(12) United States Patent
Meehl et al.

(10) Patent No.: US 9,707,276 B2
(45) Date of Patent: Jul. 18, 2017

(54) O-GLYCOSYLATED CARBOXY TERMINAL PORTION (CTP) PEPTIDE-BASED INSULIN AND INSULIN ANALOGUES

(71) Applicants: Merck Sharp & Dohme Corp., Rahway, NJ (US); Indiana University Research and Technology Corporation, Indianapolis, IN (US)

(72) Inventors: Michael Meehl, Lebanon, NH (US); Richard D. DiMarchi, Carmel, IN (US); Pengyun Li, Bloomington, IN (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/648,752

(22) PCT Filed: Nov. 22, 2013

(86) PCT No.: PCT/US2013/071384
§ 371 (c)(1),
(2) Date: Jun. 1, 2015

(87) PCT Pub. No.: WO2014/088836
PCT Pub. Date: Jun. 12, 2014

(65) Prior Publication Data
US 2015/0374795 A1    Dec. 31, 2015

Related U.S. Application Data

(60) Provisional application No. 61/732,474, filed on Dec. 3, 2012.

(51) Int. Cl.
*A61K 38/28*  (2006.01)
*A61K 38/22*  (2006.01)

(52) U.S. Cl.
CPC ............. *A61K 38/28* (2013.01); *A61K 38/22* (2013.01)

(58) Field of Classification Search
None
See application file for complete search history.

(56) References Cited

U.S. PATENT DOCUMENTS

| | | |
|---|---|---|
| 5,759,818 A | 6/1998 | Boime et al. |
| 7,259,007 B2 | 8/2007 | Bobrowicz et al. |
| 7,585,837 B2 | 9/2009 | Shechter et al. |
| 2010/0298212 A1 | 11/2010 | Maio et al. |
| 2011/0301083 A1 | 12/2011 | Zion et al. |
| 2012/0003695 A1 | 1/2012 | Davidson et al. |

FOREIGN PATENT DOCUMENTS

| | | |
|---|---|---|
| WO | 2011046855 | 4/2011 |
| WO | 2013096386 A1 | 6/2013 |

OTHER PUBLICATIONS

Lommel et al., Protein O-mannosylation: conserved from bacteria to humans, Glycobiology, May 9, 2009, vol. 19, pp. 816-828.
Fares et al., Half-Life Extension through O-Glycosylation, Therapeutic Proteins, 2012, Wiley-Blackwell, Weinheim, Germany, XP002760661, pp. 81-93.
Wildt et al., The Humanization of N-Glycosylation Pathways in Yeast, Nature Reviews, Microbiology, Nature Publishing Group, GB, vol. 3, No. 2, 2005, pp. 119-128.
Hamilton et al., Production of Complex Human Glycoproteins in yeast, Science, American Associaiton for the Advancement of Science, US, vol. 301, No. 5637, 2003, pp. 1244-1246.
Anonymous, Pichia System History: man5 man8, Pichia Pastoris Protein Expression Platform, Eukaryotic Protein Expression, 2013, pp. 1-4.
Nett et al., Characterization of the *Pichia pastoris* Protein-O-mannosyltransferase Gene Family, PLOS One, vol. 8, No. 7, 2013, pp. 1-13.
Hamilton, et al., Production of Sialylated O-linked Glycans in Pichia Pastoris, Glycobiology, Oxford University Press, US, vol. 23, No. 10, 2013, pp. 1192-1203.

*Primary Examiner* — Marcela M Cordero Garcia
*Assistant Examiner* — Catherine Mader
(74) *Attorney, Agent, or Firm* — John David Reilly; Gloria Fuentes

(57) ABSTRACT

Compositions and formulations comprising insulin or insulin analogs comprising a carboxy terminal portion (CTP) peptide comprising amino acids 112-118 to 145 of the beta subunit of human chorionic gonadotropin (hCGβ) or a partial variant thereof that includes at least one O-glycosylation site of the CTP peptide, wherein the CTP peptide of the CTP peptide-based insulin or insulin analog is O-glycosylated are described. In particular embodiments, the O-glycosylated insulin analogs are produced in vivo and in further embodiments, the O-glycosylated CTP-based insulin analogs comprise predominantly mannotriose and mannotetrose O-glycans or predominantly mannose O-glycans.

16 Claims, 20 Drawing Sheets

Glossary:
ScSUC2: S. cerevisiae Invertase
OCH1: Alpha-1,6-mannosyltransferase
KlMNN2-2: K. lactis UDP-GlcNAc transporter
BMT1: Beta-mannose-transfer (beta-mannose elimination)
BMT2: Beta-mannose-transfer (beta-mannose elimination)
BMT3: Beta-mannose-transfer (beta-mannose elimination)
BMT4: Beta-mannose-transfer (beta-mannose elimination)
MNN4L1: MNN4-like 1 (charge elimination)
MmSLC35A3: Mouse homologue of UDP-GlcNAc transporter
PNO1: Phosphomannosylation of N-linked oligosaccharides (charge elimination)
MNN4: Mannosyltransferase (charge elimination)
ScARR3: Arsenite resistance
LmSTT3d: Leishmania major N-glycan oligosaccharyltransferase

Cont. From FIG.14-1

FVNQHLCGSHLVEALYLVCGERGFFYTPKTSSSSRAPPPSLPSPSRLPGPSDTPILPQKGIVEQCCTSICSLYQLENYCN

| Das Gip Run # | Strain ID# | Plasmid ID | Occup. Mannitol/protein (mol/mol) | Chain Length | | | |
|---|---|---|---|---|---|---|---|
| | | | | Man1ol% | Man2ol% | Man3ol% | Man4ol% |
| D113901 (1/3xPMTi-4) | YGLY28024 | pGLY11167 | 2.5 | 5 | 6 | 66 | 23 |
| D113702 (1xPMTi-4) | YGLY28024 | pGLY11167 | 2.3 | 4 | 6 | 63 | 27 |

FIG.14-2

O-GLYCOSYLATED CARBOXY TERMINAL PORTION (CTP) PEPTIDE-BASED INSULIN AND INSULIN ANALOGUES

CROSS REFERENCE TO RELATED APPLICATIONS

This application claims priority to International Application No. PCT/US2013/071384, filed 22 Nov. 2013 and which claims benefit of U.S. Provisional Application No. 61/732,474 filed 3 Dec. 2012, the content of each of which is hereby incorporated by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "23093USPCT-SEQTXT-28AUG2015.txt", creation date of Aug. 28, 2015 and a size of 78 KB. This sequence listing submitted via EFS-Web is part of the specification and is herein incorporated by reference in its entirety.

BACKGROUND OF THE INVENTION (1) Field of the Invention

The present invention relates to compositions and formulations comprising insulin or insulin analogues comprising a carboxy terminal portion (CTP) peptide comprising amino acids 112-118 to 145 of the beta subunit of human chorionic gonadotropin (hCGβ) or a partial variant thereof that includes at least one O-glycosylation site of the CTP peptide, wherein the CTP peptide of the CTP peptide-based insulin or insulin analogue is O-glycosylated. In particular embodiments, the O-glycosylated insulin analogues are produced in vivo and in further embodiments, the O-glycosylated CTP-based insulin analogues comprise predominantly mannotriose and mannotetrose O-glycans or predominantly mannose O-glycans.

(2) Description of Related Art

Insulin is a peptide hormone that is essential for maintaining proper glucose levels in most higher eukaryotes, including humans. Diabetes is a disease in which the individual cannot make insulin or develops insulin resistance. Type I diabetes is a form of diabetes mellitus that results from autoimmune destruction of insulin-producing beta cells of the pancreas. Type II diabetes is a metabolic disorder that is characterized by high blood glucose in the context of insulin resistance and relative insulin deficiency. Left untreated, an individual with Type I or Type II diabetes will die. While not a cure, insulin is effective for lowering glucose in virtually all forms of diabetes. Unfortunately, its pharmacology is not glucose sensitive and as such it is capable of excessive action that can lead to life-threatening hypoglycemia. Inconsistent pharmacology is a hallmark of insulin therapy such that it is extremely difficult to normalize blood glucose without occurrence of hypoglycemia. Furthermore, native insulin is of short duration of action and requires modification to render it suitable for use in control of basal glucose. One central goal in insulin therapy is designing an insulin formulation capable of providing a once a day time action. Mechanisms for extending the action time of an insulin dosage include decreasing the solubility of insulin at the site of injection or covalently attaching sugars, polyethylene glycols, hydrophobic ligands, peptides, or proteins to the insulin.

Molecular approaches to reducing solubility of the insulin have included (1) formulating the insulin as an insoluble suspension with zinc and/or protamine, (2) increasing its isoelectric point through amino acid substitutions and/or additions, such as cationic amino acids to render the molecule insoluble at physiological pH, or (3) covalently modifying the insulin to include a hydrophobic ligand that reduces solubility of the insulin and which binds serum albumin. All of these approaches have been limited by the inherent variability that occurs with precipitation of the molecule at the site of injection, and with the subsequent re-solubilization and transport of the molecule to blood in the form of an active hormone. Even though the resolubilization of the insulin provides a longer duration of action, the insulin is still not responsive to serum glucose levels and the risk of hypoglycemia remains.

Insulin is a two chain heterodimer that is biosynthetically derived from a low potency single chain proinsulin precursor through enzymatic processing. The human insulin analogue consists of two peptide chains, an "A-chain peptide" (SEQ ID NO: 33) and "B-chain peptide" (SEQ ID NO: 25)) bound together by disulfide bonds and having a total of 51 amino acids. The C-terminal region of the B-chain and the two terminal ends of the A-chain associate in a three-dimensional structure that assembles a site for high affinity binding to the insulin receptor. The insulin molecule does not contain N-glycosylation.

Insulin molecules have been modified by linking various moieties to the molecule in an effort to modify the pharmacokinetic or pharmacodynamic properties of the molecule. For example, acylated insulin analogs have been disclosed in a number of publications, which include for example U.S. Pat. Nos. 5,693,609 and 6,011,007. PEGylated insulin analogs have been disclosed in a number of publications including, for example, U.S. Pat. Nos. 5,681,811, 6,309,633; 6,323,311; 6,890,518; 6,890,518; and, 7,585,837. Glycoconjugated insulin analogs have been disclosed in a number of publications including, for example, Internal Publication Nos. WO06082184, WO09089396, WO9010645, U.S. Pat. Nos. 3,847,890; 4,348,387; 7,531,191; and, 7,687,608. Remodeling of peptides, including insulin to include glycan structures for PEGylation and the like have been disclosed in publications including, for example, U.S. Pat. No. 7,138,371 and U.S. Published Application No. 20090053167.

BRIEF SUMMARY OF THE INVENTION

The present invention provides insulin or insulin analogues modified to include the carboxy terminal portion (CTP) peptide found at positions 112-118 to position 145 of the beta subunit of human chorionic gonadotropin (hCGβ) or a partial variant thereof that includes at least one or two O-glycosylation sites of the CTP peptide, wherein the CTP peptide is O-glycosylated. In particular aspects, the variant comprises at least two O-glycosylation sites.

The present invention further provides compositions and formulations comprising insulin and insulin analogues having an O-glycosylated CTP peptide or partial variant thereof that includes at least one or two O-glycosylation sites of the CTP peptide (hereinafter, the term "insulin and insulin analogues having an O-glycosylated CTP peptide or partial variant thereof that includes at least one or two O-glycosylation sites of the CTP peptide" may also be referred to as "CTP peptide-based insulin or insulin analogue"), methods for producing the CTP peptide-based insulin or insulin analogues in yeast, and methods for using the CTP peptide-based insulin or insulin analogues. In particular aspects of the present invention, the CTP peptide comprises the amino acid sequence SSSSKAPPPSLPSPSRLPGPSDTPILPQ (SEQ ID NO:1), which is prone to O-linked glycosylation when the protein is expressed in a eukaryotic cellular expression system. The CTP peptide may be covalently linked to the N-terminus and/or the carboxy terminus of the B-chain of a two chain insulin analog without undermining the inherent in vitro activity of the insulin analogue. In addition, the CTP peptide may also be used to connect the B and A chains of insulin to form a single chain insulin analogue while still maintaining high in vitro potency in a manner that the native proinsulin C-peptide can not.

Thus, the present invention provides insulin and insulin analogues having an O-glycosylated CTP peptide wherein the CTP peptide comprises at least one, two, three, four, or more O-glycans thereon or partial variant of the CTP peptide that includes at least one or two O-glycosylation sites of the CTP peptide. The CTP peptide-based insulin or insulin analogue molecules disclosed herein comprise one or more O-glycans linked to a serine or threonine residue of the CTP peptide in an α1-linkage wherein the O-glycan comprises one, two, three, or four mannose residues wherein the reducing end of the mannose residue is in an α1 linkage to the serine or threonine of the CTP peptide. In a further aspect, at least one O-glycan on the CTP peptide of the insulin or insulin analogue comprises a mannose, mannobiose, mannotriose, or mannotetrose O-glycan structure (See FIG. 13B).

In a further embodiment, the present invention provides compositions comprising insulin and insulin analogues having an O-glycosylated CTP peptide or partial variant thereof that includes at least one or two O-glycosylation sites of the CTP peptide thereof wherein the CTP peptide comprises one or more O-glycans thereon. In particular aspects of the invention, compositions are provided comprising insulin and insulin analogues having an O-glycosylated CTP peptide or partial variant thereof that includes at least one or two O-glycosylation sites of the CTP peptide wherein the predominant O-glycan in the composition is a mannose, mannobiose, mannotriose, or mannotetrose (See FIG. 13B). In a further aspect, the present invention provides compositions comprising insulin and insulin analogues having an O-glycosylated CTP peptide or partial variant thereof that includes at least one or two O-glycosylation sites of the CTP peptide wherein the predominant O-glycan in the composition is a mannose, mannobiose, mannotriose, or mannotetrose. In a further aspect, the present invention provides compositions comprising O-glycosylated C-terminal peptide (CTP)-based insulin or insulin analogue molecules wherein mannotriose and mannotetrose are the predominant O-glycans. In a further aspect, the present invention provides compositions comprising insulin and insulin analogues having an O-glycosylated CTP peptide or partial variant thereof that includes at least one or two O-glycosylation sites of the CTP peptide wherein mannotriose is the predominant O-glycan. In a further aspect, the present invention provides compositions comprising insulin and insulin analogues having an O-glycosylated CTP peptide or partial variant thereof that includes at least one or two O-glycosylation sites of the CTP peptide wherein mannotetrose is the predominant O-glycan.

In a further embodiment, the present invention provides compositions comprising insulin and insulin analogues having an O-glycosylated CTP peptide or partial variant thereof that includes at least one or two O-glycosylation sites of the CTP peptide and a pharmaceutically acceptable carrier or salt wherein the CTP peptide comprises one or more O-glycans thereon. In particular aspects of the invention, compositions are provided comprising insulin and insulin analogues having an O-glycosylated CTP peptide or partial variant thereof that includes at least one or two O-glycosylation sites of the CTP peptide and a pharmaceutically acceptable carrier or salt wherein the predominant O-glycan in the composition is a mannose, mannobiose, mannotriose, or mannotetrose. In a further aspect, the present invention provides compositions comprising insulin and insulin analogues having an O-glycosylated CTP peptide or partial variant thereof that includes at least one or two O-glycosylation sites of the CTP peptide and a pharmaceutically acceptable carrier or salt wherein the predominant O-glycan in the composition is a mannose, mannobiose, mannotriose, or mannotetrose. In a further aspect, the present invention provides compositions comprising insulin and insulin analogues having an O-glycosylated CTP peptide or partial variant thereof that includes at least one or two O-glycosylation sites of the CTP peptide and a pharmaceutically acceptable carrier or salt wherein mannotriose and mannotetrose are the predominant O-glycans. In a further aspect, the present invention provides compositions comprising insulin and insulin analogues having an O-glycosylated CTP peptide or partial variant thereof that includes at least one or two O-glycosylation sites of the CTP peptide and a pharmaceutically acceptable carrier or salt wherein mannotriose is the predominant O-glycan. In a further aspect, the present invention provides compositions comprising insulin and insulin analogues having an O-glycosylated CTP peptide or partial variant thereof that includes at least one or two O-glycosylation sites of the CTP peptide and a pharmaceutically acceptable carrier or salt wherein mannotetrose is the predominant O-glycan.

In a further embodiment, the present invention provides pharmaceutical compositions comprising insulin and insulin analogues having an O-glycosylated CTP peptide or partial variant thereof that includes at least one or two O-glycosylation sites of the CTP peptide and a pharmaceutically acceptable carrier or salt wherein the CTP peptide comprises one or more O-glycans thereon. In particular aspects of the invention, pharmaceutical compositions are provided comprising insulin and insulin analogues having an O-glycosylated CTP peptide or partial variant thereof that includes at least one or two O-glycosylation sites of the CTP peptide and a pharmaceutically acceptable carrier or salt wherein the predominant O-glycan in the composition is a mannose, mannobiose, mannotriose, or mannotetrose. In a further aspect, the present invention provides pharmaceutical compositions comprising insulin and insulin analogues having an O-glycosylated CTP peptide or partial variant thereof that includes at least one or two O-glycosylation sites of the CTP peptide and a pharmaceutically acceptable carrier or salt wherein the predominant O-glycan in the composition is a mannose, mannobiose, mannotriose, or mannotetrose. In a further aspect, the present invention provides pharmaceutical compositions comprising insulin and insulin analogues having an O-glycosylated CTP peptide or partial variant thereof that includes at least one or two O-glycosylation sites of the CTP peptide and a pharmaceutically acceptable carrier or salt wherein mannotriose and mannotetrose are the predominant O-glycans. In a further aspect, the present invention provides pharmaceutical compositions comprising insulin and insulin analogues having an O-glycosylated CTP peptide or partial variant thereof that includes at least one or two O-glycosylation sites of the CTP peptide and a pharmaceutically acceptable carrier or salt wherein mannotriose is the predominant O-glycan. In a further aspect, the present invention provides pharmaceutical compositions comprising insulin and insulin analogues having an O-glycosylated CTP peptide or partial variant thereof that includes at least one or two O-glycosylation sites of the CTP peptide and a pharmaceutically acceptable carrier or salt wherein mannotetrose is the predominant O-glycan.

In a further aspect of the present invention, a composition is provided comprising an O-glycosylated insulin or insulin analogue having an A-chain peptide comprising the amino acid sequence GIVEQCCTSICSLYQLENYC (SEQ ID NO: 90); a B-chain peptide comprising the amino acid sequence HLCGSHLVEALYLVCGERGFF (SEQ ID NO:3); and a CTP peptide comprising the amino acid sequence SSSSKAPPPSLPSPSRLPGPSDTPILPQ; SEQ ID NO:1), wherein at least one amino acid residue of the CTP peptide is covalently linked to an O-glycan; and wherein the insulin or insulin analogue optionally further includes up to 1, 2, 3, 4, 5, 6, 7, 8, 9, 10, 11, 12, 13, 14, 15, 16, or 17 amino acid substitutions and the CTP peptide is covalently linked by peptide bond to the N-terminus of the B-chain peptide, the C-terminus of the A-chain peptide, the C-terminus of the B chain peptide, or the CTP peptide is a connecting peptide that covalently links the B-chain peptide to the A-chain peptide to produce a single-chain insulin or insulin analogue having the structure (B-chain)-(CTP peptide)-(A-chain); and a pharmaceutically acceptable carrier or salt. The insulin or insulin analogue has three disulfide bonds: the first disulfide bond is between the cysteine residues at positions 6 and 11 of SEQ ID NO:2, the second disulfide bond is between the cysteine residues at position 3 of SEQ ID NO:3 and position 7 of SEQ ID NO:2, and the third disulfide bond is between the cysteine residues at position 15 of SEQ ID NO:3 and position 20 of SEQ ID NO:2. In further aspects, at least two, three, or four O-glycans are linked to the CTP peptide.

In a further aspect of the present invention, a pharmaceutical composition is provided comprising an O-glycosylated insulin or insulin analogue molecule having an A-chain peptide comprising the amino acid sequence GIVEQCCTSICSLYQLENYC (SEQ ID NO: 90); a B-chain peptide comprising the amino acid sequence HLCGSHLVEALYLVCGERGFF (SEQ ID NO:3); and a CTP peptide comprising the amino acid sequence SSSSKAPPPSLPSPSRLPGPSDTPILPQ; SEQ ID NO:1), wherein at least one amino acid residue of the CTP peptide is covalently linked to an O-glycan; and wherein the insulin or insulin analogue optionally further includes up to 1, 2, 3, 4, 5, 6, 7, 8, 9, 10, 11, 12, 13, 14, 15, 16, or 17 amino acid substitutions and the CTP peptide is covalently linked by peptide bond to the N-terminus of the B-chain peptide, the C-terminus of the A-chain peptide, C-terminus of the B-chain peptide, or the CTP peptide is a connecting peptide that covalently links the B-chain peptide to the A-chain peptide to produce a single-chain insulin or insulin analogue having the (B-chain)-(CTP peptide)-(A-chain); and a pharmaceutically acceptable carrier or salt. The insulin or insulin analogue has three disulfide bonds: the first disulfide bond is between the cysteine residues at positions 6 and 11 of SEQ ID NO:2, the second disulfide bond is between the cysteine residues at position 3 of SEQ ID NO:3 and position 7 of SEQ ID NO:2, and the third disulfide bond is between the cysteine residues at position 15 of SEQ ID NO:3 and position 20 of SEQ ID NO:2. In further aspects, two, three, or four O-glycans are linked to the CTP peptide.

In further aspects of any of the above embodiments, the insulin or insulin analogue is a heterodimer molecule comprising an A-chain peptide and a B-chain peptide wherein the A-chain peptide is covalently linked to the B-chain by two disulfide bonds or a single-chain molecule comprising an A-chain peptide connected to the B-chain peptide by a connecting peptide wherein the A-chain and the B-chain are covalently linked by two disulfide bonds and wherein the CTP peptide is covalently linked to the N-terminus of the B-chain or the C-terminus of the A-chain.

In further aspects of any of the above embodiments, the insulin or insulin analogue is a single-chain molecule comprising an A-chain peptide and a B-chain peptide wherein the A-chain peptide is covalently linked to the B-chain by two disulfide bonds or a single-chain molecule comprising an A-chain peptide connected to the B-chain peptide by a connecting peptide wherein the A-chain and the B-chain are covalently linked by two disulfide bonds and wherein the CTP peptide is a connecting peptide that covalently links the B-chain to the A-chain to provide the single-chain insulin or insulin analogue having the structure B-chain-CTP peptide-A-chain.

In further aspects of any of the above embodiments, the amino acids substitutions are selected from positions 5, 8, 9, 10, 12, 14, 15, 17, 18, and 21 of an A-chain peptide having the amino acid sequence shown in SEQ ID NO:2 and/or positions 1, 2, 3, 4, 5, 9, 10, 13, 14, 17, 20, 21, 22, 23, 26, 27, 28, 29, and 30 of a B-chain peptide having the amino acid sequence shown in SEQ ID NO:4.

In further aspects of any of the above embodiments, the amino acid at position 21 of the A-chain peptide is Gly and the B-chain peptide includes the dipeptide Arg-Arg covalently linked to the Thr at the position 30 of the B-chain peptide. In another aspect, the amino acids at positions 28 and 29 of the B-chain peptide are lysine and proline, respectively. In another aspect, the amino acid a position 28 of the B-chain peptide is aspartic acid. In another aspect, the amino acid a position 3 of the B-chain peptide is lysine and position 29 of the B-chain peptide is glutamic acid.

In general, the O-glycosylated CTP peptide-based insulin and insulin analogues disclosed herein have an A-chain peptide comprising 21 amino acids and a B-chain peptide comprising 30 amino acids; however, in particular aspects, the B-chain peptide lacks a threonine residue at position 30 (desB30) or in other aspects, one or more amino acids at positions 1 to 4 and/or 26 to 30 of the B-chain peptide have been deleted. In particular embodiments of the O-glycosylated CTP peptide-based heterodimer and single-chain insulin and insulin analogues, the B-chain peptide lacks amino acids 26-30 (desB26-30).

In further aspects of the compositions supra, the O-glycan occupancy is at least one mole of O-glycan per mole of C-terminal peptide (CTP)-based insulin or insulin analogue. In a further aspect, the O-glycan occupancy is at least two moles of O-glycan per mole of C-terminal peptide (CTP)-based insulin or insulin analogue. In a further aspect, the O-glycan occupancy is at least three moles of O-glycan per mole of C-terminal peptide (CTP)-based insulin or insulin analogue. In particular aspects, the O-glycan occupancy is at about one to four moles of O-glycan per mole of C-terminal peptide (CTP)-based insulin or insulin analogue.

In further aspects of the compositions supra, at least 40 mole % of the O-glycans are mannotriose or mannotetrose, at least 50 mole % of the O-glycans are mannotriose or mannotetrose, at least 60 mole % of the O-glycans are mannotriose or mannotetrose, at least 70 mole % of the O-glycans are mannotriose or mannotetrose, at least 80 mole % of the O-glycans are mannotriose or mannotetrose, at least 90 mole % of the O-glycans are mannotriose or mannotetrose, at least 95 mole % of the O-glycans are mannotriose or mannotetrose, at least 98 mole % of the O-glycans are mannotriose or mannotetrose, or at least 99 mole % of the O-glycans are mannotriose or mannotetrose.

In further aspects of the compositions supra, at least 40 mole % of the O-glycans are mannotriose and mannotetrose, at least 50 mole % of the O-glycans are mannotriose and mannotetrose, at least 60 mole % of the O-glycans are mannotriose or mannotetrose, at least 70 mole % of the O-glycans are mannotriose and mannotetrose, at least 80 mole % of the O-glycans are mannotriose and mannotetrose, at least 90 mole % of the O-glycans are mannotriose and mannotetrose, at least 95 mole % of the O-glycans are mannotriose and mannotetrose, at least 98 mole % of the O-glycans are mannotriose or mannotetrose, or at least 99 mole % of the O-glycans are mannotriose and mannotetrose.

In a further aspect of the compositions supra, at least 70%, 75%, 80%, 85%, 90%, 95%, 96%, 97%, 98%, 99%, or 100% of the CTP peptide-based insulin or insulin analogues include at least one O-glycan.

In a further aspect of the compositions supra, the mannose residues comprising the O-glycan are covalently linked to an adjacent mannose residue by an α1,2 linkage. In a further aspect, the O-glycans lack detectable mannose residues linked to an adjacent mannose residue in an β1,2-linkage and lack detectable mannose residues covalently linked to a phosphate atom. Thus, provided are composition of O-glycosylated CTP peptide-based insulin or insulin analogues that lack detectable β-linked mannose residues, phosphomannose residues, or β-linked mannose and phosphomannose residues.

The present invention further provides methods for making O-glycosylated CTP peptide-based insulin or insulin analogues in yeast or filamentous fungi host cells. In general, the host cells that are used to produce the O-glycosylated CTP peptide-based insulin or insulin analogues disclosed herein display with respect to an O-glycan on a glycoprotein little or no detectable β-mannosyltransferase activity. In another aspect, the host cells that are used to produce the O-glycosylated CTP peptide-based insulin or insulin analogues display with respect to an O-glycan on a glycoprotein little or no detectable phosphomannosyltransferase activity. In a further aspect, the host cells that are used to produce the O-glycosylated CTP peptide-based insulin or insulin analogues display with respect to an O-glycan on a glycoprotein little or no detectable phosphomannosyltransferase activity and β-mannosyltransferase activity. In particular aspects, the host cells further display with respect to an O-glycan on a glycoprotein little or no detectable initiating α1,6-mannosyltransferase activity. In a further aspect, the host cells that are used to produce the CTP peptide-based insulin or insulin analogues display with respect to an O-glycan on a glycoprotein little or no detectable phosphomannosyltransferase activity, β-mannosyltransferase activity, and initiating α1,6-mannosyltransferase activity.

Therefore, the present invention provides a method for making O-glycosylated CTP peptide-based insulin or insulin analogues in yeast or filamentous fungi host cells, comprising providing a yeast or filamentous fungus host cell that does not display detectable β-mannosyltransferase activity; transforming the host cell with a nucleic acid molecule encoding a CTP peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium.

In another embodiment, the present invention provides a method for making O-glycosylated CTP peptide-based insulin or insulin analogues in yeast or filamentous fungi host cells, comprising providing a yeast or filamentous fungus host cell that does not display detectable phosphomannosyltransferase activity; transforming the host cell with a nucleic acid molecule encoding a CTP peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium.

In a further embodiment, the present invention provides a method for making O-glycosylated CTP peptide-based insulin or insulin analogues in yeast or filamentous fungi host cells, comprising providing a yeast or filamentous fungus host cell that does not display detectable β-mannosyltransferase activity and phosphomannosyltransferase activity; transforming the host cell with a nucleic acid molecule encoding a CTP peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium.

In particular aspects of the above method, the host cell is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia minuta (Ogataea minuta, Pichia lindneri), Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum*, and *Neurospora crassa*.

The present invention further provides methods for making O-glycosylated CTP peptide-based insulin or insulin analogues in *Pichia pastoris* host cells comprising providing *Pichia pastoris* host cells wherein expression of one or more of the genes encoding β-mannosyltransferase activity is abrogated; transforming the host cell with a nucleic acid molecule encoding a CTP peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium. In a further aspect, expression of at least the BMT2 gene is abrogated. In a further aspect, expression of two or more of the BMT1, BMT2, BMT3, and BMT4 genes is abrogated. In a further aspect, expression of each of the BMT1, BMT2, BMT3, and BMT4 genes is abrogated.

The present invention further provides methods for making O-glycosylated CTP peptide-based insulin or insulin analogues in *Pichia pastoris* host cells comprising providing *Pichia pastoris* host cell wherein expression of one or more of the genes encoding phosphomannosyltransferase activity is abrogated. In a further aspect, expression of at least the PNO1 gene is abrogated; transforming the host cell with a nucleic acid molecule encoding a CTP peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium. In a further aspect, expression of the MMN4L1 genes is abrogated. In a further aspect, expression of the PNO1 and the MMN4L1 genes is abrogated. In a further aspect, expression of the MNN4 gene is abrogated. In a further aspect, expression of the PNO1, MNN4, and the MMN4L1 genes is abrogated The present invention further provides methods for making O-glycosylated CTP peptide-based insulin or insulin analogues in yeast host cells wherein expression of the OCH1 gene encoding initiating α1,6-mannosyltransferase activity is abrogated comprising transforming the host cell with a nucleic acid molecule encoding a CTP peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium.

The present invention further provides methods for making O-glycosylated CTP peptide-based insulin or insulin analogues in Pichia pastoris host cells comprising providing Pichia pastoris host cells wherein expression of one or more of the genes encoding β-mannosyltransferase activity and expression of one or more genes encoding phosphomannosyltransferase activity is abrogated; transforming the host cell with a nucleic acid molecule encoding a CTP peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium. In a further aspect, expression of at least the BMT2 gene and the PNO1 gene is abrogated. In a further aspect, expression of two or more of the BMT1, BMT2, BMT3, and BMT4 genes and the PNO1 gene is abrogated. In a further aspect, expression of each of the BMT1, BMT2, BMT3 and BMT4 genes and the PNO1 gene is abrogated. In a further aspect, expression of at least the BMT2 gene and the PNO1 and MNN4L1 genes is abrogated. In a further aspect, expression of two or more of the BMT1, BMT2, BMT3, and BMT4 genes and the PNO1 and MNN4L1 genes is abrogated. In a further aspect, expression of each of the BMT1, BMT2, BMT3, and BMT4 genes and the PNO1 and MNN4L1 genes is abrogated. In a further aspect, expression of at least the BMT2 gene and the PNO1, MNN4, and MNN4L1 genes is abrogated. In a further aspect, expression of two or more of the BMT1, BMT2, BMT3, and BMT4 genes and the PNO1 MNN4, and MNN4L1 genes is abrogated. In a further aspect, expression of each of the BMT1, BMT2, BMT3, and BMT4 genes and the PNO1 MNN4, and MNN4L1 genes is abrogated. In a further aspect of any one of the aforementioned aspects, the host further includes abrogation of expression of the OCH1 gene encoding initiating α1,6-mannosyltransferase activity.

In any of the aforementioned aspects, abrogation of expression of any of the genes recited supra may be achieved be deleting the gene or a portion thereof (e.g., open reading frame encoding the gene product or promoter) or disrupting the gene by inserting a heterologous nucleic acid molecule into the open reading frame encoding the gene product. In either case, the gene is rendered incapable of producing a gene product having detectable activity, e.g., detectable β-mannosyltransferase, phosphomannosyltransferase, or α1,6-mannosylatransferase activity, as the case may be. In other aspects, the expression of one or more of the genes recited supra is abrogated using inhibitors of gene transcription and/or mRNA translation, which includes but is not limited to chemical compounds, antisense DNA to one or more mRNA encoding the gene or genes, or siRNA to one or more mRNA encoding the gene or genes.

In a particular aspect, the β-mannosyltransferase, phosphomannosyltransferase, and/or α1,6-mannosylatransferase activity is inhibited by cultivating the host cell for a time in the presence of one or more chemical inhibitors of β-mannosyltransferase, phosphomannosyltransferase, and/or α1,6-mannosylatransferase activity, for example, the host cells are cultivated in the presence of the inhibitor at the same time or just before expression of the O-glycosylated CTP peptide-based insulin or insulin analogue is induced.

The present invention further provides lower eukaryote host cells that include a nucleic acid molecule encoding a CTP peptide-based insulin or insulin analogue. The host cells may have a genetic background as described supra. For example, the present invention provides lower eukaryote host cells that comprise a deletion or disruption of one or more genes encoding a β-mannosyltransferase activity and includes a nucleic acid molecule encoding a CTP-based insulin or insulin analogue. In another embodiment, the present invention also provides lower eukaryote host cells that comprise a deletion or disruption of one or more genes encoding a phosphomannosyltransferase activity and includes a nucleic acid molecule encoding a CTP-based insulin or insulin analogue. In a further embodiment, the present invention provides lower eukaryote host cells that comprise a deletion or disruption of one or more genes encoding a β-mannosyltransferase activity; a deletion or disruption of one or more genes encoding a phosphomannosyltransferase activity; and includes a nucleic acid molecule encoding a CTP-based insulin or insulin analogue. The embodiments the nucleic acid molecule may be integrated into the genome of the host cell or may be present in the host cell extra-chromosomally, e.g., plasmid vector, mini-chromosome, and the like.

In a further embodiment, the host cells further include a nucleic acid molecule encoding an α1,2 mannosidase activity and the host cell produces O-glycans consisting of predominantly or solely a single mannose residue. Thus, the host cell produces O-glycosylated CTP peptide-based insulin or insulin analogues having mannose O-glycan structures in which greater than 10%, 20%, 30%, 40% 50%, 60%, 70%, 80%, 90%, 95%, or 98% of the O-glycosylation sites are occupied with a mannose residue. In further embodiments, the α1,2 mannosidase activity is provided by a fusion protein comprising the catalytic domain of α1,2 mannosidase fused at its N-terminus to a heterologous cellular targeting peptide that targets the fusion protein to the secretory pathway.

The present invention further provides O-glycosylated CTP peptide-based insulin or insulin analogues as disclosed herein produced by any one of the host cells disclosed herein.

The present invention further provides nucleic acid molecules comprising an open reading frame (ORF) encoding a CTP peptide-based insulin or insulin analogue as disclosed herein. In particular aspects, the ORF encoding the CTP peptide-based insulin or insulin analogue is downstream from a second ORF on the nucleic acid molecule, which encodes a pre-propeptide, for example a Saccharomyces cerevisiae alpha mating factor, to provide a single continuous ORF encoding a fusion protein in which the pre-pro peptide is fused to the N-terminus of the CTP peptide-based insulin or insulin analogue. In a further aspect, the nucleic acid molecule encoding the CTP peptide-based insulin or insulin analogue is operably linked to an inducible promoter, for example, the Pichia pastoris AOX1 promoter. In particular aspects, the codons encoding the CTP peptide-based insulin or insulin analogue are modified to codons that are commonly used in *Pichia pastoris*. In further embodiments, the host cell further includes a nucleic acid molecule encoding an α1,2 mannosidase activity, which in further embodiments is a fusion protein comprising the catalytic domain of α1,2 mannosidase fused at its N-terminus to a heterologous cellular targeting peptide that targets the fusion protein to the secretory pathway.

Further provided is the use of an O-glycosylated CTP peptide-based insulin or insulin analogues as disclosed herein for the preparation of a medicament, composition, or formulation for the treatment of diabetes. Further provided is a composition as disclosed herein for the treatment of diabetes. For example, an O-glycosylated insulin or insulin analogue molecule having an A-chain peptide comprising the amino acid sequence GIVEQCCTSICSLYQLENYC (SEQ ID NO: 90); and a B-chain peptide comprising the amino acid sequence HLCGSHLVEALYLVCGERGFF (SEQ ID NO:3) and a CTP peptide comprising the amino acid sequence SSSSKAPPPSLPSPSRLPGPSDTPILPQ; SEQ ID NO:1), wherein at least one amino acid residue of the CTP peptide is covalently linked to an O-glycan; and wherein the insulin or insulin analogue molecule optionally further includes up to 17 amino acid substitutions and/or a polypeptide of 3 to 35 amino acids covalently linked to an N-terminus or C-terminus of the molecule; and a pharmaceutically acceptable carrier or salt for the treatment of diabetes. In further aspects, two, three, or four O-glycans are linked to the CTP peptide.

DEFINITIONS

As used herein, the term "insulin" means the active principle of the pancreas that affects the metabolism of carbohydrates in the animal body and which is of value in the treatment of diabetes mellitus. The term includes synthetic and biotechnologically derived products that are the same as, or similar to, naturally occurring insulins in structure, use, and intended effect and are of value in the treatment of diabetes mellitus.

The term "insulin" or "insulin molecule" is a generic term that designates the 51 amino acid heterodimer comprising the A-chain peptide having the amino acid sequence shown in SEQ ID NO: 2 and the B-chain peptide having the amino acid sequence shown in SEQ ID NO: 4, wherein the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond.

The term "insulin analogue" as used herein includes any heterodimer analogue or single-chain analogue that comprises one or more modification(s) of the native A-chain peptide and/or B-chain peptide. Modifications include but are not limited to substituting an amino acid for the native amino acid at a position selected from A4, A5, A8, A9, A10, A12, A13, A14, A15, A16, A17, A18, A19, A21, B1, B2, B3, B4, B5, B9, B10, B13, B14, B15, B16, B17, B18, B20, B21, B22, B23, B26, B27, B28, B29, and B30; deleting any or all of positions B1-4 and B26-30; or conjugating directly or by a polymeric or non-polymeric linker one or more acyl, polyethylglycine (PEG), or saccharide moiety (moieties); or any combination thereof. Examples of insulin analogues include but are not limited to the heterodimer and single-chain analogues disclosed in published international application WO20100080606, WO2009/099763, and WO2010080609, the disclosures of which are incorporated herein by reference. Examples of single-chain insulin analogues also include but are not limited to those disclosed in published International Applications WO9634882, WO95516708, WO2005054291, WO2006097521, WO2007104734, WO2007104736, WO2007104737, WO2007104738, WO2007096332, WO2009132129; U.S. Pat. Nos. 5,304,473 and 6,630,348; and Kristensen et al., Biochem. J. 305: 981-986 (1995), the disclosures of which are each incorporated herein by reference.

The term "insulin analogues" further includes single-chain and heterodimer polypeptide molecules that have little or no detectable activity at the insulin receptor but which have been modified to include one or more amino acid modifications or substitutions to have an activity at the insulin receptor that has at least 1%, 10%, 50%, 75%, or 90% of the activity at the insulin receptor as compared to native insulin and which further includes at least one N-linked glycosylation site. In particular aspects, the insulin analogue is a partial agonist that has from 2× to 100× less activity at the insulin receptor as does native insulin. In other aspects, the insulin analogue has enhanced activity at the insulin receptor, for example, the $IGF^{B16B17}$ derivative peptides disclosed in published international application WO2010080607 (which is incorporated herein by reference). These insulin analogues, which have reduced activity at the insulin growth hormone receptor and enhanced activity at the insulin receptor, include both heterodimers and single-chain analogues.

As used herein, the term "single-chain insulin" or "single-chain insulin analogue" encompasses a group of structurally-related proteins wherein the A-chain peptide or functional analogue and the B-chain peptide or functional analogue are covalently linked by a peptide or polypeptide of 2 to 35 amino acids or non-peptide polymeric or non-polymeric linker and which has at least 1%, 10%, 50%, 75%, or 90% of the activity of insulin at the insulin receptor as compared to native insulin. The single-chain insulin or insulin analogue further includes three disulfide bonds: the first disulfide bond is between the cysteine residues at positions 6 and 11 of the A-chain or functional analogue thereof, the second disulfide bond is between the cysteine residues at position 7 of the A-chain or functional analogue thereof and position 7 of the B-chain or functional analogue thereof, and the third disulfide bond is between the cysteine residues at position 20 of the A-chain or functional analogue thereof and position 19 of the B-chain or functional analogue thereof.

As used herein, the term "connecting peptide" or "C-peptide" refers to the connection moiety "C" of the B-C-A polypeptide sequence of a single chain preproinsulin-like molecule. Specifically, in the natural insulin chain, the C-peptide connects the amino acid at position 30 of the B-chain and the amino acid at position 1 of the A-chain. The term can refer to both the native insulin C-peptide (SEQ ID NO:5), the monkey C-peptide, and any other peptide from 3 to 35 amino acids that connects the B-chain to the A-chain thus is meant to encompass any peptide linking the B-chain peptide to the A-chain peptide in a single-chain insulin analogue (See for example, U.S. Published application Nos. 20090170750 and 20080057004 and WO9634882) and in insulin precursor molecules such as disclosed in WO9516708 and U.S. Pat. No. 7,105,314. As shown herein and disclosed in U.S. Provisional Application 61/578,052 filed 20 Dec. 2011, the connecting peptide may be the CTP peptide.

As used herein, the term "pre-proinsulin analogue precursor" refers to a fusion protein comprising a leader peptide, which targets the prepro-insulin analogue precursor to the secretory pathway of the host cell, fused to the N-terminus of a B-chain peptide or B-chain peptide analogue, which is fused to the N-terminus of a C-peptide which in turn is fused at its C-terminus to the N-terminus of an A-chain peptide or A-chain peptide analogue. The fusion protein may optionally include one or more extension or spacer peptides between the C-terminus of the leader peptide and the N-terminus of the B-chain peptide or B-chain peptide analogue. The extension or spacer peptide when present may protect the N-terminus of the B-chain or B-chain analogue from protease digestion during fermentation. The native human pre-proinsulin has the amino acid sequence shown in SEQ ID NO:6.

As used herein, the term "proinsulin analogue precursor" refers to a molecule in which the signal or pre-peptide of the pre-proinsulin analogue precursor has been removed.

As used herein, the term "insulin analogue precursor" refers to a molecule in which the propeptide of the proinsulin analogue precursor has been removed. The insulin analogue precursor may optionally include the extension or spacer peptide at the N-terminus of the B-chain peptide or B-chain peptide analogue. The insulin analogue precursor is a single-chain molecule since it includes a C-peptide; however, the insulin analogue precursor will contain correctly positioned disulphide bridges (three) as in human insulin and may by one or more subsequent chemical and/or enzymatic processes be converted into a heterodimer or single-chain insulin analogue.

As used herein, the term "leader peptide" refers to a polypeptide comprising a pre-peptide (the signal peptide) and a propeptide.

As used herein, the term "signal peptide" refers to a pre-peptide which is present as an N-terminal peptide on a precursor form of a protein. The function of the signal peptide is to facilitate translocation of the expressed polypeptide to which it is attached into the endoplasmic reticulum. The signal peptide is normally cleaved off in the course of this process. The signal peptide may be heterologous or homologous to the organism used to produce the polypeptide. A number of signal peptides which may be used include the yeast aspartic protease 3 (YAP3) signal peptide or any functional analogue (Egel-Mitani et al. YEAST 6:127 137 (1990) and U.S. Pat. No. 5,726,038) and the signal peptide of the *Saccharomyces cerevisiae* mating factor α1 gene (ScMF α 1) gene (Thorner (1981) in The Molecular Biology of the Yeast *Saccharomyces cerevisiae*, Strathern et al., eds., pp 143 180, Cold Spring Harbor Laboratory, NY and U.S. Pat. No. 4,870,008.

As used herein, the term "propeptide" refers to a peptide whose function is to allow the expressed polypeptide to which it is attached to be directed from the endoplasmic reticulum to the Golgi apparatus and further to a secretory vesicle for secretion into the culture medium (i.e., exportation of the polypeptide across the cell wall or at least through the cellular membrane into the periplasmic space of the yeast cell). The propeptide may be the ScMF al (See U.S. Pat. Nos. 4,546,082 and 4,870,008). Alternatively, the propeptide may be a synthetic propeptide, which is to say a propeptide not found in nature, including but not limited to those disclosed in U.S. Pat. Nos. 5,395,922; 5,795,746; and 5,162,498 and in WO 9832867. The propeptide will preferably contain an endopeptidase processing site at the C-terminal end, such as a Lys-Arg sequence or any functional analogue thereof.

As used herein with the term "insulin", the term "desB30" or "B(1-29)" is meant to refer to an insulin B-chain peptide lacking the B30 amino acid residue and "A(1-21)" means the insulin A chain.

As used herein, the term "immediately N-terminal to" is meant to illustrate the situation where an amino acid residue or a peptide sequence is directly linked at its C-terminal end to the N-terminal end of another amino acid residue or amino acid sequence by means of a peptide bond.

As used herein an amino acid "modification" refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

As used herein an amino acid "substitution" refers to the replacement of one amino acid residue by a different amino acid residue. Throughout the application, all references to a particular amino acid position by letter and number (e.g. position A5) refer to the amino acid at that position of either the A-chain (e.g. position A5) or the B-chain (e.g. position B5) in the respective native human insulin A-chain (SEQ ID NO: 2) or B-chain (SEQ ID NO: 4), or the corresponding amino acid position in any analogues thereof.

The term "glycoprotein" is meant to include any glycosylated insulin analogue, including single-chain insulin analogue, comprising one or more attachment groups to which one or more oligosaccharides is covalently linked thereto.

The term "recombinant host cell" ("expression host cell", "expression host system", "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism. Host cells may be yeast, fungi, mammalian cells, plant cells, insect cells, and prokaryotes and archaea that have been genetically engineered to produce glycoproteins.

When referring to "mole percent" or "mole %" of a glycan present in a preparation of a glycoprotein, the term means the molar percent of a particular glycan present in the pool of O-linked oligosaccharides released by β-elimination and then quantified by a method that is not affected by glycoform composition, (for instance, labeling the released glycan pool with a fluorescent tag such as 2-aminobenzamide and then separating by high performance liquid chromatography or capillary electrophoresis and then quantifying glycans by fluorescence intensity). In embodiments, the mole percent of a particular glycan in a preparation of glycoprotein will be between 20% and 100%, preferably above 25%, 30%, 35%, 40% or 45%, more preferably above 50%, 55%, 60%, 65% or 70% and most preferably above 75%, 80% 85%, 90% or 95%.

The term "operably linked" expression control sequences refers to a linkage in which the expression control sequence is contiguous with the gene of interest to control the gene of interest, as well as expression control sequences that act in trans or at a distance to control the gene of interest.

The term "expression control sequence" or "regulatory sequences" are used interchangeably and as used herein refer to polynucleotide sequences which are necessary to affect the expression of coding sequences to which they are operably linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "transfect", "transfection", "transfecting" and the like refer to the introduction of a heterologous nucleic acid into eukaryote cells, both higher and lower eukaryote cells. Historically, the term "transformation" has been used to describe the introduction of a nucleic acid into a prokaryote, yeast, or fungal cell; however, the term "transfection" is also used to refer to the introduction of a nucleic acid into any prokaryotic or eukaryote cell, including yeast and fungal cells. Furthermore, introduction of a heterologous nucleic acid into prokaryotic or eukaryotic cells may also occur by viral or bacterial infection or ballistic DNA transfer, and the term "transfection" is also used to refer to these methods in appropriate host cells.

The term "eukaryotic" refers to a nucleated cell or organism, and includes insect cells, plant cells, mammalian cells, animal cells and lower eukaryotic cells.

The term "lower eukaryotic cells" includes yeast and filamentous fungi. Yeast and filamentous fungi include, but are not limited to *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Yarrowia lipolytica, Candida albicans*, any *Aspergillus* sp., *Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa*.

As used herein, the term "predominantly" or variations such as "the predominant" or "which is predominant" will be understood to mean the glycan species that has the highest mole percent (%) of total O-glycans after the insulin analogue has been treated with PNGase and released glycans analyzed by mass spectroscopy, for example, MALDI-TOF MS or HPLC. In other words, the phrase "predominantly" is defined as an individual entity, such as a specific glycoform, is present in greater mole percent than any other individual entity. For example, if a composition consists of species A at 40 mole percent, species B at 35 mole percent and species C at 25 mole percent, the composition comprises predominantly species A, and species B would be the next most predominant species.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the U.S. Federal government or listed in the U.S. Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to maintaining glucose blood levels near normal levels and may include increasing or decreasing blood glucose levels depending on a given situation.

As used herein an "effective" amount or a "therapeutically effective amount" of an insulin analogue refers to a nontoxic but sufficient amount of an insulin analogue to provide the desired effect. For example one desired effect would be the prevention or treatment of hyperglycemia. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as intranasal, inhalation, subcutaneous, intramuscular, intraspinal, or intravenous.

As used herein, the term "pharmacokinetic" refers to in vivo properties of an insulin or insulin analogue commonly used in the field that relate to the liberation, absorption, distribution, metabolism, and elimination of the protein. Such pharmacokinetic properties include, but are not limited to, dose, dosing interval, concentration, elimination rate, elimination rate constant, area under curve, volume of distribution, clearance in any tissue or cell, proteolytic degradation in blood, bioavailability, binding to plasma, half-life, first-pass elimination, extraction ratio, $C_{max}$, $t_{max}$, $C_{min}$, rate of absorption, and fluctuation.

As used herein, the term "pharmacodynamic" refers to in vivo properties of an insulin or insulin analogue commonly used in the field that relate to the physiological effects of the protein. Such pharmacokinetic properties include, but are not limited to, maximal glucose infusion rate, time to maximal glucose infusion rate, and area under the glucose infusion rate curve.

Figures 1, 14:
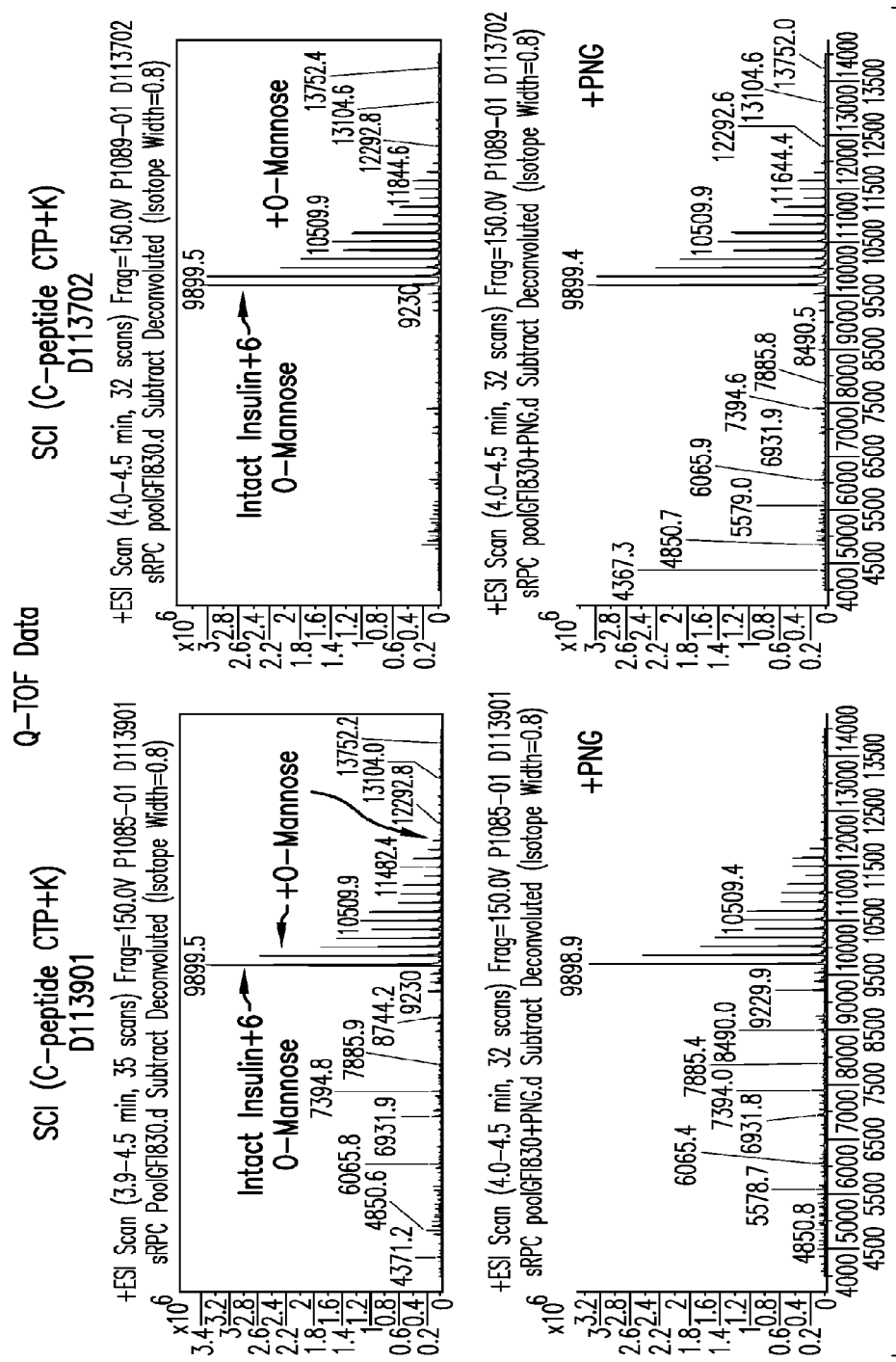

FIG. 14 shows Q-TOF analysis of O-glycosylated CTP peptide-based insulin analogues D113901 and D113702 (SCI:C peptide CTP; SEQ ID NO:45). The top panel shows the O-glycan profile prior to PNGase (PNG) treatment and the bottom panel shows the profile after PNGase treatment. The table shows the O-glycan occupancy and chain length for the analogues.

Figure 15:
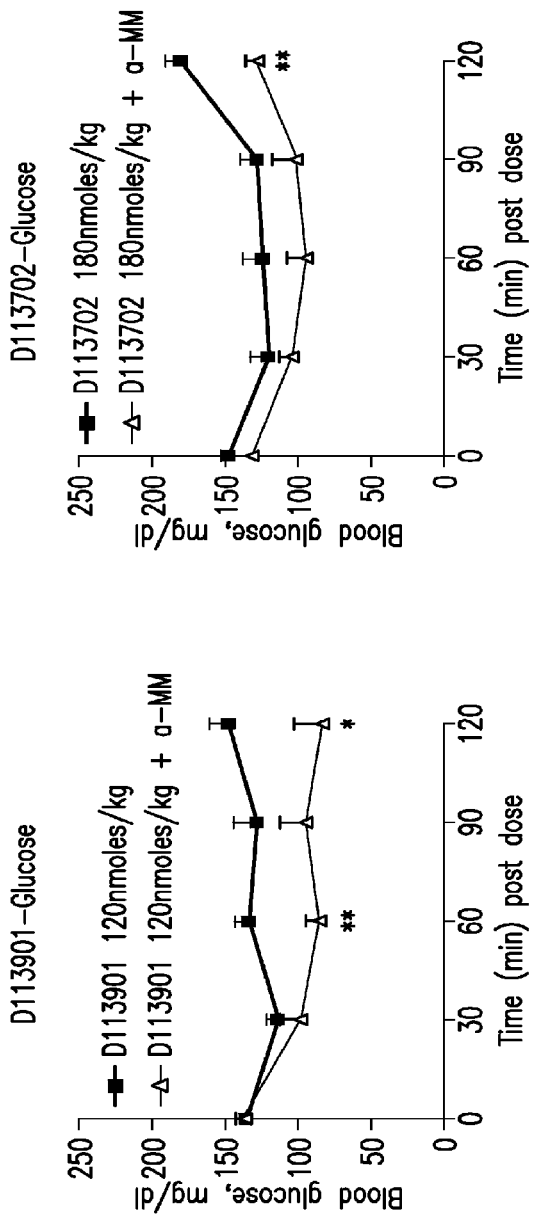

FIG. 15 shows the effect of O-glycosylated CTP peptide-based analogues D113901 and D113702 with and without α-methyl-mannose (α-MM) on blood glucose levels over time in non-diabetic C57BL/6 mice.

Figure 16:
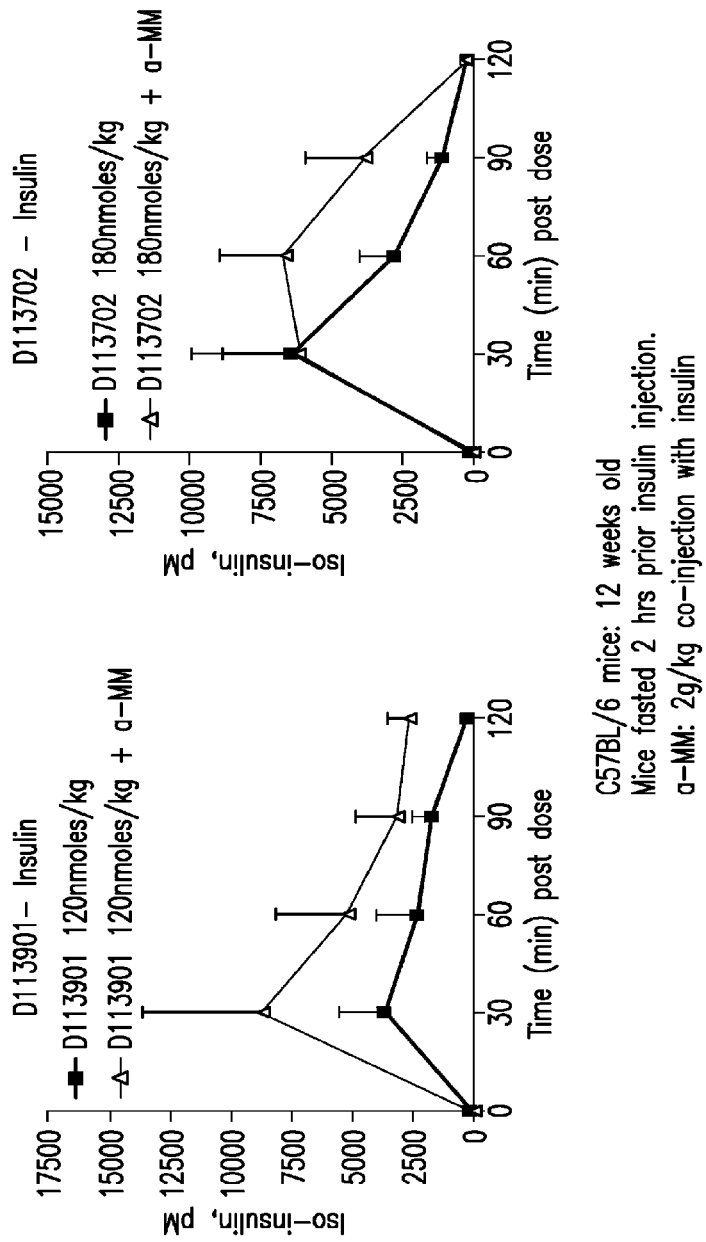

FIG. 16 shows the effect of O-glycosylated CTP peptide-based analogues D113901 and D113702 with and without α-MM on plasma insulin levels over time in the C57BL/6 mice.

Figure 17:
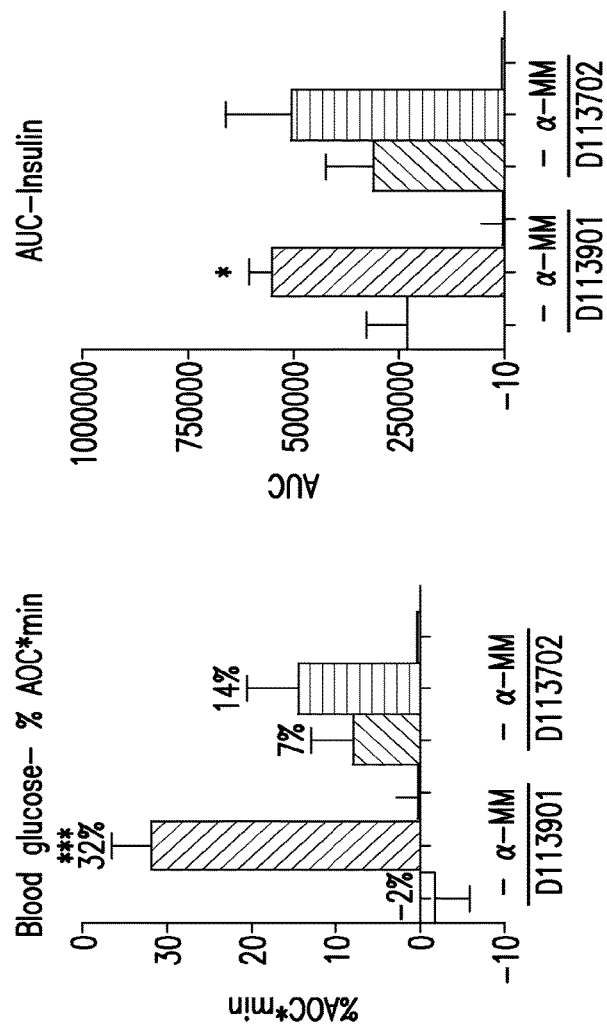

FIG. 17 shows the effect of O-glycosylated CTP peptide-based analogues D113901 and D113702 with and without α-MM on blood glucose % AOC and plasma insulin AUC in the C57BL/6 mice. (AUC refers to "area under the curve")

DETAILED DESCRIPTION OF THE INVENTION

The present invention provides O-glycosylated insulin or insulin analogue molecules, compositions and pharmaceutical formulations comprising O-glycosylated insulin or insulin analogue molecules, methods for producing the O-glycosylated insulin or insulin analogues, and methods for using the O-glycosylated insulin or insulin analogues. The O-glycosylated insulin or insulin analogues have at least one pharmacodynamic (PD) or pharmacokinetic (PK) property modified by the O-glycosylation. Compositions and formulations comprising the O-glycosylated insulin or insulin analogues described herein may be useful in treatments and therapies for diabetes.

Insulin produced in humans or mammals does not naturally contain O-linked glycosylation; therefore, in the present invention, the insulin or insulin analogue is modified to include the carboxy terminal portion (CTP) peptide found at positions 112-118 to position 145 of the beta subunit of human chorionic gonadotropin (hCGβ) or a partial variant thereof that includes at least one or two O-glycosylation sites of the CTP peptide. The CTP peptide has been used in the art to modify biologically active molecules at the N-terminus or C-terminus to alter their in vivo clearance patterns. Use of the CTP peptide to extend serum half-life of biologically active molecules has been the object of a number of U.S. patents (See for example, U.S. Pat. Nos. 5,705,478; 5,712,122; 5,759,818; 5,585,345; 6,225,449; 6,635,256; 6,987,172; and 7,442, 376).

In particular aspects of the present invention, the CTP peptide comprises the amino acid sequence SSSSKAPPPSLPSPSRLPGPSDTPILPQ (SEQ ID NO:1). The CTP peptide has a propensity to be O-glycosylated in mammalian host cells and as shown herein, is capable of being O-glycosylated in lower eukaryotes as well. In mammalian host cells, the CTP peptide is O-glycosylated at the serine residues at positions 4, 10, 15, and 21 of SEQ ID NO:1.

Figure 12:
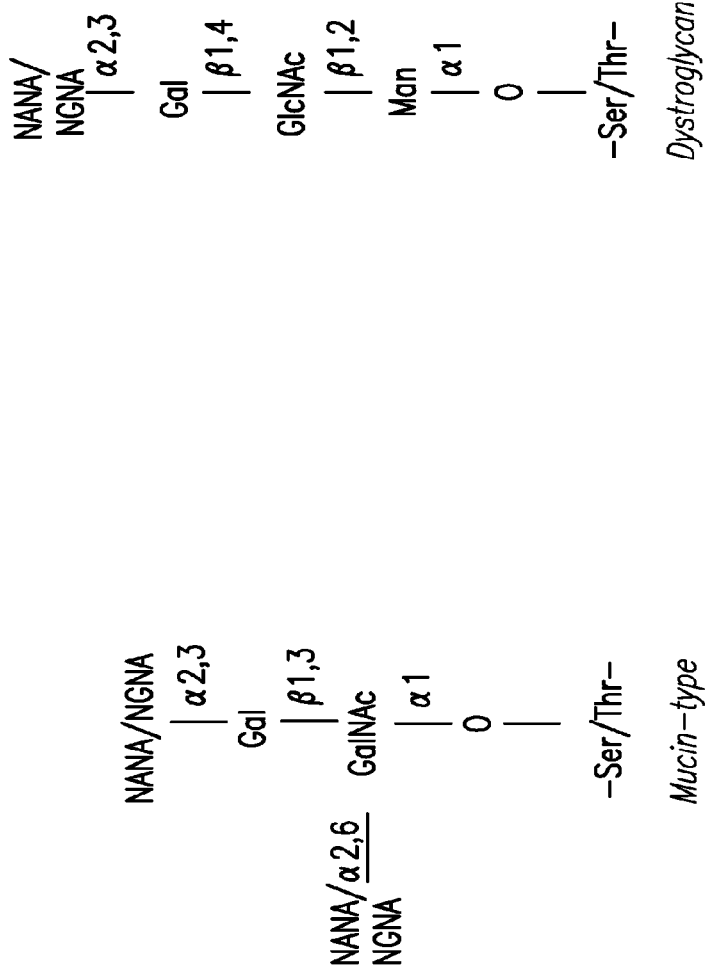
FIG. 12 shows a comparison of mucin-type O-glycosylation to dystroglycan-type O-glycosylation.

In eukaryotes, N-linked glycans and O-linked glycans are the two major types of glycosylation. N-linked glycosylation (N-glycosylation) is characterized by the β-glycosylamine linkage of N-acetylglucosamine (GlcNac) to asparagine (Asn) (Spiro, Glycobiol. 12: 43R-56R (2002)). It has been well established that the consensus sequence motif Asn-Xaa-Ser/Thr is essential in N-glycosylation (Blom et al., Proteomics 4: 1633-1649 (2004)). The most abundant form of O-linked glycosylation (O-glycosylation) is of the mucin-type, which is characterized by α-N-acetylgalactosamine (GalNAc) attached to the hydroxyl group of serine/threonine (Ser/Thr) side chains by the enzyme UDP-N-acetyl-D-galactosaminepolypeptide N-acetylgalactosaminyltransferase (Hang & Bertozzi, Bioorg. Med. Chem. 13: 5021-5034 (2005); Julenius et al., Glycobiol. 15: 153-164 (2005); FIG. 12). Mucin-type O-glycans can further include galactose and sialic acid residues. Mucin-type O-glycosylation is commonly found in many secreted and membrane-bound mucins in mammal, although it also exists in other higher eukaryotes (Hanish, Biol Chem. 382: 143-149 (2001)). As the main component of mucus, a gel playing crucial role in defending epithelial surface against pathogens and environmental injury, mucins are in charge of organizing the framework and conferring the rheological property of mucus. Beyond the above properties exhibited by mucins, mucin-type O-glycosylation is also known to modulate various protein functions in vivo (Hang & Bertozzi, Bioorg. Med. Chem. 13: 5021-5034 (2005)). For instance, mucin-like glycans can serve as receptor-binding ligands during an inflammatory response (McEver & Cummings, J. Chin. Invest. 100: 485-491 (1997)).

Another form of O-glycosylation is that of the O-mannose-type glycosylation (T. Endo, BBA 1473: 237-246 (1999)). In mammalian organisms this form of glycosylation can be sub-divided into two forms. The first form is the addition of a single mannose to a serine or threonine residue of a protein. This is a rare occurrence but has been demonstrated to occur on a few proteins, e.g., IgG$_2$ light chain (Martinez et al, J. Chromatogr. A. 1156: 183-187 (2007)). A more common form of O-mannose-type glycosylation in mammalian systems is that of the dystroglycan-type, which is characterized by β-N-acetylglucosamine (GlcNAc) attached to a mannose residue attached to the hydroxyl group of serine/threonine side chains in an α1 linkage by an O-linked mannose β1,2-N-acetylglucosaminyltransferase 1 (POMGnT1) (T. Endo, BBA 1473: 237-246 (1999); FIG. 12). Dystroglycan-type O-glycans can further include galactose and sialic acid residues. Unlike N-glycosylation, the consensus motif has not been identified in the sequence context of mucin or dystroglycan O-glycosylation sites.

Mucin-type O-glycosylation is primarily found on cell surface proteins and secreted proteins. Dystroglycan-type O-glycosylation is primarily associated with proteins comprising the extracellular matrix. Both mucin- and dystroglycan-type O-glycans may possess terminal sialic acid residues. As shown in FIG. 12, the terminal sialic acid residues are in α2,3 linkage with the preceding galactose residue. In some instances, as shown in FIG. 12, mucin-type O-glycans can also possess a branched α2,6 sialic acid residue. The sialic acid present on each type of structure on glycoproteins obtained from recombinant non-human cell lines can include mixtures of N-acetylneuraminic acid (NANA) and N-glycolylneuraminic acid (NGNA). However, in contrast to glycoproteins obtained from mammalian cells, the sialic acid present on each type of structure on glycoproteins obtained from human cells is composed of NANA. Thus, glycoprotein compositions obtained from mammalian cell culture include sialylated O-glycans that have a structure associated with glycoproteins produced in non-human mammalian cells.

Figure 13A:
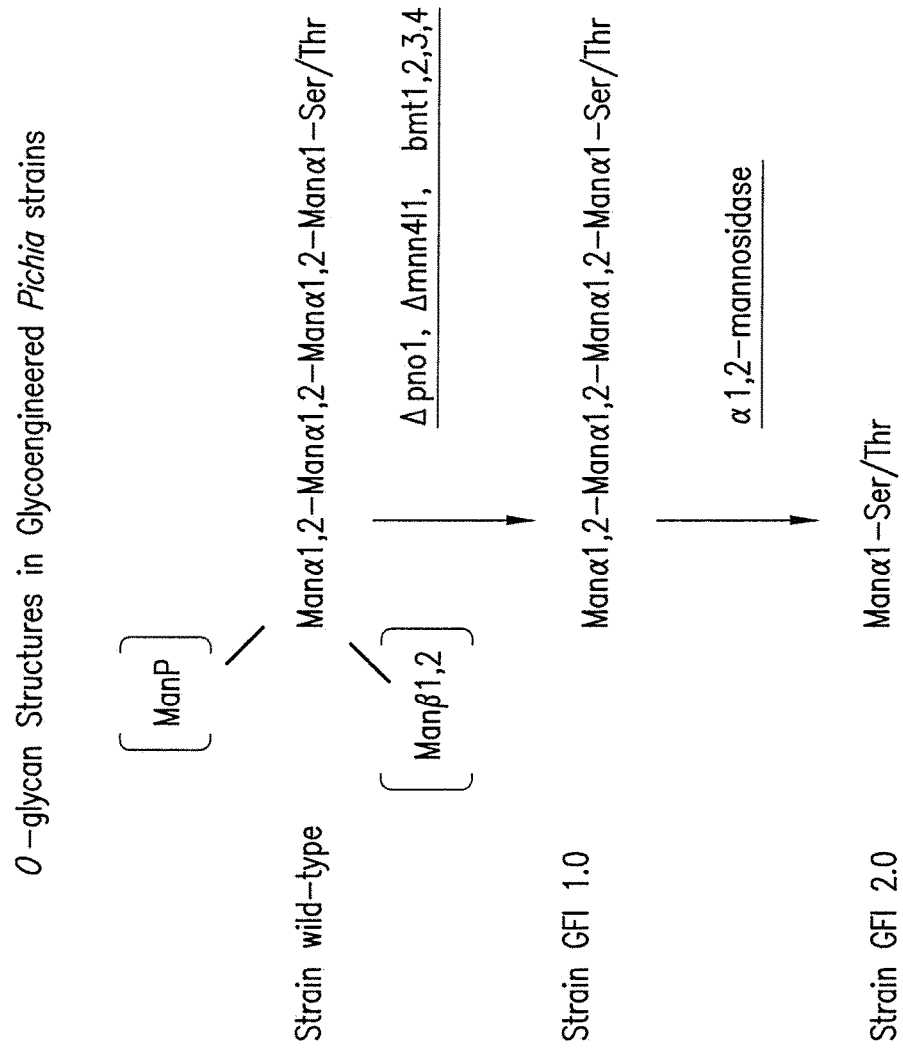
FIG. 13A shows the structure of O-glycans typically produced in wild-type *Pichia pastoris* compared to the mannotetrose O-glycan produced in *Pichia pastoris* genetically engineered to lack detectable β-mannosyltransferase activity and phosphomannosyltransferase activity (GFI strain 1.0) or the mannose O-glycan produced in *Pichia pastoris* genetically engineered to lack detectable β-mannosyltransferase activity and phosphomannosyltransferase activity and to express an α1,2-mannosyltransferase activity (GFI strain 2.0). Not shown for GFI strain 1.0 are mannose, mannobiose, or mannotriose O-glycans.

In contrast to human and mammalian systems, in fungi such as *Saccharomyces cerevisiae* and *Pichia pastoris*, O-glycosylation produces O-glycans that can include up to five or six mannose residues (See for example, Tanner & Lehle, Biochim. Biophys. Acta 906: 81-89 (1987); Herscovics & Orlean, FASEB J. 7: 540-550 (1993); Trimble et al., GlycoBiol. 14: 265-274 (2004); Lommel & Strahl, Glycobiol. 19: 816-828 (2009)). Wild-type *Pichia pastoris* as shown in FIG. 13A can produce O-mannose-type O-glycans consisting of up to six mannose residues in which the terminal mannose residue can be phosphorylated. By abrogating phosphomannosyltransferase activity and β-mannosyltransferase activity in the *Pichia pastoris*, which results in charge-free O-glycans without β-linked mannose residues, and cultivating the *Pichia pastoris* lacking phosphomannosyltransferase activity and β-mannosyltransferase activity in the presence of a protein PMT inhibitor, which reduces O-glycosylation site occupancy, and a secreted α1,2-mannosidase, which reduces the chain length of the charge-free O-glycans, O-mannose reduced glycans (or mannose-reduced O-glycans) can be produced (See U.S. Published Application No. 20090170159 and U.S. Pat. Nos. 7,259,007 and 7,465,577). The consensus motif has not been identified in the sequence context of fungal O-glycosylation sites.

Figure 13B:
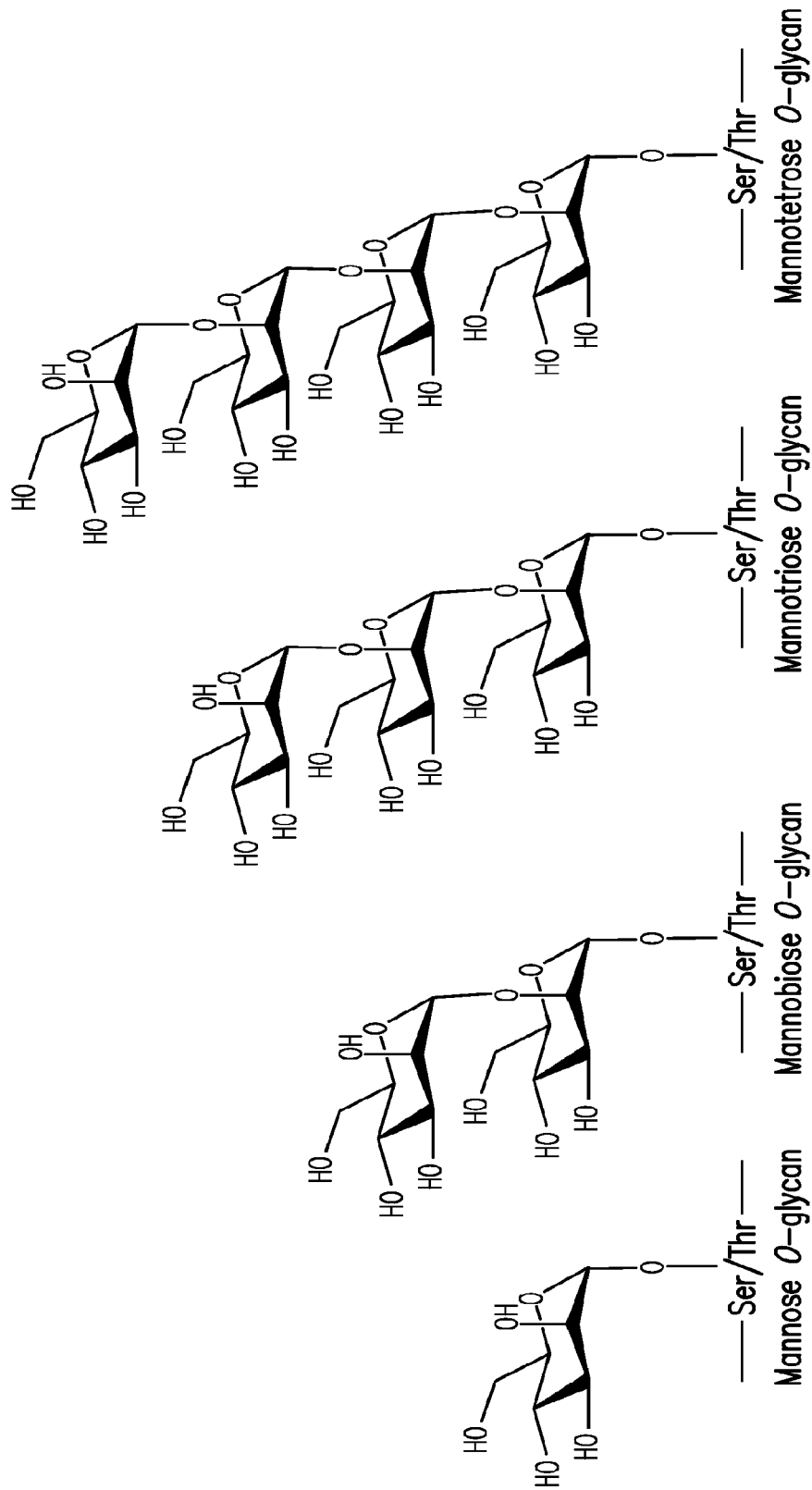
FIG. 13B shows the structure of mannose, mannobiose, mannotriose, and mannotetrose O-glycans produced in host cells that do not display with respect to an O-glycan on a protein detectable β-mannosyltransferase activity and phosphomannosyltransferase activity, e.g., *Pichia pastoris* genetically engineered to lack detectable β-mannosyltransferase activity and phosphomannosyltransferase activity (GFI strain 1.0).

The present invention provides insulin and insulin analogues comprising at least one carboxy terminus portion (CTP) peptide found at positions 112-118 to position 145 of the beta subunit of human chorionic gonadotropin (hCGβ) or a partial variant thereof that includes at least one or two O-glycosylation sites of the CTP peptide covalently linked to the insulin or insulin analogue by an amide (peptide) bond wherein the CTP peptide or partial variant thereof is O-glycosylated with O-glycans wherein each O-glycan thereon comprises one, two, three, or four mannose residues (mannose, mannobiose, mannotriose, or mannotetrose O-glycan structure, respectively. (Structures shown in FIG. 13B). The mannose at the reducing end of the O-glycan is covalently linked to a serine or threonine residue of the CTP peptide or partial variant thereof in an α1 linkage. Each additional mannose residue is linked at its reducing end to the non-reducing end of the preceding mannose residue in an α1,2 linkage. In a further embodiment, at least one, two, three, or four O-glycosylation site(s) of the CTP peptide selected from positions 1, 2, 3, 4, 10, 13, 15, 21, and 23 of the sequence SSSSKAPPPSLPSPSRLPGPSDTPILPQ (SEQ ID NO:1) is(are) occupied with an O-glycan. In a particular embodiment, at least one of the serine residues selected from positions 4, 10, 15, and 21 of the sequence SSSSKAPPPSLPSPSRLPGPSDTPILPQ (SEQ ID NO:1) is(are) occupied with an O-glycan. In a particular embodiment, at least two of the serine residues selected from positions 4, 10, 15, and 21 of the sequence SSSSKAPPPSLPSPSRLPGPSDTPILPQ (SEQ ID NO:1) are occupied with an O-glycan. In a particular embodiment, at least three of the serine residues selected from positions 4, 10, 15, and 21 of the sequence SSSSKAPPPSLPSPSRLPGPSDTPILPQ (SEQ ID NO:1) are occupied with an O-glycan. In a particular embodiment, the serine residues at positions 4, 10, 15, and 21 of the sequence SSSSKAPPPSLPSPSRLPGPSDTPILPQ (SEQ ID NO:1) are each occupied with an O-glycan.

In some embodiments, the C-terminus and/or the N-terminus of the CTP peptide may further include one or two basic amino acids, e.g., Lys or Arg, Lys-Arg, or Arg-Arg. For example, in particular aspects the CTP peptide comprises the amino acid sequence SSSSKAPPPSLPSPSRLPGPSDTPILPQK (SEQ ID NO:91), SSSSKAPPPSLPSPSRLPGPSDTPILPQR (SEQ ID NO:92), SSSSKAPPPSLPSPSRLPGPSDTPILPQKR (SEQ ID NO:93), or SSSSKAPPPSLPSPSRLPGPSDTPILPQRR (SEQ ID NO:94). In a further embodiment, at least two O-glycosylation sites of the CTP peptide are occupied with an O-glycan. In a further still embodiment, at least three O-glycosylation sites of the CTP peptide are occupied with an O-glycan. In a further still embodiment, at least four O-glycosylation sites of the CTP peptide are occupied with an O-glycan. In a further embodiment, the insulin and insulin analogue comprises a portion of at least one carboxy terminus portion (CTP) peptide provided that the portion of the CTP peptide comprises at least one O-glycosylation site. In particular embodiments, the O-glycans thereon consist of mannose, mannobiose, mannotriose, and/or mannotetrose structures and lack fucose, N-acetylglucosamine (GlcNAc), galactose, and/or sialic acid (NANA and/or NGNA) residues.

In a further embodiment, at least one CTP peptide or a partial variant thereof that includes at least one or two O-glycosylation sites of the CTP peptide is covalently linked at its C-terminus to the N-terminus of the B-chain or the A-chain. In another embodiment, at least one CTP peptide or partial variant thereof that includes at least one or two O-glycosylation sites of the CTP peptide is covalently linked at its N-terminus to the C-terminus of the A-chain or B-chain. In a further embodiment, at least one CTP peptide or partial variant thereof that includes at least one or two O-glycosylation sites of the CTP peptide is covalently linked at its C-terminus to the N-terminus of the B-chain or the A-chain and at least one CTP peptide or partial variant thereof that includes at least one or two O-glycosylation sites of the CTP peptide is covalently linked at its N-terminus to the C-terminus of the A-chain or B-chain. In a further embodiment, at least one CTP peptide or partial variant thereof that includes at least one or two O-glycosylation sites of the CTP peptide is covalently linked at its C-terminus to the N-terminus of the B-chain and at least one CTP peptide or partial variant thereof that includes at least one or two O-glycosylation sites of the CTP peptide is covalently linked at its N-terminus to the C-terminus of the A-chain or B-chain peptide. In a further embodiment, at least one CTP peptide or partial variant thereof that includes at least one or two O-glycosylation sites of the CTP peptide is covalently linked at its C-terminus to the N-terminus of the A-chain and at least one CTP peptide or partial variant thereof that includes at least one or two O-glycosylation sites of the CTP peptide is covalently linked at its N-terminus to the C-terminus of the A-chain or B-chain. In a further embodiment, at least one CTP peptide or partial variant thereof that includes at least one or two O-glycosylation sites of the CTP peptide is covalently linked at its C-terminus to the N-terminus of the B-chain and at least one CTP peptide or partial variant thereof that includes at least one or two O-glycosylation sites of the CTP peptide is covalently linked at its N-terminus to the C-terminus of the B-chain. In a further embodiment, at least one CTP peptide or partial variant thereof that includes at least one or two O-glycosylation sites of the CTP peptide is covalently linked at its C-terminus to the N-terminus of the A-chain and at least one CTP peptide or partial variant thereof that includes at least one or two O-glycosylation sites of the CTP peptide is covalently linked at its N-terminus to the C-terminus of the A-chain. In a further embodiment, at least one CTP peptide or partial variant thereof that includes at least one or two O-glycosylation sites of the CTP peptide is covalently linked at its C-terminus to the N-terminus of the A-chain and at least one CTP peptide or partial variant thereof that includes at least one or two O-glycosylation sites of the CTP peptide is covalently linked at its N-terminus to the C-terminus of the B-chain. In a further embodiment, at least one CTP peptide or partial variant thereof that includes at least one or two O-glycosylation sites of the CTP peptide is covalently linked at its C-terminus to the N-terminus of the B-chain and at least one CTP peptide or partial variant thereof that includes at least one or two O-glycosylation sites of the CTP peptide is covalently linked at its N-terminus to the C-terminus of the A-chain. In further aspects of the above embodiments, an intervening peptide of one, two, three, four, five, six, or seven to 20 amino acids is positioned between the CTP peptide or partial variant thereof that includes at least one or two O-glycosylation sites of the CTP peptide and the terminus of the A-chain or B-chain. In the above embodiments, the insulin or insulin analogue may be a heterodimer molecule or a single chain molecule. In either the heterodimer or single-chain aspect, the A-chain and B-chain are covalently linked to each other by disulfide linkages.

In a further embodiment, the O-glycosylated CTP peptide-based insulin or insulin analogue is a single chain molecule and the CTP peptide or partial variant thereof that includes at least one or two O-glycosylation sites of the CTP peptide connects the A-chain and the B-chain to provide a molecule comprising the structure: (B-chain)-(CTP peptide)-(A-chain) in which at least one O-glycan is linked to the CTP peptide or partial variant thereof that includes at least one or two O-glycosylation sites of the CTP peptide and wherein each O-glycan thereon comprises one or more mannose residues. In a further embodiment, the O-glycosylated CTP peptide-based single-chain insulin or insulin analogue further comprises at least one CTP peptide or partial variant thereof that includes at least one or two O-glycosylation sites of the CTP peptide covalently linked to the N-terminus of the B-chain and/or C-terminus of the A-chain.

In embodiments where the connecting peptide is not the CTP peptide, the connecting peptide may vary from 3 amino acid residues and up to a length corresponding to the length of the natural C-peptide in human insulin. The non-CTP connecting peptide is however normally shorter than the human C-peptide and will typically have a length from 3 to about 35, from 3 to about 30, from 4 to about 35, from 4 to about 30, from 5 to about 35, from 5 to about 30, from 6 to about 35 or from 6 to about 30, from 3 to about 25, from 3 to about 20, from 4 to about 25, from 4 to about 20, from 5 to about 25, from 5 to about 20, from 6 to about 25 or from 6 to about 20, from 3 to about 15, from 3 to about 10, from 4 to about 15, from 4 to about 10, from 5 to about 15, from 5 to about 10, from 6 to about 15 or from 6 to about 10, or from 6-9, 6-8, 6-7, 7-8, 7-9, or 7-10 amino acid residues in the peptide chain. Single-chain peptides have been disclosed in U.S. Published Application No. 20080057004, U.S. Pat. No. 6,630,348, International Application Nos. WO2005054291, WO2007104734, WO2010080609, WO20100099601, and WO2011159895, each of which is incorporated herein by reference. Further provided are compositions and formulations of the above comprising a pharmaceutically acceptable carrier, salt, or combination thereof.

In particular embodiments, the connecting peptide comprises the formula Gly-$Z^1$-Gly-$Z^2$ wherein $Z^1$ is Ala or another amino acid except for tyrosine, and $Z^2$ is a peptide of 2-35 amino acids.

In particular embodiments, the connecting peptide is GAGSSSRRAPQT (SEQ INO:56), GAGSSSSRRA (SEQ INO:57), GAGSSSSRR (SEQ INO:58), GGGPRR (SEQ ID NO:59), GGGPGAG (SEQ ID NO:60), GGGGGKR (SEQ ID NO:61), or GGGPGKR (SEQ ID NO:62).

In particular embodiments, the connecting peptide is VGLSSGQ (SEQ INO:63) or TGLGSGR (SEQ INO:64). In other aspects, the connecting peptide is RRGPGGG (SEQ INO:65), RRGGGGG (SEQ INO:66), GGAPGDVKR (SEQ INO:67), RRAPGDVGG (SEQ INO:68), GGYPGDVLR (SEQ INO:69), RRYPGDVGG (SEQ INO:70), GGHPGDVR (SEQ INO:71), or RRHPGDVGG (SEQ INO:72).

In particular embodiments of the O-glycosylated heterodimer or single-chain insulin analogues, the O-glycosylated insulin or insulin analogue has an A-chain peptide comprising at least the amino acid sequence GIVEQCCTSICSLYQLENYC (SEQ ID NO: 90); a B-chain peptide comprising at least the amino acid sequence HLCGSHLVEALYLVCGERGFF (SEQ ID NO:3), and a carboxy terminal portion (CTP) peptide comprising amino acids 112-118 to 145 of the beta subunit of human chorionic gonadotropin (hCGβ) or a partial variant thereof that includes at least one or two O-glycosylation sites of the CTP peptide, wherein at least one amino acid residue of the CTP peptide or a partial variant thereof that includes at least one or two O-glycosylation sites of the CTP peptide is covalently linked to an O-glycan; and wherein the insulin or insulin analogue optionally further includes up to 1, 2, 3, 4, 5, 6, 7, 8, 9, 10, 11, 12, 13, 14, 15, 16, or 17 amino acid substitutions in the native amino acid sequence of the A-chain peptide and/or the B-chain peptide; and the CTP peptide or a partial variant thereof that includes at least one or two O-glycosylation sites of the CTP peptide is covalently linked by peptide bond to the N-terminus of the B-chain, the C-terminus of the A-chain, or the CTP peptide or a partial variant thereof that includes at least one or two O-glycosylation sites of the CTP peptide is a connecting peptide that covalently links the B-chain to the A-chain to produce a single-chain insulin or insulin analogue having the structure (B-chain)-(CTP peptide)-(A-chain). The insulin or insulin analogue has three disulfide bonds: the first disulfide bond is between the cysteine residues at positions 6 and 11 of SEQ ID NO:90, the second disulfide bond is between the cysteine residues at position 3 of SEQ ID NO:3 and position 7 of SEQ ID NO:90, and the third disulfide bond is between the cysteine residues at position 15 of SEQ ID NO:3 and position 20 of SEQ ID NO:90.

The present invention further provides compositions and pharmaceutical compositions comprising one or more species of the O-glycosylated CTP peptide-based heterodimer or single-chain insulin or insulin analogues disclosed herein, which may further include a pharmaceutically acceptable carrier. The compositions of O-glycosylated CTP peptide-based heterodimer or single-chain insulin or insulin analogues may comprise predominantly mannose, mannobiose, mannotriose, or mannotetrose O-glycans. In a further aspect, the predominant O-glycan is mannotriose or mannotetrose. In a further aspect, the predominant O-glycan is a combination of mannotriose and mannotetrose. In a further aspect, the predominant O-glycan is mannose with little or no detectable mannobiose, mannotriose, or mannotetrose.

In further aspects of the compositions supra, at least 40 mole % of the O-glycans are mannotriose or mannotetrose, at least 50 mole % of the O-glycans are mannotriose or mannotetrose, at least 60 mole % of the O-glycans are mannotriose or mannotetrose, at least 70 mole % of the O-glycans are mannotriose or mannotetrose, at least 80 mole % of the O-glycans are mannotriose or mannotetrose, at least 90 mole % of the O-glycans are mannotriose or mannotetrose, at least 95 mole % of the O-glycans are mannotriose or mannotetrose, at least 98 mole % of the O-glycans are mannotriose or mannotetrose, or at least 99 mole % of the O-glycans are mannotriose or mannotetrose.

In further aspects of the compositions supra, at least 40 mole % of the O-glycans are mannotriose and mannotetrose, at least 50 mole % of the O-glycans are mannotriose and mannotetrose, at least 60 mole % of the O-glycans are mannotriose or mannotetrose, at least 70 mole % of the O-glycans are mannotriose and mannotetrose, at least 80 mole % of the O-glycans are mannotriose and mannotetrose, at least 90 mole % of the O-glycans are mannotriose and mannotetrose, at least 95 mole % of the O-glycans are mannotriose and mannotetrose, at least 98 mole % of the O-glycans are mannotriose or mannotetrose, or at least 99 mole % of the O-glycans are mannotriose and mannotetrose.

In a further aspect of the compositions supra, at least 70%, 75%, 80%, 85%, 90%, 95%, 96%, 97%, 98%, 99%, or 100% of the O-glycosylated CTP peptide-based heterodimer or single-chain insulin or insulin analogues include at least one O-glycan. In a further aspect of the compositions supra, at least 70%, 75%, 80%, 85%, 90%, 95%, 96%, 97%, 98%, 99%, or 100% of the O-glycosylated CTP peptide-based heterodimer or single-chain insulin or insulin analogues include two or more O-glycans. In a further aspect of the compositions supra, at least 70%, 75%, 80%, 85%, 90%, 95%, 96%, 97%, 98%, 99%, or 100% of the O-glycosylated CTP peptide-based heterodimer or single-chain insulin or insulin analogues include three or more O-glycans. In a further aspect of the compositions supra, at least 70%, 75%, 80%, 85%, 90%, 95%, 96%, 97%, 98%, 99%, or 100% of the O-glycosylated CTP peptide-based heterodimer or single-chain insulin or insulin analogues include two or more O-glycans. In a further aspect of the compositions supra, at least 70%, 75%, 80%, 85%, 90%, 95%, 96%, 97%, 98%, 99%, or 100% of the O-glycosylated CTP peptide-based heterodimer or single-chain insulin or insulin analogues include four O-glycans.

In a further aspect of the compositions supra, the predominant species of O-glycosylated CTP peptide-based heterodimer or single-chain insulin or insulin analogue in the composition comprises at least six molecules of mannose per molecule of protein (O-glycosylated CTP peptide-based heterodimer or single-chain insulin or insulin analogue). A predominant species comprising six molecules of mannose per molecule of protein may have any combination of O-glycosylation site occupancy and chain length. For example, if one site is occupied with an O-glycan of four mannose residues (mannotetrose) then (i) another site may be occupied with an O-glycan of two mannose residues (mannobiose) or (ii) two other sites may be occupied with O-glycans of one mannose each. As another example, if one site is occupied with an O-glycan of three mannose residues (mannotriose) then (i) another site may be occupied with an O-glycan of three mannose residues (mannotriose) or (ii) two other sites may be occupied with O-glycans, one occupied with mannose and the other occupied with mannobiose or (iii) each of three other sites may each be occupied with an O-glycan of one mannose residue. As another example, if one site is occupied with an O-glycan of two mannose residues (mannobiose) then (i) another two sites may each be occupied with an O-glycan of two mannose residues (mannobiose) or (ii) two other sites may each be occupied with O-glycans, one occupied with mannose and the other occupied with mannobiose.

The O-linked glycan may confer one or more beneficial properties to the O-glycosylated CTP peptide-based insulin or insulin analogue compared to a non-glycosylated insulin or insulin analogue, including but not limited to, (i) enhanced or extended pharmacokinetic (PK) properties, (ii) enhanced pharmacodynamic (PD) properties, (iii) reduced side effects such as hypoglycemia, (iv) enable the O-glycosylated CTP peptide-based insulin or insulin analogue to display saccharide-responsive or sensitive activity, (v) display a reduced affinity to the insulin-like growth factor 1 receptor (IGF1R) compared to affinity to the insulin receptor (IR), (vi) display preferential binding to either the IR-A or IR-B, (vii) display an increased on-rate, decreased on-rate, and/or reduced off-rate to the insulin receptor, and/or (viii) altered route of delivery, for example oral, nasal, or pulmonary administration verses subcutaneous, intravenous, or intramuscular administration.

An O-glycosylated CTP peptide-based insulin or insulin analogue may confer one or more of the above attributes and may provide a significant improvement over current diabetes therapy. For example, O-glycans are known to alter the PK/PD properties of therapeutic proteins (See for example, U.S. Pat. No. 6,689,365). Currently marketed insulin therapy consists of recombinant human insulin and mutated variants of human insulin called insulin analogues. These analogues exhibit altered in vitro and in vivo properties due to the combination of the amino acid mutation(s) and formulation buffers. The addition of an O-glycan to insulin as disclosed herein adds another dimension for modulating insulin action in the body that is lacking in all current insulin therapies. Insulin conjugated to a saccharide or oligosaccharide moiety either directly or by means of polymeric or non-polymeric linker has been described previously, for example in U.S. Pat. No. 3,847,890; U.S. Pat. No. 7,317,000; Int. Pub. Nos. WO8100354; WO8401896; WO9010645; WO2004056311; WO2007047977; WO2010088294; and EP0119650). A feature of the O-glycosylated insulin analogues disclosed herein is that the O-glycan attached thereto in a naturally occurring linkage, which is a natural chemical bond that can be produced in vivo by any organism with O-linked glycosylation capabilities.

For over three decades, insulin researchers have described attaching a saccharide to insulin using a chemical linker or ex vivo enzymatic reaction in an attempt to improve upon existing insulin therapy. The concept of chemical attachment of a sugar moiety to insulin was first introduced in 1979 by Michael Brownlee as a mechanism to modulate insulin bioavailability as a function of the physiological blood glucose level (Brownlee & Cerami, Science 206: 1190 (1979)). A major limitation of the Brownlee proposal was toxicity of concanavalin A, to which the glycosylated insulin derivative interacted. There have been reports in the literature describing the presence of an O-linked mannose glycan on insulin produced in yeast, but this glycan was considered a contaminant to be removed (Kannan et al., Rapid Commun. Mass Spectrom. 23: 1035 (2009); International Publication Nos. WO9952934 and WO2009104199). Therefore, in one embodiment, the present invention provides O-glycosylated CTP peptide-based insulin or insulin analogues (either in the precursor form or mature form, in a heterodimer form, or in a single-chain chain form) to which at least one O-glycan is attached in vivo and wherein the O-glycan alters at least one therapeutic property of the O-glycosylated insulin or insulin analogue, for example, rendering the insulin or insulin analogue into a molecule that is has at least one modified pharmacokinetic (PK) and/or pharmacodynamic property (PD); for example, extended serum half-life, improved stability on solution, capable of being a saccharide-regulated insulin, or the like.

Currently, *Escherichia coli*, *Saccharomyces cerevisiae*, and *Pichia pastoris* are used to produce commercially available recombinant insulins and insulin analogues. Of these three organisms, only the yeasts *Saccharomyces cerevisiae* and *Pichia pastoris* have the innate ability to add an O-glycan to a protein. In general, O-glycosylation in yeast results in the production of glycoproteins in which the O-glycans thereon that have a fungal-type high mannose structure. Over the past decade yeast strains have been constructed in which the glycosylation pattern has been altered from the endogenous glycosylation pattern. For example, using the glycoengineered *Pichia pastoris* strains as disclosed herein, the O-glycan composition may be pre-determined and controlled. Thus, the glycoengineered yeast platform, is well suited for producing O-glycosylated insulin and insulin analogues. While O-glycosylated insulin may be expressed in mammalian cell culture, it currently appears to be an unfeasible means for recombinantly producing insulin since mammalian cell cultures routinely require the addition of insulin for optimal cell viability and fitness. Since insulin is metabolized in a normal mammalian cell fermentation process, the secreted O-glycosylated insulin analogue may likely be utilized by the cells resulting in reduced yield of the O-glycosylated insulin analogue. A further disadvantage to the use of mammalian cell culture is the current inability to modify or customize the glycan profile to the same extent as has been done in yeast cell culture (Sethuraman & Stadheim, Curr. Opin. Biotechnol. 17: 341 (2006)).

There are many advantages to producing the O-glycosylated insulin analogues as described herein. Genetically engineered (or glycoengineered) *Pichia pastoris* provides the attractive properties of other yeast-based insulin production systems for insulin, including fermentability and yield. Genetic engineering allows for in vivo maturation of insulin precursor to eliminate process steps of enzymatic reactions and purifications. Pertaining to in vivo O-glycosylation, glycoengineered *Pichia pastoris* does not require the chemical synthesis or sourcing of the O-glycan moiety, as the yeast cell is the source of the glycan, which may result in improved yield and lower cost of goods. As described herein, glycoengineered *Pichia pastoris* strains can be selected that express O-glycosylated CTP peptide-based insulin or insulin analogues with O-glycans of various mannose chain lengths and various degrees of site occupancy, which may be costly to synthesize using in vitro reactions. Moreover, a linker domain and non-natural glycans may in some cases be more immunogenic than an O-linked O-glycan and thereby reduce the effectiveness of the insulin therapy. Finally, an O-linked glycan structure on insulin may be further modified by enzymatic or chemical reactions to greatly expand the amount of O-glycan analogues that may be screened. As such, the optimal O-glycan may be identified more rapidly and with less cost than using purely synthetic strategies.

I. Insulin Analogues

In various embodiments of the in vivo O-glycosylated CTP peptide-based insulin or insulin analogues disclosed herein, the insulin analogue may include a substitution at position B28 to an amino acid residue such as lysine or aspartic acid. For example, insulin lispro (HUMALOG) is a rapid acting insulin analogue in which the penultimate lysine and proline residues on the C-terminal end of the B-peptide have been reversed (LysB28ProB29-human insulin; SEQ ID NO:2 and SEQ ID NO:73), which reduces the formation of insulin multimers, and insulin aspart (NOVOLOG) is another rapid acting insulin mutant in which the proline at position B28 has been substituted with aspartic acid (AspB28-human insulin; SEQ ID NO:2 and SEQ ID NO:74), which also results in reduced formation of multimers. Therefore, those O-glycosylated CTP peptide-based insulin or insulin analogue disclosed herein in which the lysine residue at amino acid at position 28 has been replaced with another amino acid may have reduced ability to form multimers and thus, may exhibit a fast-acting profile. In some embodiments, the mutation at positions B28 and/or B29 may be accompanied by one or more mutations elsewhere in the insulin polypeptide. For example, insulin glulisine (APIDRA) is yet another rapid acting insulin mutant in which asparagine at position B3 has been replaced by a lysine residue and lysine at position B29 has been replaced with a glutamic acid residue (LysB3GluB29-human insulin; SEQ ID NO:2 and SEQ ID NO:75).

In various embodiments, the O-glycosylated CTP peptide-based insulin or insulin analogue has an isoelectric point that has been shifted relative to human insulin. In some embodiments, the shift in isoelectric point is achieved by adding one or more arginine, lysine, or histidine residues to the N-terminus of the insulin A-chain peptide and/or the C-terminus of the insulin B-chain peptide. Examples of such insulin polypeptides include ArgA0-human insulin (SEQ ID NO:79 and SEQ ID NO:4), ArgB31ArgB32-human insulin (SEQ ID NO:2 and SEQ ID NO:78), GlyA21ArgB31ArgB32-human insulin (SEQ ID NO:77 and SEQ ID NO:78), ArgA0ArgB31ArgB32-human insulin (SEQ ID NO:79 and SEQ ID NO:78), and ArgA0GlyA21ArgB31ArgB32-human insulin (SEQ ID NO:80 and SEQ ID NO:78). By way of further example, insulin glargine (LANTUS) is an exemplary long-acting insulin analogue in which AsnA21 has been replaced by glycine, and two arginine residues have been covalently linked to the C-terminus of the B-peptide. The effect of these amino acid changes was to shift the isoelectric point of the molecule, thereby producing a molecule that is soluble at acidic pH (e.g., pH 4 to 6.5) but insoluble at physiological pH. When a solution of insulin glargine is injected into the muscle, the pH of the solution is neutralized and the insulin glargine forms microprecipitates that slowly release the insulin glargine over the 24 hour period following injection with no pronounced insulin peak and thus a reduced risk of inducing hypoglycemia. This profile allows a once-daily dosing to provide a patient's basal insulin. Thus, in some embodiments, the insulin analogue comprises an A-chain peptide wherein the amino acid at position A21 is glycine and a B-chain peptide wherein the amino acids at position B31 and B32 are arginine. The present disclosure encompasses all single and multiple combinations of these mutations and any other mutations that are described herein (e.g., GlyA21-human insulin, GlyA21ArgB31-human insulin, ArgB31ArgB32-human insulin, ArgB31-human insulin).

In various embodiments, the O-glycosylated CTP peptide-based insulin or insulin analogue lacks one or more amino acids at the N- or C-terminus of the B-chain. For example, in certain embodiments, the B-chain peptide lacks at least one B1, B2, B3, B26, B27, B28, B29, or B30 residue. In particular embodiments, the B-chain peptide lacks a combination of residues. For example, the B-chain may lack amino acid residues B1-B2, B1-B3, B1-B4, B29-B30, B28-B30, B27-B30 and/or B26-B30. In some embodiments, these deletions may apply to any of the aforementioned insulin analogues (e.g., without limitation to produce des(B29)-insulin lispro, des(B30)-insulin aspart, and the like. In embodiments, where the In some embodiments, the O-glycosylated CTP peptide-based insulin or insulin analogue contains additional amino acid residues on the N- or C-terminus of the A-chain peptide or B-chain. In some embodiments, one or more amino acid residues are located at positions A0, A22, B0 and/or B31. In some embodiments, one or more amino acid residues are located at position A0. In some embodiments, one or more amino acid residues are located at position A22. In some embodiments, one or more amino acid residues are located at position B0. In some embodiments, one or more amino acid residues are located at position B31. In particular embodiments, the glycosylated insulin or insulin analogue does not include any additional amino acid residues at positions A0, A22, B0 or B31.

In particular embodiments, one or more amidated amino acids of the O-glycosylated CTP peptide-based insulin or insulin analogue are replaced with an acidic amino acid, or another amino acid. For example, the asparagine at positions other than the position glycosylated may be replaced with aspartic acid or glutamic acid, or another residue. Likewise, glutamine may be replaced with aspartic acid or glutamic acid, or another residue. In particular, AsnA18, AsnA21, or AsnB3, or any combination of those residues, may be replaced by aspartic acid or glutamic acid, or another residue. GlnA15 or GlnB4, or both, may be replaced by aspartic acid or glutamic acid, or another residue. In particular embodiments, the insulin analogues have an aspartic acid, or another residue, at position A21 or aspartic acid, or another residue, at position B3, or both.

One skilled in the art will recognize that it is possible to replace yet other amino acids in the O-glycosylated CTP peptide-based insulin or insulin analogue with other amino acids while retaining biological activity of the molecule. For example, without limitation, the following modifications are also widely accepted in the art: replacement of the histidine residue of position B10 with aspartic acid (HisB10 to AspB10); replacement of the phenylalanine residue at position B1 with aspartic acid (PheB1 to AspB1); replacement of the threonine residue at position B30 with alanine (ThrB30 to AlaB30); replacement of the tyrosine residue at position B26 with alanine (TyrB26 to AlaB26); and replacement of the serine residue at position B9 with aspartic acid (SerB9 to AspB9).

In various embodiments, the O-glycosylated CTP peptide-based insulin or insulin analogue has a protracted profile of action. Thus, in certain embodiments, the O-glycosylated CTP peptide-based insulin or insulin analogue may be acylated with a fatty acid. That is, an amide bond is formed between an amino group on the insulin analogue and the carboxylic acid group of the fatty acid. The amino group may be the alpha-amino group of an N-terminal amino acid of the insulin analogue, or may be the epsilon-amino group of a lysine residue of the insulin analogue. The O-glycosylated CTP peptide-based insulin or insulin analogue may be acylated at one or more of the three amino groups that are present in wild-type human insulin or may be acylated on lysine residue that has been introduced into the wild-type human insulin sequence. In particular embodiments, the O-glycosylated CTP peptide-based insulin or insulin analogue may be acylated at position B1. In certain embodiments, the O-glycosylated CTP peptide-based insulin or insulin analogue may be acylated at position B29. In certain embodiments, the fatty acid is selected from myristic acid ($C_{14}$), pentadecylic acid ($C_{15}$), palmitic acid ($C_{16}$), heptadecylic acid ($C_{17}$) and stearic acid ($C_{18}$). For example, insulin detemir (LEVEMIR) is a long acting insulin mutant in which ThrB30 has been deleted (desB30) and a $C_{14}$ fatty acid chain (myristic acid) has been attached to LysB29 via a γE linker (SEQ ID NO:2 and SEQ ID NO:81) and insulin degludec is a long acting insulin mutant in which ThrB30 has been deleted and a $C_{16}$ fatty acid chain (palmitic acid) has been attached to LysB29 via a γE linker (SEQ ID NO:2 and SEQ ID NO:76).

The O-glycosylated CTP peptide-based insulin or insulin analogue comprising one or more O-linked glycosylation sites, includes heterodimer analogues and single-chain analogues that comprise modified derivatives of the native A-chain and/or B-chain, including modification of the amino acid at position A19, B16 or B25 to a 4-amino phenylalanine or one or more amino acid substitutions at positions selected from A5, A8, A9, A10, A12, A13, A14, A15, A17, A18, A21, B1, B2, B3, B4, B5, B9, B10, B13, B14, B16, B17, B18, B20, B21, B22, B23, B26, B27, B28, B29 and B30 or deletions of any or all of positions B1-4 and B26-30. Examples of insulin analogues can be found for example in published International Application WO9634882, WO95516708; WO20100080606, WO2009/099763, and WO2010080609, U.S. Pat. No. 6,630,348, and Kristensen et al., Biochem. J. 305: 981-986 (1995), the disclosures of which are incorporated herein by reference). In further embodiments, the O-glycosylated CTP peptide-based insulin or insulin analogue may be acylated and/or pegylated.

In some embodiments, the N-terminus of the A-peptide, the N-terminus of the B-peptide, the epsilon-amino group of Lys at position B29 or any other available amino group in the O-glycosylated CTP peptide-based insulin or insulin analogue is covalently linked to a fatty acid moiety of general formula:

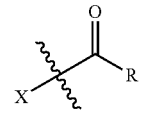

wherein X is an amino group of the insulin polypeptide and R is H or a $C_{1-30}$ alkyl group and the insulin analogue comprises one or more N-linked glycosylation sites. In some embodiments, R is a $C_{1-20}$ alkyl group, a $C_{3-19}$ alkyl group, a $C_{5-18}$ alkyl group, a $C_{6-17}$ alkyl group, a $C_{8-16}$ alkyl group, a $C_{10-15}$ alkyl group, or a $C_{12-14}$ alkyl group. In certain embodiments, the insulin polypeptide is conjugated to the moiety at the A1 position. In particular embodiments, the insulin polypeptide is conjugated to the moiety at the B1 position. In particular embodiments, the insulin polypeptide is conjugated to the moiety at the epsilon-amino group of Lys at position B29. In particular embodiments, position B28 of the O-glycosylated CTP peptide-based insulin or insulin analogue is Lys and the epsilon-amino group of $Lys^{B28}$ is conjugated to the fatty acid moiety. In particular embodiments, position B3 of the O-glycosylated CTP peptide-based insulin or insulin analogue is Lys and the epsilon-amino group of $Lys^{B3}$ is conjugated to the fatty acid moiety. In some embodiments, the fatty acid chain is 8-20 carbons long. In particular embodiments, the fatty acid is octanoic acid (C8), nonanoic acid (C9), decanoic acid (C10), undecanoic acid (C11), dodecanoic acid (C12), or tridecanoic acid (C13). In certain embodiments, the fatty acid is myristic acid (C14), pentadecanoic acid (C15), palmitic acid (C16), heptadecanoic acid (C17), stearic acid (C18), nonadecanoic acid (C19), or arachidic acid (C20).

In particular embodiments, the O-glycosylated CTP peptide-based insulin or insulin analogue comprises the mutations and/or chemical modifications of one of the following insulin analogues: Lys$^{B28}$Pro$^{B29}$-human insulin (insulin lispro), Asp$^{B28}$-human insulin (insulin aspart), Lys$^{B3}$Glu$^{B29}$-human insulin (insulin glulisine), Arg$^{B31}$Arg$^{B32}$-human insulin (insulin glargine), N$^{\epsilon B29}$-myristoyl-des(B30)-human insulin (insulin detemir), Ala$^{B26}$-human insulin, Asp$^{B1}$-human insulin, Arg$^{A0}$-human insulin, Asp$^{B1}$Glu$^{B13}$-human insulin, Gly$^{A21}$-human insulin, Gly$^{A21}$Arg$^{B31}$Arg$^{B32}$-human insulin, Arg$^{A0}$Arg$^{B31}$Arg$^{B32}$-human insulin, Arg$^{A0}$Gly$^{A21}$Arg$^{B31}$Arg$^{B32}$-human insulin, des(B30)-human insulin, des(B27)-human insulin, des(B28-B30)-human insulin, des(B1)-human insulin, des(B1-B3)-human insulin.

In particular embodiments, an O-glycosylated CTP peptide-based insulin or insulin analogue comprises the mutations and/or chemical modifications of one of the following insulin analogues: N$^{\epsilon B29}$-palmitoyl-human insulin, N$^{\epsilon B29}$-myrisotyl-human insulin, N$^{\epsilon B28}$-palmitoyl-Lys$^{B28}$Pro$^{B29}$-human insulin, N$^{\epsilon B28}$-myristoyl-Lys$^{B28}$Pro$^{B29}$-human insulin. In particular embodiments, the glycosylated insulin analogue comprises at least one N-glycan as disclosed herein attached to the asparagine residue comprising an N-linked glycosylation site.

In particular embodiments, the O-glycosylated CTP peptide-based insulin or insulin analogue comprises the mutations and/or chemical modifications of one of the following insulin analogues: N$^{\epsilon B29}$-palmitoyl-des(B30)-human insulin, N$^{\epsilon B30}$-myristoyl-Thr$^{B29}$Lys$^{B30}$-human insulin, N$^{\epsilon B30}$-palmitoyl-Thr$^{B29}$Lys$^{B30}$-human insulin, N$^{\epsilon B29}$-(N-palmitoyl-γ-glutamyl)-des(B30)-human insulin, N$^{\epsilon B29}$-(N-lithocolyl-γ-glutamyl)-des(B30)-human insulin, N$^{\epsilon B29}$-(ω-carboxyheptadecanoyl)-des(B30)-human insulin, N$^{\epsilon B29}$-(ω-carboxyheptadecanoyl)-human insulin.

In particular embodiments, the O-glycosylated CTP peptide-based insulin or insulin analogue comprises the mutations and/or chemical modifications of one of the following insulin analogues: N$^{\epsilon B29}$-octanoyl-human insulin, N$^{\epsilon B29}$-myristoyl-GlyA21ArgB31Arg$^{B31}$-human insulin, N$^{\epsilon B29}$-myristoyl-Gly$^{A21}$ Gln$^{B3}$ Arg$^{B31}$ Arg$^{B32}$-human insulin, N$^{\epsilon B29}$-myristoyl-Arg$^{A0}$Gly$^{A21}$ Arg$^{B31}$ Arg$^{B32}$-human insulin, N$^{\epsilon B29}$-Arg$^{A0}$Gly$^{A21}$Gln$^{B3}$Arg$^{B31}$Arg$^{B32}$-human insulin, N$^{\epsilon B29}$-myristoyl-Arg$^{A0}$Gly$^{A21}$Asp$^{B3}$Arg$^{B31}$Arg$^{B32}$-human insulin, N$^{\epsilon B29}$-myristoyl-Arg$^{B31}$ Arg$^{B32}$-human insulin, N$^{\epsilon B29}$myristoyl-Arg$^{A0}$ Arg$^{B31}$ Arg$^{B32}$-human insulin, N$^{\epsilon B29}$-octanoyl-Gly$^{A21}$Arg$^{B31}$ Arg$^{B32}$-human insulin, N$^{\epsilon B29}$-octanoyl-Gly$^{A21}$ Gln$^{B3}$Arg$^{B31}$ Arg$^{B32}$-human insulin, N$^{\epsilon B29}$-octanoyl-Arg$^{A0}$Gly$^{A21}$Arg$^{B31}$Arg$^{B32}$-human insulin, N$^{\epsilon B29}$-octanoyl-Arg$^{A0}$Gly$^{A21}$Gln$^{B3}$Arg$^{B31}$Arg$^{B32}$-human insulin, N$^{\epsilon B29}$-octanoyl-Arg$^{B0}$Gly$^{A21}$Asp$^{B3}$Arg$^{B31}$Arg$^{B32}$-human insulin, N$^{\epsilon B29}$-octanoyl-Arg$^{B31}$Arg$^{B32}$-human insulin, N$^{\epsilon B29}$-octanoyl-Arg$^{A0}$Arg$^{B31}$Arg$^{B32}$-human insulin.

In particular embodiments, the O-glycosylated CTP peptide-based insulin or insulin analogue comprises the mutations and/or chemical modifications of one of the following insulin polypeptides: N$^{\epsilon B28}$-myristoyl-Gly$^{A21}$Lys$^{B28}$Pro$^{B29}$Arg$^{B31}$Arg$^{B32}$-human insulin, N$^{\epsilon B28}$-myristoyl-Gly$^{A21}$Gln$^{B3}$Lys$^{B28}$Pro$^{B30}$Arg$^{B31}$Arg$^{B32}$-human insulin, N$^{\epsilon B28}$-myristoyl-Arg$^{A0}$Gly$^{A21}$Lys$^{B28}$Pro$^{B29}$Arg$^{B31}$Arg$^{B32}$-human insulin, N$^{\epsilon B28}$-myristoyl-Arg$^{A0}$Gly$^{A21}$Gln$^{B3}$Lys$^{B28}$Pro$^{B29}$Arg$^{B31}$Arg$^{B32}$-human insulin, N$^{\epsilon B28}$-myristoyl-Arg$^{A0}$Gly$^{A21}$Asp$^{B3}$Lys$^{B28}$Pro$^{B29}$Arg$^{B31}$Arg$^{B32}$-human insulin, N$^{\epsilon B28}$-myristoyl-Lys$^{B28}$Pro$^{B29}$Arg$^{B31}$Arg$^{B32}$-human insulin, N$^{\epsilon B28}$-myristoyl-arg$^{A0}$Lys$^{B28}$Pro$^{B29}$Arg$^{B31}$Arg$^{B32}$-human insulin, N$^{\epsilon B28}$-octanoyl-Gly$^{A21}$Lys$^{B28}$Pro$^{B29}$Arg$^{B31}$Arg$^{B32}$-human insulin.

In particular embodiments, the O-glycosylated CTP peptide-based insulin or insulin analogue comprises the mutations and/or chemical modifications of one of the following insulin analogues: N$^{\epsilon B28}$-octanoyl-Gly$^{A21}$Gln$^{B3}$Lys$^{B28}$Pro$^{B29}$ Arg$^{B31}$ Arg$^{B32}$-human insulin, N$^{\epsilon B28}$-octanoyl-Arg$^{A0}$Gly$^{A21}$Lys$^{B28}$Pro$^{B29}$Arg$^{B31}$Arg$^{B32}$-human insulin, N$^{\epsilon B28}$-octanoyl-Arg$^{A0}$Gly$^{A21}$Gln$^{B3}$Lys$^{B28}$Pro$^{B29}$Arg$^{B31}$Arg$^{B32}$-human insulin, N$^{\epsilon B28}$-octanoyl-Arg$^{A0}$Gly$^{A21}$Asp$^{B3}$Lys$^{B28}$Pro$^{B29}$Arg$^{B31}$Arg$^{B32}$-human insulin, N$^{\epsilon B28}$-octanoyl-Lys$^{B28}$Pro$^{B29}$Arg$^{B31}$Arg$^{B32}$-human insulin, N$^{\epsilon B28}$-octanoyl-Arg$^{A0}$Lys$^{B28}$Pro$^{B29}$Arg$^{B31}$Arg$^{B32}$-human insulin.

In particular embodiments, the O-glycosylated CTP peptide-based insulin or insulin analogue comprises the mutations and/or chemical modifications of one of the following insulin analogues: N$^{\epsilon B29}$-tridecanoyl-des(B30)-human insulin, N$^{\epsilon B29}$-tetradecanoyl-des(B30)-human insulin, N$^{\epsilon B29}$-decanoyl-des(B30)-human insulin, N$^{\epsilon B29}$-dodecanoyl-des (B30)-human insulin N$^{\epsilon B29}$-tridecanoyl-Gly$^{A21}$-des(B30)-human insulin, N$^{\epsilon B29}$-tetradecanoyl-Gly$^{A21}$-des(B30)-human insulin, N$^{\epsilon B29}$-decanoyl-Gly$^{A21}$-des(B30)-human insulin, N$^{\epsilon B29}$-dodecanoyl-Gly$^{A21}$-des(B30)-human insulin, N$^{\epsilon B29}$-tridecanoyl-Gly$^{A21}$Gln$^{B3}$-des(B30)-human insulin, N$^{\epsilon B29}$-tetradecanoyl-Gly$^{A21}$Gln$^{B3}$-des(B30)-human insulin, N$^{\epsilon B29}$-decanoyl-Gly$^{A21}$Gln$^{B3}$-des(B30)-human insulin N$^{\epsilon B29}$-dodecanoyl-Gly$^{A21}$-Gln$^{B3}$-des (B30)-human insulin, N$^{\epsilon B29}$-tridecanoyl-Ala$^{A21}$-des(B30)-human insulin, N$^{\epsilon B29}$-tetradecanoyl-Ala$^{A21}$-des(B30)-human insulin, N$^{\epsilon B29}$-decanoyl-Ala$^{A21}$-des(B30)-human insulin, N$^{\epsilon B29}$-dodecanoyl-Ala$^{A21}$-des(B30)-human insulin, N$^{\epsilon B29}$-tridecanoyl-Ala$^{A21}$-Gln$^{B3}$-des(B30)-human insulin, N$^{\epsilon B29}$-tetradecanoyl-Ala$^{A21}$Gln$^{B3}$-des(B30)-human insulin, N$^{\epsilon B29}$-decanoyl-Ala$^{A21}$Gln$^{B3}$-des(B30)-human insulin, N$^{\epsilon B29}$-dodecanoyl-Ala$^{A21}$Gln$^{B3}$-des (B30)-human insulin, N$^{\epsilon B29}$-tridecanoyl-Gln$^{B3}$-des(B30)-human insulin, N$^{\epsilon B29}$-tetradecanoyl-Gln$^{B3}$-des(B30)-human insulin, N$^{\epsilon B29}$-decanoyl-Gln$^{B3}$-des(B30)-human insulin, N$^{\epsilon B29}$-dodecanoyl-Gln$^{B3}$-des(B30)-human insulin.

In particular embodiments, the O-glycosylated CTP peptide-based insulin or insulin analogue comprises the mutations and/or chemical modifications of one of the following insulin analogues: N$^{\epsilon B29}$-tridecanoyl-Gly$^{A21}$-human insulin, N$^{\epsilon B29}$-tetradecanoyl-Gly$^{A21}$-human insulin, N$^{\epsilon B29}$-decanoyl-Gly$^{A21}$-human insulin, N$^{\epsilon B29}$-dodecanoyl-Gly$^{A21}$-human insulin, N$^{\epsilon B29}$-tridecanoyl-Ala$^{A21}$-human insulin, N$^{\epsilon B29}$-tetradecanoyl-Ala$^{A21}$-human insulin, N$^{\epsilon B29}$-decanoyl-Ala$^{A21}$-human insulin, N$^{\epsilon B29}$-dodecanoyl-Ala$^{A21}$-human insulin In particular embodiments, the O-glycosylated CTP peptide-based insulin or insulin analogue comprises the mutations and/or chemical modifications of one of the following insulin analogues: N$^{\epsilon B29}$-tridecanoyl-Gly$^{A21}$Gln$^{B3}$-human insulin, N$^{\epsilon B29}$-tetradecanoyl-Gly$^{A21}$Gln$^{B3}$-human insulin, N$^{\epsilon B29}$-decanoyl-Gly$^{A21}$Gln$^{B3}$-human insulin, N$^{\epsilon B29}$-dodecanoyl-Gly$^{A21}$Gln$^{B3}$-human insulin, N$^{\epsilon B29}$-tridecanoyl-Ala$^{A21}$Gln$^{B3}$-human insulin, N$^{\epsilon B29}$-tetradecanoyl-Ala$^{A21}$Gln$^{B3}$-human insulin, N$^{\epsilon B29}$-decanoyl-Ala$^{A21}$Gln$^{B3}$-human insulin, N$^{\epsilon B29}$-dodecanoyl-Ala$^{A21}$Gln$^{B3}$-human insulin.

In particular embodiments, the O-glycosylated CTP peptide-based insulin or insulin analogue comprises the mutations and/or chemical modifications of one of the following insulin analogues: N$^{\epsilon B29}$-tridecanoyl-Gln$^{B3}$-human insulin, N$^{\epsilon B29}$-tetradecanoyl-Gln$^{B3}$-human insulin, N$^{\epsilon B29}$-decanoyl-Gln$^{B3}$-human insulin, N$^{\epsilon B29}$-dodecanoyl-Gln$^{B3}$-human insulin.

In particular embodiments, the O-glycosylated CTP peptide-based insulin or insulin analogue comprises the mutations and/or chemical modifications of one of the following insulin analogues: $N^{\epsilon B29}$-tridecanoyl-Glu$^{B30}$-human insulin, $N^{\epsilon B29}$-tetradecanoyl-Glu$^{B30}$-human insulin, $N^{\epsilon B29}$-decanoyl-Glu$^{B30}$-human insulin, $N^{\epsilon B29}$-dodecanoyl-Glu$^{B30}$-human insulin.

In particular embodiments, the O-glycosylated CTP peptide-based insulin or insulin analogue comprises the mutations and/or chemical modifications of one of the following insulin analogues: $N^{\epsilon B29}$-tridecanoyl-Gly$^{A21}$Glu$^{B30}$-human insulin, $N^{\epsilon B29}$-tetradecanoyl-Gly$^{A21}$Glu$^{B30}$-human insulin, $N^{\epsilon B29}$-decanoyl-Gly$^{A21}$Glu$^{B30}$-human insulin, $N^{\epsilon B29}$-dodecanoyl-Gly$^{A21}$Glu$^{B30}$-human insulin.

In particular embodiments, the O-glycosylated CTP peptide-based insulin or insulin analogue comprises the mutations and/or chemical modifications of one of the following insulin analogues: $N^{\epsilon B29}$-tridecanoyl-Gly$^{A21}$Gln$^{B3}$Glu$^{B30}$-human insulin, $N^{\epsilon B29}$-tetradecanoyl-Gly$^{A21}$Gln$^{B3}$Glu$^{B30}$-human insulin, $N^{\epsilon B29}$-decanoyl-Gly$^{A21}$Gln$^{B3}$Glu$^{B30}$-human insulin, $N^{\epsilon B29}$-dodecanoyl-Gly$^{A21}$Gln$^{B3}$Glu$^{B30}$-human insulin, $N^{\epsilon B29}$-tridecanoyl-Ala$^{A21}$Glu$^{B30}$-human insulin, $N^{\epsilon B29}$-tetradecanoyl-Ala$^{A21}$Glu$^{B30}$-human insulin, $N^{\epsilon B29}$-decanoyl-Ala$^{A21}$Glu$^{B30}$-human insulin, $N^{\epsilon B29}$-dodecanoyl-Ala$^{A21}$Glu$^{B30}$-human insulin, $N^{\epsilon B29}$-tridecanoyl-Ala$^{A21}$Gln$^{B3}$Glu$^{B30}$-human insulin, $N^{\epsilon B29}$-tetradecanoyl-Ala$^{A21}$Gln$^{B3}$Glu$^{B30}$-human insulin, $N^{\epsilon B29}$-decanoyl-Ala$^{A21}$Gln$^{B3}$Glu$^{B30}$-human insulin, $N^{\epsilon B29}$-dodecanoyl-Ala$^{A21}$Gln$^{B3}$Glu$^{B30}$-human insulin.

In particular embodiments, the O-glycosylated CTP peptide-based insulin or insulin analogue comprises the mutations and/or chemical modifications of one of the following insulin analogues: $N^{\epsilon B29}$-tridecanoyl-Gln$^{B3}$Glu$^{B30}$-human insulin, $N^{\epsilon B29}$-tetradecanoyl-Gln$^{B3}$Glu$^{B30}$-human insulin, $N^{\epsilon B29}$-decanoyl-Gln$^{B3}$Glu$^{B30}$-human insulin, $N^{\epsilon B29}$-dodecanoyl-Gln$^{B3}$Glu$^{B30}$-human insulin.

In particular embodiments, the O-glycosylated CTP peptide-based insulin or insulin analogue comprises the mutations and/or chemical modifications of one of the following insulin analogues: $N^{\epsilon B29}$-formyl-human insulin, $N^{\alpha B1}$-formyl-human insulin, $N^{\alpha A1}$-formyl-human insulin, $N^{\epsilon B29}$-formyl-$N^{\alpha B1}$-formyl-human insulin, $N^{\epsilon B29}$-formyl-$N^{\alpha A1}$-formyl-human insulin, $N^{\alpha A1}$-formyl-$N^{\alpha B1}$-formyl-human insulin, $N^{\epsilon B29}$-formyl-$N^{\alpha A1}$-formyl-$N^{\alpha B1}$-formyl-human insulin.

In particular embodiments, the O-glycosylated CTP peptide-based insulin or insulin analogue comprises the mutations and/or chemical modifications of one of the following insulin analogues: $N^{\epsilon B29}$-acetyl-human insulin, $N^{\alpha B1}$-acetyl-human insulin, $N^{\alpha A1}$-acetyl-human insulin, $N^{\epsilon B29}$-acetyl-$N^{\alpha B1}$-acetyl-human insulin, $N^{\epsilon B29}$-acetyl-$N^{\alpha A1}$-acetyl-human insulin, $N^{\alpha A1}$-acetyl-$N^{\alpha B1}$-acetyl-human insulin, $N^{\epsilon B29}$-acetyl-$N^{\alpha A1}$-acetyl-$N^{\alpha B1}$-acetyl-human insulin.

In particular embodiments, the O-glycosylated CTP peptide-based insulin or insulin analogue comprises the mutations and/or chemical modifications of one of the following insulin analogues: $N^{\epsilon B29}$-propionyl-human insulin, $N^{\alpha B1}$-propionyl-human insulin, $N^{\alpha A1}$-propionyl-human insulin, $N^{\epsilon B29}$-acetyl-$N^{\alpha B1}$-propionyl-human insulin, $N^{\epsilon B29}$-propionyl-$N^{\alpha A1}$-propionyl-human insulin, $N^{\alpha A1}$-propionyl-$N^{\alpha B1}$-propionyl-human insulin, $N^{\epsilon B29}$-propionyl-$N^{\alpha A1}$-propionyl-$N^{\alpha B1}$-propionyl-human insulin.

In particular embodiments, an O-glycosylated CTP peptide-based insulin or insulin analogue of the present disclosure comprises the mutations and/or chemical modifications of one of the following insulin analogues: $N^{\epsilon B29}$-butyryl-human insulin, $N^{\alpha B1}$-butyryl-human insulin, $N^{\alpha A1}$-butyryl-human insulin, $N^{\epsilon B29}$-butyryl-$N^{\alpha B1}$-butyryl-human insulin, $N^{\epsilon B29}$-butyryl-$N^{\alpha A1}$-butyryl-human insulin, $N^{\alpha A1}$-butyryl-$N^{\alpha B1}$-butyryl-human insulin, $N^{\epsilon B29}$-butyryl-$N^{\alpha A1}$-butyryl-$N^{\alpha B1}$-butyryl-human insulin.

In particular embodiments, the O-glycosylated CTP peptide-based insulin or insulin analogue comprises the mutations and/or chemical modifications of one of the following insulin analogues: $N^{\epsilon B29}$-pentanoyl-human insulin, $N^{\alpha B1}$-pentanoyl-human insulin, $N^{\alpha A1}$-pentanoyl-human insulin, $N^{\epsilon B29}$-pentanoyl-$N^{\alpha B1}$-pentanoyl-human insulin, $N^{\epsilon B29}$-pentanoyl-$N^{\alpha A1}$-pentanoyl-human insulin, $N^{\alpha A1}$-pentanoyl-$N^{\alpha B1}$-pentanoyl-human insulin, $N^{\epsilon B29}$-pentanoyl-pentanoyl-$N^{\alpha B1}$-pentanoyl-human insulin.

In particular embodiments, the O-glycosylated CTP peptide-based insulin or insulin analogue comprises the mutations and/or chemical modifications of one of the following insulin analogues: $N^{\epsilon B29}$-hexanoyl-human insulin, $N^{\alpha B1}$-hexanoyl-human insulin, $N^{\alpha A1}$-hexanoyl-human insulin $N^{\epsilon B29}$-hexanoyl-$N^{\alpha B1}$-hexanoyl-human insulin, $N^{\epsilon B29}$-hexanoyl-$N^{\alpha A1}$-hexanoyl-human insulin, $N^{\alpha A1}$-hexanoyl-$N^{\alpha B1}$-hexanoyl-human insulin, $N^{\epsilon B29}$-hexanoyl-$N^{\alpha A1}$-hexanoyl-$N^{\alpha B1}$-hexanoyl-human insulin.

In particular embodiments, the O-glycosylated CTP peptide-based insulin or insulin analogue comprises the mutations and/or chemical modifications of one of the following insulin analogues: $N^{\epsilon B29}$-heptanoyl-human insulin, $N^{\alpha A1}$-heptanoyl-human insulin, $N^{\alpha A1}$-heptanoyl-human insulin, $N^{\epsilon B29}$-heptanoyl-$N^{\alpha B1}$-heptanoyl-human insulin, $N^{\epsilon B29}$-heptanoyl-$N^{\alpha A1}$-heptanoyl-human insulin, $N^{\alpha A1}$-heptanoyl-$N^{\alpha B1}$-heptanoyl-human insulin, $N^{\epsilon B29}$-heptanoyl-$N^{\alpha A1}$-heptanoyl-$N^{\alpha B1}$-heptanoyl-human insulin.

In particular embodiments, the O-glycosylated CTP peptide-based insulin or insulin analogue comprises the mutations and/or chemical modifications of one of the following insulin analogues: $N^{\alpha B1}$-octanoyl-human insulin, $N^{\alpha A1}$-octanoyl-human insulin, $N^{\epsilon B29}$-octanoyl-$N^{\alpha B1}$-octanoyl-human insulin, $N^{\epsilon B29}$-octanoyl-$N^{\alpha A1}$-octanoyl-human insulin, $N^{\alpha A1}$-octanoyl-$N^{\alpha B1}$-octanoyl-human insulin, $N^{\epsilon B29}$-octanoyl-$N^{\alpha A1}$-octanoyl-$N^{\alpha B1}$-octanoyl-human insulin.

In particular embodiments, the O-glycosylated CTP peptide-based insulin or insulin analogue comprises the mutations and/or chemical modifications of one of the following insulin analogues: $N^{\epsilon B29}$-nonanoyl-human insulin, $N^{\alpha B1}$-nonanoyl-human insulin, $N^{\alpha A1}$-nonanoyl-human insulin, $N^{\epsilon B29}$-nonanoyl-$N^{\alpha B1}$-nonanoyl-human insulin, $N^{\epsilon B29}$-nonanoyl-$N^{\alpha A1}$-nonanoyl-human insulin, $N^{\alpha A1}$-nonanoyl-$N^{\alpha B1}$-nonanoyl-human insulin, $N^{\epsilon B29}$-nonanoyl-$N^{\alpha A1}$-nonanoyl-$N^{\alpha B1}$-nonanoyl-human insulin.

In particular embodiments, the O-glycosylated CTP peptide-based insulin or insulin analogue comprises the mutations and/or chemical modifications of one of the following insulin analogues: $N^{\epsilon B29}$-decanoyl-human insulin, $N^{\alpha B1}$-decanoyl-human insulin, $N^{\alpha A1}$-decanoyl-human insulin, $N^{\epsilon B29}$-decanoyl-$N^{\alpha B1}$-decanoyl-human insulin, $N^{\epsilon B29}$-decanoyl-$N^{\alpha A1}$-decanoyl-human insulin, $N^{\alpha A1}$-decanoyl-$N^{\alpha B1}$-decanoyl-human insulin, $N^{\epsilon B29}$-decanoyl-$N^{\alpha A1}$-decanoyl-$N^{\alpha B1}$-decanoyl-human insulin.

In particular embodiments, O-glycosylated CTP peptide-based insulin or insulin analogue comprises the mutations and/or chemical modifications of one of the following insulin analogues: $N^{\epsilon B28}$-formyl-Lys$^{B28}$Pro$^{B29}$-human insulin, $N^{\alpha B1}$-formyl-Lys$^{B28}$Pro$^{B29}$-human insulin, $N^{\alpha A1}$-formyl-Lys$^{B28}$Pro$^{B29}$-human insulin, $N^{\epsilon B28}$-formyl-$N^{\alpha A1}$-formyl-Lys$^{B28}$Pro$^{B29}$-human insulin, $N^{\epsilon B28}$-formyl-$N^{\alpha A1}$-formyl-Lys$^{B28}$Pro$^{B29}$-human insulin, $N^{\alpha A1}$-formyl-$N^{\alpha B1}$-formyl-Lys$^{B28}$Pro$^{B29}$-human insulin, $N^{\epsilon B28}$-formyl-$N^{\alpha A1}$-formyl-$N^{\alpha B1}$-formyl-Lys$^{B28}$Pro$^{B29}$-human insulin, $N^{\epsilon B29}$- acetyl-Lys$^{B28}$Pro$^{B29}$-human insulin, N$^{\alpha B1}$-acetyl-Lys$^{B28}$Pro$^{B29}$-human insulin, N$^{\alpha A1}$-acetyl-Lys$^{B28}$Pro$^{B29}$-human insulin, N$^{\epsilon B28}$-acetyl-N$^{\alpha B1}$-acetyl-Lys$^{B28}$Pro$^{B29}$-human insulin.

In particular embodiments, the O-glycosylated CTP peptide-based insulin or insulin analogue comprises the mutations and/or chemical modifications of one of the following insulin analogues: N$^{\epsilon B28}$-acetyl-N$^{\alpha A1}$-acetyl-Lys$^{B28}$Pro$^{B29}$-human insulin, N$^{\alpha A1}$-acetyl-N$^{\alpha B1}$-acetyl-Lys$^{B28}$Pro$^{B29}$-human insulin, N$^{\epsilon B28}$-acetyl-N$^{\alpha A1}$-acetyl-N$^{\alpha B1}$-acetyl-Lys$^{B28}$Pro$^{B29}$-human insulin.

In particular embodiments, the O-glycosylated CTP peptide-based insulin or insulin analogue comprises the mutations and/or chemical modifications of one of the following insulin analogues: N$^{\epsilon B28}$-propionyl-Lys$^{B28}$Pro$^{B29}$-human insulin, N$^{\alpha B1}$-propionyl-Lys$^{B28}$Pro$^{B29}$-human insulin N$^{\alpha A1}$-propionyl-Lys$^{B28}$Pro$^{B29}$-human insulin, N$^{\epsilon B28}$-propionyl-N$^{\alpha B1}$-propionyl-Lys$^{B28}$Pro$^{B29}$-human insulin, N$^{\epsilon B28}$-propionyl-N$^{\alpha A1}$-propionyl-Lys$^{B28}$Pro$^{B29}$-human insulin, N$^{\alpha A1}$-propionyl-N$^{\alpha B1}$-propionyl-Lys$^{B28}$Pro$^{B29}$-human insulin, N$^{\epsilon B28}$-propionyl-N$^{\alpha A1}$-propionyl-N$^{\alpha B1}$-propionyl-Lys$^{B28}$Pro$^{B29}$-human insulin.

In particular embodiments, the O-glycosylated CTP peptide-based insulin or insulin analogue comprises the mutations and/or chemical modifications of one of the following insulin analogues: N$^{\epsilon B28}$-butyryl-Lys$^{B28}$Pro$^{B29}$-human insulin, N$^{\alpha B1}$-butyryl-Lys$^{B28}$Pro$^{B29}$-human insulin, N$^{\alpha A1}$-butyryl-Lys$^{B28}$Pro$^{B29}$-human insulin, N$^{\epsilon B28}$-butyryl-N$^{\alpha B1}$-butyryl-Lys$^{B28}$Pro$^{B29}$-human insulin, N$^{\epsilon B28}$-butyryl-N$^{\alpha A1}$-butyryl-Lys$^{B28}$Pro$^{B29}$-human insulin, N$^{\alpha A1}$-butyryl-N$^{\alpha B1}$-butyryl-Lys$^{B28}$Pro$^{B29}$-human insulin, N$^{\epsilon B28}$-butyryl-N$^{\alpha A1}$-butyryl-N$^{\alpha B1}$-butyryl-Lys$^{B28}$Pro$^{B29}$-human insulin.

In particular embodiments, the O-glycosylated CTP peptide-based insulin or insulin analogue comprises the mutations and/or chemical modifications of one of the following insulin analogues: N$^{\epsilon B28}$-pentanoyl-Lys$^{B28}$Pro$^{B29}$-human insulin, N$^{\alpha B1}$-pentanoyl-Lys$^{B28}$Pro$^{B29}$-human insulin N$^{\alpha A1}$-pentanoyl-Lys$^{B28}$Pro$^{B29}$-human insulin, N$^{\epsilon B28}$-pentanoyl-N$^{\alpha B1}$-pentanoyl-Lys$^{B28}$Pro$^{B29}$-human insulin, N$^{\epsilon B28}$-pentanoyl-N$^{\alpha A1}$-pentanoyl-Lys$^{B28}$Pro$^{B29}$-human insulin, N$^{\alpha A1}$-pentanoyl-N$^{\alpha B1}$-pentanoyl-Lys$^{B28}$Pro$^{B29}$-human insulin, N$^{\epsilon B28}$-pentanoyl-N$^{\alpha A1}$-pentanoyl-N$^{\alpha B1}$-pentanoyl-Lys$^{B28}$Pro$^{B29}$-human insulin.

In particular embodiments, the O-glycosylated CTP peptide-based insulin or insulin analogue comprises the mutations and/or chemical modifications of one of the following insulin analogues: N$^{\epsilon B28}$-hexanoyl-Lys$^{B28}$Pro$^{B29}$-human insulin, N$^{\alpha B1}$-hexanoyl-Lys$^{B28}$Pro$^{B29}$-human insulin N$^{\alpha A1}$-hexanoyl-Lys$^{B28}$Pro$^{B29}$-human insulin, N$^{\epsilon B28}$-hexanoyl-N$^{\alpha B1}$-hexanoyl-Lys$^{B28}$Pro$^{B29}$-human insulin, N$^{\epsilon B28}$-hexanoyl-N$^{\alpha A1}$-hexanoyl-Lys$^{B28}$Pro$^{B29}$-human insulin, N$^{\alpha A1}$-hexanoyl-N$^{\alpha B1}$-hexanoyl-Lys$^{B28}$Pro$^{B29}$-human insulin, N$^{\epsilon B28}$-hexanoyl-N$^{\alpha A1}$-hexanoyl-N$^{\alpha B1}$-hexanoyl-Lys$^{B28}$Pro$^{B29}$-human insulin.

In particular embodiments, the O-glycosylated CTP peptide-based insulin or insulin analogue comprises the mutations and/or chemical modifications of one of the following insulin analogues: N$^{\epsilon B28}$-heptanoyl-Lys$^{B28}$Pro$^{B29}$-human insulin, N$^{\alpha B1}$-heptanoyl-Lys$^{B28}$Pro$^{B29}$-human insulin N$^{\alpha A1}$-heptanoyl-Lys$^{B28}$Pro$^{B29}$-human insulin, N$^{\epsilon B28}$-heptanoyl-N$^{\alpha B1}$-heptanoyl-Lys$^{B28}$Pro$^{B29}$-human insulin, N$^{\epsilon B28}$-heptanoyl-N$^{\alpha A1}$-heptanoyl-Lys$^{B28}$Pro$^{B29}$-human insulin, N$^{\alpha A1}$-heptanoyl-N$^{\alpha B1}$-heptanoyl-Lys$^{B28}$Pro$^{B29}$-human insulin, N$^{\epsilon B28}$-heptanoyl-N$^{\alpha A1}$-heptanoyl-N$^{\alpha B1}$-heptanoyl-Lys$^{B28}$Pro$^{B29}$-human insulin.

In particular embodiments, the O-glycosylated CTP peptide-based insulin or insulin analogue comprises the mutations and/or chemical modifications of one of the following insulin analogues: N$^{\epsilon B28}$-octanoyl-Lys$^{B28}$Pro$^{B29}$-human insulin, N$^{\alpha B1}$-octanoyl-Lys$^{B28}$Pro$^{B29}$-human insulin, N$^{\alpha A1}$-octanoyl-Lys$^{B28}$Pro$^{B29}$-human insulin, N$^{\epsilon B28}$-octanoyl-N$^{\alpha B1}$-octanoyl-Lys$^{B28}$Pro$^{B29}$-human insulin, N$^{\epsilon B28}$-octanoyl-N$^{\alpha A1}$-octanoyl-Lys$^{B28}$Pro$^{B29}$-human insulin, N$^{\alpha A1}$-octanoyl-N$^{\alpha B1}$-octanoyl-Lys$^{B28}$Pro$^{B29}$-human insulin, N$^{\epsilon B28}$-octanoyl-N$^{\alpha A1}$-octanoyl-N$^{\alpha B1}$-octanoyl-Lys$^{B28}$Pro$^{B29}$-human insulin.

In particular embodiments, the O-glycosylated CTP peptide-based insulin or insulin analogue comprises the mutations and/or chemical modifications of one of the following insulin analogues: N$^{\epsilon B28}$-nonanoyl-Lys$^{B28}$Pro$^{B29}$-human insulin, N$^{\alpha B1}$-nonanoyl-Lys$^{B28}$Pro$^{B29}$-human insulin N$^{\alpha A1}$-nonanoyl-Lys$^{B28}$Pro$^{B29}$-human insulin, N$^{\epsilon B28}$-nonanoyl-N$^{\alpha B1}$-nonanoyl-Lys$^{B28}$Pro$^{B29}$-human insulin, N$^{\epsilon B28}$-nonanoyl-N$^{\alpha A1}$-nonanoyl-Lys$^{B28}$Pro$^{B29}$-human insulin, N$^{\alpha A1}$-nonanoyl-N$^{\alpha B1}$-nonanoyl-Lys$^{B28}$Pro$^{B29}$-human insulin, N$^{\epsilon B28}$-nonanoyl-N$^{\alpha A1}$-nonanoyl-N$^{\alpha B1}$-nonanoyl-Lys$^{B28}$Pro$^{B29}$-human insulin.

In particular embodiments, the O-glycosylated CTP peptide-based insulin or insulin analogue comprises the mutations and/or chemical modifications of one of the following insulin analogues: N$^{\epsilon B28}$-decanoyl-Lys$^{B28}$Pro$^{B29}$-human insulin, N$^{\alpha B1}$-decanoyl-Lys$^{B28}$Pro$^{B29}$-human insulin, N$^{\alpha A1}$-decanoyl-Lys$^{B28}$Pro$^{B29}$-human insulin, N$^{\epsilon B28}$-decanoyl-N$^{\alpha A1}$-decanoyl-Lys$^{B28}$Pro$^{B29}$-human insulin, N$^{\epsilon B28}$-decanoyl-N$^{\alpha A1}$-decanoyl-Lys$^{B28}$Pro$^{B29}$-human insulin, N$^{\alpha A1}$-decanoyl-N$^{\alpha B1}$-decanoyl-Lys$^{B28}$Pro$^{B29}$-human insulin, N$^{\epsilon B28}$-decanoyl-N$^{\alpha A1}$-decanoyl-N$^{\alpha B1}$-decanoyl-Lys$^{B28}$Pro$^{B29}$-human insulin.

In particular embodiments, the O-glycosylated CTP peptide-based insulin or insulin analogue comprises the mutations and/or chemical modifications of one of the following insulin analogues: N$^{\epsilon B29}$-pentanoyl-Gly$^{A21}$Arg$^{B31}$Arg$^{B32}$-human insulin, N$^{\alpha B1}$-hexanoyl-Gly$^{A21}$Arg$^{B31}$Arg$^{B32}$-human insulin, N$^{\alpha A1}$-heptanoyl-Gly$^{A21}$Arg$^{B31}$Arg$^{B32}$-human insulin, N$^{\epsilon B29}$-octanoyl-N$^{\alpha B1}$-octanoyl-Gly$^{A21}$Arg$^{B31}$Arg$^{B32}$-human insulin, N$^{\epsilon B29}$-propionyl-N$^{\alpha A1}$-propionyl-Gly$^{A21}$Arg$^{B31}$Arg$^{B32}$-human insulin, N$^{\alpha A1}$-acetyl-N$^{\alpha B1}$-acetyl-Gly$^{A21}$Arg$^{B31}$Arg$^{B32}$-human insulin, N$^{\epsilon B28}$-formyl-N$^{\alpha A1}$-formyl-N$^{\alpha B1}$-formyl-Gly$^{A21}$Arg$^{B31}$Arg$^{B32}$-human insulin, N$^{\alpha B1}$-formyl-des(B26)-human insulin, N$^{\alpha B1}$-acetyl-Asp$^{B28}$-human insulin, N$^{\epsilon B29}$-propionyl-N$^{\alpha A1}$-propionyl-N$^{\alpha B1}$-propionyl-Asp$^{B1}$ Asp$^{B3}$ Asp$^{B21}$-human insulin, N$^{\epsilon B29}$-pentanoyl-Gly$^{A21}$-human insulin, N$^{\alpha B1}$-hexanoyl-Gly$^{A21}$-human insulin, N$^{\alpha A1}$-heptanoyl-Gly$^{A21}$-human insulin, N$^{\epsilon B29}$-octanoyl-N$^{\alpha B1}$-octanoyl-Gly$^{A21}$-human insulin, N$^{\epsilon B29}$-propionyl-N$^{\alpha A1}$-propionyl-Gly$^{A21}$-human insulin, N$^{\alpha A1}$-acetyl-N$^{\alpha B1}$-acetyl-Gly$^{A21}$-human insulin, N$^{\epsilon B29}$-formyl-N$^{\alpha A1}$-formyl-N$^{\alpha B1}$-formyl-Gly$^{A21}$-human insulin, N$^{\epsilon B29}$-butyryl-des(B30)-human insulin, N$^{\alpha B1}$-butyryl-des(B30)-human insulin, N$^{\alpha A1}$-butyryl-des(B30)-human insulin, N$^{\epsilon B29}$-butyryl-N$^{\alpha B1}$-butyryl-des(B30)-human insulin, N$^{\epsilon B29}$-butyryl-N$^{\alpha A1}$-butyryl-des(B30)-human insulin, N$^{\alpha A1}$-butyryl-N$^{\alpha B1}$-butyryl-des(B30)-human insulin, N$^{\epsilon B29}$-butyryl-N$^{\alpha A1}$-butyryl-N$^{\alpha B1}$-butyryl-des(B30)-human insulin.

The O-glycosylated CTP peptide-based insulin or insulin analogues further include modified forms of non-human insulins (e.g., porcine insulin, bovine insulin, rabbit insulin, sheep insulin, etc.) that comprise any one of the aforementioned mutations and/or chemical modifications. These and other modified insulin molecules are described in detail in U.S. Pat. Nos. 6,906,028; 6,551,992; 6,465,426; 6,444,641; 6,335,316; 6,268,335; 6,051,551; 6,034,054; 5,952,297; 5,922,675; 5,747,642; 5,693,609; 5,650,486; 5,547,929;

5,504,188; 5,474,978; 5,461,031; and 4,421,685; and in U.S. Pat. Nos. 7,387,996; 6,869,930; 6,174,856; 6,011,007; 5,866,538; and 5,750,497, the entire disclosures of which are hereby incorporated by reference.

In various embodiments, the O-glycosylated CTP peptide-based insulin or insulin analogue disclosed herein include the three wild-type disulfide bridges (i.e., one between position 7 of the A-chain and position 7 of the B-chain, a second between position 20 of the A-chain and position 19 of the B-chain, and a third between positions 6 and 11 of the A-chain).

In some embodiments, the O-glycosylated CTP peptide-based insulin or insulin analogue is modified and/or mutated to reduce its affinity for the insulin receptor. Without wishing to be bound to a particular theory, it is believed that attenuating the receptor affinity of an insulin molecule through modification (e.g., acylation) or mutation may decrease the rate at which the insulin molecule is eliminated from blood. In some embodiments, a decreased insulin receptor affinity in vitro translates into a superior in vivo activity for the O-glycosylated CTP peptide-based insulin or insulin analogue.

II. Integration of Insulin Protein Engineering and Glycodesign a. Pharmacokinetic (PK)/Pharmacodynamic (PD) Improvements The quality of life for type I diabetics was significantly improved with the introduction of insulin glargine, a once-daily insulin analogue that provides a basal level of insulin in the patient. Due to repetitive blood monitoring and subcutaneous injections that type I diabetics must endure, reduced frequency of injections would be a welcomed advancement in diabetes treatment. Improving the pharmacokinetic profile to meet a once daily injection is greatly sought after for any new insulin treatment. In fact, once-monthly insulin has recently been reported in an animal model (Gupta et al., Proc. Natl. Acad. Sci. USA 107: 13246 (2010); U.S. Pub. Application No. 20090090258818). While many strategies are being pursued to improve the PK profile of insulin, the O-glycosylated CTP peptide-based insulin or insulin analogue disclosed herein may provide benefits to the diabetic patient not achievable with other strategies.

b. Saccharide-Responsive or -Sensitive O-Glycosylated CTP Peptide-Based Insulin or Insulin Analogue The concept of modulating insulin bioavailability as a function of the physiological blood glucose level by chemical attachment of a sugar moiety to insulin was first introduced in 1979 by Michael Brownlee (Brownlee & Cerami, op. cit.). A major limitation of the concept was toxicity of concanavalin A to which the glycosylated insulin derivative interacted. Since this initial report, many reports have been published on potential improvements for glucose-regulated insulin but no reports to date have attached the sugar via in vivo O-linked glycosylation (Liu et al., Bioconjug. Chem. 8: 664 (1997)).

Since Brownlee's concept in 1979, a number of different strategies have evolved to sequester insulin in an insulin reservoir when blood glucose levels are low. These include the mannose-binding lectin concanavalin A, which was demonstrated to release a bound insulin-sugar complex with high blood glucose concentrations. More recently, U.S. Pat. No. 7,531,191 and International Application Nos. WO2010088261 and WO2010088286, which are incorporated by reference herein, all disclose systems in which microparticles comprising an insulin-saccharide conjugate bound to an exogenous multivalent saccharide-binding molecule (e.g., lectin or modified lectin) can be administered to a patient wherein the amount and duration of insulin-saccharide conjugate released from the microparticle is a function of the serum concentration of a saccharide such as glucose. Other strategies include utilizing modified lectins, endogenous receptors, endogenous lectins, and/or sugar-binding proteins. Such examples include modified ConA molecules, mannose-binding lectin, mannose receptor, mannose-binding protein, and DC-SIGN. For example, U.S. Published Application No. 20110301083 discloses that when certain insulin-conjugates were modified to include high affinity saccharide ligands they could be made to exhibit PK/PD profiles that responded to saccharide concentration changes even in the absence of an exogenous multivalent saccharide-binding molecule such as Con A.

Saccharide-responsive or -sensitive insulin is one therapeutic mechanism that may mimic the physiologic pulsation of endogenous insulin release. A major stimulus that triggers insulin release from pancreatic beta cells is high blood glucose. In a similar mechanism, therapeutic glycosylated insulin that is released from protected pools into circulation by high glucose concentrations may function in an oscillatory fashion. O-glycosylated CTP peptide-based insulin or insulin analogues may function in a manner in vivo that supports a saccharide-responsive or -sensitive insulin therapy. As shown in FIGS. 15-17, the PD of an O-glycosylated CTP peptide-based insulin or insulin analogue administered to a non-diabetic mouse was sensitive to the serum level of α-methylmannose, an inhibitor of the binding of various lectins to various saccharides such as mannose, to the mouse (as shown in U.S. Pub. Application No. 20110301083).

Therefore, in particular embodiments, the heterodimer or single-chain O-glycosylated CTP peptide-based insulin or insulin analogue display at least one PK and/or PD property that is responsive or sensitive to the serum concentration of a saccharide, e.g., glucose, fucose, GlcNAc, galactose, or α-methylmannose. In a further embodiment, provided is a saccharide-responsive or -sensitive O-glycosylated CTP peptide-based insulin or insulin analogue comprising a native A-chain peptide and B-chain peptide, or analogue thereof comprising 1, 2, 3, 4, 5, or more amino acid substitutions and/or deletions. In general, the PK and/or PD of the saccharide-responsive or -sensitive O-glycosylated CTP peptide-based insulin or insulin analogue herein administered to an individual is affected by the serum concentration of a saccharide, e.g., glucose, fucose, GlcNAc, galactose, or α-methylmannose in the individual. The serum concentration of the saccharide may be effected by administering the saccharide to the individual or it may be affected by the physiological state of the individual.

c. Long-Acting Saccharide-Responsive or -Sensitive O-Glycosylated CTP Peptide-Based Insulin or Insulin Analogue The function of saccharide-responsive or sensitive insulin, as described above, may be further optimized to reduce the number of doses per day. For example, further provided is a saccharide-responsive O-glycosylated CTP peptide-based insulin or insulin analogue that further includes the physiochemical properties of insulin glargine, which acts as a basal insulin therapy by virtue of its insolubility at neutral pH. The consequence of neutral pH insolubility is a slow resolubilization process in the subcutaneous depot that enables once-a-day injection. Insulin glargine was modified to include two arginine residues at the end of the B-chain and substitute asparagine for glycine at the end of the A-chain. These three changes increase the pI of the protein such that it is soluble in low pH formulation buffer but insoluble at the physiological pH. These changes may be incorporated into a saccharide-responsive or sensitive saccharide-responsive O-glycosylated CTP peptide-based insulin or insulin analogue as disclosed herein. An O-glycosylated CTP peptide-based insulin or insulin analogue with a pI similar to insulin glargine may provide a long-acting saccharide-responsive or sensitive insulin therapy.

h. O-Glycosylated CTP Peptide-Based Insulin or Insulin Analogue PD and PK

In the various embodiments disclosed herein, the pharmacokinetic and/or pharmacodynamic behavior of an O-glycosylated CTP peptide-based insulin or insulin analogue as disclosed herein may be modified by variations in the serum concentration of a saccharide, including but not limited to glucose and alpha-methyl-mannose.

For example, from a pharmacokinetic (PK) perspective, the serum concentration curve may shift upward when the serum concentration of the saccharide (e.g., glucose) increases or when the serum concentration of the saccharide crosses a threshold (e.g., is higher than normal glucose levels).

In particular embodiments, the serum concentration curve of an O-glycosylated CTP peptide-based insulin or insulin analogue as disclosed herein is substantially different when administered to the mammal under fasted and hyperglycemic conditions. As used herein, the term "substantially different" means that the two curves are statistically different as determined by a student t-test ($p<0.05$). As used herein, the term "fasted conditions" means that the serum concentration curve was obtained by combining data from five or more fasted non-diabetic individuals. In particular embodiments, a fasted non-diabetic individual is a randomly selected 18-30 year old human who presents with no diabetic symptoms at the time blood is drawn and who has not eaten within 12 hours of the time blood is drawn. As used herein, the term "hyperglycemic conditions" means that the serum concentration curve was obtained by combining data from five or more fasted non-diabetic individuals in which hyperglycemic conditions (glucose Cmax at least 100 mg/dL above the mean glucose concentration observed under fasted conditions) is induced by concurrent administration of an in vivo or in vitro glycosylated insulin analogue as disclosed herein and glucose.

Concurrent administration of an O-glycosylated CTP peptide-based insulin or insulin analogue as disclosed herein and glucose simply requires that the glucose Cmax occur during the period when the O-glycosylated insulin analogue is present at a detectable level in the serum. For example, a glucose injection (or ingestion) could be timed to occur shortly before, at the same time or shortly after the glycosylated insulin analogue is administered. In particular embodiments, the O-glycosylated CTP peptide-based insulin or insulin analogue as disclosed herein and glucose are administered by different routes or at different locations. For example, in particular embodiments, the O-glycosylated CTP peptide-based insulin or insulin analogue as disclosed herein is administered subcutaneously while glucose is administered orally or intravenously.

In particular embodiments, the serum Cmax of the O-glycosylated CTP peptide-based insulin or insulin analogue as disclosed herein is higher under hyperglycemic conditions as compared to fasted conditions. Additionally or alternatively, in particular embodiments, the serum area under the curve (AUC) of the glycosylated insulin analogue is higher under hyperglycemic conditions as compared to fasted conditions. In various embodiments, the serum elimination rate of the glycosylated insulin analogue is slower under hyperglycemic conditions as compared to fasted conditions. In particular embodiments, the serum concentration curve of the glycosylated insulin analogue can be fit to a two-compartment bi-exponential model with one short and one long half-life. The long half-life may be particularly sensitive to glucose concentration. Thus, in particular embodiments, the long half-life is longer under hyperglycemic conditions as compared to fasted conditions. In particular embodiments, the fasted conditions involve a glucose Cmax of less than 100 mg/dL (e.g., 80 mg/dL, 70 mg/dL, 60 mg/dL, 50 mg/dL, etc.). In particular embodiments, the hyperglycemic conditions involve a glucose Cmax in excess of 200 mg/dL (e.g., 300 mg/dL, 400 mg/dL, 500 mg/dL, 600 mg/dL, etc.). It will be appreciated that other PK parameters such as mean serum residence time (MRT), mean serum absorption time (MAT), etc. could be used instead of or in conjunction with any of the aforementioned parameters.

The normal range of glucose concentrations in humans, dogs, cats, and rats is 60 to 200 mg/dL. One skilled in the art will be able to extrapolate the following values for species with different normal ranges (e.g., the normal range of glucose concentrations in miniature pigs is 40 to 150 mg/dl). In general, glucose concentrations below 50 mg/dL are considered hypoglycemic and glucose concentrations above 200 mg/dL are considered hyperglycemic. In particular embodiments, the PK properties of the O-glycosylated CTP peptide-based insulin or insulin analogue as disclosed herein may be tested using a glucose clamp method (see Examples) and the serum concentration curve of the O-glycosylated CTP peptide-based insulin or insulin analogue as disclosed herein may be substantially different when administered at glucose concentrations of 50 and 200 mg/dL, 50 and 300 mg/dL, 50 and 400 mg/dL, 50 and 500 mg/dL, 50 and 600 mg/dL, 100 and 200 mg/dL, 100 and 300 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc. Additionally or alternatively, the serum Tmax, serum Cmax, mean serum residence time (MRT), mean serum absorption time (MAT) and/or serum half-life may be substantially different at the two glucose concentrations. As discussed below, in particular embodiments, 100 mg/dL and 300 mg/dL may be used as comparative glucose concentrations. It is to be understood however that the present disclosure encompasses each of these embodiments with an alternative pair of comparative glucose concentrations including, without limitation, any one of the following pairs: 50 and 200 mg/dL, 50 and 300 mg/dL, 50 and 400 mg/dL, 50 and 500 mg/dL, 50 and 600 mg/dL, 100 and 200 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc. Thus, in particular embodiments, the Cmax of the N-glycosylated insulin analogue is higher when administered to the mammal at the higher of the two glucose concentrations (e.g., 300 vs. 100 mg/dL glucose).

In particular embodiments, the Cmax of the O-glycosylated CTP peptide-based insulin or insulin analogue as disclosed herein is at least 50% (e.g., at least 100%, at least 200% or at least 400%) higher when administered to the mammal at the higher of the two glucose concentrations (e.g., 300 vs. 100 mg/dL glucose). In particular embodiments, the AUC of the O-glycosylated CTP peptide-based insulin or insulin analogue as disclosed herein is higher when administered to the mammal at the higher of the two glucose concentrations (e.g., 300 vs. 100 mg/dL glucose). In particular embodiments, the AUC of the O-glycosylated CTP peptide-based insulin or insulin analogue as disclosed herein is at least 50% (e.g., at least e.g., at least 100%, at least 200% or at least 400%) higher when administered to the mammal at the higher of the two glucose concentrations (e.g., 300 vs. 100 mg/dL glucose).

In particular embodiments, the serum elimination rate of the O-glycosylated CTP peptide-based insulin or insulin analogue as disclosed herein is slower when administered to the mammal at the higher of the two glucose concentrations (e.g., 300 vs. 100 mg/dL glucose). In certain embodiments, the serum elimination rate of the N-glycosylated insulin analogue is at least 25% (e.g., at least 50%, at least 100%, at least 200%, or at least 400%) faster when administered to the mammal at the lower of the two glucose concentrations (e.g., 100 vs. 300 mg/dL glucose).

In particular embodiments, the serum concentration curve of an O-glycosylated CTP peptide-based insulin or insulin analogue as disclosed herein may be fit using a two-compartment bi-exponential model with one short and one long half-life. The long half-life may be particularly sensitive to glucose concentration. Thus, in particular embodiments, the long half-life is longer when administered to the mammal at the higher of the two glucose concentrations (e.g., 300 vs. 100 mg/dL glucose).

In particular embodiments, the long half-life is at least 50% (e.g., at least 100%, at least 200% or at least 400%) longer when administered to the mammal at the higher of the two glucose concentrations (e.g., 300 vs. 100 mg/dL glucose).

In particular embodiments, provided is a method in which the serum concentration curve of an O-glycosylated CTP peptide-based insulin or insulin analogue as disclosed herein is obtained at two different glucose concentrations (e.g., 300 vs. 100 mg/dL glucose); the two curves are fit using a two-compartment bi-exponential model with one short and one long half-life; and the long half-lives obtained under the two glucose concentrations are compared. In particular embodiments, this method may be used as an assay for testing or comparing the glucose sensitivity of one or more O-glycosylated CTP peptide-based insulin or insulin analogue as disclosed herein.

In particular embodiments, provided is a method in which the serum concentration curves of an O-glycosylated CTP peptide-based insulin or insulin analogue as disclosed herein and a non-glycosylated version of the insulin are obtained under the same conditions (for example, fasted conditions); the two curves are fit using a two-compartment bi-exponential model with one short and one long half-life; and the long half-lives obtained for the an O-glycosylated CTP peptide-based insulin or insulin analogue as disclosed herein and non-glycosylated version are compared. In particular embodiments, this method may be used as an assay for identifying an O-glycosylated CTP peptide-based insulin or insulin analogue as disclosed herein that are cleared more rapidly than the non-glycosylated version or native insulin.

In particular embodiments, the serum concentration curve of an O-glycosylated CTP peptide-based insulin or insulin analogue as disclosed herein is substantially the same as the serum concentration curve of a non-glycosylated version of the analogue when administered to the mammal under hyperglycemic conditions. As used herein, the term "substantially the same" means that there is no statistical difference between the two curves as determined by a student t-test (p>0.05). In particular embodiments, the serum concentration curve of the O-glycosylated CTP peptide-based insulin or insulin analogue as disclosed herein is substantially different from the serum concentration curve of a non-glycosylated version of the analogue when administered under fasted conditions. In particular embodiments, the serum concentration curve of the an O-glycosylated CTP peptide-based insulin or insulin analogue as disclosed herein is substantially the same as the serum concentration curve of a non-glycosylated version of the analogue when administered under hyperglycemic conditions and substantially different when administered under fasted conditions.

In particular embodiments, the hyperglycemic conditions involve a glucose Cmax in excess of 200 mg/dL (e.g., 300 mg/dL, 400 mg/dL, 500 mg/dL, 600 mg/dL, etc.). In particular embodiments, the fasted conditions involve a glucose Cmax of less than 100 mg/dL (e.g., 80 mg/dL, 70 mg/dL, 60 mg/dL, 50 mg/dL, etc.). It will be appreciated that any of the aforementioned PK parameters such as serum Tmax, serum Cmax, AUC, mean serum residence time (MRT), mean serum absorption time (MAT) and/or serum half-life could be compared.

From a pharmacodynamic (PD) perspective, the bioactivity of the an O-glycosylated CTP peptide-based insulin or insulin analogue as disclosed herein may increase when the glucose concentration increases or when the glucose concentration crosses a threshold, for example, is higher than normal glucose levels. In particular embodiments, the bioactivity of an O-glycosylated CTP peptide-based insulin or insulin analogue as disclosed herein is lower when administered under fasted conditions as compared to hyperglycemic conditions.

In particular embodiments, the fasted conditions involve a glucose Cmax of less than 100 mg/dL (e.g., 80 mg/dL, 70 mg/dL, 60 mg/dL, 50 mg/dL, etc.). In particular embodiments, the hyperglycemic conditions involve a glucose Cmax in excess of 200 mg/dL (e.g., 300 mg/dL, 400 mg/dL, 500 mg/dL, 600 mg/dL, etc.).

In particular embodiments, the PD properties of an O-glycosylated CTP peptide-based insulin or insulin analogue as disclosed herein may be tested by measuring the glucose infusion rate (GIR) required to maintain a steady glucose concentration. According to such embodiments, the bioactivity of the O-glycosylated CTP peptide-based insulin or insulin analogue as disclosed herein may be substantially different when administered at glucose concentrations of 50 and 200 mg/dL, 50 and 300 mg/dL, 50 and 400 mg/dL, 50 and 500 mg/dL, 50 and 600 mg/dL, 100 and 200 mg/dL, 100 and 300 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc. Thus, in particular embodiments, the bioactivity of an O-glycosylated CTP peptide-based insulin or insulin analogue as disclosed herein is higher when administered to the mammal at the higher of the two glucose concentrations (e.g., 300 vs. 100 mg/dL glucose). In certain embodiments, the bioactivity of the O-glycosylated CTP peptide-based insulin or insulin analogue is at least 25% (e.g., at least 50% or at least 100%) higher when administered to the mammal at the higher of the two glucose concentrations (e.g., 300 vs. 100 mg/dL glucose).

The PD behavior for the O-glycosylated CTP peptide-based insulin or insulin analogue as disclosed herein can be observed by comparing the time to reach minimum blood glucose concentration (Tnadir), the duration over which the blood glucose level remains below a certain percentage of the initial value (e.g., 70% of initial value or 10 T70% BGL), etc. In general, it will be appreciated that any of the PK and PD characteristics discussed herein can be determined according to any of a variety of published pharmacokinetic and pharmacodynamic methods (e.g., see Baudys et al., Bioconjugate Chem. 9: 176-183 (1998) for methods suitable for subcutaneous delivery). It is also to be understood that the PK and/or PD properties may be measured in any mammal (e.g., a human, a rat, a cat, a minipig, a dog, etc.).

In particular embodiments, PK and/or PD properties are measured in a human. In particular embodiments, PK and/or PD properties are measured in a rat. In particular embodiments, PK and/or PD properties are measured in a minipig. In particular embodiments, PK and/or PD properties are measured in a dog. It will also be appreciated that while the foregoing was described in the context of saccharide-responsive or -sensitive O-glycosylated CTP peptide-based insulin or insulin analogue as disclosed herein, the same properties and assays apply to an O-glycosylated CTP peptide-based insulin or insulin analogue as disclosed herein that are responsive to serum concentrations of other saccharides including exogenous saccharides, e.g., mannose, L-fucose, N-acetyl glucosamine, alpha-methyl mannose, etc. In some aspects, instead of comparing PK and/or PD properties under fasted and hyperglycemic conditions, the PK and/or PD properties may be compared under fasted conditions with and without administration of the exogenous saccharide. It is to be understood that O-glycosylated CTP peptide-based insulin or insulin analogues as disclosed herein may be designed that respond to different Cmax values of a given exogenous saccharide.

III. Host Cells for Making O-Glycosylated CTP Peptide-Based Insulin or Insulin Analogues In general, bacterial cells such as *E. coli* and yeast cells such as *Saccharomyces cerevisiae* or *Pichia pastoris* have been used for the commercial production of insulin and insulin analogues. For example, Thin et al., Proc. Natl. Acad. Sci. USA 83: 6766-6770 (1986), U.S. Pat. Nos. 4,916,212; 5,618,913; and 7,105,314 disclose producing insulin in *Saccharomyces cerevisiae* and WO2009104199 discloses producing insulin in *Pichia pastoris*. Production of insulin in *E. coli* has been disclosed in numerous publications including Chan et al., Proc. Natl. Acad. Sci. USA 78: 5401-5404 (1981) and U.S. Pat. No. 5,227,293. The advantage of producing insulin in a yeast host is that the insulin molecule is secreted from the host cell in a properly folded configuration with the correct disulfide linkages, which can then be processed enzymatically in vitro to produce an insulin heterodimers. In contrast, insulin produced in *E. coli* is not processed in vivo. Instead, it is sequestered in inclusion bodies in an improperly folded configuration. The inclusion bodies are harvested from the cells and processed in vitro in a series of reactions to produce an insulin heterodimers in the proper configuration. While insulin is not normally considered a glycoprotein since it lacks N-linked and O-linked glycosylation sites, when insulin is produced in yeast but not *E. coli*, a small population of the insulin synthesized appears to be O-glycosylated. These O-glycosylated molecules are considered to be a contaminant in which methods for its removal have been developed (See for example, U.S. Pat. No. 6,180,757 and WO2009104199).

In particular aspects of the invention, the host cell is a yeast cell or filamentous fungus host cell. Yeast and filamentous fungi host cells include, but are not limited to *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Yarrowia lipolytica, Hansenula polymorpha*, any *Kluyveromyces* sp., *Candida albicans*, any *Aspergillus* sp., *Aspergillus nidulans, Aspergillus niger, Aspergillus oryzae, Fusarium* sp., *Fusarium gramineum, Fusarium venenatum, Physcomitrella patens, Chrysosporium lucknowense, Trichoderma reesei*, and *Neurospora crassa*. In general, the host cell selected or chosen to produce the O-glycosylated CTP peptide-based insulin or insulin analogues herein does not display with respect to an O-glycan on a glycoprotein detectable β1,2-linked mannose and/or phosphomannose activity. In host cells that typically display detectable β1,2-linked mannose and/or phosphomannose activity, the host cell is genetically engineered to not display with respect to an O-glycan on a glycoprotein detectable β1,2-linked mannose and/or phosphomannose activity and thus produce glycoproteins that lack detectable β1,2-linked mannose and/or phosphomannose residues.

In particular embodiments, the host cell is a yeast host cell, for example, *Saccharomyces cerevisiae, Yarrowia lipolytica*, methylotrophic yeast such as *Pichia pastoris* or *Ogataea minuta*, mutants thereof, and genetically engineered variants thereof that produce glycoproteins that lack detectable β1,2-linked mannose or phosphomannose residues. In this manner, glycoprotein compositions can be produced in which a specific desired glycoform is predominant in the composition.

Use of lower eukaryotic host cells such as yeast are further advantageous in that these cells may be able to produce relatively homogenous compositions of glycoprotein, such that the predominant glycoform of the glycoprotein may be present as greater than 30 mole % of the glycoforms in the composition. In particular aspects, the predominant glycoform may be present in greater than 40 mole %, 50 mole %, 60 mole %, 70 mole % and, most preferably, greater than 80 mole % of the glycoprotein present in the composition. Such can be achieved by eliminating selected endogenous glycosylation enzymes.

In particular aspects of the present invention, host cells for producing O-glycosylated CTP peptide-based insulin or insulin analogues include *Pichia pastoris* strains that have been genetically engineered to lack detectable phosphomannosyltransferase activity by deleting or disrupting expression of one or both of the phosphomannosyltransferase genes PNO1 and MNN4B (See for example, U.S. Pat. Nos. 7,198,921 and 7,259,007; the disclosures of which are all incorporated herein by reference), which in further aspects can also include deleting or disrupting expression of the MNN4A gene. Disruption includes disrupting the open reading frame encoding the particular enzymes or disrupting expression of the open reading frame or abrogating translation of RNAs encoding one or more of the β-mannosyltransferases and/or phosphomannosyltransferases using interfering RNA, antisense RNA, or the like. The host cells can further include any one of the aforementioned host cells modified to produce particular N-glycan structures.

To reduce or eliminate the likelihood of O-glycans with 3-linked mannose residues, which are resistant to α-mannosidases, the recombinant glycoengineered *Pichia pastoris* host cells for producing O-glycosylated CTP peptide-based insulin or insulin analogues are genetically engineered to lack detectable α-mannosidase-resistant O-glycans, which may be achieved by deleting or disrupting one or more of the β-mannosyltransferase genes (e.g., BMT1, BMT2, BMT3, and BMT4)(See, U.S. Pat. No. 7,465,577, U.S. Pat. No. 7,713,719, and Published International Application No. WO2011046855, each of which is incorporated herein by reference). The deletion or disruption of BMT2 and one or more of BMT1, BMT3, and BMT4 also reduces or eliminates detectable cross-reactivity of compositions comprising the glycoprotein to antibodies against host cell protein. In particular aspects, the host cell lacks detectable expression of BMT2, BMT1, BMT3, and BMT4.

In a further embodiment, the host cell does not display initiating α1,6-mannosyl transferase activity with respect to an N-glycan on a glycoprotein. For example, in yeast such an α1,6-mannosyl transferase activity is encoded by the OCH1 gene and deletion or disruption of expression of the OCH1 gene (och1Δ) inhibits the production of high mannose or hypermannosylated N-glycans in yeast such as *Pichia pastoris* or *Saccharomyces cerevisiae*. (See for example, Gerngross et al. in U.S. Pat. No. 7,029,872; Contreras et al. in U.S. Pat. No. 6,803,225; and Chiba et al. in EP1211310B1 the disclosures of which are incorporated herein by reference). Thus, in one embodiment, the host cell for producing the O-glycosylated CTP peptide-based insulin or insulin analogues comprises a deletion or disruption of expression of the OCH1 gene (och1Δ) and includes a nucleic acid molecule encoding an insulin or insulin analogue having at least one CTP peptide.

Yield of glycoprotein can in some situations be improved by overexpressing nucleic acid molecules encoding mammalian or human chaperone proteins or replacing the genes encoding one or more endogenous chaperone proteins with nucleic acid molecules encoding one or more mammalian or human chaperone proteins. In addition, the expression of mammalian or human chaperone proteins in the host cell also appears to control O-glycosylation in the cell. Thus, further included are the host cells herein wherein the function of at least one endogenous gene encoding a chaperone protein has been reduced or eliminated, and a vector encoding at least one mammalian or human homolog of the chaperone protein is expressed in the host cell. Also included are host cells in which the endogenous host cell chaperones and the mammalian or human chaperone proteins are expressed. In further aspects, the lower eukaryotic host cell is a yeast or filamentous fungi host cell. Examples of the use of chaperones of host cells in which human chaperone proteins are introduced to improve the yield and reduce or control O-glycosylation of recombinant proteins has been disclosed in Published International Application No. WO 2009105357 and WO2010019487 (the disclosures of which are incorporated herein by reference).

In some embodiments, the host cell may further include a nucleic acid molecule encoding a heterologous single-subunit oligosaccharyltransferase, which is capable of functionally suppressing a lethal mutation of one or more essential subunits comprising the endogenous host cell hetero-oligomeric oligosaccharyltransferase (OTase) complex, is overexpressed in the recombinant host cell either before or simultaneously with the expression of the glycoprotein in the host cell. The *Leishmania major* STT3A protein, *Leishmania major* STT3B protein, and *Leishmania major* STT3D protein, are single-subunit oligosaccharyltransferases that have been shown to suppress the lethal phenotype of a deletion of the STT3 locus in *Saccharomyces cerevisiae* (Naseb et al., Molec. Biol. Cell 19: 3758-3768 (2008)). Naseb et al. (ibid.) further showed that the *Leishmania major* STT3D protein could suppress the lethal phenotype of a deletion of the WBP1, OST1, SWP1, or OST2 loci. Hese et al. (Glycobiology 19: 160-171 (2009)) teaches that the *Leishmania major* STT3A (STT3-1), STT3B (STT3-2), and STT3D (STT3-4) proteins can functionally complement deletions of the OST2, SWP1, and WBP1 loci. As shown in PCT/US2011/25878 (Published International Application No. WO2011106389, which is incorporated herein by reference), the *Leishmania major* STT3D (LmSTT3D) protein is a heterologous single-subunit oligosaccharyltransferases that is capable of suppressing a lethal phenotype of a Δstt3 mutation and at least one lethal phenotype of a Δwbp1, Δost1, Δswp1, and Δost2 mutation.

Thus, further provided is a yeast or filamentous fungus host cell, comprising a first nucleic acid molecule encoding a heterologous single-subunit oligosaccharyltransferase; and a second nucleic acid molecule encoding an insulin or insulin analogue comprising at least one CTP peptide; and wherein the endogenous host cell genes encoding the proteins comprising the oligosaccharyltransferase (OTase) complex are expressed. This includes expression of the endogenous STT3 gene, which in yeast is the STT3 gene.

In general, in the above methods and host cells, the single-subunit oligosaccharyltransferase is capable of functionally suppressing the lethal phenotype of a mutation of at least one essential protein of the OTase complex. In further aspects, the essential protein of the OTase complex is encoded by the STT3 locus, WBP1 locus, OST1 locus, SWP1 locus, or OST2 locus, or homologue thereof. In further aspects, the for example single-subunit oligosaccharyltransferase is the *Leishmania major* STT3D protein.

In some embodiments, the host cells are grown in the presence of a Pmtp inhibitor, which may include but is not limited to benzylidene thiazolidinediones. Examples of benzylidene thiazolidinediones that can be used are 5-[[3,4-bis (phenylmethoxy)phenyl]methylene]-4-oxo-2-thioxo-3-thiazolidineacetic Acid; 5-[[3-(1-Phenylethoxy)-4-(2-phenylethoxy)]phenyl]methylene]-4-oxo-2-thioxo-3-thiazolidineacetic Acid; and 5-[[3-(1-Phenyl-2-hydroxy) ethoxy)-4-(2-phenylethoxy)]phenyl]methylene]-4-oxo-2-thioxo-3-thiazolidineacetic Acid. Use of the Pmtp inhibitor may reduce unwanted or inappropriate O-glycosylation within the amino acid sequences of the A-chain or B-chain.

Therefore, the present invention provides lower eukaryote host cells that display with respect to an O-glycan on a glycoprotein little or no detectable β-mannosyltransferase activity and comprise a nucleic acid molecule encoding a CTP peptide-based insulin or insulin analogue. In another embodiment, the present invention also provides lower eukaryote host cells that that display with respect to an O-glycan on a glycoprotein little or no detectable phosphomannosyltransferase activity and comprise a nucleic acid molecule encoding a CTP peptide-based insulin or insulin analogue. In a further embodiment, the present invention provides lower eukaryote host cells that display with respect to an O-glycan on a glycoprotein little or no detectable β-mannosyltransferase activity and little or no detectable phosphomannosyltransferase activity and comprise a nucleic acid molecule encoding a CTP peptide-based insulin or insulin analogue. The embodiments the nucleic acid molecule may be integrated into the genome of the host cell or may be present in the host cell extra-chromosomally, e.g., plasmid vector, mini-chromosome, and the like.

The present invention further provides lower eukaryote host cells that comprise a deletion or disruption of one or more genes encoding a β-mannosyltransferase activity and includes a nucleic acid molecule encoding a CTP peptide-based insulin or insulin analogue. In another embodiment, the present invention also provides lower eukaryote host cells that comprise a deletion or disruption of one or more genes encoding a phosphomannosyltransferase activity and includes a nucleic acid molecule encoding a CTP peptide-based insulin or insulin analogue. In a further embodiment, the present invention provides lower eukaryote host cells that comprise a deletion or disruption of one or more genes encoding a β-mannosyltransferase activity; a deletion or disruption of one or more genes encoding a phosphomannosyltransferase activity; and includes a nucleic acid molecule encoding a CTP peptide-based insulin or insulin analogue. The embodiments the nucleic acid molecule may be integrated into the genome of the host cell or may be present in the host cell extra-chromosomally, e.g., plasmid vector, mini-chromosome, and the like.

The present invention further provides Pichia pastoris host cells comprising a deletion or disruption of expression of one or more of the genes encoding β-mannosyltransferase activity and a nucleic acid molecule encoding a CTP peptide-based insulin or insulin analogue. In a further aspect, expression of at least the BMT2 gene is deleted or disrupted. In a further aspect, expression of two or more of the BMT1, BMT2, BMT3, and BMT4 genes is abrogated. In a further aspect, expression of each of the BMT1, BMT2, BMT3, and BMT4 genes is abrogated.

The present invention further provides Pichia pastoris host cells comprising deletion or disruption of expression of one or more of the genes encoding phosphomannosyltransferase activity a nucleic acid molecule encoding a CTP peptide-based insulin or insulin analogue. In a further aspect, expression of the MMN4L1 genes is abrogated. In a further aspect, expression of the PNO1 and the MMN4L1 genes is deleted or disrupted. In a further aspect, expression of the MNN4 gene is abrogated. In a further aspect, expression of the PNO1, MNN4, and the MMN4L1 genes is abrogated.

The present invention further provides yeast host cells comprising a deletion or disruption of expression of the OCH1 gene encoding initiating α1,6-mannosyltransferase activity and a nucleic acid molecule encoding a CTP peptide-based insulin or insulin analogue.

The present invention further provides Pichia pastoris host cells comprising a deletion or disruption of expression of one or more of the genes encoding β-mannosyltransferase activity and deletion or disruption of expression of one or more genes encoding phosphomannosyltransferase activity and a nucleic acid molecule encoding a CTP peptide-based insulin or insulin analogue. In a further aspect, expression of at least the BMT2 gene and the PNO1 gene is deleted or disrupted. In a further aspect, expression of two or more of the BMT1, BMT2, BMT3, and BMT4 genes and the PNO1 gene is deleted or disrupted. In a further aspect, expression of each of the BMT1, BMT2, BMT3, and BMT4 genes and the PNO1 gene is deleted or disrupted. In a further aspect, expression of at least the BMT2 gene and the PNO1 and MNN4L1 genes is deleted or disrupted. In a further aspect, expression of two or more of the BMT1, BMT2, BMT3, and BMT4 genes and the PNO1 and MNN4L1 genes is deleted or disrupted. In a further aspect, expression of each of the BMT1, BMT2, BMT3, and BMT4 genes and the PNO1 and MNN4L1 genes is deleted or disrupted. In a further aspect, expression of at least the BMT2 gene and the PNO1, MNN4, and MNN4L1 genes is deleted or disrupted. In a further aspect, expression of two or more of the BMT1, BMT2, BMT3, and BMT4 genes and the PNO1 MNN4, and MNN4L1 genes is deleted or disrupted. In a further aspect, expression of each of the BMT1, BMT2, BMT3, and BMT4 genes and the PNO1 MNN4, and MNN4L1 genes is deleted or disrupted. In a further aspect of any one of the aforementioned aspects, the host further includes deletion or disruption of expression of the OCH1 gene encoding initiating α1,6-mannosyltransferase activity.

The present invention further provides methods for making O-glycosylated CTP peptide-based insulin or insulin analogues in yeast or filamentous fungi host cells. In general, the host cells that are used to produce the O-glycosylated CTP peptide-based insulin or insulin analogues disclosed herein display with respect to an O-glycan on a glycoprotein little or no detectable β-mannosyltransferase activity. In another aspect, the host cells that are used to produce the O-glycosylated CTP peptide-based insulin or insulin analogues display with respect to an O-glycan on a glycoprotein little or no detectable phosphomannosyltransferase activity. In a further aspect, the host cells that are used to produce the O-glycosylated CTP peptide-based insulin or insulin analogues display with respect to an O-glycan on a glycoprotein little or no detectable phosphomannosyltransferase activity and β-mannosyltransferase activity. In particular aspects, the host cells further display with respect to an O-glycan on a glycoprotein little or no detectable initiating α1,6-mannosyltransferase activity. In a further aspect, the host cells that are used to produce the CTP peptide-based insulin or insulin analogues display with respect to an O-glycan on a glycoprotein little or no detectable phosphomannosyltransferase activity, β-mannosyltransferase activity, and initiating α1,6-mannosyltransferase activity.

Therefore, the present invention provides a method for making O-glycosylated CTP peptide-based insulin or insulin analogues in yeast or filamentous fungi host cells, comprising providing a yeast or filamentous fungus host cell that does not display detectable β-mannosyltransferase activity; transforming the host cell with a nucleic acid molecule encoding a CTP peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium.

In another embodiment, the present invention provides a method for making O-glycosylated CTP peptide-based insulin or insulin analogues in yeast or filamentous fungi host cells, comprising providing a yeast or filamentous fungus host cell that does not display detectable phosphomannosyltransferase activity; transforming the host cell with a nucleic acid molecule encoding a CTP peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium.

In a further embodiment, the present invention provides a method for making O-glycosylated CTP peptide-based insulin or insulin analogues in yeast or filamentous fungi host cells, comprising providing a yeast or filamentous fungus host cell that does not display detectable β-mannosyltransferase activity and phosphomannosyltransferase activity; transforming the host cell with a nucleic acid molecule encoding a CTP peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium.

In particular aspects of the above method, the host cell is selected from the group consisting of Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia minuta (Ogataea minuta, Pichia lindneri), Pichia sp., Saccharomyces cerevisiae, Saccharomyces sp., Hansenula polymorpha, Kluyveromyces sp., Kluyveromyces lactis, Candida albicans, Aspergillus nidulans, *Aspergillus niger, Aspergillus oryzae, Trichoderma reesei, Chrysosporium lucknowense, Fusarium* sp., *Fusarium gramineum, Fusarium venenatum*, and *Neurospora crassa*.

The present invention further provides methods for making O-glycosylated CTP peptide-based insulin or insulin analogues in *Pichia* sp. host cells comprising providing *Pichia* sp. host cells wherein expression of one or more of the genes encoding β-mannosyltransferase activity is deleted or disrupted; transforming the host cell with a nucleic acid molecule encoding a CTP peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium. In a further aspect, expression of at least the BMT2 gene is deleted or disrupted. In a further aspect, expression of two or more of the BMT1, BMT2, BMT3, and BMT4 genes is abrogated. In a further aspect, expression of each of the BMT1, BMT2, BMT3, and BMT4 genes is deleted or disrupted.

The present invention further provides methods for making O-glycosylated CTP peptide-based insulin or insulin analogues in *Pichia* sp. host cells comprising providing *Pichia* sp. host cell wherein expression of one or more of the genes encoding phosphomannosyltransferase activity is deleted or disrupted. In a further aspect, expression of at least the PNO1 gene is deleted or disrupted; transforming the host cell with a nucleic acid molecule encoding a CTP peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium. In a further aspect, expression of the MMN4L1 genes is deleted or disrupted. In a further aspect, expression of the PNO1 and the MMN4L1 genes is abrogated. In a further aspect, expression of the MNN4 gene is deleted or disrupted. In a further aspect, expression of the PNO1, MNN4, and the MMN4L1 genes is deleted or disrupted.

The present invention further provides methods for making O-glycosylated CTP peptide-based insulin or insulin analogues in yeast host cells wherein expression of the OCH1 gene encoding initiating α1,6-mannosyltransferase activity is deleted or disrupted comprising transforming the host cell with a nucleic acid molecule encoding a CTP host peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium.

The present invention further provides methods for making O-glycosylated CTP peptide-based insulin or insulin analogues in *Pichia* sp. host cells comprising providing *Pichia* sp. host cells wherein expression of one or more of the genes encoding β-mannosyltransferase activity and expression of one or more genes encoding phosphomannosyltransferase activity is abrogated; transforming the host cell with a nucleic acid molecule encoding a CTP peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium. In a further aspect, expression of at least the BMT2 gene and the PNO1 gene is abrogated. In a further aspect, expression of two or more of the BMT1, BMT2, BMT3, and BMT4 genes and the PNO1 gene is abrogated. In a further aspect, expression of each of the BMT1, BMT2, BMT3, and BMT4 genes and the PNO1 gene is abrogated. In a further aspect, expression of at least the BMT2 gene and the PNO1 and MNN4L1 genes is abrogated. In a further aspect, expression of two or more of the BMT1, BMT2, BMT3, and BMT4 genes and the PNO1 and MNN4L1 genes is abrogated. In a further aspect, expression of each of the BMT1, BMT2, BMT3, and BMT4 genes and the PNO1 and MNN4L1 genes is abrogated. In a further aspect, expression of at least the BMT2 gene and the PNO1, MNN4, and MNN4L1 genes is abrogated. In a further aspect, expression of two or more of the BMT1, BMT2, BMT3, and BMT4 genes and the PNO1 MNN4, and MNN4L1 genes is abrogated. In a further aspect, expression of each of the BMT1, BMT2, BMT3, and BMT4 genes and the PNO1 MNN4, and MNN4L1 genes is abrogated. In a further aspect of any one of the aforementioned aspects, the host further includes abrogation of expression of the OCH1 gene encoding initiating α1,6-mannosyltransferase activity.

The present invention further provides methods for making O-glycosylated CTP peptide-based insulin or insulin analogues in *Pichia pastoris* host cells comprising providing *Pichia pastoris* host cells wherein expression of one or more of the genes encoding β-mannosyltransferase activity is deleted or disrupted; transforming the host cell with a nucleic acid molecule encoding a CTP peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium. In a further aspect, expression of at least the BMT2 gene is deleted or disrupted. In a further aspect, expression of two or more of the BMT1, BMT2, BMT3, and BMT4 genes is abrogated. In a further aspect, expression of each of the BMT1, BMT2, BMT3, and BMT4 genes is deleted or disrupted.

The present invention further provides methods for making O-glycosylated CTP peptide-based insulin or insulin analogues in *Pichia pastoris* host cells comprising providing *Pichia pastoris* host cell wherein expression of one or more of the genes encoding phosphomannosyltransferase activity is deleted or disrupted. In a further aspect, expression of at least the PNO1 gene is deleted or disrupted; transforming the host cell with a nucleic acid molecule encoding a CTP peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium. In a further aspect, expression of the MMN4L1 genes is deleted or disrupted. In a further aspect, expression of the PNO1 and the MMN4L1 genes is abrogated. In a further aspect, expression of the MNN4 gene is deleted or disrupted. In a further aspect, expression of the PNO1, MNN4, and the MMN4L1 genes is deleted or disrupted.

The present invention further provides methods for making O-glycosylated CTP peptide-based insulin or insulin analogues in *Pichia pastoris* host cells comprising providing *Pichia pastoris* host cells wherein expression of one or more of the genes encoding (3-mannosyltransferase activity and expression of one or more genes encoding phosphomannosyltransferase activity are abrogated; transforming the host cell with a nucleic acid molecule encoding a CTP peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium. In a further aspect, expression of at least the BMT2 gene and the PNO1 gene are abrogated. In a further aspect, expression of two or more of the BMT1, BMT2, BMT3, and BMT4 genes and the PNO1 gene is abrogated. In a further aspect, expression of each of the BMT1, BMT2, BMT3, and BMT4 genes and the PNO1 gene is abrogated. In a further aspect, expression of at least the BMT2 gene and the PNO1 and MNN4L1 genes is abrogated. In a further aspect, expression of two or more of the BMT1, BMT2, BMT3, and BMT4 genes and the PNO1 and MNN4L1 genes is abrogated. In a further aspect, expression of each of the BMT1, BMT2, BMT3, and BMT4 genes and the PNO1 and MNN4L1 genes is abrogated. In a further aspect, expression of at least the BMT2 gene and the PNO1, MNN4, and MNN4L1 genes is abrogated. In a further aspect, expression of two or more of the BMT1, BMT2, BMT3, and BMT4 genes and the PNO1 MNN4, and MNN4L1 genes is abrogated. In a further aspect, expression of each of the BMT1, BMT2, BMT3, and BMT4 genes and the PNO1 MNN4, and MNN4L1 genes is abrogated. In a further aspect of any one of the aforementioned aspects, the host further includes abrogation of expression of the OCH1 gene encoding initiating α1,6-mannosyltransferase activity.

In any of the aforementioned aspects, deletion or disruption of expression of any of the genes recited supra may be achieved be deleting the gene or partial variant thereof that includes at least one or two O-glycosylation sites of the CTP peptide or disrupting the gene by inserting a heterologous nucleic acid molecule into the open reading frame encoding the β-mannosyltransferase activity. In either case, the gene deleted or disrupted is rendered incapable of producing a protein product having β-mannosyltransferase, phosphomannosyltransferase, or α1,6-mannosylatransferase activity, as the case may be. In other aspects, the activity of one or more of the genes recited supra is disrupted using inhibitors, which includes but is not limited to chemical compounds, antisense DNA to one or more mRNA encoding the gene or genes, or siRNA to one or more mRNA encoding the gene or genes.

In a further aspect of the above host cells or methods using the host cells, the host cell is genetically engineered to produce O-glycans that comprise predominantly a single mannose residue, e.g., mannose O-glycan. Thus, the host cells may further include a nucleic acid molecule encoding an α1,2-mannosidase activity. In a further aspect, the nucleic acid molecule encodes a fusion protein encoding a chimeric α1,2-mannosidase comprising the catalytic domain of an α1,2-mannosidase operably linked or fused to a heterologous cellular targeting peptide that targets the chimeric α1,2-mannosidase to the secretory pathway. In particular aspects, the cellular targeting peptide fused to the α1,2-mannosidase catalytic domain is the *Saccharomyces cerevisiae* alpha mating factor pre signal peptide (SEQ ID NO:86) encoded by SEQ ID NO:85 or the pre-propeptide (SEQ ID NO:7) encoded by SEQ ID NO:41. In particular aspects, a fungal α1,2-mannosidase catalytic domain is fused to the cellular targeting peptide that targets the secretory pathway and directs the fusion protein for secretion from the host cell. In general, the α1,2-mannosidase activity is capable of trimming O-glycans on a glycoprotein as it traverses the secretory pathway and may further trim O-glycans on the glycoprotein extracellularly. In particular aspects, the α-1, 2-mannosidase is selected from a *Coccidioides* sp., *Trichoderma* sp., *Saccharomyces* sp., or *Aspergillus* sp. In particular aspects, the α1,2-mannosidase is selected from *Coccidioides immitis, Coccidioides posadasii, Trichoderma reesei, Saccharomyces cerevisiea,* or *Aspergillus niger*. In a further aspect, the α1,2-mannosidase catalytic domain is from *Trichoderma reesei* and may encoded by the nucleotide sequence shown in SEQ ID NO:87.

In particular aspects of the present invention, further provided are methods for making O-glycosylated CTP peptide-based insulin or insulin analogues in *Pichia pastoris* host cells wherein expression of the host cell OCH1 gene encoding initiating α1,6-mannosyltransferase activity is deleted or disrupted comprising transforming the host cell with a nucleic acid molecule encoding a CTP peptide-based insulin or insulin analogue; cultivating the transformed host cells in a medium and under conditions to express the CTP peptide-based insulin or insulin analogue in the host cell; and recovering the O-glycosylated CTP peptide-based insulin or insulin analogue from the medium.

Promoters are DNA sequence elements for controlling gene expression. In particular, promoters specify transcription initiation sites and can include a TATA box and upstream promoter elements. The promoters selected are those which would be expected to be operable in the particular host system selected. For example, yeast promoters are used when a yeast such as *Saccharomyces cerevisiae, Kluyveromyces lactis, Ogataea minuta,* or *Pichia pastoris* is the host cell whereas fungal promoters would be used in host cells such as *Aspergillus niger, Neurospora crassa,* or *Tricoderma reesei*. Examples of yeast promoters include but are not limited to the GAPDH, AOX1, SEC4, HH1, PMA1, OCH1, GAL1, PGK, GAP, TPI, CYC1, ADH2, PHO5, CUP1, MFα1, FLD1, PMA1, PDI, TEF, RPL10, and GUT1 promoters. Romanos et al., Yeast 8: 423-488 (1992) provide a review of yeast promoters and expression vectors. Hartner et al., Nucl. Acid Res. 36: e76 (pub on-line 6 Jun. 2008) describes a library of promoters for fine-tuned expression of heterologous proteins in *Pichia pastoris*.

The promoters that are operably linked to the nucleic acid molecules disclosed herein can be constitutive promoters or inducible promoters. An inducible promoter, for example the AOX1 promoter, is a promoter that directs transcription at an increased or decreased rate upon binding of a transcription factor in response to an inducer. Transcription factors as used herein include any factor that can bind to a regulatory or control region of a promoter and thereby affect transcription. The RNA synthesis or the promoter binding ability of a transcription factor within the host cell can be controlled by exposing the host to an inducer or removing an inducer from the host cell medium. Accordingly, to regulate expression of an inducible promoter, an inducer is added or removed from the growth medium of the host cell. Such inducers can include sugars, phosphate, alcohol, metal ions, hormones, heat, cold and the like. For example, commonly used inducers in yeast are glucose, galactose, alcohol, and the like.

Transcription termination sequences that are selected are those that are operable in the particular host cell selected. For example, yeast transcription termination sequences are used in expression vectors when a yeast host cell such as *Saccharomyces cerevisiae, Kluyveromyces lactis,* or *Pichia pastoris* is the host cell whereas fungal transcription termination sequences would be used in host cells such as *Aspergillus niger, Neurospora crassa,* or *Tricoderma reesei*. Transcription termination sequences include but are not limited to the *Saccharomyces cerevisiae* CYC transcription termination sequence (ScCYC TT), the *Pichia pastoris* ALG3 transcription termination sequence (ALG3 TT), the *Pichia pastoris* ALG6 transcription termination sequence (ALG6 TT), the *Pichia pastoris* ALG12 transcription termination sequence (ALG12 TT), the *Pichia pastoris* AOX1 transcription termination sequence (AOX1 TT), the *Pichia pastoris* OCH1 transcription termination sequence (OCH1 TT) and *Pichia pastoris* PMA1 transcription termination sequence (PMA1 TT). Other transcription termination sequences can be found in the examples and in the art.

For genetically engineering yeast, selectable markers can be used to construct the recombinant host cells include drug resistance markers and genetic functions which allow the yeast host cell to synthesize essential cellular nutrients, e.g. amino acids. Drug resistance markers which are commonly used in yeast include chloramphenicol, kanamycin, methotrexate, G418 (geneticin), Zeocin, and the like. Genetic functions which allow the yeast host cell to synthesize essential cellular nutrients are used with available yeast strains having auxotrophic mutations in the corresponding genomic function. Common yeast selectable markers provide genetic functions for synthesizing leucine (LEU2), tryptophan (TRP1 and TRP2), proline (PRO1), uracil (URA3, URA5, URA6), histidine (HIS3), lysine (LYS2), adenine (ADE1 or ADE2), and the like. Other yeast selectable markers include the ARR3 gene from *S. cerevisiae*, which confers arsenite resistance to yeast cells that are grown in the presence of arsenite (Bobrowicz et al., Yeast, 13:819-828 (1997); Wysocki et al., J. Biol. Chem. 272: 30061-30066 (1997)). A number of suitable integration sites include those enumerated in U.S. Pat. No. 7,479,389 (the disclosure of which is incorporated herein by reference) and include homologs to loci known for *Saccharomyces cerevisiae* and other yeast or fungi. Methods for integrating vectors into yeast are well known (See for example, U.S. Pat. No. 7,479,389, U.S. Pat. No. 7,514,253, U.S. Published Application No. 2009012400, and WO2009/085135; the disclosures of which are all incorporated herein by reference). Examples of insertion sites include, but are not limited to, *Pichia* ADE genes; *Pichia* TRP (including TRP1 through TRP2) genes; *Pichia* MCA genes; *Pichia* CYM genes; *Pichia* PEP genes; *Pichia* PRB genes; and *Pichia* LEU genes. The *Pichia* ADE1 and ARG4 genes have been described in Lin Cereghino et al., Gene 263:159-169 (2001) and U.S. Pat. No. 4,818,700 (the disclosure of which is incorporated herein by reference), the HIS3 and TRP1 genes have been described in Cosano et al., Yeast 14:861-867 (1998), HIS4 has been described in GenBank Accession No. X56180.

The transformation of the yeast cells is well known in the art and may for instance be effected by protoplast formation followed by transformation in a manner known per se. The medium used to cultivate the cells may be any conventional medium suitable for growing yeast organisms. A significant proportion of the secreted O-glycosylated CTP peptide-based insulin or insulin analogue precursor, which will be present in the medium in correctly processed form and may be recovered from the medium by various procedures including but not limited to separating the yeast cells from the medium by centrifugation, filtration, or catching the insulin precursor by an ion exchange matrix or by a reverse phase absorption matrix, precipitating the proteinaceous components of the supernatant or filtrate by means of a salt, e g ammonium sulphate, followed by purification by a variety of chromatographic procedures, e.g. ion exchange chromatography, affinity chromatography, or the like.

The secreted O-glycosylated CTP peptide-based insulin or insulin analogue molecule may be a precursor molecule that may optionally include an N-terminal extension or spacer peptide, as described in U.S. Pat. No. 5,395,922 and European Patent No. 765,395A, both of which are herein specifically incorporated by reference. The N-terminal extension or spacer is a peptide that is positioned between the signal peptide or propeptide and the N-terminus of the B-chain. Following removal of the signal peptide and propeptide during passage through the secretory pathway, the N-terminal extension peptide remains attached to the N-glycosylated insulin precursor. Thus, during fermentation, the N-terminal end of the B-chain may be protected against the proteolytic activity of yeast proteases. The presence of an N-terminal extension or spacer peptide may also serve as a protection of the N-terminal amino group during chemical processing of the protein, i.e., it may serve as a substitute for a BOC (t-butyl-oxycarbonyl) or similar protecting group. The N-terminal extension or spacer may be removed from the recovered O-glycosylated CTP peptide-based insulin or insulin analogue precursor by means of a proteolytic enzyme which is specific for a basic amino acid (e.g., Lys) so that the terminal extension is cleaved off at the Lys residue. Examples of such proteolytic enzymes are trypsin, *Achromobacter lyticus* protease, or *Lysobacter enzymogenes* endoprotease Lys-C.

After secretion into the culture medium and recovery, the O-glycosylated CTP peptide-based insulin or insulin analogue precursor may be subjected to various in vitro procedures to remove the optional N-terminal extension or spacer peptide and the C-peptide in the case where the CTP peptide is not a connecting peptide to produce a desB30 O-glycosylated CTP peptide-based insulin or insulin analogue. The desB30 O-glycosylated CTP peptide-based insulin or insulin analogue may then be converted into B30 insulin by adding a Thr in position B30. Conversion of the O-glycosylated CTP peptide-based insulin or insulin analogue precursor into a B30 heterodimer by digesting the O-glycosylated CTP peptide-based insulin or insulin analogue precursor with trypsin or Lys-C in the presence of an L-threonine ester followed by conversion of the threonine ester to L-threonine by basic or acid hydrolysis as described in U.S. Pat. No. 4,343,898 or 4,916,212, the disclosures of which are incorporated by reference hereinto. The O-glycosylated CTP peptide-based insulin or insulin analogue desB30 insulin may also be converted into an acylated derivative as disclosed in U.S. Pat. No. 5,750,497 and U.S. Pat. No. 5,905,140, the disclosures of which are incorporated by reference hereinto.

The present invention further provides nucleic acid molecules comprising an open reading frame (ORF) encoding a CTP peptide-based insulin or insulin analogue as disclosed herein. In particular aspects, the ORF encoding the CTP peptide-based insulin or insulin analogue is in frame to and downstream from a second ORF on the nucleic acid molecule, which encodes a pre-propeptide, for example a *Saccharomyces cerevisiae* alpha mating factor pre-propeptide, to provide a single continuous ORF encoding a fusion protein in which the pre-pro peptide is fused to the N-terminus of the CTP peptide-based insulin or insulin analogue. In a further aspect, the nucleic acid molecule encoding the CTP peptide-based insulin or insulin analogue is operably linked to an inducible promoter, for example, the *Pichia pastoris* AOX1 promoter. In particular aspects, the codons encoding the CTP peptide-based insulin or insulin analogue are modified to codons that are commonly used in *Pichia pastoris*.

The propeptide may be the *Saccharomyces cerevisiae* alpha mating factor pre-propeptide having the amino acid sequence shown in SEQ ID NO:7, which may be encoded by the nucleic acid sequence shown in SEQ ID NO:41) (See U.S. Pat. Nos. 4,546,082 and 4,870,008). Alternatively, the pro-peptide may be a synthetic propeptide, which is to say a propeptide not found in nature, including but not limited to those disclosed in U.S. Pat. Nos. 5,395,922; 5,795,746; and 5,162,498 and in WO 9832867. The propeptide will preferably contain an endopeptidase processing site at the C-terminal end, such as a Lys-Arg sequence or any functional analogue thereof. In another embodiment, the pre-propeptide may comprise Yps1ss single sequence peptide having the amino acid sequence MKLKTVRSAVLSS-LFASQVLG (SEQ ID NO:26) fused to the N-terminus of the TA57 propeptide having the amino acid sequence QPID-DTESQTTSVNLMADDTESAFATQTNSGGLDVVGLIS-MAKR (SEQ ID NO:82). Optionally, an N-terminal spacer having the amino acid sequence EEGEPK (SEQ ID NO:83) may be fused to the C-terminal amino acid of the pre-propeptide. The Yps1ss peptide is a synthetic leader or signal peptide disclosed in U.S. Pat. Nos. 5,639,642 and 5,726,038, and which are hereby incorporated herein by reference. The TA57 propeptide and N-terminal spacer have been described by Kjeldsen et al., Gene 170:107-112 (1996) and in U.S. Pat. Nos. 6,777,207, and 6,214,547, and which are hereby incorporated herein in by reference.

VI. Sustained Release Formulations

In certain embodiments it may be advantageous to administer an O-glycosylated CTP peptide-based insulin or insulin analogue in a sustained fashion (i.e., in a form that exhibits an absorption profile that is more sustained than soluble recombinant human insulin). This will provide a sustained level of glycosylated insulin that can respond to fluctuations in glucose on a timescale that it more closely related to the typical glucose fluctuation timescale (i.e., hours rather than minutes). In certain embodiments, the sustained release formulation may exhibit a zero-order release of the glycosylated insulin when administered to a mammal under non-hyperglycemic conditions (i.e., fasted conditions). It will be appreciated that any formulation that provides a sustained absorption profile may be used. In certain embodiments this may be achieved by combining the glycosylated insulin with other ingredients that slow its release properties into systemic circulation. For example, PZI (protamine zinc insulin) formulations may be used for this purpose. In some cases, the zinc content is in the range of about 0.05 to about 0.5 mg zinc/mg glycosylated insulin.

Thus, in certain embodiments, a formulation of the present disclosure includes from about 0.05 to about 10 mg protamine/mg glycosylated insulin or insulin analogue. For example, from about 0.2 to about 10 mg protamine/mg O-glycosylated CTP peptide-based insulin or insulin analogue, e.g., about 1 to about 5 mg protamine/mg O-glycosylated insulin or insulin analogue.

In certain embodiments, a formulation of the present disclosure includes from about 0.006 to about 0.5 mg zinc/mg glycosylated insulin or insulin analogue. For example, from about 0.05 to about 0.5 mg zinc/mg glycosylated insulin or insulin analogue, e.g., about 0.1 to about 0.25 mg zinc/mg O-glycosylated CTP peptide-based insulin or insulin analogue.

In certain embodiments, a formulation of the present disclosure includes protamine and zinc in a ratio (w/w) in the range of about 100:1 to about 5:1, for example, from about 50:1 to 20 about 5:1, e.g., about 40:1 to about 10:1. In certain embodiments, a PZI formulation of the present disclosure includes protamine and zinc in a ratio (w/w) in the range of about 20:1 to about 5:1, for example, about 20:1 to about 10:1, about 20:1 to about 15:1, about 15:1 to about 5:1, about 10:1 to about 5:1, about 10:1 to about 15:1.

In certain embodiments a formulation of the present disclosure includes an antimicrobial preservative (e.g., m-cresol, phenol, methylparaben, or propylparaben). In certain embodiments the antimicrobial preservative is m-cresol. For example, in certain embodiments, a formulation may include from about 0.1 to about 1.0% v/v m-cresol. For example, from about 0.1 to about 0.5% v/v m-cresol, e.g., about 0.15 to about 0.35% v/v m-cresol.

In certain embodiments a formulation of the present disclosure includes a polyol as isotonic agent (e.g., mannitol, propylene glycol or glycerol). In certain embodiments the isotonic agent is glycerol. In certain embodiments, the isotonic agent is a salt, e.g., NaCl. For example, a formulation may comprise from about 0.05 to about 0.5 M NaCl, e.g., from about 0.05 to about 0.25 M NaCl or from about 0.1 to about 0.2 M NaCl.

In certain embodiments a formulation of the present disclosure includes an amount of non-glycosylated insulin or insulin analogue. In certain embodiments, a formulation includes a molar ratio of glycosylated insulin analogue to non-glycosylated insulin or insulin analogue in the range of about 100:1 to 1:1, e.g., about 50:1 to 2:1 or about 25:1 to 2:1.

The present disclosure also encompasses the use of standard sustained (also called extended) release formulations that are well known in the art of small molecule formulation (e.g., see *Remington's Pharmaceutical Sciences,* 19th ed., Mack Publishing Co., Easton, Pa., 1995).

The present disclosure also encompasses the use of devices that rely on pumps or hindered diffusion to deliver a glycosylated insulin analogue on a gradual basis. In certain embodiments, a long acting formulation may (additionally or alternatively) be provided by modifying the insulin to be long-lasting. For example, the insulin analogue may be insulin glargine or insulin detemir. Insulin glargine is an exemplary long acting insulin analogue in which Asn-A21 has been replaced by glycine, and two arginines have been added to the C-terminus of the B-chain. The effect of these changes is to shift the isoelectric point, producing a solution that is completely soluble at pH 4. Insulin detemir is another long acting insulin analogue in which Thr-B30 has been deleted, and a C14 fatty acid chain has been attached to Lys-B29.

The following examples are intended to promote a further understanding of the present invention.

Example 1

This example illustrates the construction of plasmid expression vectors encoding human insulin analogues comprising a CTP peptide. These expression vectors have been designed for protein expression in *Pichia pastoris*; however, the nucleic acid molecules encoding the recited insulin analogue A- and B-chain peptides can be incorporated into expression vectors designed for protein expression in other host cells capable of producing O-glycosylated glycoproteins, for example, mammalian cells and fungal, plant, insect, or bacterial cells.

The expression vectors disclosed below encode a pre-proinsulin analogue precursor molecule comprising a CTP peptide at the N-terminus and/or as a connecting peptide. During expression of the vector encoding the pre-proinsulin analogue precursor in the yeast host cell, the pre-proinsulin analogue precursor is transported to the secretory pathway where the signal peptide is removed and the molecule is processed into a glycosylated proinsulin analogue precursor that is folded into a structure held together by disulfide bonds that has the same configuration as that for native human insulin. The O-glycosylated CTP peptide-based insulin or insulin analogue precursor is transported through the secretory pathway and then directed to vesicles where the propetide is removed to form an O-glycosylated CTP peptide-based insulin or insulin analogue precursor molecule or O-glycosylated CTP peptide-based insulin or insulin analogue single-chain molecule that is then secreted from the host cell where in the case of the precursor molecule, it may be further processed in vitro using trypsin or endoproteinase Lys-C digestion to produce an O-glycosylated CTP peptide-based insulin or insulin analogue heterodimer.

Figure 1:
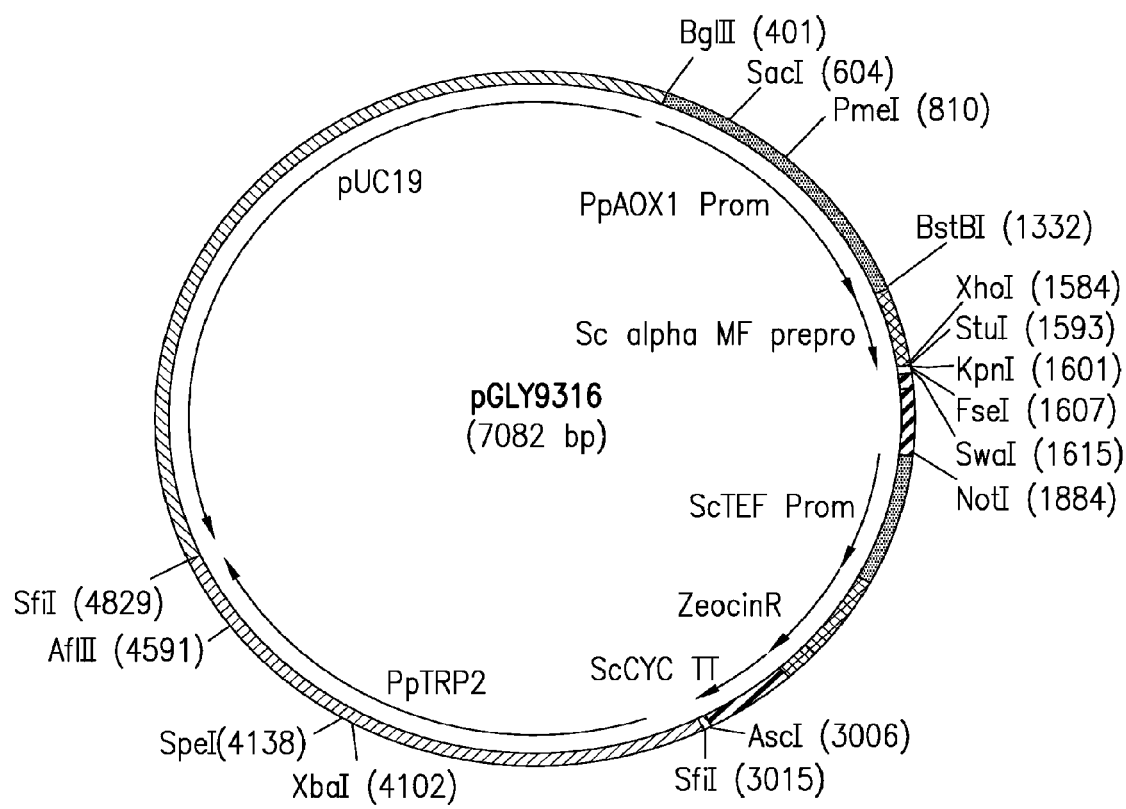
FIG. 1 shows map of plasmid pGLY9316, which is a roll-in integration plasmid that targets the TRP2 or AOX1 loci, includes an empty expression cassette utilizing the *S. cerevisiae* alpha mating factor signal sequence.

Plasmid pGLY9316 (FIG. 1) is an empty expression plasmid that was used to generate the insulin expression plasmids listed in Table 1. Plasmid pGLY9316 comprises a nucleic acid molecule encoding the *S. cerevisiae* alpha mating factor signal sequence and propeptide (SEQ ID NO:7 encoded by SEQ ID NO:41) operably linked upstream to the *Pichia pastoris* AOX1 promoter (SEQ ID NO:8) and downstream to a multiple cloning site and *Pichia pastoris* AOX1 transcription termination sequence (SEQ ID NO:9). The plasmid further comprises an expression cassette encoding the Zeocin resistance selection marker (SEQ ID NO:10) operably linked to the *S. cerevisiae* TEF1 promoter (SEQ ID NO:11) and *S. cerevisiae* CYC transcription termination sequence (SEQ ID NO:12). The plasmid vector targets the TRP2 locus (SEQ ID NO:13) or AOX1 promoter (SEQ ID NO:8) for integration. To generate the expression plasmids shown in Table 1, nucleic acid molecules encoding the listed insulin/CTP analogues were inserted into the multiple cloning site in frame with the open reading frame encoding the *S. cerevisiae* alpha mating factor signal sequence and propeptide to encode a fusion protein comprising the *S. cerevisiae* alpha mating factor signal sequence and propeptide fused to the N-terminus of the B-chain peptide. The codons encoding the insulin/CTP were optimized for expression in *Pichia pastoris*. For each open reading frame (ORF) encoding the insulin/CTP, the 5' end of the ORF was linked to the nucleotide sequence GAGTCCTCTT (SEQ ID NO:54) and the 3' end of the ORF was linked to the nucleotide sequence TAATAGGGCCGGCC (SEQ ID NO:55).

The descendent insulin precursor expression plasmids, as listed in Table 1, were constructed by inserting the nucleic acid molecule encoding the insulin/CTP analogue and digested with MlyI and FseI between the StuI and FseI restriction enzyme sites in the multiple cloning site of the expression plasmid pGLY9316.

TABLE 1

| Expression vector | Description | Nucleic acid sequence SEQ ID NO: | Amino acid sequence SEQ ID NO: |
|---|---|---|---|
| pGLY11165 | SCI (C peptide replaced with CTP) | 42 | 43 |
| pGLY11167 | SCI (C-peptide replaced with CTP + K) | 44 | 45 |
| pGLY11169 | SCI (N-spacer is CTP) | 46 | 47 |
| pGLY11171 | SCI (N-spacer is CTP + K) | 48 | 49 |
| pGLY11173 | SCI (N-spacer is CTP; C-peptide replaced with CTP) | 50 | 51 |
| pGLY11175 | SCI (N-spacer is CTP; C-peptide replaced with CTP + K) | 52 | 53 |

The codons encoding the insulin/CTP were optimized for expression in *Pichia pastoris*. For each open reading frame (ORF) encoding the insulin/CTP, the 5' end of the ORF was linked to the nucleotide sequence GAGTCCTCTT (SEQ ID NO: 54) and the 3' end of the ORF was linked to the nucleotide sequence TAATAGGGCCGGCC (SEQ ID NO: 55).
SCI = single-chain insulin
CTP + K = CTP peptide with a C-terminal lysine residue The expression vector containing the expression cassette encoding the pre-proinsulin analogue precursor is transformed into a yeast host cell where it integrates into the host cell genome and the pre-proinsulin analogue precursor is expressed from the expression cassette integrated into the host cell genome. The pre-proinsulin analogue precursor targets the secretory pathway where it is folded with disulfide linkages and O-glycosylated. The proinsulin analogue precursor is then transported to vesicles where the propeptide is removed and the pre-O-glycosylated CTP peptide-based proinsulin analogue precursor is secreted from the host cell into the culture medium where it may be purified. In the case where the connecting peptide is the CTP peptide with one or two basic amino acid residues at the C-terminal end (e.g., CTP+K having the amino acid sequence SEQ ID NO:91) or a connecting peptide other than CTP peptide having a terminal Lys, e.g., AAK (SEQ ID NO:84), and the CTP peptide is at the N-terminus of the B-chain (N-spacer), the precursor may be further processed in vitro (ex-cellularly) to provide an O-glycosylated CTP peptide-based insulin analogue heterodimer in which the CTP peptide is at the C-terminus of the B-chain peptide or the N-terminus of the B-chain peptide, respectively. The heterodimer insulin analogues that are produced following in vitro processing with trypsin or endoproteinase Lys-C lack the B30 Tyrosine residue, thus the insulin analogues are desB30 analogues. However, as known in the art, desB30 insulin analogues have an activity at the insulin receptor that is not substantially different from that of native insulin. For insulin analogues in which the connecting peptide is the CTP peptide, the O-glycosylated CTP peptide-based insulin analogue is a single-chain molecule.

Example 2

Figure 2A:
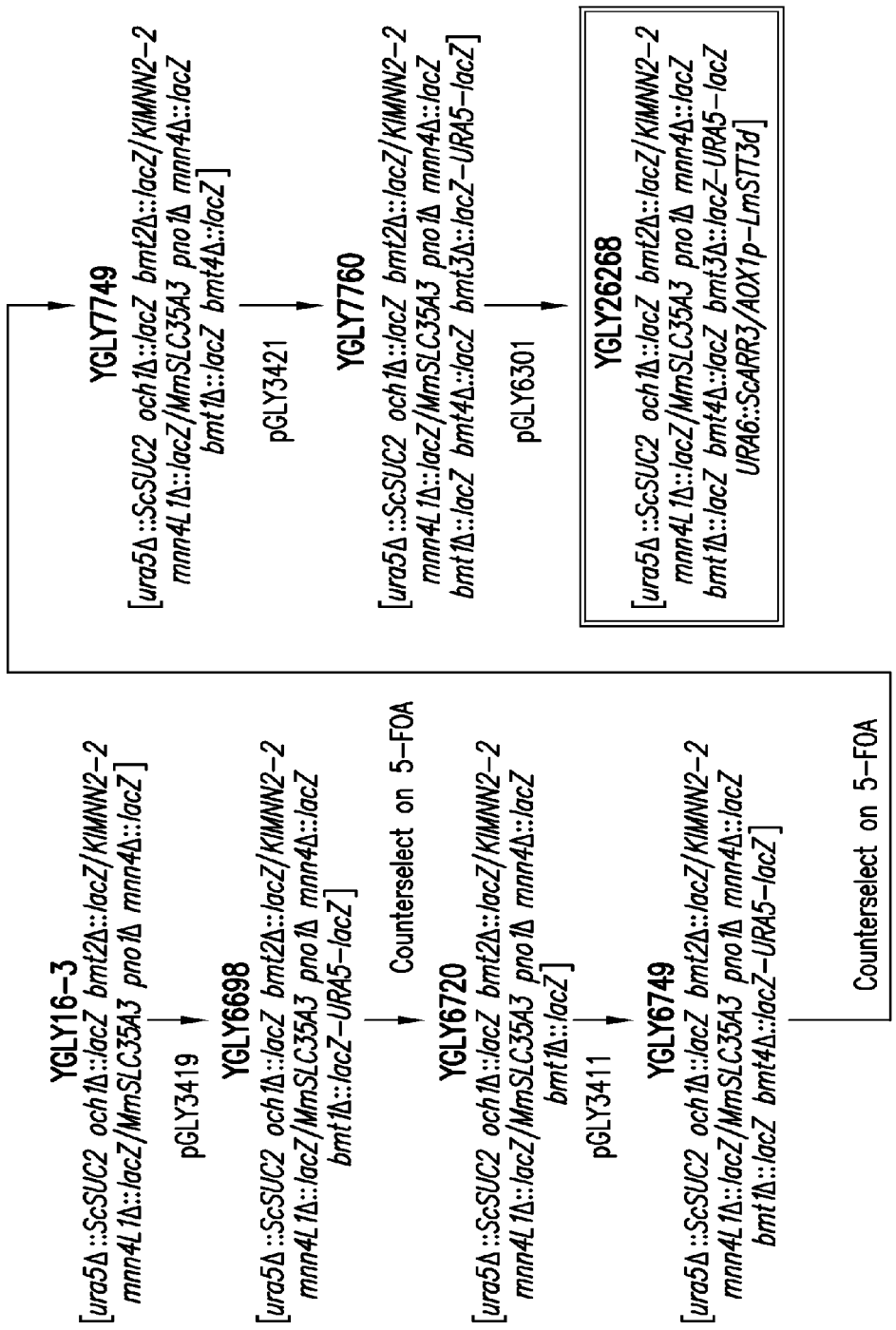
FIG. 2 shows the construction of strain YGLY26268.

To test expression and glycosylation of the CTP peptide-based insulin or insulin analogues, *Pichia pastoris* strain YGLY26268 was constructed as illustrated schematically in FIG. 2. Briefly, the strain was constructed as follows.

Yeast strains were transformed by electroporation (using standard techniques as recommended by the manufacturer of the electroporator BioRad). In general, yeast transformations were as follows. *P. pastoris* strains were grown in 50 mL YPD media (yeast extract (1%), peptone (2%), dextrose (2%)) overnight to an optical density ("OD") of between about 0.2 to 6. After incubation on ice for 30 minutes, cells were pelleted by centrifugation at 2500-3000 rpm for 5 minutes. Media was removed and the cells washed three times with ice cold sterile 1M sorbitol before resuspension in 0.5 ml ice cold sterile 1M sorbitol. Ten µL DNA (5-20 µg) and 100 µL cell suspension was combined in an electroporation cuvette and incubated for 5 minutes on ice. Electroporation was in a Bio-Rad GenePulser Xcell following the preset *Pichia pastoris* protocol (2 kV, 25 µF, 200Ω), immediately followed by the addition of 1 mL YPDS recovery media (YPD media plus 1 M sorbitol). The transformed cells were allowed to recover for four hours to overnight at room temperature (26° C.) before plating the cells on selective media.

Figure 3:
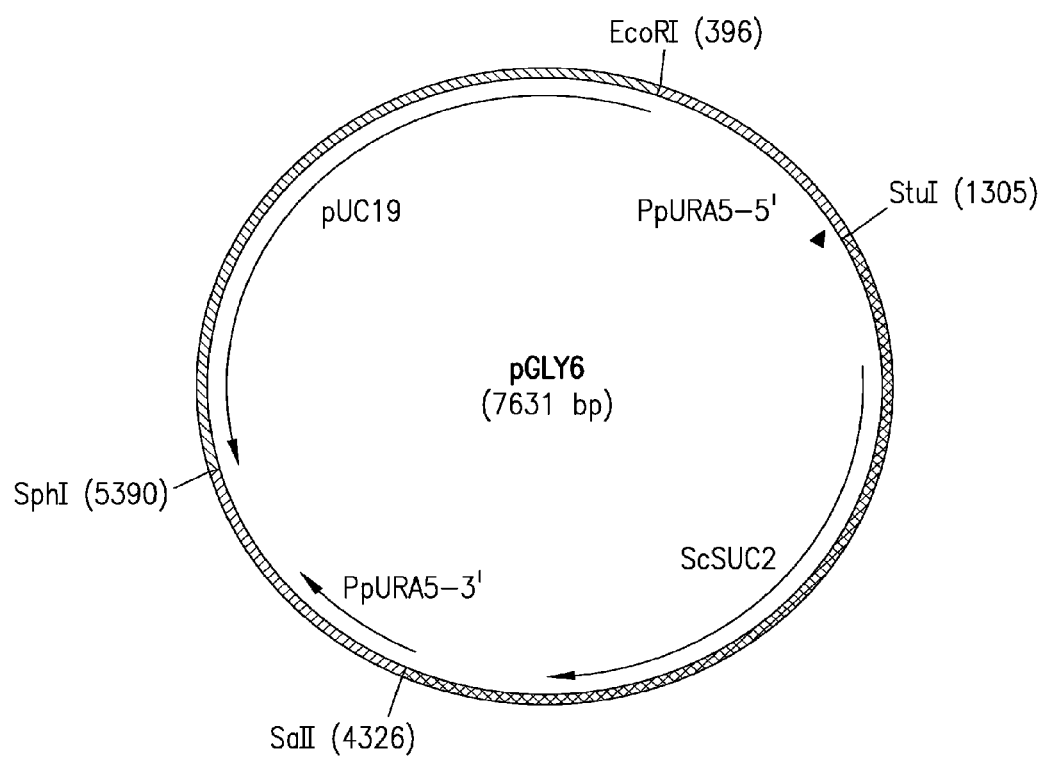
FIG. 3 shows a map of plasmid pGLY6. Plasmid pGLY6 is an integration vector that targets the URA5 locus and contains a nucleic acid molecule comprising the *S. cerevisiae* invertase gene or transcription unit (ScSUC2) flanked on one side by a nucleic acid molecule comprising a nucleotide sequence from the 5' region of the *P. pastoris* URA5 gene (PpURA5-5') and on the other side by a nucleic acid molecule comprising the a nucleotide sequence from the 3' region of the *P. pastoris* URA5 gene (PpURA5-3').

Plasmid pGLY6 (Figure-3) is an integration vector that targets the URA5 locus. It contains a nucleic acid molecule comprising the *S. cerevisiae* invertase gene or transcription unit (ScSUC2; SEQ ID NO:14) flanked on one side by a nucleic acid molecule comprising a nucleotide sequence from the 5' region of the *P. pastoris* URA5 gene (SEQ ID NO:15) and on the other side by a nucleic acid molecule comprising the nucleotide sequence from the 3' region of the *P. pastoris* URA5 gene (SEQ ID NO:16). Plasmid pGLY6 was linearized and the linearized plasmid transformed into wild-type strain NRRL-Y 11430 to produce a number of strains in which the ScSUC2 gene was inserted into the URA5 locus by double-crossover homologous recombination. Strain YGLY1-3 was selected from the strains produced and is auxotrophic for uracil.

Figure 4:
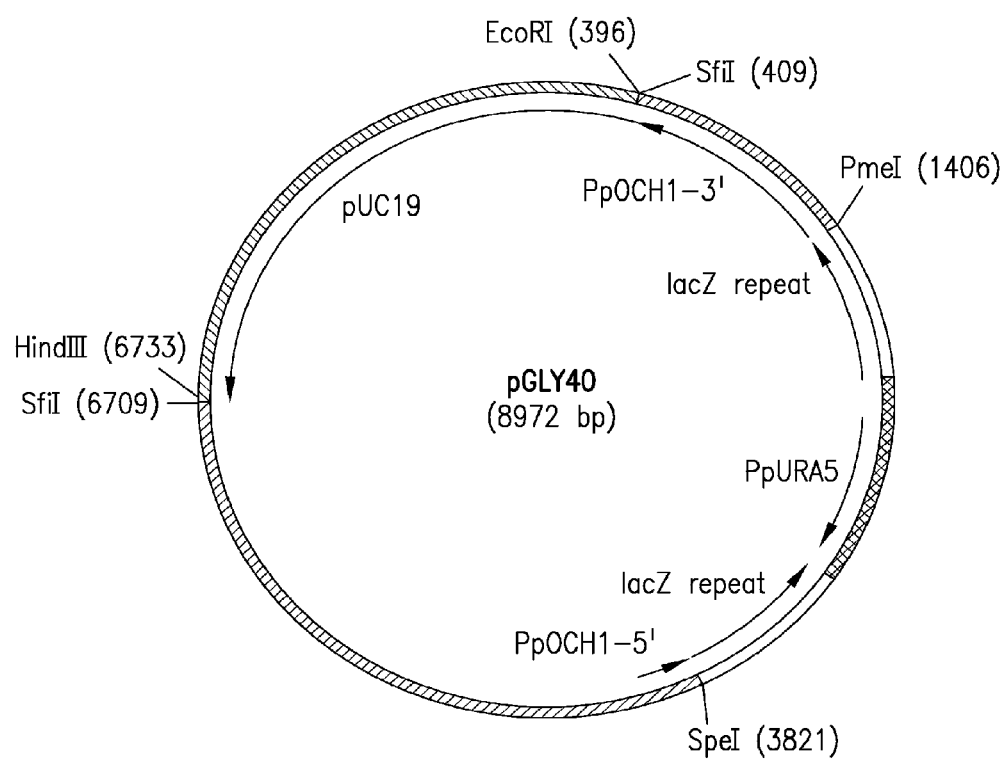
FIG. 4 shows a map of plasmid pGLY40. Plasmid pGLY40 is an integration vector that targets the OCH1 locus and contains a nucleic acid molecule comprising the *P. pastoris* URA5 gene or transcription unit (PpURA5) flanked by nucleic acid molecules comprising lacZ repeats (lacZ repeat) which in turn is flanked on one side by a nucleic acid molecule comprising a nucleotide sequence from the 5' region of the OCH1 gene (PpOCH1-5') and on the other side by a nucleic acid molecule comprising a nucleotide sequence from the 3' region of the OCH1 gene (PpOCH1-3').

Plasmid pGLY40 (FIG. 4) is an integration vector that targets the OCH1 locus and contains a nucleic acid molecule comprising the *P. pastoris* URA5 gene or transcription unit (SEQ ID NO:17) flanked by nucleic acid molecules comprising lacZ repeats (SEQ ID NO:18) which in turn is flanked on one side by a nucleic acid molecule comprising a nucleotide sequence from the 5' region of the OCH1 gene (SEQ ID NO:19) and on the other side by a nucleic acid molecule comprising a nucleotide sequence from the 3' region of the OCH1 gene (SEQ ID NO:20). Plasmid pGLY40 was linearized with SfiI and the linearized plasmid transformed into strain YGLY1-3 to produce a number of strains in which the URA5 gene flanked by the lacZ repeats has been inserted into the OCH1 locus by double-crossover homologous recombination. Strain YGLY2-3 was selected from the strains produced and is prototrophic for URA5. Strain YGLY2-3 was counterselected in the presence of 5-fluoroorotic acid (5-FOA) to produce a number of strains in which the URA5 gene has been lost and only the lacZ repeats remain in the OCH1 locus. This renders the strain auxotrophic for uracil. Strain YGLY4-3 was selected.

Figure 5:
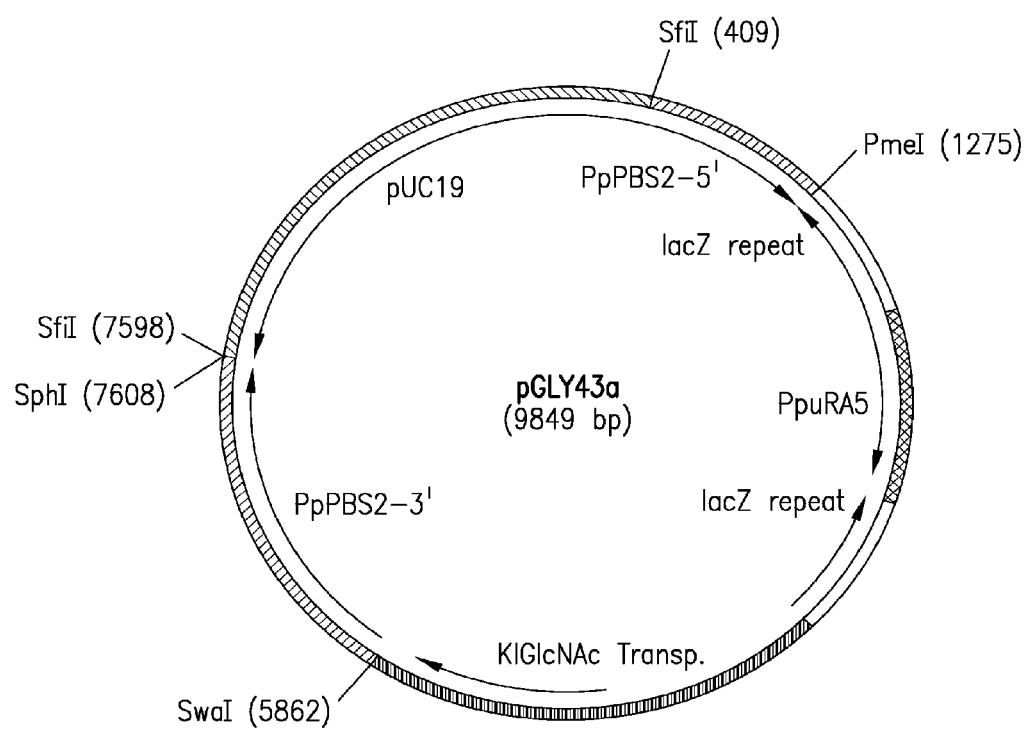
FIG. 5 shows a map of plasmid pGLY43a. Plasmid pGLY43a is an integration vector that targets the BMT2 locus and contains a nucleic acid molecule comprising the *K. lactis* UDP-N-acetylglucosamine (UDP-GlcNAc) transporter gene or transcription unit (KlGlcNAc Transp.) adjacent to a nucleic acid molecule comprising the *P. pastoris* URA5 gene or transcription unit (PpURA5) flanked by nucleic acid molecules comprising lacZ repeats (lacZ repeat). The adjacent genes are flanked on one side by a nucleic acid molecule comprising a nucleotide sequence from the 5' region of the BMT2 gene (PpPBS2-5') and on the other side by a nucleic acid molecule comprising a nucleotide sequence from the 3' region of the BMT2 gene (PpPBS2-3').

Plasmid pGLY43a (FIG. 5) is an integration vector that targets the BMT2 locus and contains a nucleic acid molecule comprising the *K. lactis* UDP-N-acetylglucosamine (UDP-GlcNAc) transporter gene or transcription unit (KlMNN2-2, SEQ ID NO:21) adjacent to a nucleic acid molecule comprising the *P. pastoris* URA5 gene or transcription unit flanked by nucleic acid molecules comprising lacZ repeats. The adjacent genes are flanked on one side by a nucleic acid molecule comprising a nucleotide sequence from the 5' region of the BMT2 gene (SEQ ID NO: 22) and on the other side by a nucleic acid molecule comprising a nucleotide sequence from the 3' region of the BMT2 gene (SEQ ID NO:23). Plasmid pGLY43a was linearized with SfiI and the linearized plasmid transformed into strain YGLY4-3 to produce to produce a number of strains in which the KlMNN2-2 gene and URA5 gene flanked by the lacZ repeats has been inserted into the BMT2 locus by double-crossover homologous recombination. The BMT2 gene has been disclosed in Mille et al., J. Biol. Chem. 283: 9724-9736 (2008) and U.S. Pat. No. 7,465,557. Strain YGLY6-3 was selected from the strains produced and is prototrophic for uracil. Strain YGLY6-3 was counterselected in the presence of 5-FOA to produce strains in which the URA5 gene has been lost and only the lacZ repeats remain. This renders the strain auxotrophic for uracil. Strain YGLY8-3 was selected.

Figure 6:
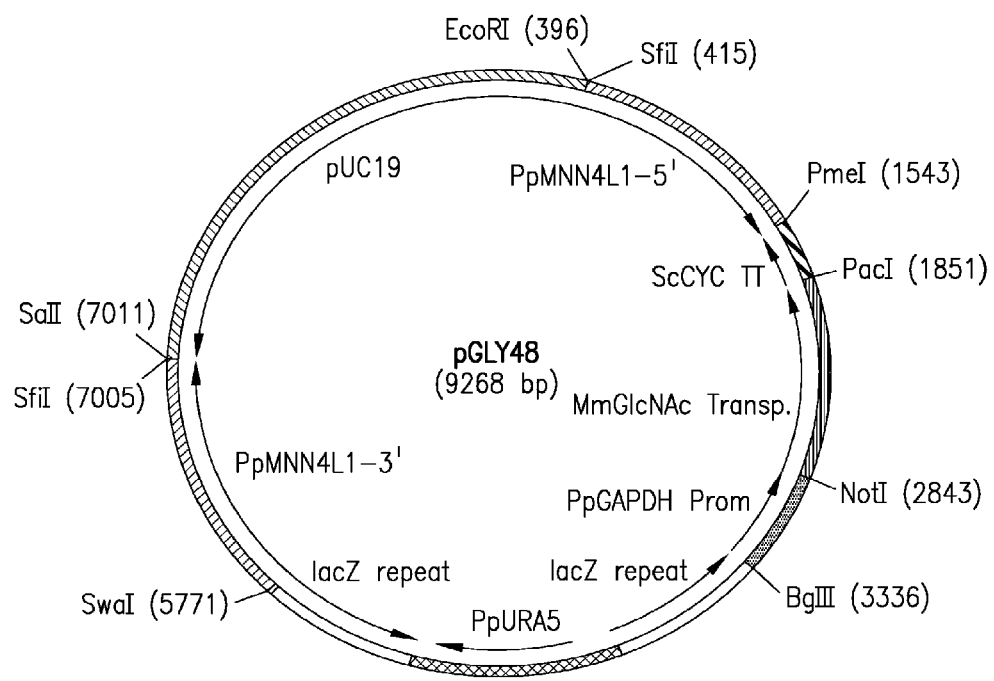
FIG. 6 shows a map of plasmid pGLY48. Plasmid pGLY48 is an integration vector that targets the MNN4L1 locus and contains an expression cassette comprising a nucleic acid molecule encoding the mouse homologue of the UDP-GlcNAc transporter (MmGlcNAc Transp.) open reading frame (ORF) operably linked at the 5' end to a nucleic acid molecule comprising the *P. pastoris* GAPDH promoter (PpGAPDH Prom) and at the 3' end to a nucleic acid molecule comprising the *S. cerevisiae* CYC termination sequence (ScCYC TT) adjacent to a nucleic acid molecule comprising the *P. pastoris* URA5 gene or transcription unit (PpURA5) flanked by lacZ repeats (lacZ repeat) and in which the expression cassettes together are flanked on one side by a nucleic acid molecule comprising a nucleotide sequence from the 5' region of the *P. pastoris* MNN4L1 gene (PpMNN4L1-5') and on the other side by a nucleic acid molecule comprising a nucleotide sequence from the 3' region of the MNN4L1 gene (PpMNN4L1-3').

Plasmid pGLY48 (FIG. 6) is an integration vector that targets the MNN4L1 locus and contains an expression cassette comprising a nucleic acid molecule encoding the mouse homologue of the UDP-GlcNAc transporter (SEQ ID NO:24) open reading frame (ORF) operably linked at the 5' end to a nucleic acid molecule comprising the *P. pastoris* GAPDH promoter (SEQ ID NO:25) and at the 3' end to a nucleic acid molecule comprising the *S. cerevisiae* CYC termination sequences (SEQ ID NO:12) adjacent to a nucleic acid molecule comprising the *P. pastoris* URA5 gene flanked by lacZ repeats and in which the expression cassettes together are flanked on one side by a nucleic acid molecule comprising a nucleotide sequence from the 5' region of the *P. pastoris* MNN4L1 gene (SEQ ID NO:27) and on the other side by a nucleic acid molecule comprising a nucleotide sequence from the 3' region of the MNN4L1 gene (SEQ ID NO:28). Plasmid pGLY48 was linearized with SfiI and the linearized plasmid transformed into strain YGLY8-3 to produce a number of strains in which the expression cassette encoding the mouse UDP-GlcNAc transporter and the URA5 gene have been inserted into the MNN4L1 locus by double-crossover homologous recombination. The MNN4L1 gene (also referred to as MNN4B) has been disclosed in U.S. Pat. No. 7,259,007. Strain YGLY10-3 was selected from the strains produced and then counterselected in the presence of 5-FOA to produce a number of strains in which the URA5 gene has been lost and only the lacZ repeats remain. Strain YGLY12-3 was selected.

Figure 7:
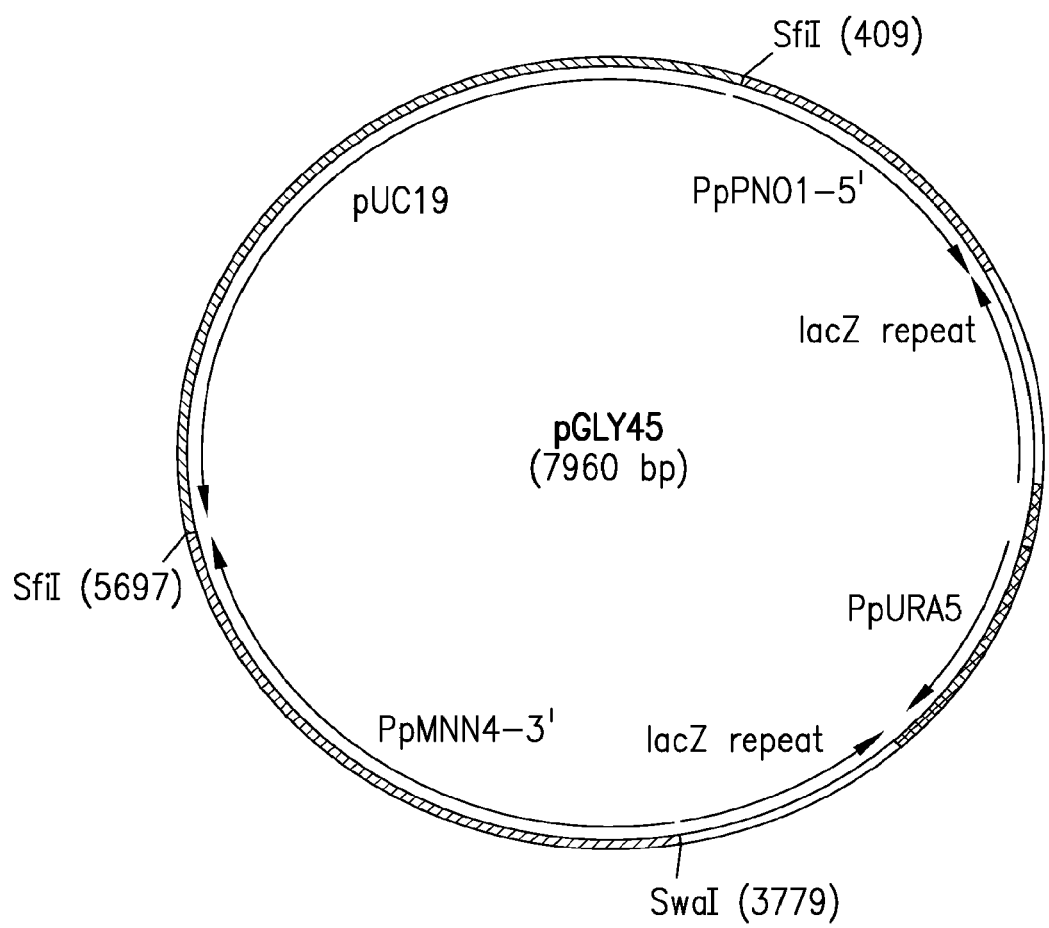
FIG. 7 shows as map of plasmid pGLY45. Plasmid pGLY45 is an integration vector that targets the PNO1/MNN4 loci contains a nucleic acid molecule comprising the *P. pastoris* URA5 gene or transcription unit (PpURA5) flanked by nucleic acid molecules comprising lacZ repeats (lacZ repeat) which in turn is flanked on one side by a nucleic acid molecule comprising a nucleotide sequence from the 5' region of the PNO1 gene (PpPNO1-5') and on the other side by a nucleic acid molecule comprising a nucleotide sequence from the 3' region of the MNN4 gene (PpMNN4-3').

Plasmid pGLY45 (FIG. 7) is an integration vector that targets the PNO1/MNN4 loci and contains a nucleic acid molecule comprising the *P. pastoris* URA5 gene or transcription unit flanked by nucleic acid molecules comprising lacZ repeats which in turn is flanked on one side by a nucleic acid molecule comprising a nucleotide sequence from the 5' region of the PNO1 gene (SEQ ID NO:29) and on the other side by a nucleic acid molecule comprising a nucleotide sequence from the 3' region of the MNN4 gene (SEQ ID NO:30). Plasmid pGLY45 was linearized with SfiI and the linearized plasmid transformed into strain YGLY12-3 to produce a number of strains in which the URA5 gene flanked by the lacZ repeats has been inserted into the PNO1/MNN4 loci by double-crossover homologous recombination. The PNO1 gene has been disclosed in U.S. Pat. No. 7,198,921 and the MNN4 gene (also referred to as MNN4B) has been disclosed in U.S. Pat. No. 7,259,007. Strain YGLY14-3 was selected from the strains produced and then counterselected in the presence of 5-FOA to produce a number of strains in which the URA5 gene has been lost and only the lacZ repeats remain. Strain YGLY16-3 was selected.

Figure 8:
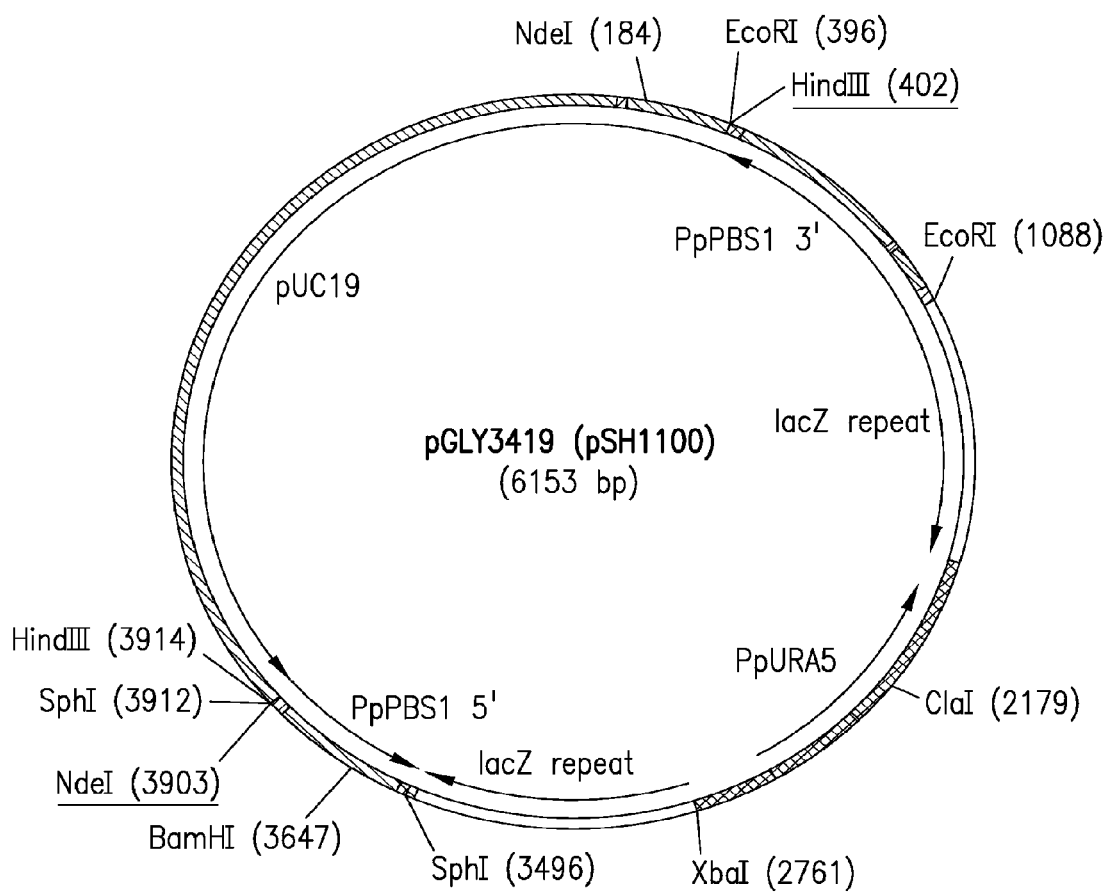
FIG. 8 shows a map of plasmid pGLY3419 (pSH1110). Plasmid pGLY3430 (pSH1115) is an integration vector that contains an expression cassette comprising the *P. pastoris* URA5 gene or transcription unit (PpURA5) flanked by lacZ repeats (lacZ repeat) flanked on one side with the 5' nucleotide sequence of the *P. pastoris* BMT1 gene (PBS1 5') and on the other side with the 3' nucleotide sequence of the *P. pastoris* BMT1 gene (PBS1 3')

Plasmid pGLY3419 (FIG. 8) is an integration vector that contains an expression cassette comprising the *P. pastoris* URA5 gene flanked by lacZ repeats flanked on one side with the 5' nucleotide sequence of the *P. pastoris* BMT1 gene (SEQ ID NO:31) and on the other side with the 3' nucleotide sequence of the *P. pastoris* BMT1 gene (SEQ ID NO:32). Plasmid pGLY3419 was linearized and the linearized plasmid transformed into strain YGLY16-3 to produce a number of strains in which the URA5 expression cassette has been inserted into the BMT1 locus by double-crossover homologous recombination. The strains YGLY6698 and YGLY6697 were selected from the strains produced and are prototrophic for uracil, adenine, histidine, proline, arginine, and tryptophan. The strains were then counterselected in the presence of 5-FOA to produce a number of strains now auxotrophic for uridine. Strains YGLY6720 and YGLY6719 were selected.

Figure 9:
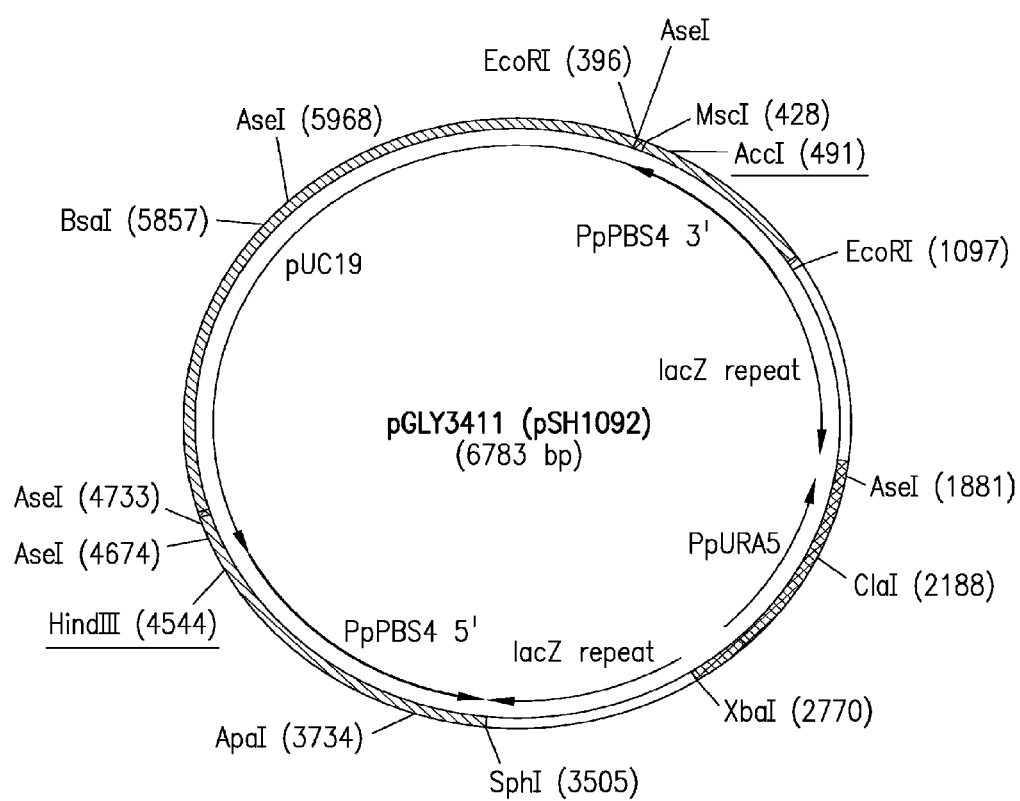
FIG. 9 shows a map of plasmid pGLY3411 (pSH1092). Plasmid pGLY3411 (pSH1092) is an integration vector that contains the expression cassette comprising the *P. pastoris* URA5 gene or transcription unit (PpURA5) flanked by lacZ repeats (lacZ repeat) flanked on one side with the 5' nucleotide sequence of the *P. pastoris* BMT4 gene (PpPBS4 5') and on the other side with the 3' nucleotide sequence of the *P. pastoris* BMT4 gene (PpPBS4 3').

Plasmid pGLY3411 (FIG. 9) is an integration vector that contains the expression cassette comprising the *P. pastoris* URA5 gene flanked by lacZ repeats flanked on one side with the 5' nucleotide sequence of the *P. pastoris* BMT4 gene (SEQ ID NO:33) and on the other side with the 3' nucleotide sequence of the *P. pastoris* BMT4 gene (SEQ ID NO:34). Plasmid pGLY3411 was linearized and the linearized plasmid transformed into YGLY6720 and YGLY6719 to produce a number of strains in which the URA5 expression cassette has been inserted into the BMT4 locus by double-crossover homologous recombination. Strain YGLY6749 and YGLY6743 were selected from the strains produced and are prototrophic for uracil, adenine, histidine, proline, arginine, and tryptophan. The strains were then counterselected in the presence of 5-FOA to produce a number of strains now auxotrophic for uridine of which strains YGLY7749 and YGLY6773 were selected.

Figure 10:
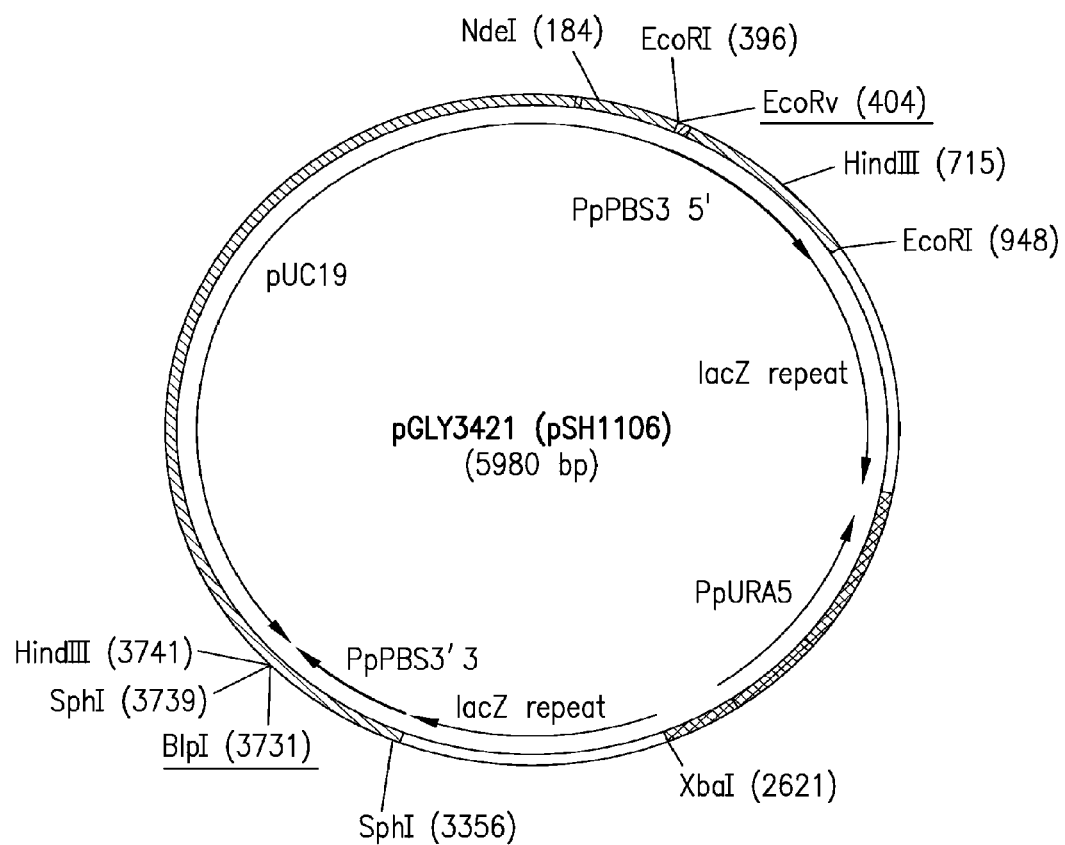
FIG. 10 shows a map of plasmid pGLY3421 (pSH1106). Plasmid pGLY4472 (pSH1186) contains an expression cassette comprising the *P. pastoris* URA5 gene or transcription unit (PpURA5) flanked by lacZ repeats (lacZ repeat) flanked on one side with the 5' nucleotide sequence of the *P. pastoris* BMT3 gene (PpPBS3 5') and on the other side with the 3' nucleotide sequence of the *P. pastoris* BMT3 gene (PpPBS3 3').

Plasmid pGLY3421 (FIG. 10) is an integration vector that contains an expression cassette comprising the *P. pastoris* URA5 gene flanked by lacZ repeats flanked on one side with the 5' nucleotide sequence of the *P. pastoris* BMT3 gene (SEQ ID NO:35) and on the other side with the 3' nucleotide sequence of the *P. pastoris* BMT3 gene (SEQ ID NO:36). Plasmid pGLY3419 was linearized and the linearized plasmid transformed into strain YGLY7749 and YGLY6773 to produce a number of strains in which the URA5 expression cassette has been inserted into the BMT1 locus by double-crossover homologous recombination. Strains YGLY7760 and YGLY7754 were selected from the strains produced and are prototrophic for uracil, adenine, histidine, proline, arginine, and tryptophan.

Figure 11:
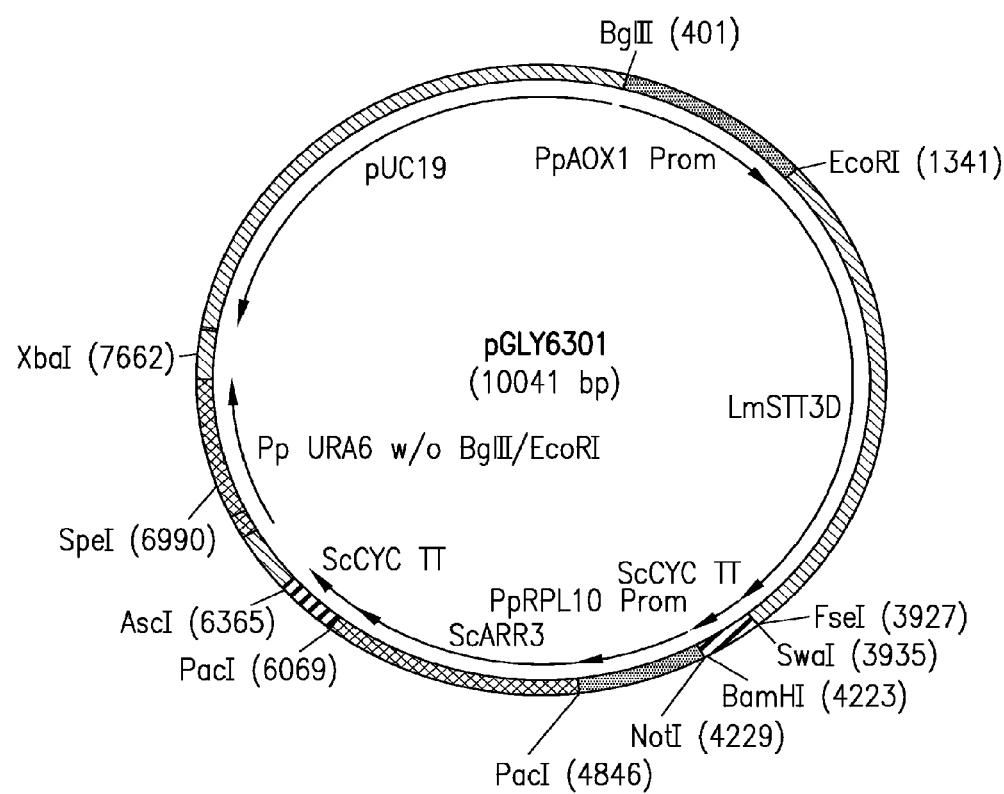
FIG. 11 shows a map of plasmid pGLY6301. Plasmid pGLY6301 is an integration plasmid that expresses the LmSTT3D and targets the URA6 locus in *P. pastoris*. The expression cassette encoding the LmSTT3D comprises a nucleic acid molecule encoding the LmSTT3D ORF codon-optimized for optimal expression in P. operably linked at the 5' end to a nucleic acid molecule that has the inducible *P. pastoris* AOX1 promoter sequence and at the 3' end to a nucleic acid molecule that has the *S. cerevisiae* CYC transcription termination sequence and for selection, the plasmid contains a nucleic acid molecule comprising the *S. cerevisiae* ARR3 gene to confer arsenite resistance.

Plasmid pGLY6301 (FIG. 11) is a roll-in integration plasmid that targets the URA6 locus in *P. pastoris*. The expression cassette encoding the LmSTT3D comprises a nucleic acid molecule encoding the LmSTT3D ORF codon-optimized for effective expression in *P. pastoris* (SEQ ID NO:37) operably linked at the 5' end to a nucleic acid molecule that has the inducible *P. pastoris* AOX1 promoter sequence (SEQ ID NO:8) and at the 3' end to a nucleic acid molecule that has the *S. cerevisiae* CYC transcription termination sequence (SEQ ID NO:12). For selecting transformants, the plasmid comprises an expression cassette encoding the *S. cerevisiae* ARR3 ORF in which the nucleic acid molecule encoding the ORF (SEQ ID NO:38) is operably linked at the 5' end to a nucleic acid molecule having the *P. pastoris* RPL10 promoter sequence (SEQ ID NO:39) and at the 3' end to a nucleic acid molecule having the *S. cerevisiae* CYC transcription termination sequence (SEQ ID NO:12). The plasmid further includes a nucleic acid molecule for targeting the URA6 locus (SEQ ID NO:40). Strain YGLY7760 was transformed with pGLY6301 to produce a number of strains of which strain YGLY26268 was selected.

Example 3

The strains capable of producing the various O-glycosylated CTP peptide-based insulin analogues may be grown as follows. The primary culture is prepared by inoculating two 2.8 liter (L) baffled Fernbach flasks containing 500 mL of BSGY media with a 2 mL Research Cell Bank of the relevant strain. After 48 hours of incubation, the cells are transferred to inoculate the bioreactor. The fermentation batch media contains: 40 g glycerol (Sigma Aldrich, St. Louis, Mo.), 18.2 g sorbitol (Acros Organics, Geel, Belgium), 2.3 g mono-basic potassium phosphate, (Fisher Scientific, Fair Lawn, N.J.) 11.9 g di-basic potassium phosphate (EMD, Gibbstown, N.J.), 10 g Yeast Extract (Sensient, Milwaukee, Wis.), 20 g Hy-Soy (Sheffield Bioscience, Norwich, N.Y.), 13.4 g YNB (BD, Franklin Lakes, N.J.), and $4 \times 10^{-3}$ g biotin (Sigma-Aldrich, St. Louis, Mo.) per liter of medium.

Fermentations may be conducted in 15 L dished-bottom glass autoclavable and 40 L SIP bioreactors (8 L & 20 L starting volume respectively) (Applikon, Foster City, Calif.).

The DasGip Protocol for growing the recombinant host cells is substantially as follows.

The inoculum seed flasks are inoculated from yeast patches (isolated from a single colony) on agar plates into 0.1 L of 4% BSGY (no maltitol) in a 0.5-L baffled flask. Seed flasks are grown at 180 rpm and 24° C. (Innova 44, New Brunswick Scientific) for 48 hours.

Cultivations are done in 1 L (fedbatch-pro, DASGIP BioTools) bioreactors. Vessels are charged with 0.54 L of 0.22 µm filtered 4% BSGY media (with 4 drops/L Sigma 204 antifoam) and autoclaved at 121° C. for 60 minutes. After sterilization and cooling; the aeration, agitation and temperatures are set to 0.7 vvm, 400 rpm and 24° C., respectively. The pH is adjusted to and controlled at 6.5 using 30% ammonium hydroxide.

Inoculation of a prepared bioreactor is done aseptically with 60 mL from a seed flask. Agitation is ramped to maintain 20% dissolved oxygen (DO) saturation. After the initial glycerol charge is consumed, denoted by a sharp increase in the dissolved oxygen, a 50% w/w glycerol solution containing 5 mg/L biotin and 32.3 mg/L (or 10.8 mg/L) PMTi-4 is triggered to feed at 3.68 mL/hr for eight hours. During the glycerol fed-batch phase 0.375 mL of PTM2 salts are injected manually. Completion of the glycerol fed-batch is followed by a 0.5 hour starvation period and initiation of the induction phase. A continuous feed of a 50% v/v methanol solution containing 2.5 mg/L biotin and 6.25 mL/L PTM2 salts is started at a flat rate of 2.16 mL/hour. Injections of 0.25 mL of 1.9 mg/mL (1×) or 0.63 mg/mL (⅓×) PMTi-4 (in methanol) are added after each 24 hours of induction. In general, individual fermentations are harvested within 36-110 hours of induction. The culture broth is clarified by centrifugation (Sorvall Evolution RC, Thermo Scientific) at 8500 rpm for 40 min and the resulting supernatant was submitted for purification.

TABLE 2

| 4% BSGY with maltitol | |
|---|---|
| Component | Concentration (g/L) |
| KH$_2$PO$_4$ (monobasic) | 11.9 |
| K$_2$HPO$_4$ (dibasic) | 2.5 |
| maltitol | 50 |
| Yeast Extract | 10 |
| Soytone | 20 |
| Glycerol | 40 |
| YNB | 13.4 |
| Biotin | 20 (ml/L) |
| Anti-foam | 8 drops/L* |

Solution to be autoclaved once made

TABLE 3

PTM2 Salts

| Component | Concentration (g/L) |
|---|---|
| $CuSO_4$—$5H_2O$ | 1.50 |
| NaI | 0.08 |
| $MnSO_4$—$H_2O$ | 1.81 |
| $H_3BO_4$ | 0.02 |
| $FeSO_4$—$7H_2O$ | 6.50 |
| $ZnCl_2$ | 2.00 |
| $CoCl_2$—$6H_2O$ | 0.50 |
| $Na_2MoO_4$—$2H_2O$ | 0.20 |
| Biotin (dry stock) | 0.20 |
| 98% $H_2SO_4$ | 5 mL/L |

Dissolve in 80% of the desired total volume of DI water.
Once dissolved make up to final total volume with DI water
Filter under vacuum through 0.22 micron filter into sterile bottle.
Label with Solution Name, Batch Number, and Date. Store at 4° C.

PMTi-4 is a PMT inhibitor disclosed in U.S. Published Application No. 20110076721 as Example 4 compound and has the structure

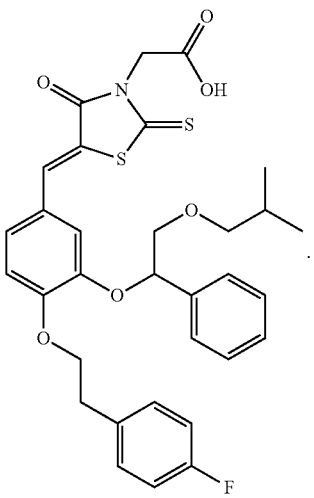 [SMILES: CC(C)COCC(Oc1cc(/C=C2\SC(=S)N(CC(=O)O)C2=O)ccc1OCCc1ccc(F)cc1)c1ccccc1]

Example 4

In this example, a single-chain insulin molecule comprising an O-glycosylated CTP connecting peptide (SCI:C peptide CTP with a K at the junction of the CTP peptide and the a-chain; See SEQ ID NO:45) was produced in *Pichia pastoris* host cells grown in the presence of a Pmti-4 at 1× (Das Gip Run # D113901) or ⅓× (Das Gip run # D113702) as described above.

To purify the O-glycosylated CTP peptide-based single-chain insulin (SCI) analogues, supernatant medium is clarified by centrifugation for 15 min at 13,000 g in a Sorvall Evolution RC (kendo, Asheville, N.C.), followed by pH adjustment to 4.5 and filtered using a Sartopore 2 0.2 μm (Sartorius Biotech Inc). The filtrate is loaded to a Capto MMC column, a multimodal cation exchanger chromatography resin (GE Healthcare, Piscataway, N.J.) adjusted to the same pH. The pool obtained after elution at pH 7 is collected and loaded into a RESOURCE RPC column (Amersham Biosciences, Piscataway, N.J.), a reverse-phase column chromatography packed with SOURCE 15RPC, a polymeric, reversed-phase chromatography medium based on rigid, monodisperse 15 μm beads made of polystyrene/divinylbenzene. The resin is equilibrated at pH 3.5 and eluted using step elution from 12.5% to 20% 2-propanol at the same pH.

Quadrupole Time-of-Flight (Q-TOF) Mass Spectrometry (MS) Analysis

Protein quality and glycosylation of insulin analogs are analyzed using a liquid chromatography-mass spectrometry (LC-MS) system that comprises the Agilent Q-TOF 6520 mass spectrometer (Santa Clara, Calif.), Agilent 1200 HPLC system, and Waters MassPREP™ on-line desalting cartridge (Milford, Mass.). The mass spectrometer is operated in a positive mode with collected mass range form 600-2700 m/z in profile format. The temperature of dual electrospray ionization (ESI) source is set at 350° C., the drying gas was set at 13 L/hour, the nebulizer is set at 45 psig (0.41 MPa). The voltages for Vcap, Fragmentor, and Skimmer are set at 4500, 150, and 30 respectively. Insulin analogue samples are loaded onto the LC-MS and desalted with 100% Buffer A (0.1% formic in water) flowing at 1 mL/min for two minutes and then eluted with 100% Buffer B (0.1% formic acid, 10% water, and 90% acetonitrile) at 0.4 mL/minute for five minutes. The collected MS data are deconvoluted through Mass Hunter BioConfirm software.

FIG. 14 shows Q-TOF MS analysis of D113901 and D113702. The top panels show that the predominant O-glycosylated species corresponds to a molecule having six mannose residues thereon and is at position 9899.5. Each successive lesser peak moving to the right corresponds to an O-glycosylated species with successively an additional mannose residue. For example, the peak at position 10509.9 corresponds to a species with 11 mannose residues and the peak at position 11482.4 corresponds to a species with 17 mannose residues. The lower panels show the profile after treating the insulin molecules with PNGase (PNG). PNGase will remove N-glycans from glycoproteins; however, O-glycans are refractory to PNGase activity. The lower panel shows that the Q-TOF MS profile does not change following PNGase treatment, which indicates that the profile is showing O-glycans and does not contain any N-glycans.

Keeping in mind that the maximum chain length for an O-glycan in the host cells used to produce the O-glycosylated CTP peptide-based insulin analogues is four mannose residues (mannotetrose) and the CTP peptide has four O-glycosylation sites, the six mannose residues of the predominant species may be distributed over the four O-glycosylation sites as follows: (i) mannotetrose occupying one site and mannobiose occupying one of the other three sites, (ii) mannotetrose occupying one site and mannose occupying two of the other three sites, (iii) mannotriose occupying one site and a mannose residue occupying each of the other three sites, (iv) mannotriose occupying one site and mannotriose occupying one of the other three sites, (v) mannotriose occupying one site, mannobiose occupying a second site, and mannose occupying a third site, (vi) mannobiose occupying each of three sites, or (vii) mannobiose occupying two sites and mannose occupying each of the other two sites.

The table in FIG. 14 shows that mole mannitol per mole protein in the compositions is about 2.3 to 2.5 indicating that there are about 2-3 moles of O-glycan per mole of protein. The table also shows that the predominant O-glycan in the compositions is mannotriose with mannotetrose the second most abundant species and minor amounts of mannose and mannobiose. The table also shows that a three-fold increase in the Pmtp inhibitors had little affect on O-glycan occupancy or O-glycan chain length.

Table 4 summarizes the O-glycan analysis of D113901 and D113702 above compared to Humulin (recombinant human insulin) and to D113903 having an N-spacer CTP. The table shows that for the species not treated with an α1,2-mannosidase, the predominant O-glycan is mannotriose with mannotetrose the second most abundant O-glycan. The table also shows that D113901 treated with a *T. reesei* chimeric α1,2-mannosidase in vitro provides compositions where the predominant O-glycan chain length was one mannose residue with no detectable mannobiose, mannotriose, or mannotetrose.

TABLE 4

| Insulin Sample | O-glycan Occupancy (mol/mol) | Chain Length (% man1/2/3/4) | Binding to insulin receptor IC50 (nM) |
|---|---|---|---|
| Humulin | — | — | 0.4 |
| D113901 (SCI with C-peptide CTP + K and O-glycosylated) | 2.5 | 5/6/66/33 | 8.7 |
| D113702 (SCI with C-peptide CTP + K and O-glycosylated) | 2.3 | 4/6/63/27 | 11.4 |
| D113903 (SCI with N-spacer CTP and O-glycosylated) | 1.8 | 1/4/63/32 | Not tested |
| D113901 (SCI with C-peptide CTP + K and O-glycosylated) treated with α1,2-mannosidase | 2.6 | 100/0/0 | 4.1 |

Example 5

To study the potential for the O-glycosylated CTP peptide based insulin analogues to display saccharide responsiveness or sensitivity, C57BL/6 mice at 12 to 13 weeks of age were fasted two hours before being dosed with O-glycosylated CTP peptide based analogues D113901 or D113702 in saline by subcutaneous (s.c.) injection. At the same time, animals received intraperitoneal (i.p.) administration of α-methylmannose (α-MM) solution (21.5% w/v in saline, 10 ml/kg) or vehicle. Blood glucose was measured using a glucometer (OneTouch Ultra LifeScan; Milpitas, Calif.) at time 0 and then 30, 60, 90, and 120 minutes post injection. Glucose Area-Over-the-Curve (AOC) was calculated using values normalized to glucose of time 0 (as 100%). Insulin was measured with the iso-insulin ELISA kit. The results shown in FIG. 15, FIG. 16, and FIG. 17 and indicate that the molecules are responsive or sensitive to the serum concentration of α-MM.

Example 6

To provide a *Pichia pastoris* strain capable of producing glycoproteins that have O-glycans that are predominantly one mannose residue in length, Strain YGL7760 or YGLY26268 is transformed with a plasmid vector comprising expression cassettes encoding (1) the *T. reesei* α-1,2-mannosidase catalytic domain fused at the N-terminus to *S. cerevisiae* αMATpre signal peptide (aMATTrMan) to target the chimeric protein to the secretory pathway and secretion from the cell and (2) the *P. pastoris* URA5 gene or transcription unit. The expression cassette encoding the aMAT-TrMan comprises a nucleic acid molecule encoding the *T. reesei* catalytic domain (SEQ ID NO:87) fused at the 5' end to a nucleic acid molecule encoding the *S. cerevisiae* αMATpre signal peptide (SEQ ID NO:85 encoding amino acid sequence SEQ ID NO:86), which is operably linked at the 5' end to a nucleic acid molecule comprising the *P. pastoris* AOX1 promoter and at the 3' end to a nucleic acid molecule comprising the *S. cerevisiae* CYC transcription termination sequence. The URA5 expression cassette comprises a nucleic acid molecule comprising the *P. pastoris* URA5 gene or transcription unit flanked by nucleic acid molecules comprising lacZ repeats. The cassette further provides nucleotide sequences to target the vector to a particular locus in the *Pichia pastoris* genome. For example, the two tandem cassettes may be flanked on one side by a nucleic acid molecule comprising a nucleotide sequence from the 5' region of the PRO1 gene (SEQ ID NO:88) and on the other side by a nucleic acid molecule comprising a nucleotide sequence from the 3' region of the PRO1 gene (SEQ ID NO:89). Strains comprising the expression cassette integrated into the genome may be selected and transformed with a plasmid vector encoding a CTP peptide-based insulin or insulin analogue.

Expression of a CTP peptide-based insulin or insulin analogue in the above strain under conditions as described above produces an O-glycosylated CTP peptide-based insulin or insulin analogue wherein the predominant O-glycan structure is mannose.

SEQUENCES

Sequences that were used to produce some of the strains disclosed in the Examples are provided in the following table.

Table of Sequences

| SEQ ID NO: | Description | Sequence |
|---|---|---|
| 1 | Human CTP peptide | SSSSKAPPPSLPSPSRLPGPSDTPILPQ |
| 2 | Human insulin A chain | GIVEQCCTSICSLYQLENYCN |
| 3 | B-chain peptide core sequence | HLCGSHLVEALYLVCGERGFF |
| 4 | Human insulin B chain | FVNQHLCGSHLVEALYLVCGERGFFYTPKT |
| 5 | Human insulin C chain | RREAEDLQVGQVELGGGPGAGSLQPLALEGSLQKR |

Table of Sequences

| SEQ ID NO: | Description | Sequence |
|---|---|---|
| 6 | Human pre-proinsulin | MALWMRLLPLLALLALWGPDPAAAFVNQHLCGSHLVEALYLVCGE RGFFYTPKTRREAEDLQVGQVELGGGPGAGSLQPLALEGSLQKR GIVEQCCTSICSLYQLENYCN |
| 7 | Sc alpha mating factor signal sequence and pro-peptide | MRFPSIFTAVLFAASSALAAPVNTTTEDETAQIPAEAVIGYLDLEGDF DVAVLPFSNSTNNGLLFINTTIASIAAKEEGVSLEKR |
| 8 | Pp AOX1 promoter | AACATCCAAAGACGAAAGGTTGAATGAAACCTTTTTGCCATCCG ACATCCACAGGTCCATTCTCACACATAAGTGCCAAACGCAACAG GAGGGGATACACTAGCAGCAGACCGTTGCAAACGCAGGACCTC CACTCCTCTTCTCCTCAACACCCACTTTTGCCATCGAAAAACCAG CCCAGTTATTGGGCTTGATTGGAGCTCGCTCATTCCAATTCCTT CTATTAGGCTACTAACACCATGACTTTATTAGCCTGTCTATCCTG GCCCCCCTGGCGAGGTTCATGTTTGTTTATTTCCGAATGCAACA AGCTCCGCATTACACCCGAACATCACTCCAGATGAGGGCTTTCT GAGTGTGGGGTCAAATAGTTTCATGTTCCCCAAATGGCCCAAAA CTGACAGTTTAAACGCTGTCTTGGAACCTAATATGACAAAAGCG TGATCTCATCCAAGATGAACTAAGTTTGGTTCGTTGAAATGCTAA CGGCCAGTTGGTCAAAAAGAAACTTCCAAAAGTCGGCATACCGT TTGTCTTGTTTGGTATTGATTGACGAATGCTCAAAAATAATCTCA TTAATGCTTAGCGCAGTCTCTCTATCGCTTCTGAACCCCGGTGC ACCTGTGCCGAAACGCAAATGGGGAAACACCCGCTTTTTGGATG ATTATGCATTGTCTCCACATTGTATGCTTCCAAGATTCTGGTGGG AATACTGCTGATAGCCTAACGTTCATGATCAAAATTTAACTGTTC TAACCCCTACTTGACAGCAATATATAAACAGAAGGAAGCTGCCC TGTCTTAAACCTTTTTTTTTATCATCATTATTAGCTTACTTTCATAA TTGCGACTGGTTCCAATTGACAAGCTTTTGATTTTAACGACTTTT AACGACAACTTGAGAAGATCAAAAAACAACTAATTATTCGAAACG |
| 9 | PpAOX1 TT | TCAAGAGGATGTCAGAATGCCATTTGCCTGAGAGATGCAGGCTT CATTTTGATACTTTTTTATTTGTAACCTATATAGTATAGGATTTTTT TTGTCATTTTGTTTCTTCTCGTACGAGCTTGCTCCTGATCAGCCT ATCTCGCAGCTGATGAATATCTTGTGGTAGGGGTTTGGGAAAAT CATTCGAGTTTGATGTTTTTCTTGGTATTTCCCACTCCTCTTCAG AGTACAGAAGATTAAGTGAGACGTTCGTTTGTGCA |
| 10 | Sequence of the Sh ble ORF (Zeocin resistance marker): | ATGGCCAAGTTGACCAGTGCCGTTCCGGTGCTCACCGCGCGCG ACGTCGCCGGAGCGGTCGAGTTCTGGACCGACCGGCTCGGGT TCTCCCGGGACTTCGTGGAGGACGACTTCGCCGGTGTGGTCCG GGACGACGTGACCCTGTTCATCAGCGCGGTCCAGGACCAGGTG GTGCCGGACAACACCCTGGCCTGGGTGTGGGTGCGCGGCCTG GACGAGCTGTACGCCGAGTGGTCGGAGGTCGTGTCCACGAACT TCCGGGACGCCTCCGGGCCGGCCATGACCGAGATCGGCGAGC AGCCGTGGGGGCGGGAGTTCGCCCTGCGCGACCCGGCCGGCA ACTGCGTGCACTTCGTGGCCGAGGAGCAGGACTGA |
| 11 | ScTEF1 promoter | GATCCCCCACACACCATAGCTTCAAAATGTTTCTACTCCTTTTTT ACTCTTCCAGATTTTCTCGGACTCCGCGCATCGCCGTACCACTT CAAAACACCCAAGCACAGCATACTAAATTTCCCCTCTTTCTTCCT CTAGGGTGTCGTTAATTACCCGTACTAAAGGTTTGGAAAAGAAA AAAGAGACCGCCTCGTTTCTTTTTCTTCGTCGAAAAAGGCAATAA AAATTTTTATCACGTTTCTTTTTCTTGAAAATTTTTTTTTTGATTT TTTTCTCTTTCGATGACCTCCCATTGATATTTAAGTTAATAAACGG TCTTCAATTTCTCAAGTTTCAGTTTCATTTTTCTTGTTCTATTACAA CTTTTTTTACTTCTTGCTCATTAGAAAGAAAGCATAGCAATCTAAT CTAAGTTTTAATTACAAA |
| 12 | ScCYC TT | ACAGGCCCCTTTTCCTTTGTCGATATCATGTAATTAGTTATGTCA CGCTTACATTCACGCCCTCCTCCCACATCCGCTCTAACCGAAAA GGAAGGAGTTAGACAACCTGAAGTCTAGGTCCCTATTTATTTTTT TTAATAGTTATGTTAGTATTAAGAACGTTATTTATATTTCAAATTTT TCTTTTTTTTCTGTACAAACGCGTGTACGCATGTAACATTATACT GAAAACCTTGCTTGAGAAGGTTTTGGGACGCTCGAAGGCTTTAA TTTGCAAGCTGCCGGCTCTTAAG |
| 13 | Sequence of the PpTRP2 gene integration locus: | GGTTTCTCAATTACTATATACTACTAACCATTTACCTGTAGCGTAT TTCTTTTCCCTCTTCGCGAAAGCTCAAGGGCATCTTCTTGACTCA TGAAAAATATCTGGATTTCTTCTGACAGATCATCACCCTTGAGCC CAACTCTCTAGCCTATGAGTGTAAGTGATAGTCATCTTGCAACA GATTATTTTGGAACGCAACTAACAAAGCAGATACACCCTTCAGC |

| SEQ ID NO: | Description | Sequence |
|---|---|---|
| | | AGAATCCTTTCTGGATATTGTGAAGAATGATCGCCAAAGTCACA<br>GTCCTGAGACAGTTCCTAATCTTTACCCCATTTACAAGTTCATCC<br>AATCAGACTTCTTAACGCCTCATCTGGCTTATATCAAGCTTACCA<br>ACAGTTCAGAAACTCCCAGTCCAAGTTTCTTGCTTGAAAGTGCG<br>AAGAATGGTGACACCGTTGACAGGTACACCTTTATGGGACATTC<br>CCCCAGAAAAATAATCAAGACTGGGCCTTTAGAGGGTGCTGAAG<br>TTGACCCCTTGGTGCTTCTGGAAAAAGAACTGAAGGGCACCAGA<br>CAAGCGCAACTTCCTGGTATTCCTCGTCTAAGTGGTGGTGCCAT<br>AGGATACATCTCGTACGATTGTATTAAGTACTTTGAACCAAAAC<br>TGAAAGAAAACTGAAAGATGTTTTGCAACTTCCGGAAGCAGCTT<br>TGATGTTGTTCGACACGATCGTGGCTTTTGACAATGTTTATCAAA<br>GATTCCAGGTAATTGGAAACGTTTCTCTATCCGTTGATGACTCG<br>GACGAAGCTATTCTTGAGAAATATTATAAGACAAGAGAAGAAGT<br>GGAAAAGATCAGTAAAGTGGTATTTGACAATAAAACTGTTCCCTA<br>CTATGAACAGAAAGATATTATTCAAGGCCAAACGTTCACCTCTAA<br>TATTGGTCAGGAGGGTATGAAAACCATGTTCGCAAGCTGAAAG<br>AACATATTCTGAAAGGAGACATCTTCCAAGCTGTTCCCTCTCAAA<br>GGGTAGCCAGGCCGACCTCATTGCACCCTTTCAACATCTATCGT<br>CATTTGAGAACTGTCAATCCTTCTCCATACATGTTCTATATTGAC<br>TATCTAGACTTCCAAGTTGTTGGTGCTTCACCTGAATTACTAGTT<br>AAATCCGACAACAACAACAAAATCATCACACATCCTATTGCTGGA<br>ACTCTTCCCAGAGGTAAAACTATCGAAGAGGACGACAATTATGC<br>TAAGCAATTGAAGTCGTCTTTGAAAGACAGGGCCGAGCACGTCA<br>TGCTGGTAGATTTGGCCAGAAATGATATTAACCGTGTGTGTGAG<br>CCCACCAGTACCACGGTTGATCGTTTATTGACTGTGGAGAGATT<br>TTCTCATGTGATGCATCTTGTGTCAGAAGTCAGTGGAACATTGA<br>GACCAAACAAGACTCGCTTCGATGCTTTCAGATCCATTTTCCCA<br>GCAGGAACCGTCTCCGGTGCTCCGAAGGTAAGAGCAATGCAAC<br>TCATAGGAGAATTGGAAGGAGAAAAGAGAGGTGTTTATGCGGG<br>GGCCGTAGGACACTGGTCGTACGATGGAAAATCGATGGACACA<br>TGTATTGCCTTAAGAACAATGGTCGTCAAGGACGGTGTCGCTTA<br>CCTTCAAGCCGGAGGTGGAATTGTCTACGATTCTGACCCCTATG<br>ACGAGTACATCGAAACCATGAACAAAATGAGATCCAACAATAAC<br>ACCATCTTGGAGGCTGAGAAAATCTGGACCGATAGGTTGGCCA<br>GAGACGAGAATCAAAGTGAATCCGAAGAAAACGATCAATGAACG<br>GAGGACGTAAGTAGGAATTTATG |
| 14 | *S. cerevisiae* invertase gene (ScSUC2) ORF underlined | AGGCCTCGCAACAACCTATAATTGAGTTAAGTGCCTTTCCAAGC<br>TAAAAAGTTTGAGGTTATAGGGGCTTAGCATCCACACGTCACAA<br>TCTCGGGTATCGAGTATAGTATGTAGAATTACGGCAGGAGGTTT<br>CCCAATGAACAAAGGACAGGGGCACGGTGAGCTGTCGAAGGTA<br>TCCATTTTATCATGTTTCGTTTGTACAAGCACGACATACTAAGAC<br>ATTTACCGTATGGGAGTTGTTGTCCTAGCGTAGTTCTCGCTCCC<br>CCAGCAAAGCTCAAAAAGTACGTCATTTAGAATAGTTTGTGAG<br>CAAATTACCAGTCGGTATGCTACGTTAGAAAGGCCCACAGTATT<br>CTTCTACCAAAGGCGTGCCTTTGTTGAACTCGATCCATTATGAG<br>GGCTTCCATTATTCCCCGCATTTTTATTACTCTGAACAGGAATAA<br>AAAGAAAAAACCCAGTTTAGGAAATTATCCGGGGCGAAGAAAT<br>ACGCGTAGCGTTAATCGACCCCACGTCCAGGGTTTTTCCATGGA<br>GGTTTCTGGAAAAACTGACGAGGAATGTGATTATAAATCCCTTTA<br>TGTGATGTCTAAGACTTTTAAGGTACGCCCGATGTTTGCCTATTA<br>CCATCATAGAGACGTTTCTTTTCGAGGAATGCTTAAACGACTTTG<br>TTTGACAAAAATGTTGCCTAAGGGCTCTATAGTAAACCATTTGGA<br>AGAAAGATTTGACGACTTTTTTTTTTTGGATTTCGATCCTATAATC<br>CTTCCTCCTGAAAAGAAACATATAAATAGATATGTATTATTCTTCA<br>AAACATTCTCTTGTTCTTGTGCTTTTTTTTACCATATATCTTACTT<br>TTTTTTTTCTCTCAGAGAAACAAGCAAAACAAAAAGCTTTTCTTTT<br>CACTAACGTATATGATGCTTTTGCAAGCTTTCCTTTTCCTTTTGG<br>CTGGTTTTGCAGCCAAAATATCTGCATCAATGACAAACGAAACTA<br>GCGATAGACCTTTGGTCCACTTCACACCCAACAAGGGCTGGATG<br>AATGACCCAAATGGGTTGTGGTACGATGAAAAAGATGCCAAATG<br>GCATCTGTACTTTCAATACAACCCAAATGACACCGTATGGGGTA<br>CGCCATTGTTTGGGGCCATGCTACTTCCGATGATTTGACTAATT<br>GGGAAGATCAACCCATTGCTATCGCTCCCAAGCGTAACGATTCA<br>GGTGCTTTCTCTGGCTCCATGGTGGTTGATTACAACAACACGAG<br>TGGGTTTTTCAATGATACTATTGATCCAAGACAAAGATGCGTTGC<br>GATTTGGACTTATAACACTCCTGAAAGTGAAGAGCAATACATTAG<br>CTATTCTCTTGATGGTGGTTACACTTTTACTGAATACCAAAAGAA<br>CCCTGTTTTAGCTGCCAACTCCACTCAATTCAGAGATCCAAAGG<br>TGTTCTGGTATGAACCTTCTCAAAAATGGATTATGACGGCTGCC<br>AAATCACAAGACTACAAAATTGAAATTTACTCCTCTGATGACTTG<br>AAGTCCTGGAAGCTAGAATCTGCATTTGCCAATGAAGGTTTCTTA<br>GGCTACCAATACGAATGTCCAGGTTTGATTGAAGTCCCAACTGA |

Table of Sequences

| SEQ ID NO: | Description | Sequence |
|---|---|---|
| | | GCAAGATCCTTCCAAATCTTATTGGGTCATGTTTATTTCTATCAA<br>CCCAGGTGCACCTGCTGGCGGTTCCTTCAACCAATATTTTGTTG<br>GATCCTTCAATGGTACTCATTTTGAAGCGTTTGACAATCAATCTA<br>GAGTGGTAGATTTTGGTAAGGACTACTATGCCTTGCAAACTTTCT<br>TCAACACTGACCCAACCTACGGTTCAGCATTAGGTATTGCCTGG<br>GCTTCAAACTGGGAGTACAGTGCCTTTGTCCCAACTAACCCATG<br>GAGATCATCCATGTCTTTGGTCCGCAAGTTTTCTTTGAACACTGA<br>ATATCAAGCTAATCCAGAGACTGAATTGATCAATTTGAAAGCCGA<br>ACCAATATTGAACATTAGTAATGCTGGTCCCTGGTCTCGTTTTGC<br>TACTAACACAACTCTAACTAAGGCCAATTCTTACAATGTCGATTT<br>GAGCAACTCGACTGGTACCCTAGAGTTTGAGTTGGTTTACGCTG<br>TTAACACCACACAAACCATATCCAAATCCGTCTTTGCCGACTTAT<br>CACTTTGGTTCAAGGGTTTAGAAGATCCTGAAGAATATTTGAGAA<br>TGGGTTTTGAAGTCAGTGCTTCTTCCTTCTTTTTGGACCGTGGTA<br>ACTCTAAGGTCAAGTTTGTCAAGGAGAACCCATATTTCACAAACA<br>GAATGTCTGTCAACAACCAACCATTCAAGTCTGAGAACGACCTA<br>AGTTACTATAAAGTGTACGGCCTACTGGATCAAAACATCTTGGAA<br>TTGTACTTCAACGATGGAGATGTGGTTTCTACAAATACCTACTTC<br>ATGACCACCGGTAACGCTCTAGGATCTGTGAACATGACCACTGG<br>TGTCGATAATTTGTTCTACATTGACAAGTTCCAAGTAAGGGAAGT<br>AAAATAGAGGTTATAAAACTTATTGTCTTTTTTATTTTTTTCAAAA<br>GCCATTCTAAAGGGCTTTAGCTAACGAGTGACGAATGTAAAACT<br>TTATGATTTCAAAGAATACCTCCAAACCATTGAAAATGTATTTTTA<br>TTTTTATTTTCTCCCGACCCCAGTTACCTGGAATTTGTTCTTTATG<br>TACTTTATATAAGTATAATTCTCTTAAAAATTTTTACTACTTTGCAA<br>TAGACATCATTTTTTCACGTAATAAACCCACAATCGTAATGTAGT<br>TGCCTTACACTACTAGGATGGACCTTTTTGCCTTTATCTGTTTTG<br>TTACTGACACAATGAAACCGGGTAAAGTATTAGTTATGTGAAAAT<br>TTAAAAGCATTAAGTAGAAGTATACCATATTGTAAAAAAAAAAG<br>CGTTGTCTTCTACGTAAAAGTGTTCTCAAAAAGAAGTAGTGAGG<br>GAAATGGATACCAAGCTATCTGTAACAGGAGCTAAAAAATCTCA<br>GGGAAAAGCTTCTGGTTTGGGAAACGGTCGAC |
| 15 | Sequence of the 5'-Region used for knock out of PpURA5: | ATCGGCCTTTGTTGATGCAAGTTTTACGTGGATCATGGACTAAG<br>GAGTTTTATTTGGACCAAGTTCATCGTCCTAGACATTACGGAAAG<br>GGTTCTGCTCCTCTTTTTGGAAACTTTTTGGAACCTCTGAGTATG<br>ACAGCTTGGTGGATTGTACCCATGGTATGGCTTCCTGTGAATTT<br>CTATTTTTTCTACATTGGATTCACCAATCAAAACAAATTAGTCGC<br>CATGGCTTTTTGGCTTTTGGGTCTATTTGTTTGGACCTTCTTGGA<br>ATATGCTTTGCATAGATTTTTGTTCCACTTGGACTACTATCTTCCA<br>GAGAATCAAATTGCATTTACCATTCATTTCTTATTGCATGGGATA<br>CACCACTATTTACCAATGGATAAATACAGATTGGTGATGCCACCT<br>ACACTTTTCATTGTACTTTGCTACCCAATCAAGACGCTCGTCTTT<br>TCTGTTCTACCATATTACATGGCTTGTTCTGGATTTGCAGGTGGA<br>TTCCTGGGCTATATCATGTATGATGTCACTCATTACGTTCTGCAT<br>CACTCCAAGCTGCCTCGTTATTTCCAAGAGTTGAAGAAATATCAT<br>TTGGAACATCACTACAAGAATTACGAGTTAGGCTTTGGTGTCACT<br>TCCAAATTCTGGGACAAAGTCTTTGGGACTTATCTGGGTCCAGA<br>CGATGTGTATCAAAAGACAAATTAGAGTATTTATAAAGTTATGTA<br>AGCAAATAGGGGCTAATAGGGAAAGAAAAATTTTGGTTCTTTATC<br>AGAGCTGGCTCGCGCGCAGTGTTTTTCGTGCTCCTTTGTAATAG<br>TCATTTTTGACTACTGTTCAGATTGAAATCACATTGAAGATGTCA<br>CTCGAGGGGTACCAAAAAAGGTTTTTGGATGCTGCAGTGGCTTC<br>GC |
| 16 | Sequence of the 3'-Region used for knock out of PpURA5: | GGTCTTTTCAACAAAGCTCCATTAGTGAGTCAGCTGGCTGAATC<br>TTATGCACAGGCCATCATTAACAGCAACCTGGAGATAGACGTTG<br>TATTTGGACCAGCTTATAAAGGTATTCCTTTGGCTGCTATTACCG<br>TGTTGAAGTTGTACGAGCTCGGCGGCAAAAAATACGAAAATGTC<br>GGATATGCGTTCAATAGAAAAGAAAAGAAAGACCACGGAGAAGG<br>TGGAAGCATCGTTGGAGAAAGTCTAAAGAATAAAAGAGTACTGA<br>TTATCGATGATGTGATGACTGCAGGTACTGCTATCAACGAAGCA<br>TTTGCTATAATTGGAGCTGAAGGTGGGAGAGTTGAAGGTAGTAT<br>TATTGCCCTAGATAGAATGGAGACTACAGGAGATGACTCAAATA<br>CCAGTGCTACCCAGGCTGTTAGTCAGAGATATGGTACCCCTGTC<br>TTGAGTATAGTGACATTGGACCATATTGTGGCCCATTTGGGCGA<br>AACTTTCACAGCAGACGAGAAATCTCAAATGGAAACGTATAGAA<br>AAAAGTATTTGCCCAAATAAGTATGAATCTGCTTCGAATGAATGA<br>ATTAATCCAATTATCTTCTCACCATTATTTTCTTCTGTTTCGGAGC<br>TTTGGGCACGGCGGCGGGTGGTGCGGGCTCAGGTTCCCTTTCA<br>TAAACAGATTTAGTACTTGGATGCTTAATAGTGAATGGCGAATGC<br>AAAGGAACAATTTCGTTCATCTTTAACCCTTTCACTCGGGGTACA<br>CGTTCTGGAATGTACCCGCCCTGTTGCAACTCAGGTGGACCGG |

Table of Sequences

| SEQ ID NO: | Description | Sequence |
|---|---|---|
| | | GCAATTCTTGAACTTTCTGTAACGTTGTTGGATGTTCAACCAGAA ATTGTCCTACCAACTGTATTAGTTTCCTTTTGGTCTTATATTGTC ATCGAGATACTTCCCACTCTCCTTGATAGCCACTCTCACTCTTCC TGGATTACCAAAATCTTGAGGATGAGTCTTTTCAGGCTCCAGGA TGCAAGGTATATCCAAGTACCTGCAAGCATCTAATATTGTCTTTG CCAGGGGGTTCTCCACACCATACTCCTTTTGGCGCATGC |
| 17 | Sequence of the PpURA5 auxotrophic marker: | TCTAGAGGGACTTATCTGGGTCCAGACGATGTGTATCAAAAGAC AAATTAGAGTATTTATAAAGTTATGTAAGCAAATAGGGGCTAATA GGGAAAGAAAAATTTTGGTTCTTTATCAGAGCTGGCTCGCGCGC AGTGTTTTTCGTGCTCCTTTGTAATAGTCATTTTTGACTACTGTTC AGATTGAAATCACATTGAAGATGTCACTGGAGGGGTACCAAAAA AGGTTTTTGGATGCTGCAGTGGCTTCGCAGGCCTTGAAGTTTGG AACTTTCACCTTGAAAAGTGGAAGACAGTCTCCATACTTCTTTAA CATGGGTCTTTTCAACAAAGCTCCATTAGTGAGTCAGCTGGCTG AATCTTATGCTCAGGCCATCATTAACAGCAACCTGGAGATAGAC GTTGTATTTGGACCAGCTTATAAAGGTATTCCTTTGGCTGCTATT ACCGTGTTGAAGTTGTACGAGCTGGGCGGCAAAAAATACGAAAA TGTCGGATATGCGTTCAATAGAAAAGAAAAGAAAGACCACGGAG AAGGTGGAAGCATCGTTGGAGAAAGTCTAAAGAATAAAAGAGTA CTGATTATCGATGATGTGATGACTGCAGGTACTGCTATCAACGA AGCATTTGCTATAATTGGAGCTGAAGGTGGGAGAGTTGAAGGTT GTATTATTGCCCTAGATAGAATGGAGACTACAGGAGATGACTCA AATACCAGTGCTACCCAGGCTGTTAGTCAGAGATATGGTACCCC TGTCTTGAGTATAGTGACATTGGACCATATTGTGGCCCATTTGG GCGAAACTTTCACAGCAGACGAGAAATCTCAAATGGAAACGTAT AGAAAAAAGTATTTGCCCAAATAAGTATGAATCTGCTTCGAATGA ATGAATTAATCCAATTATCTTCTCACCATTATTTTCTTCTGTTTCG GAGCTTTGGGCACGGCGGCGGATCC |
| 18 | Sequence of the part of the Ec lacZ gene that was used to construct the PpURA5 blaster (recyclable auxotrophic marker) | CCTGCACTGGATGGTGGCGCTGGATGGTAAGCCGCTGGCAAGC GGTGAAGTGCCTCTGGATGTCGCTCCACAAGGTAAACAGTTGAT TGAACTGCCTGAACTACCGCAGCCGGAGAGCGCCGGGCAACTC TGGCTCACAGTACGCGTAGTGCAACCGAACGCGACCGCATGGT CAGAAGCCGGGCACATCAGCGCCTGGCAGCAGTGGCGTCTGG CGGAAAACCTCAGTGTGACGCTCCCCGCCGCGTCCCACGCCAT CCCGCATCTGACCACCAGCGAAATGGATTTTTGCATCGAGCTGG GTAATAAGCGTTGGCAATTTAACCGCCAGTCAGGCTTTCTTTCA CAGATGTGGATTGGCGATAAAAAACAACTGCTGACGCCGCTGC GCGATCAGTTCACCCGTGCACCGCTGGATAACGACATTGGCGT AAGTGAAGCGACCCGCATTGACCCTAACGCCTGGGTCGAACGC TGGAAGGCGGCGGGCCATTACCAGGCCGAAGCAGCGTTGTTGC AGTGCACGGCAGATACACTTGCTGATGCGGTGCTGATTACGAC CGCTCACGCGTGGCAGCATCAGGGGAAAACCTTATTTATCAGCC GGAAAACCTACCGGATTGATGGTAGTGGTCAAATGGCGATTACC GTTGATGTTGAAGTGGCGAGCGATACACCGCATCCGGCGCGGA TTGGCCTGAACTGCCAG |
| 19 | Sequence of the 5'-Region used for knock out of PpOCH1: | AAAACCTTTTTTCCTATTCAAACACAAGGCATTGCTTCAACACGT GTGCGTATCCTTAACACAGATACTCCATACTTCTAATAATGTGAT AGACGAATACAAAGATGTTCACTCTGTGTTGTGTCTACAAGCATT TCTTATTCTGATTGGGGATATTCTAGTTACAGCACTAAACAACTG GCGATACAAACTTAAATTAAATAATCCGAATCTAGAAAATGAACT TTTGGATGGTCCGCCTGTTGGTTGGATAAATCAATACCGATTAAA TGGATTCTATTCCAATGAGAGAGTAATCCAAGACACTCTGATGTC AATAATCATTTGCTTGCAACAACAAACCCGTCATCTAATCAAAGG GTTTGATGAGGCTTACCTTCAATTGCAGATAAACTCATTGCTGTC CACTGCTGTATTATGTGAGAATATGGGTGATGAATCTGGTCTTCT CCACTCAGCTAACATGGCTGTTTGGGCAAAGGTGGTACAATTAT ACGGAGATCAGGCAATAGTGAAATTGTTGAATATGGCTACTGGA CGATGCTTCAAGGATGTACGTCTAGTAGGAGCCGTGGGAAGATT GCTGGCAGAACCAGTTGGCACGTCGCAACAATCCCCAAGAAAT GAAATAAGTGAAAACGTAACGTCAAAGACAGCAATGGAGTCAAT ATTGATAACACCACTGGCAGAGCGGTTCGTACGTCGTTTTGGAG CCGATATGAGGCTCAGCGTGCTAACAGCACGATTGACAAGAAG ACTCTCGAGTGACAGTAGGTTGAGTAAAGTATTCGCTTAGATTC CCAACCTTCGTTTTATTCTTTCGTAGACAAAGAAGCTGCATGCGA ACATAGGGACAACTTTTATAAATCCAATTGTCAAACCAACGTAAA ACCCTCTGGCACCATTTTCAACATATATTTGTGAAGCAGTACGCA ATATCGATAAATACTCACCGTTGTTTGTAACAGCCCCAACTTGCA TACGCCTTCTAATGACCTCAAATGGATAAGCCGCAGCTTGTGCT AACATACCAGCAGCACCGCCCGCGGTCAGCTGCGCCCACACAT ATAAAGGCAATCTACGATCATGGGAGGAATTAGTTTTGACCGTC |

| SEQ ID NO: | Description | Sequence |
|---|---|---|
| | | AGGTCTTCAAGAGTTTTGAACTCTTCTTCTTGAACTGTGTAACCT<br>TTTAAATGACGGGATCTAAATACGTCATGGATGAGATCATGTGT<br>GTAAAAACTGACTCCAGCATATGGAATCATTCCAAAGATTGTAG<br>GAGCGAACCCACGATAAAAGTTTCCCAACCTTGCCAAAGTGTCT<br>AATGCTGTGACTTGAAATCTGGGTTCCTCGTTGAAGACCCTGCG<br>TACTATGCCCAAAAACTTTCCTCCACGAGCCCTATTAACTTCTCT<br>ATGAGTTTCAAATGCCAAACGGACACGGATTAGGTCCAATGGGT<br>AAGTGAAAAACACAGAGCAAACCCCAGCTAATGAGCCGGCCAG<br>TAACCGTCTTGGAGCTGTTTCATAAGAGTCATTAGGGATCAATAA<br>CGTTCTAATCTGTTCATAACATACAAATTTTATGGCTGCATAGGG<br>AAAAATTCTCAACAGGGTAGCCGAATGACCCTGATATAGACCTG<br>CGACACCATCATACCCATAGATCTGCCTGACAGCCTTAAAGAGC<br>CCGCTAAAGACCCGGAAAACCGAGAGAACTCTGGATTAGCAG<br>TCTGAAAAAGAATCTTCACTCTGTCTAGTGGAGCAATTAATGTCT<br>TAGCGGCACTTCCTGCTACTCCGCCAGCTACTCCTGAATAGATC<br>ACATACTGCAAAGACTGCTTGTCGATGACCTTGGGGTTATTTAG<br>CTTCAAGGGCAATTTTTGGGACATTTTGGACACAGGAGACTCAG<br>AAACAGACACAGAGCGTTCTGAGTCCTGGTGCTCCTGACGTAG<br>GCCTAGAACAGGAATTATTGGCTTTATTTGTTTGTCCATTTCATA<br>GGCTTGGGGTAATAGATAGATGACAGAGAAATAGAGAAGACCTA<br>ATATTTTTTGTTCATGGCAAATCGCGGGTTCGCGGTCGGGTCAC<br>ACACGGAGAAGTAATGAGAAGAGCTGGTAATCTGGGGTAAAAG<br>GGTTCAAAAGAAGGTCGCCTGGTAGGGATGCAATACAAGGTTGT<br>CTTGGAGTTTACATTGACCAGATGATTTGGCTTTTTCTCTGTTCA<br>ATTCACATTTTTCAGCGAGAATCGGATTGACGGAGAAATGGCGG<br>GGTGTGGGGTGGATAGATGGCAGAAATGCTCGCAATCACCGCG<br>AAAGAAAGACTTTATGGAATAGAACTACTGGGTGGTGTAAGGAT<br>TACATAGCTAGTCCAATGGAGTCCGTTGGAAAGGTAAGAAGAAG<br>CTAAAACCGGCTAAGTAACTAGGGAAGAATGATCAGACTTTGAT<br>TTGATGAGGTCTGAAAATACTCTGCTGCTTTTTCAGTTGCTTTTT<br>CCCTGCAACCTATCATTTTCCTTTTCATAAGCCTGCCTTTTCTGT<br>TTTCACTTATATGAGTTCCGCCGAGACTTCCCCAAATTCTCTCCT<br>GGAACATTCTCTATCGCTCTCCTTCCAAGTTGCGCCCCCTGGCA<br>CTGCCTAGTAATATTACCACGCGACTTATATTCAGTTCCACAATT<br>TCCAGTGTTCGTAGCAAATATCATCAGCCATGGCGAAGGCAGAT<br>GGCAGTTTGCTCTACTATAATCCTCACAATCCACCCAGAAGGTA<br>TTACTTCTACATGGCTATATTCGCCGTTTCTGTCATTTGCGTTTT<br>GTACGGACCCTCACAACAATTATCATCTCCAAAAATAGACTATGA<br>TCCATTGACGCTCCGATCACTTGATTTGAAGACTTTGGAAGCTC<br>CTTCACAGTTGAGTCCAGGCACCGTAGAAGATAATCTTCG |
| 20 | Sequence of the 3'-Region used for knock out of PpOCH1: | AAAGCTAGAGTAAAATAGATATAGCGAGATTAGAGAATGAATACC<br>TTCTTCTAAGCGATCGTCCGTCATCATAGAATATCATGGACTGTA<br>TAGTTTTTTTTTTGTACATATAATGATTAAACGGTCATCCAACATC<br>TCGTTGACAGATCTCTCAGTACGCGAAATCCCTGACTATCAAAG<br>CAAGAACCGATGAAGAAAAAAACAACAGTAACCCAAACACCACA<br>ACAAACACTTTATCTTCTCCCCCCCAACACCAATCATCAAAGAGA<br>TGTCGGAACCAAACACCAAGAAGCAAAAACTAACCCCATATAAA<br>AACATCCTGGTAGATAATGCTGGTAACCCGCTCTCCTTCCATATT<br>CTGGGCTACTTCACGAAGTCTGACCGGTCTCAGTTGATCAACAT<br>GATCCTCGAAATGGGTGGCAAGATCGTTCCAGACCTGCCTCCTC<br>TGGTAGATGGAGTGTTGTTTTTGACAGGGGATTACAAGTCTATT<br>GATGAAGATACCCTAAAGCAACTGGGGGACGTTCCAATATACAG<br>AGACTCCTTCATCTACCAGTGTTTTGTGCACAAGACATCTCTTCC<br>CATTGACACTTTCCGAATTGACAAGAACGTCGACTTGGCTCAAG<br>ATTTGATCAATAGGGCCCTTCAAGAGTCTGTGGATCATGTCACTT<br>CTGCCAGCACAGCTGCAGCTGCTGCTGTTGTTGTCGCTACCAAC<br>GGCCTGTCTTCTAAACCAGACGCTCGTACTAGCAAAATACAGTT<br>CACTCCCGAAGAAGATCGTTTTATTCTTGACTTTGTTAGGAGAAA<br>TCCTAAACGAAGAAACACACATCAACTGTACACTGAGCTCGCTC<br>AGCACATGAAAAACCATACGAATCATTCTATCCGCCACAGATTTC<br>GTCGTAATCTTTCCGCTCAACTTGATTGGGTTTATGATATCGATC<br>CATTGACCAACCAACCTCGAAAAGATGAAAACGGGAACTACATC<br>AAGGTACAAGGCCTTCCA |
| 21 | *K. lactis* UDP-GlcNAc transporter gene (KlMNN2-2) ORF underlined | AAACGTAACGCCTGGCACTCTATTTTCTCAAACTTCTGGGACGG<br>AAGAGCTAAATATTGTGTTGCTTGAACAAACCCAAAAAACAAAA<br>AAATGAACAAACTAAAACTACACCTAAATAAACCGTGTGTAAAAC<br>GTAGTACCATATTACTAGAAAAGATCACAAGTGTATCACACATGT<br>GCATCTCATATTACATCTTTTATCCAATCCATTCTCTCTATCCCGT<br>CTGTTCCTGTCAGATTCTTTTTCCATAAAAAGAAGAAGACCCCGA<br>ATCTCACCGGTACAATGCAAAACTGCTGAAAAAAAAAGAAAGTT<br>CACTGGATACGGGAACAGTGCCAGTAGGCTTCACCACATGGAC |

Table of Sequences

| SEQ ID NO: | Description | Sequence |
|---|---|---|
| | | AAAACAATTGACGATAAAATAAGCAGGTGAGCTTCTTTTTCAAGT<br>CACGATCCCTTTATGTCTCAGAAACAATATATACAAGCTAAACCC<br>TTTTGAACCAGTTCTCTCTTCATAGTTATGTTCACATAAATTGCG<br>GGAACAAGACTCCGCTGGCTGTCAGGTACACGTTGTAACGTTTT<br>CGTCCGCCCAATTATTAGCACAACATTGGCAAAAAGAAAAACTG<br>CTCGTTTTCTCTACAGGTAAATTACAATTTTTTTCAGTAATTTTCG<br>CTGAAAAATTTAAAGGGCAGGAAAAAAAGACGATCTCGACTTTG<br>CATAGATGCAAGAACTGTGGTCAAAACTTGAAATAGTAATTTTGC<br>TGTGCGTGAACTAATAAATATATATATATATATATATATATATTTGT<br>GTATTTTGTATATGTAATTGTGCACGTCTTGGCTATTGGATATAA<br>GATTTTCGCGGGTTGATGACATAGAGCGTGTACTACTGTAATAG<br>TTGTATATTCAAAAGCTGCTGCGTGGAGAAAGACTAAAATAGATA<br>AAAAGCACACATTTTGACTTCGGTACCGTCAACTTAGTGGGACA<br>GTCTTTTATATTTGGTGTAAGCTCATTTCTGGTACTATTCGAAAC<br>AGAACAGTGTTTTCTGTATTACCGTCCAATCGTTTGTCATGAGTT<br>TTGTATTGATTTTGTCGTTAGTGTTCGGAGGATGTTGTTCCAATG<br>TGATTAGTTTCGAGCACATGGTGCAAGGCAGCAATATAAATTTG<br>GGAAATATTGTTACATTCACTCAATTCGTGTCTGTGACGCTAATT<br>CAGTTGCCCAATGCTTTGGACTTCTCTCACTTTCCGTTTAGGTTG<br>CGACCTAGACACATTCCTCTTAAGATCCATATGTTAGCTGTGTTT<br>TTGTTCTTTACCAGTTCAGTCGCCAATAACAGTGTGTTTAAATTT<br>GACATTTCCGTTCCGATTCATATTATCATTAGATTTTCAGGTACC<br>ACTTTGACGATGATAATAGGTTGGGCTGTTTGTAATAAGAGGTA<br>CTCCAAACTTCAGGTGCAATCTGCCATCATTATGACGCTTGGTG<br>CGATTGTCGCATCATTATACCGTGACAAAGAATTTTCAATGGACA<br>GTTTAAAGTTGAATACGGATTCAGTGGGTATGACCCAAAAATCTA<br>TGTTTGGTATCTTTGTTGTGCTAGTGGCCACTGCCTTGATGTCAT<br>TGTTGTCGTTGCTCAACGAATGGACGTATAACAAGTACGGGAAA<br>CATTGGAAAGAAACTTTGTTCTATTCGCATTTCTTGGCTCTACCG<br>TTGTTTATGTTGGGGTACACAAGGCTCAGAGACGAATTCAGAGA<br>CCTCTTAATTTCCTCAGACTCAATGGATATTCCTATTGTTAAATTA<br>CCAATTGCTACGAAACTTTTCATGCTAATAGCAAATAACGTGACC<br>CAGTTCATTTGTATCAAAGGTGTTAACATGCTAGCTAGTAACACG<br>GATGCTTTGACACTTTCTGTCGTGCTTCTAGTGCGTAAATTTGTT<br>AGTCTTTTACTCAGTGTCTACATCTACAAGAACGTCCTATCCGTG<br>ACTGCATACCTAGGGACCATCACCGTGTTCCTGGGAGCTGGTTT<br>GTATTCATATGGTTCGGTCAAAACTGCACTGCCTCGCTGAAACA<br>ATCCACGTCTGTATGATACTCGTTTCAGAATTTTTTTGATTTTCTG<br>CCCGGATATGGTTTCTCATCTTTACAATCGCATTCTTAATTATACC<br>AGAACGTAATTCAATGATCCCAGTGACTCGTAACTCTTATATGTC<br>AATTTAAGC |
| 22 | Sequence of the 5'-Region used for knock out of PpBMT2: | GGCCGAGCGGGCCTAGATTTTCACTACAAATTTCAAAACTACGC<br>GGATTTATTGTCTCAGAGAGCAATTTGGCATTTCTGAGCGTAGC<br>AGGAGGCTTCATAAGATTGTATAGGACCGTACCAACAAATTGCC<br>GAGGCACAACACGGTATGCTGTGCACTTATGTGGCTACTTCCCT<br>ACAACGGAATGAAACCTTCCTCTTTCCGCTTAAACGAGAAAGTG<br>TGTCGCAATTGAATGCAGGTGCCTGTGCGCCTTGGTGTATTGTT<br>TTTGAGGGCCCAATTTATCAGGCGCCTTTTTTCTTGGTTGTTTTC<br>CCTTAGCCTCAAGCAAGGTTGGTCTATTTCATCTCCGCTTCTATA<br>CCGTGCCTGATACTGTTGGATGAGAACACGACTCAACTTCCTGC<br>TGCTCTGTATTGCCAGTGTTTTGTCTGTGATTTGGATCGGAGTC<br>CTCCTTACTTGGAATGATAATAATCTTGGCGGAATCTCCCTAAAC<br>GGAGGCAAGGATTCTGCCTATGATGATCTGCTATCATTGGGAAG<br>CTTCAACGACATGGAGGTCGACTCCTATGTCACCAACATCTACG<br>ACAATGCTCCAGTGCTAGGATGTACGGATTTGTCTTATCATGGA<br>TTGTTGAAAGTCACCCCAAAGCATGACTTAGCTTGCGATTTGGA<br>GTTCATAAGAGCTCAGATTTTGGACATTGACGTTTACTCCGCCAT<br>AAAAGACTTAGAAGATAAAGCCTTGACTGTAAAACAAAAGGTTGA<br>AAAACACTGGTTTACGTTTTATGGTAGTTCAGTCTTTCTGCCCGA<br>ACACGATGTGCATTACCTGGTTAGACGAGTCATCTTTTCGGCTG<br>AAGGAAAGGCGAACTCTCCAGTAACATC |
| 23 | Sequence of the 3'-Region used for knock out of PpBMT2: | CCATATGATGGGTGTTTGCTCACTCGTATGGATCAAAATTCCATG<br>GTTTCTTCTGTACAACTTGTACACTTATTTGGACTTTTCTAACGGT<br>TTTTCTGGTGATTTGAGAAGTCCTTATTTTGGTGTTCGCAGCTTA<br>TCCGTGATTGAACCATCAGAAATACTGCAGCTCGTTATCTAGTTT<br>CAGAATGTGTTGTAGAATACAATCAATTCTGAGTCTAGTTTGGGT<br>GGGTCTTGGCGACGGGACCGTTATATGCATCTATGCAGTGTTAA<br>GGTACATAGAATGAAAATGTAGGGGTTAATCGAAAGCATCGTTA<br>ATTTCAGTAGAACGTAGTTCTATTCCCTACCCAAATAATTTGCCA<br>AGAATGCTTCGTATCCACATACGCAGTGGACGTAGCAAATTTCA<br>CTTTGGACTGTGACCTCAAGTCGTTATCTTCTACTTGGACATTGA |

Table of Sequences

| SEQ ID NO: | Description | Sequence |
|---|---|---|
| | | TGGTCATTACGTAATCCACAAAGAATTGGATAGCCTCTCGTTTTA<br>TCTAGTGCACAGCCTAATAGCACTTAAGTAAGAGCAATGGACAA<br>ATTTGCATAGACATTGAGCTAGATACGTAACTCAGATCTTGTTCA<br>CTCATGGTGTACTCGAAGTACTGCTGGAACCGTTACCTCTTATC<br>ATTTCGCTACTGGCTCGTGAAACTACTGGATGAAAAAAAAAAA<br>GAGCTGAAAGCGAGATCATCCCATTTTGTCATCATACAAATTCAC<br>GCTTGCAGTTTTGCTTCGTTAACAAGACAAGATGTCTTTATCAAA<br>GACCCGTTTTTTCTTCTTGAAGAATACTTCCCTGTTGAGCACATG<br>CAAACCATATTTATCTCAGATTTCACTCAACTTGGGTGCTTCCAA<br>GAGAAGTAAAATTCTTCCCACTGCATCAACTTCCAAGAAACCCG<br>TAGACCAGTTTCTCTTCAGCCAAAAGAAGTTGCTCGCCGATCAC<br>CGCGGTAACAGAGGAGTCAGAAGGTTTCACACCCTTCCATCCC<br>GATTTCAAAGTCAAAGTGCTGCGTTGAACCAAGGTTTTCAGGTT<br>GCCAAAGCCCAGTCTGCAAAAACTAGTTCCAAATGGCCTATTAA<br>TTCCCATAAAAGTGTTGGCTACGTATGTATCGGTACCTCCATTCT<br>GGTATTTGCTATTGTTGTCGTTGGTGGGTTGACTAGACTGACCG<br>AATCCGGTCTTTCCATAACGGAGTGGAAACCTATCACTGGTTCG<br>GTTCCCCCACTGACTGAGGAAGACTGGAAGTTGGAATTTGAAAA<br>ATACAAACAAAGCCCTGAGTTTCAGGAACTAAATTCTCACATAAC<br>ATTGGAAGAGTTCAAGTTTATATTTTCCATGGAATGGGGACATAG<br>ATTGTTGGGAAGGGTCATCGGCCTGTCGTTTGTTCTTCCCACGT<br>TTTACTTCATTGCCCGTCGAAAGTGTTCCAAAGATGTTGCATTGA<br>AACTGCTTGCAATATGCTCTATGATAGGATTCCAAGGTTTCATCG<br>GCTGGTGGATGGTGTATTCCGGATTGGACAAACAGCAATTGGCT<br>GAACGTAACTCCAAACCAACTGTGTCTCCATATCGCTTAACTACC<br>CATCTTGGAACTGCATTTGTTATTTACTGTTACATGATTTACACA<br>GGGCTTCAAGTTTTGAAGAACTATAAGATCATGAAACAGCCTGA<br>AGCGTATGTTCAAATTTTCAAGCAAATTGCGTCTCCAAAATTGAA<br>AACTTTCAAGAGACTCTCTTCAGTTCTATTAGGCCTGGTG |
| 24 | DNA encodes MmSLC35A3 UDP-GlcNAc transporter | ATGTCTGCCAACCTAAAATATCTTTCCTTGGGAATTTTGGTGTTT<br>CAGACTACCAGTCTGGTTCTAACGATGCGGTATTCTAGGACTTT<br>AAAAGAGGAGGGGCCTCGTTATCTGTCTTCTACAGCAGTGGTTG<br>TGGCTGAATTTTTGAAGATAATGGCCTGCATCTTTTTAGTCTACA<br>AAGACAGTAAGTGTAGTGTGAGAGCACTGAATAGAGTACTGCAT<br>GATGAAATTCTTAATAAGCCCATGGAAACCCTGAAGCTCGCTAT<br>CCCGTCAGGGATATATACTCTTCAGAACAACTTACTCTATGTGG<br>CACTGTCAAACCTAGATGCAGCCACTTACCAGGTTACATATCAG<br>TTGAAAATACTTACAACAGCATTATTTTCTGTGTCTATGCTTGGTA<br>AAAAATTAGGTGTGTACCAGTGGCTCTCCCTAGTAATTCTGATG<br>GCAGGAGTTGCTTTTGTACAGTGGCCTTCAGATTCTCAAGAGCT<br>GAACTCTAAGGACCTTTCAACAGGCTCACAGTTTGTAGGCCTCA<br>TGGCAGTTCTCACAGCCTGTTTTTCAAGTGGCTTTGCTGGAGTT<br>TATTTTGAGAAAATCTTAAAAGAAACAAAACAGTCAGTATGGATA<br>AGGAACATTCAACTTGGTTTCTTTGGAAGTATATTTGGATTAATG<br>GGTGTATACGTTTATGATGGAGAATTGGTCTCAAAGAATGGATTT<br>TTTCAGGGATATAATCAACTGACGTGGATAGTTGTTGCTCTGCA<br>GGCACTTGGAGGCCTTGTAATAGCTGCTGTCATCAAATATGCAG<br>ATAACATTTTAAAAGGATTTGCGACCTCCTTATCCATAATATTGTC<br>AACAATAATATCTTATTTTTGGTTGCAAGATTTTGTGCCAACCAG<br>TGTCTTTTTCCTTGGAGCCATCCTTGTAATAGCAGCTACTTTCTT<br>GTATGGTTACGATCCCAAACCTGCAGGAAATCCCACTAAAGCAT<br>AG |
| 25 | PpGAPDH promoter | TTTTTGTAGAAATGTCTTGGTGTCCTCGTCCAATCAGGTAGCCAT<br>CTCTGAAATATCTGGCTCCGTTGCAACTCCGAACGACCTGCTGG<br>CAACGTAAAATTCTCCGGGGTAAAACTTAAATGTGGAGTAATGG<br>AACCAGAAACGTCTCTTCCCTTCTCTCTCCTTCCACCGCCCGTT<br>ACCGTCCCTAGGAAATTTTACTCTGCTGGAGAGCTTCTTCTACG<br>GCCCCCTTGCAGCAATGCTCTTCCCAGCATTACGTTGCGGGTAA<br>AACGGAGGTCGTGTACCCGACCTAGCAGCCCAGGGATGGAAAA<br>GTCCCGGCCGTCGCTGGCAATAATAGCGGGCGGACGCATGTCA<br>TGAGATTATTGGAAACCACCAGAATCGAATATAAAAGGCGAACA<br>CCITTCCCAATTTTGGITTCTCCTGACCCAAAGACTTTAAATTTAA<br>TTTATTTGTCCCTATTTCAATCAATTGAACAACTATCAAAACACA |
| 26 | Ypslss | MKLKTVRSAVLSSLFASQVLG |
| 27 | Sequence of the 5'-Region used for knock out of PpMNN4L1: | GATCTGGCCATTGTGAAACTTGACACTAAAGACAAAACTCTTAGA<br>GTTTCCAATCACTTAGGAGACGATGTTTCCTACAACGAGTACGA<br>TCCCTCATTGATCATGAGCAATTTGTATGTGAAAAAAGTCATCGA<br>CCTTGACACCTTGGATAAAAGGGCTGGAGGAGGTGGAACCACC<br>TGTGCAGGCGGTCTGAAAGTGTTCAAGTACGGATCTACTACCAA |

Table of Sequences

| SEQ ID NO: | Description | Sequence |
|---|---|---|
| | | ATATACATCTGGTAACCTGAACGGCGTCAGGTTAGTATACTGGA ACGAAGGAAAGTTGCAAAGCTCCAAATTTGTGGTTCGATCCTCT AATTACTCTCAAAAGCTTGGAGGAAACAGCAACGCCGAATCAAT TGACAACAATGGTGTGGGTTTTGCCTCAGCTGGAGACTCAGGC GCATGGATTCTTTCCAAGCTACAAGATGTTAGGGAGTACCAGTC ATTCACTGAAAAGCTAGGTGAAGCTACGATGAGCATTTTCGATTT CCACGGTCTTAAACAGGAGACTTCTACTACAGGGCTTGGGGTAG TTGGTATGATTCATTCTTACGACGGTGAGTTCAAACAGTTTGGTT TGTTCACTCCAATGACATCTATTCTACAAAGACTTCAACGAGTGA CCAATGTAGAATGGTGTGTAGCGGGTTGCGAAGATGGGGATGT GGACACTGAAGGAGAACACGAATTGAGTGATTTGGAACAACTGC ATATGCATAGTGATTCCGACTAGTCAGGCAAGAGAGAGCCCTCA AATTTACCTCTCTGCCCCTCCTCACTCCTTTTGGTACGCATAATT GCAGTATAAAGAACTTGCTGCCAGCCAGTAATCTTATTTCATACG CAGTTCTATATAGCACATAATCTTGCTTGTATGTATGAAATTTACC GCGTTTTAGTTGAAATTGTTTATGTTGTGTGCCTTGCATGAAATC TCTCGTTAGCCCTATCCTTACATTTAACTGGTCTCAAAACCTCTA CCAATTCCATTGCTGTACAACAATATGAGGCGGCATTACTGTAG GGTTGGAAAAAAATTGTCATTCCAGCTAGAGATCACACGACTTC ATCACGCTTATTGCTCCTCATTGCTAAATCATTTACTCTTGACTTC GACCCAGAAAAGTTCGCC |
| 28 | Sequence of the 3'-Region used for knock out of PpMNN4L1: | GCATGTCAAACTTGAACACAACGACTAGATAGTTGTTTTTTCTAT ATAAAACGAAACGTTATCATCTTTAATAATCATTGAGGTTTACCCT TATAGTTCCGTATTTTCGTTTCCAAACTTAGTAATCTTTTGGAAAT ATCATCAAAGCTGGTGCCAATCTTCTTGTTTGAAGTTTCAAACTG CTCCACCAAGCTACTTAGAGACTGTTCTAGGTCTGAAGCAACTT CGAACACAGAGACAGCTGCCGCCGATTGTTCTTTTTTGTGTTTTT CTTCTGGAAGAGGGGCATCATCTTGTATGTCCAATGCCCGTATC CTTTCTGAGTTGTCCGACACATTGTCCTTCGAAGAGTTTCCTGAC ATTGGGCTTCTTCTATCCGTGTATTAATTTTGGGTTAAGTTCCTC GTTTGCATAGCAGTGGATACCTCGATTTTTTTGGCTCCTATTTAC CTGACATAATATTCTACTATAATCCAACTTGGACGCGTCATCTAT GATAACTAGGCTCTCCTTTGTTCAAAGGGGACGTCTTCATAATC CACTGGCACGAAGTAAGTCTGCAACGAGGCGGCTTTTGCAACA GAACGATAGTGTCGTTTCGTACTTGGACTATGCTAAACAAAAGG ATCTGTCAAACATTTCAACCGTGTTTCAAGGCACTCTTTACGAAT TATCGACCAAGACCTTCCTAGACGAACATTTCAACATATCCAGG CTACTGCTTCAAGGTGGTGCAAATGATAAAGGTATAGATATTAGA TGTGTTTGGGACCTAAAACAGTTCTTGCCTGAAGATTCCCTTGA GCAACAGGCTTCAATAGCCAAGTTAGAGAAGCAGTACCAAATCG GTAACAAAAGGGGGAAGCATATAAAACCTTTACTATTGCGACAA AATCCATCCTTGAAAGTAAAGCTGTTTGTTCAATGTAAAGCATAC GAAACGAAGGAGGTAGATCCTAAGATGGTTAGAGAACTTAACGG GACATACTCCAGCTGCATCCCATATTACGATCGCTGGAAGACTT TTTTCATGTACGTATCGCCCACCAACCTTTCAAAGCAAGCTAGGT ATGATTTTGACAGTTCTCACAATCCATTGGTTTTCATGCAACTTG AAAAAACCCAACTCAAACTTCATGGGGATCCATACAATGTAAATC ATTACGAGAGGGCGAGGTTGAAAAGTTTCCATTGCAATCACGTC GCATCATGGCTACTGAAAGGCCTTAAC |
| 29 | Sequence of the 5'-Region used for knock out of PpPNO1 and PpMNN4: | TCATTCTATATGTTCAAGAAAAGGGTAGTGAAAGGAAAGAAAAG GCATATAGGCGAGGGAGAGTTAGCTAGCATACAAGATAATGAAG GATCAATAGCGGTAGTTAAAGTGCACAAGAAAAGAGCACCTGTT GAGGCTGATGATAAAGCTCCAATTACATTGCCACAGAGAAACAC AGTAACAGAAATAGGAGGGGATGCACCACGAGAAGAGCATTCA GTGAACAACTTTGCCAAATTCATAACCCCAAGCGCTAATAAGCC AATGTCAAAGTCGGCTACTAACATTAATAGTACAACAACTATCGA TTTTCAACCAGATGTTTGCAAGGACTACAAACAGACAGGTTACT GCGGATATGGTGACACTTGTAAGTTTTTGCACCTGAGGGATGAT TTCAAACAGGGATGGAAATTAGATAGGGAGTGGGAAAATGTCCA AAAGAAGAAGCATAATACTCTCAAAGGGGTTAAGGAGATCCAAA TGTTTAATGAAGATGAGCTCAAAGATATCCCGTTTAAATGCATTA TATGCAAAGGAGATTACAAATCACCCGTGAAAACTTCTTGCAATC ATTATTTTTGCGAACAATGTTTCCTGCAACGGTCAAGAAGAAAC CAAATTGTATTATATGTGGCAGAGACACTTTAGGAGTTGCTTTAC CAGCAAAGAAGTTGTCCCAATTTCTGGCTAAGATACATAATAATG AAAGTAATAAAGTTTAGTAATTGCATTGCGTTGACTATTGATTGC ATTGATGTCGTGTGATACTTTCACCGAAAAAAAACACGAAGCGC AATAGGAGCGGTTGCATATTAGTCCCCAAAGCTATTTAATTGTGC CTGAAACTGTTTTTTAAGCTCATCAAGCATAATTGTATGCATTGC GACGTAACCAACGTTTAGGCGCAGTTTAATCATAGCCCACTGCT AAGCC |

| SEQ ID NO: | Description | Sequence |
|---|---|---|
| 30 | Sequence of the 3'-Region used for knock out of PpPNO1 and PpMNN4: | CGGAGGAATGCAAATAATAATCTCCTTAATTACCCACTGATAAGC
TCAAGAGACGCGGTTTGAAAACGATATAATGAATCATTTGGATTT
TATAATAAACCCTGACAGTTTTTCCACTGTATTGTTTTAACACTCA
TTGGAAGCTGTATTGATTCTAAGAAGCTAGAAATCAATACGGCC
ATACAAAAGATGACATTGAATAAGCACCGGCTTTTTTGATTAGCA
TATACCTTAAAGCATGCATTCATGGCTACATAGTTGTTAAAGGGC
TTCTTCCATTATCAGTATAATGAATTACATAATCATGCACTTATAT
TTGCCCATCTCTGTTCTCTCACTCTTGCCTGGGTATATTCTATGA
AATTGCGTATAGCGTGTCTCCAGTTGAACCCCAAGCTTGGCGAG
TTTGAAGAGAATGCTAACCTTGCGTATTCCTTGCTTCAGGAAACA
TTCAAGGAGAAACAGGTCAAGAAGCCAAACATTTTGATCCTTCC
CGAGTTAGCATTGACTGGCTACAATTTTCAAAGCCAGCAGCGGA
TAGAGCCTTTTTTGGAGGAAACAACCAAGGGAGCTAGTACCCAA
TGGGCTCAAAAAGTATCCAAGACGTGGGATTGCTTTACTTTAATA
GGATACCCAGAAAAAAGTTTAGAGAGCCCTCCCCGTATTTACAA
CAGTGCGGTACTTGTATCGCCTCAGGGAAAAGTAATGAACAACT
ACAGAAAGTCCTTCTTGTATGAAGCTGATGAACATTGGGGATGT
TCGGAATCTTCTGATGGGTTTCAAACAGTAGATTTATTAATTGAA
GGAAAGACTGTAAAGACATCATTTGGAATTTGCATGGATTTGAAT
CCTTATAAATTTGAAGCTCCATTCACAGACTTCGAGTTCAGTGGC
CATTGCTTGAAAACCGGTACAAGACTCATTTTGTGCCCAATGGC
CTGGTTGTCCCCTCTATCGCCTTCCATTAAAAAGGATCTTAGTGA
TATAGAGAAAAGCAGACTTCAAAAGTTCTACCTTGAAAAAATAGA
TACCCCGGAATTTGACGTTAATTACGAATTGAAAAAAGATGAAGT
ATTGCCCACCCGTATGAATGAAACGTTGGAAACAATTGACTTTG
AGCCTTCAAAACCGGACTACTCTAATATAAATTATTGGATACTAA
GGTTTTTTCCCTTTCTGACTCATGTCTATAAACGAGATGTGCTCA
AAGAGAATGCAGTTGCAGTCTTATGCAACCGAGTTGGCATTGAG
AGTGATGTCTTGTACGGAGGATCAACCACGATTCTAAACTTCAAT
GGTAAGTTAGCATCGACACAAGAGGAGCTGGAGTTGTACGGGC
AGACTAATAGTCTCAACCCCAGTGTGGAAGTATTGGGGGCCCTT
GGCATGGGTCAACAGGGAATTCTAGTACGAGACATTGAATTAAC
ATAATATACAATATACAATAAACACAAATAAAGAATACAAGCCTG
ACAAAAATTCACAAATTATTGCCTAGACTTGTCGTTATCAGCAGC
GACCTTTTTCCAATGCTCAATTTCACGATATGCCTTTTCTAGCTC
TGCTTTAAGCTTCTCATTGGAATTGGCTAACTCGTTGACTGCTTG
GTCAGTGATGAGTTTCTCCAAGGTCCATTTCTCGATGTTGTTGTT
TTCGTTTTCCTTTAATCTCTTGATATAATCAACAGCCTTCTTTAAT
ATCTGAGCCTTGTTCGAGTCCCCTGTTGGCAACAGAGCGGCCA
GTTCCTTTATTCCGTGGTTTATATTTTCTCTTCTACGCCTTTCTAC
TTCTTTGTGATTCTCTTTACGCATCTTATGCCATTCTTCAGAACCA
GTGGCTGGCTTAACCGAATAGCCAGAGCCTGAAGAAGCCGCAC
TAGAAGAAGCAGTGGCATTGTTGACTATGG |
| 31 | Sequence of the 5'-Region used for knock out of BMT1 | CATATGGTGAGAGCCGTTCTGCACAACTAGATGTTTTCGAGCTT
CGCATTGTTTCCTGCAGCTCGACTATTGAATTAAGATTTCCGGAT
ATCTCCAATCTCACAAAAACTTATGTTGACCACGTGCTTTCCTGA
GGCGAGGTGTTTTATATGCAAGCTGCCAAAAATGGAAAACGAAT
GGCCATTTTTCGCCCAGGCAAATTATTCGATTACTGCTGTCATAA
AGACAGTGTTGCAAGGCTCACATTTTTTTTAGGATCCGAGATAA
AGTGAATACAGGACAGCTTATCTCTATATCTTGTACCATTCGTGA
ATCTTAAGAGTTCGGTTAGGGGGACTCTAGTTGAGGGTTGGCAC
TCACGTATGGCTGGGCGCAGAAATAAAATTCAGGCGCAGCAGC
ACTTATCGATG |
| 32 | Sequence of the 3'-Region used for knock out of BMT1 | GAATTCACAGTTATAAATAAAAACAAAAACTCAAAAAGTTTGGGC
TCCACAAAATAACTTAATTTAAATTTTTGTCTAATAAATGAATGTA
ATTCCAAGATTATGTGATGCAAGCACAGTATGCTTCAGCCCTAT
GCAGCTACTAATGTCAATCTCGCCTGCGAGCGGGCCTAGATTTT
CACTACAAATTTCAAAACTACGCGGATTTATTGTCTCAGAGAGCA
ATTTGGCATTTCTGAGCGTAGCAGGAGGCTTCATAAGATTGTAT
AGGACCGTACCAACAAATTGCCGAGGCACAACACGGTATGCTG
TGCACTTATGTGGCTACTTCCCTACAACGGAATGAAACCTTCCT
CTTTCCGCTTAAACGAGAAAGTGTGTCGCAATTGAATGCAGGTG
CCTGTGCGCCTTGGTGTATTGTTTTTGAGGGCCCAATTTATCAG
GCGCCTTTTTTCTTGGTTGTTTTCCCTTAGCCTCAAGCAAGGTTG
GTCTATTTCATCTCCGCTTCTATACCGTGCCTGATACTGTTGGAT
GAGAACACGACTCAACTTCCTGCTGCTCTGTATTGCCAGTGTTT
TGTCTGTGATTTGGATCGGAGTCCTCCTTACTTGGAATGATAATA
ATCTTGGCGGAATCTCCCTAAACGGAGGCAAGGATTCTGCCTAT
GATGATCTGCTATCATTGGGAAGCTT |

-continued

Table of Sequences

| SEQ ID NO: | Description | Sequence |
|---|---|---|
| 33 | Sequence of the 5'-Region used for knock out of BMT4 | AAGCTTGTTCACCGTTGGGACTTTTCCGTGGACAATGTTGACTA<br>CTCCAGGAGGGATTCCAGCTTTCTCTACTAGCTCAGCAATAATC<br>AATGCAGCCCCAGGCGCCCGTTCTGATGGCTTGATGACCGTTG<br>TATTGCCTGTCACTATAGCCAGGGGTAGGGTCCATAAAGGAATC<br>ATAGCAGGGAAATTAAAAGGGCATATTGATGCAATCACTCCCAA<br>TGGCTCTCTTGCCATTGAAGTCTCCATATCAGCACTAACTTCCAA<br>GAAGGACCCCTTCAAGTCTGACGTGATAGAGCACGCTTGCTCTG<br>CCACCTGTAGTCCTCTCAAAACGTCACCTTGTGCATCAGCAAAG<br>ACTTTACCTTGCTCCAATACTATGACGGAGGCAATTCTGTCAAAA<br>TTCTCTCTCAGCAATTCAACCAACTTGAAAGCAAATTGCTGTCTC<br>TTGATGATGGAGACTTTTTTCCAAGATTGAAATGCAATGTGGGAC<br>GACTCAATTGCTTCTTCCAGCTCCTCTTCGGTTGATTGAGGAACT<br>TTTGAAACCACAAAATTGGTCGTTGGGTCATGTACATCAAACCAT<br>TCTGTAGATTTAGATTCGACGAAAGCGTTGTTGATGAAGGAAAA<br>GGTTGGATACGGTTTGTCGGTCTCTTTGGTATGGCCGGTGGGG<br>TATGCAATTGCAGTAGAAGATAATTGGACAGCCATTGTTGAAGG<br>TAGAGAAAAGGTCAGGGAACTTGGGGGTTATTTATACCATTTTA<br>CCCCACAAATAACAACTGAAAAGTACCCATTCCATAGTGAGAGG<br>TAACCGACGGAAAAAGACGGGCCCATGTTCTGGGACCAATAGA<br>ACTGTGTAATCCATTGGGACTAATCAACAGACGATTGGCAATATA<br>ATGAAATAGTTCGTTGAAAAGCCACGTCAGCTGTCTTTTCATTAA<br>CTTTGGTCGGACACAACATTTTCTACTGTTGTATCTGTCCTACTT<br>TGCTTATCATCTGCCACAGGGCAAGTGGATTTCCTTCTCGCGCG<br>GCTGGGTGAAAACGGTTAACGTGAA |
| 34 | Sequence of the 3'-Region used for knock out of BMT4 | GCCTTGGGGGACTTCAAGTCTTTGCTAGAAACTAGATGAGGTCA<br>GGCCCTCTTATGGTTGTGTCCCAATTGGGCAATTTCACTCACCT<br>AAAAAGCATGACAATTATTTAGCGAAATAGGTAGTATATTTTCCC<br>TCATCTCCCAAGCAGTTTCGTTTTTGCATCCATATCTCTCAAATG<br>AGCAGCTACGACTCATTAGAACCAGAGTCAAGTAGGGGTGAGC<br>TCAGTCATCAGCCTTCGTTTCTAAAACGATTGAGTTCTTTTGTTG<br>CTACAGGAAGCGCCCTAGGGAACTTTCGCACTTTGGAAATAGAT<br>TTTGATGACCAAGAGCGGGAGTTGATATTAGAGAGGCTGTCCAA<br>AGTACATGGGATCAGGCCGGCCAAATTGATTGGTGTGACTAAAC<br>CATTGTGTACTTGGACACTCTATTACAAAAGCGAAGATGATTTGA<br>AGTATTACAAGTCCCGAAGTGTTAGAGGATTCTATCGAGCCCAG<br>AATGAAATCATCAACCGTTATCAGCAGATTGATAAACTCTTGGAA<br>AGCGGTATCCCATTTTCATTATTGAAGAACTACGATAATGAAGAT<br>GTGAGAGACGGCGACCCTCTGAACGTAGACGAAGAAACAAATC<br>TACTTTTGGGGTACAATAGAGAAAGTGAATCAAGGGAGGTATTT<br>GTGGCCATAATACTCAACTCTATCATTAATG |
| 35 | Sequence of the 5'-Region used for knock out of BMT3 | GATATCTCCCTGGGGACAATATGTGTTGCAACTGTTCGTTGTTG<br>GTGCCCCAGTCCCCCAACCGGTACTAATCGGTCTATGTTCCCGT<br>AACTCATATTCGGTTAGAACTAGAACAATAAGTGCATCATTGTTC<br>AACATTGTGGTTCAATTGTCGAACATTGCTGGTGCTTATATCTAC<br>AGGGAAGACGATAAGCCTTTGTACAAGAGAGGTAACAGACAGTT<br>AATTGGTATTTCTTTGGGAGTCGTTGCCCTCTACGTTGTCTCCAA<br>GACATACTACATTCTGAGAAACAGATGGAAGACTCAAAAATGGG<br>AGAAGCTTAGTGAAGAAGAGAAAGTTGCCTACTTGGACAGAGCT<br>GAGAAGGAGAACCTGGGTTCTAAGAGGCTGGACTTTTTGTTCGA<br>GAGTTAAACTGCATAATTTTTTCTAAGTAAATTTCATAGTTATGAA<br>ATTTCTGCAGCTTAGTGTTTACTGCATCGTTTACTGCATCACCCT<br>GTAAATAATGTGAGCTTTTTCCTTCCATTGCTTGGTATCTTCCTT<br>GCTGCTGTTT |
| 36 | Sequence of the 3'-Region used for knock out of BMT3 | ACAAAACAGTCATGTACAGAACTAACGCCTTTAAGATGCAGACC<br>ACTGAAAAGAATTGGGTCCCATTTTTCTTGAAAGACGACCAGGA<br>ATCTGTCCATTTTGTTTACTCGTTCAATCCTCTGAGAGTACTCAA<br>CTGCAGTCTTGATAACGGTGCATGTGATGTTCTATTTGAGTTACC<br>ACATGATTTTGGCATGTCTTCCGAGCTACGTGGTGCCACTCCTA<br>TGCTCAATCTTCCTCAGGCAATCCCGATGGCAGACGACAAAGAA<br>ATTTGGGTTTCATTCCCAAGAACGAGAATATCAGATTGCGGGTG<br>TTCTGAAACAATGTACAGGCCAATGTTAATGCTTTTTGTTAGAGA<br>AGGAACAAACTTTTTTGCTGAGC |
| 37 | *Leishmania major* STT3D (DNA) | ATGGGTAAAAGAAAGGGAAACTCCTTGGGAGATTCTGGTTCTGC<br>TGCTACTGCTTCCAGAGAGGCTTCTGCTCAAGCTGAAGATGCTG<br>CTTCCCAGACTAAGACTGCTTCTCCACCTGCTAAGGTTATCTTGT<br>TGCCAAAGACTTTGACTGACGAGAAGGACTTCATCGGTATCTTC<br>CCATTTCCATTCTGGCCAGTTCACTTCGTTTTGACTGTTGTTGCT<br>TTGTTCGTTTTGGCTGCTTCCTGTTTCCAGGCTTTCACTGTTAGA<br>ATGGATCTCCGTTCAAATCTACGGTTACTTGATCCACGAATTTGAC |

| SEQ ID NO: | Description | Sequence |
|---|---|---|
| | | CCATGGTTCAACTACAGAGCTGCTGAGTACATGTCTACTCACGG<br>ATGGAGTGCTTTTTTCTCCTGGTTCGATTACATGTCCTGGTATCC<br>ATTGGGTAGACCAGTTGGTTCTACTACTTACCCAGGATTGCAGT<br>TGACTGCTGTTGCTATCCATAGAGCTTTGGCTGCTGCTGGAATG<br>CCAATGTCCTTGAACAATGTTTGTGTTTGATGCCAGCTTGGTTT<br>GGTGCTATCGCTACTGCTACTTTGGCTTTCTGTACTTACGAGGC<br>TTCTGGTTCTACTGTTGCTGCTGCTGCAGCTGCTTTGTCCTTCTC<br>CATTATCCCTGCTCACTTGATGAGATCCATGGCTGGTGAGTTCG<br>ACAACGAGTGTATTGCTGTTGCTGCTATGTTGTTGACTTTCTACT<br>GTTGGGTTCGTTCCTTGAGAACTAGATCCTCCTGGCCAATCGGT<br>GTTTTGACAGGTGTTGCTTACGGTTACATGGCTGCTGCTTGGGG<br>AGGTTACATCTTCGTTTTGAACATGGTTGCTATGCACGCTGGTAT<br>CTCTTCTATGGTTGACTGGGCTAGAAACACTTACAACCCATCCTT<br>GTTGAGAGCTTACACTTTGTTCTACGTTGTTGGTACTGCTATCGC<br>TGTTTGTGTTCCACCAGTTGGAATGTCTCCATTCAAGTCCTTGGA<br>GCAGTTGGGAGCTTTGTTGGTTTTGGTTTTCTTGTGTGGATTGC<br>AAGTTTGTGAGGTTTTGAGAGCTAGAGCTGGTGTTGAAGTTAGA<br>TCCAGAGCTAATTTCAAGATCAGAGTTAGAGTTTTCTCCGTTATG<br>GCTGGTGTTGCTGCTTTGGCTATCTCTGTTTTGGCTCCAACTGG<br>TTACTTTGGTCCATTGTCTGTTAGAGTTAGAGCTTTGTTTGTTGA<br>GCACACTAGAACTGGTAACCCATTGGTTGACTCCGTTGCTGAAC<br>ATCAACCAGCTTCTCCAGAGGCTATGTGGGCTTTCTTGCATGTT<br>TGTGGTGTTACTTGGGGATTGGGTTCCATTGTTTTGGCTGTTTC<br>CACTTTCGTTCACTACTCCCCATCTAAGGTTTTCTGGTTGTTGAA<br>CTCCGGTGCTGTTTACTACTTCTCCACTAGAATGGCTAGATTGTT<br>GTTGTTGTCCGGTCCAGCTGCTTGTTTGTCCACTGGTATCTTCG<br>TTGGTACTATCTTGGAGGCTGCTGTTCAATTGTCTTTCTGGGACT<br>CCGATGCTACTAAGGCTAAGAAGCAGCAAAAGCAGGCTCAAAG<br>ACACCAAAGAGGTGCTGGTAAAGGTTCTGGTAGAGATGACGCTA<br>AGAACGCTACTACTGCTAGAGCTTTCTGTGACGTTTTCGCTGGT<br>TCTTCTTTGGCTTGGGGTCACAGAATGGTTTTGTCCATTGCTATG<br>TGGGCTTTGGTTACTACTACTGCTGTTTCCTTCTTCTTCCTCCGAA<br>TTTGCTTCTCACTCCACTAAGTTCGCTGAACAATCCTCCAACCCA<br>ATGATCGTTTTCGCTGCTGTTGTTCAGAACAGAGCTACTGGAAA<br>GCCAATGAACTTGTTGGTTGACGACTACTTGAAGGCTTACGAGT<br>GGTTGAGAGACTCTACTCCAGAGGACGCTAGAGTTTTGGCTTGG<br>TGGGACTACGGTTACCAAATCACTGGTATCGGTAACAGAACTTC<br>CTTGGCTGATGGTAACACTTGGAACCACGAGCACATTGCTACTA<br>TCGGAAAGATGTTGACTTCCCCAGTTGTTGAAGCTCACTCCCTT<br>GTTAGACACATGGCTGACTACGTTTTGATTTGGGCTGGTCAATC<br>TGGTGACTTGATGAAGTCTCCACACATGGCTAGAATCGGTAACT<br>CTGTTTACCACGACATTTGTCCAGATGACCCATTGTGTCAGCAAT<br>TCGGTTTCCACAGAAACGATTACTCCAGACCAACTCCAATGATG<br>AGAGCTTCCTTGTTGTACAACTTGCACGAGGCTGGAAAAAGAAA<br>GGGTGTTAAGGTTAACCCATCTTTGTTCCAAGAGGTTTACTCCTC<br>CAAGTACGGACTTGTTAGAATCTTCAAGGTTATGAACGTTTCCG<br>CTGAGTCTAAGAAGTGGGTTGCAGACCCAGCTAACAGAGTTTGT<br>CACCCACCTGGTTCTTGGATTTGTCCTGGTCAATACCCACCTGC<br>TAAAGAAATCCAAGAGATGTTGGCTCACAGAGTTCCATTCGACC<br>AGGTTACAAACGCTGACAGAAAGAACAATGTTGGTTCCTACCAA<br>GAGGAATACATGAGAAGAATGAGAGAGTCCGAGAACAGAAGAT<br>AATAG |
| 38 | ScARR3 ORF | ATGTCAGAAGATCAAAAAAGTGAAAATTCCGTACCTTCTAAGGTT<br>AATATGGTGAATCGCACCGATATACTGACTACGATCAAGTCATT<br>GTCATGGCTTGACTTGATGTTGCCATTTACTATAATTCTCTCCAT<br>AATCATTGCAGTAATAATTTCTGTCTATGTGCCTTCTTCCCGTCA<br>CACTTTTGACGCTGAAGGTCATCCCAATCTAATGGGAGTGTCCA<br>TTCCTTTGACTGTTGGTATGATTGTAATGATGATTCCCCCGATCT<br>GCAAAGTTTCCTGGGAGTCTATTCACAAGTACTTCTACAGGAGC<br>TATATAAGGAAGCAACTAGCCCTCTCGTTATTTTGAATTGGGTC<br>ATCGGTCCTTTGTTGATGACAGCATTGGCGTGGATGGCGCTATT<br>CGATTATAAGGAATACCGTCAAGGCATTATTATGATCGGAGTAG<br>CTAGATGCATTGCCATGGTGCTAATTTGGAATCAGATTGCTGGA<br>GGGAGACAATGATCTCTGCGTCGTGCTTGTTATTACAAACTCGCT<br>TTTACAGATGGTATTATATGCACCATTGCAGATATTTTACTGTTAT<br>GTTATTTCTCATGACCACCTGAATACTTCAAATAGGGTATTATTC<br>GAAGAGGTTGCAAAGTCTGTCGGAGTTTTCTCGGCATACCACT<br>GGGAATTGGCATTATCATACGTTTGGGAAGTCTTACCATAGCTG<br>GTAAAAGTAATTATGAAAAATACATTTTGAGATTTATTTCTCCATG<br>GGCAATGATCGGATTTCATTACACTTTATTTGTTATTTTTATTAGT<br>AGAGGTTATCAATTTATCCACGAAATTGGTTCTGCAATATTGTGC<br>TTTGTCCCATTGGTGCTTTACTTCTTTATTGCATGGTTTTTGACCT |

| SEQ ID NO: | Description | Sequence |
|---|---|---|
| | | TCGCATTAATGAGGTACTTATCAATATCTAGGAGTGATACACAAA GAGAATGTAGCTGTGACCAAGAACTACTTTTAAAGAGGGTCTGG GGAAGAAAGTCTTGTGAAGCTAGCTTTTCTATTACGATGACGCA ATGTTTCACTATGGCTTCAAATAATTTTGAACTATCCCTGGCAAT TGCTATTTCCTTATATGGTAACAATAGCAAGCAAGCAATAGCTGC AACATTTGGGCCGTTGCTAGAAGTTCCAATTTTATTGATTTTGGC AATAGTCGCGAGAATCCTTAAACCATATTATATATGGAACAATAG AAATTAA |
| 39 | PpRPL10 promoter | GTTCTTCGCTTGGTCTTGTATCTCCTTACACTGTATCTTCCCATT TGCGTTTAGGTGGTTATCAAAAACTAAAAGGAAAAATTTCAGATG TTTATCTCTAAGGTTTTTTCTTTTTACAGTATAACACGTGATGCGT CACGTGGTACTAGATTACGTAAGTTATTTTGGTCCGGTGGGTAA GTGGGTAAGAATAGAAAGCATGAAGGTTTACAAAAACGCAGTCA CGAATTATTGCTACTTCGAGCTTGGAACCACCCCAAAGATTATAT TGTACTGATGCACTACCTTCTCGATTTTGCTCCTCCAAGAACCTA CGAAAAACATTTCTTGAGCCTTTTCAACCTAGACTACACATCAAG TTATTTAAGGTATGTTCCGTTAACATGTAAGAAAAGGAGAGGATA GATCGTTTATGGGGTACGTCGCCTGATTCAAGCGTGACCATTCG AAGAATAGGCCTTCGAAAGCTGAATAAAGCAAATGTCAGTTGCG ATTGGTATGCTGACAAATTAGCATAAAAAGCAATAGACTTTCTAA CCACCTGTTTTTTTCCTTTTACTTTATTTATATTTTGCCACCGTAC TAACAAGTTCAGACAAA |
| 40 | URA6 region | CAAATGCAAGAGGACATTAGAAATGTGTTTGGTAAGAACATGAA GCCGGAGGCATACAAACGATTCACAGATTTGAAGGAGGAAAACA AACTGCATCCACCGGAAGTGCCAGCAGCCGTGTATGCCAACCT TGCTCTCAAAGGCATTCCTACGGATCTGAGTGGGAAATATCTGA GATTCACAGACCCACTATTGGAACAGTACCAAACCTAGTTTGGC CGATCCATGATTATGTAATGCATATAGTTTTTGTCGATGCTCACC CGTTTCGAGTCTGTCTCGTATCGTCTTACGTATAAGTTCAAGCAT GTTTACCAGGTCTGTTAGAAACTCCTTTGTGAGGGCAGGACCTA TTCGTCTCGGTCCCGTTGTTTCTAAGAGACTGTACAGCCAAGCG CAGAATGGTGGCATTAACCATAAGAGGATTCTGATCGGACTTGG TCTATTGGCTATTGGAACCACCCTTTACGGGACAACCAACCCTA CCAAGACTCCTATTGCATTTGTGGAACCAGCCACGGAAAGAGCG TTTAAGGACGGAGACGTCTCTGTGATTTTTGTTCTCGGAGGTCC AGGAGCTGGAAAAGGTACCCAATGTGCCAAACTAGTGAGTAATT ACGGATTTGTTCACCTGTCAGCTGGAGACTTGTTACGTGCAGAA CAGAAGAGGGAGGGGTCTAAGTATGGAGAGATGATTTCCCAGT ATATCAGAGATGGACTGATAGTACCTCAAGAGGTCACCATTGCG CTCTTGGAGCAGGCCATGAAGGAAAACTTCGAGAAAGGGAAGA CACGGTTCTTGATTGATGGATTCCCTCGTAAGATGGACCAGGCC AAAACTTTTGAGGAAAAAGTCGCAAAGTCCAAGGTGACACTTTT CTTTGATTGTCCCGAATCAGTGCTCCTTGAGAGATTACTTAAAAG AGGACAGACAAGCGGAAGAGAGGATGATAATGCGGAGAGTATC AAAAAAAAGATTCAAACATTCGTGGAAACTTCGATGCCTGTGGT GGACTATTTCGGGAAGCAAGGACGCGTITTGAAGGTATCTTGTG ACCACCCTGTGGATCAAGTGTATTCACAGGTTGTGTCGGTGCTA AAAGAGAAGGGGATCTTTGCCGATAACGAGACGGAGAATAAATA A |
| 41 | DNA encodes *Saccharomyces cerevisiae* mating factor pre-propeptide | ATGAGATTTCCTTCAATTTTTACTGCAGTTTTATTCGCAGCATCCT CCGCATTAGCTGCTCCAGTCAACACTACAACAGAAGATGAAACG GCACAAATTCCGGCTGAAGCTGTCATCGGTTACTCAGATTTAGA AGGGGATTTCGATGTTGCTGTTTTGCCATTTTCCAACAGCACAAA TAACGGGTTATTGTTTATAAATACTACTATTGCCAGCATTGCTGC TAAAGAAGAAGGGGTATCTCTCGAGAAAAGG |
| 42 | DNA encodes SCI (C peptide CTP) | TTTGTTAACCAACATTTGTGTGGTTCTCACCTTGTTGAAGCTTTG TACCTTGTCTGCGGAGAGAGAGGATTTTTCTATACTCCTAAGAC ATCTTCCTCAAGTAAAGCCCCACCTCCATCATTGCCTTCTCCATC CAGACTTCCTGGTCCATCCGATACCCCTATTTTGCCACAAGGAA TCGTCGAACAGTGTTGCACTTCAATTTGTAGTTTGTACCAGCTTG AGAACTATTGCAAT |
| 43 | SCI (C peptide CTP) | FVNQHLCGSHLVEALYLVCGERGFFYTPKTSSSSKAPPPSLPSPSR LPGPSDTPILPQGIVEQCCTSICSLYQLENYCN |
| 44 | DNA encodes SCI (C peptide CTP + K) | TTTGTTAACCAACATTTGTGTGGTTCTCACCTTGTTGAAGCTTTG TACCTTGTCTGCGGAGAGAGAGGATTTTTCTATACTCCTAAGAC ATCTTCCTCAAGTAGAGCCCCACCTCCATCATTGCCTTCTCCATC CAGACTTCCTGGTCCATCCGATACCCCTATTTTGCCACAAAAAG |

Table of Sequences

| SEQ ID NO: | Description | Sequence |
|---|---|---|
| | | GAATCGTCGAACAGTGTTGCACTTCAATTTGTAGTTTGTACCAGC TTGAGAACTATTGCAAT |
| 45 | SCI (C peptide CTP + K) | FVNQHLCGSHLVEALYLVCGERGFFYTPKTSSSSRAPPPSLPSPSR LPGPSDTPILPQKGIVEQCCTSICSLYQLENYCN |
| 46 | DNA encodes SCI (N-spacer CTP) | TCTTCCTCAAGTAGAGCACCACCTCCATCATTGCCTTCTCCATCC AGACTTCCTGGTCCATCCGATACCCCTATTTTGCCACAATTTGTT AACCAGCATTTGTGTGGATCTCACCTTGTTGAAGCTTTGTACCTT GTCTGCGGAGAGAGAGGATTTTTCTATACTCCTAAGACAGCTGC CAAAGGTATTGTCGAACAATGTTGCACTTCAATCTGTAGTTTGTA CCAGCTTGAGAACTATTGCAAT |
| 47 | SCI (N-spacer CTP) | SSSSRAPPPSLPSPSRLPGPSDTPILPQFVNQHLCGSHLVEALYLV CGERGFFYTPKTAAKGIVEQCCTSICSLYQLENYCN |
| 48 | DNA encodes SCI (N-spacer CTP + K) | TCTTCCTCAAGTAGAGCACCACCTCCATCATTGCCTTCTCCATCC AGACTTCCTGGTCCATCCGATACCCCTATTTTGCCACAAAAGTTT GTTAACCAGCATTTGTGTGGATCTCACCTTGTTGAAGCTTTGTAC CTTGTCTGCGGAGAGAGAGGATTTTTCTATACTCCTAAGACAGC TGCCAAAGGTATTGTCGAACAATGTTGCACTTCAATCTGTAGTTT GTACCAGCTTGAGAACTATTGCAAT |
| 49 | SCI (N-spacer CTP + K) | SSSSRAPPPSLPSPSRLPGPSDTPILPQKFVNQHLCGSHLVEALYL VCGERGFFYTPKTAAKGIVEQCCTSICSLYQLENYCN |
| 50 | DNA encodes SCI (N-spacer CTP; C-peptide CTP) | TCTTCCTCAAGTAAGGCTCCACCTCCATCATTGCCATCTCCTTCC AGACTTCCAGGTCCTAGTGATACAACCAATTTTGCCTCAATTTGTT AACCAGCATTTGTGTGGATCTCACCTTGTTGAAGCTTTGTACCTT GTCTGCGGAGAGAGAGGATTTTTCTATACTCCAAAGACATCTTC CTCAAGTAAAGCCCCTCCACCTTCCTTGCCATCACCTAGTAGAC TTCCAGGTCCTTCTGACACCCCAATTTTGCCTCAAGGAATCGTC GAACAGTGTTGCACTTCTATCTGTTCCTTGTACCAACTTGAGAAC TATTGCAAT |
| 51 | SCI (N-spacer CTP; C-peptide CTP) | SSSSKAPPPSLPSPSRLPGPSDTPILPQFVNQHLCGSHLVEALYLV CGERGFFYTPKTSSSSKAPPPSLPSPSRLPGPSDTPILPQGIVEQC CTSICSLYQLENYCN |
| 52 | DNA encodes SCI (N-spacer CTP; C-peptide CTP + K) | TCTTCTTCTTCTAGAGCCCCACCTCCATCATTGCCATCTCCTTCC AGACTTCCAGGTCCTAGTGATACACCAATTTTGCCTCAATTTGTT AACCAGCATTTGTGTGGATCTCACCTTGTTGAAGCTTTGTACCTT GTCTGCGGAGAGAGAGGATTTTTCTATACTCCAAAGACATCTTC CTCAAGTAGAGCCCCTCCACCTTCCTTGCCATCACCTAGTAGAC TTCCAGGTCCTTCTGACACCCCAATTTTGCCTCAAAAAGGAATC GTCGAACAGTGTTGCACTTCTATCTGTTCCTTGTACCAACTTGAG AACTATTGCAAT |
| 53 | SCI (N-spacer CTP; C-peptide CTP + K) | SSSSRAPPPSLPSPSRLPGPSDTPILPQFVNQHLCGSHLVEALYLV CGERGFFYTPKTSSSSRAPPPSLPSPSRLPGPSDTPILPQKGIVEQ CCTSICSLYQLENYCN |
| 54 | 5'MyII leader sequence | GAGTCCTCTT |
| 55 | 3'stop-stop-FseI sequence | TAATAGGGCCGGCC |
| 56 | Connecting peptide | GAGSSSRRAPQT |
| 57 | Connecting peptide | GAGSSSRRA |
| 58 | Connecting peptide | GAGSSSRR |
| 59 | Connecting peptide | GGGPRR |
| 60 | Connecting peptide | GGGPGAG |

Table of Sequences

| SEQ ID NO: | Description | Sequence |
|---|---|---|
| 61 | Connecting peptide | GGGGGKR |
| 62 | Connecting peptide | GGGPGKR |
| 63 | Connecting peptide | VGLSSGQ |
| 64 | Connecting peptide | TGLGSGR |
| 65 | Connecting peptide | RRGPGGG |
| 66 | Connecting peptide | RRGGGGG |
| 67 | Connecting peptide | GGAPGDVKR |
| 68 | Connecting peptide | RRAPGDVGG |
| 69 | Connecting peptide | GGYPGDVLR |
| 70 | Connecting peptide | RRYPGDVGG |
| 71 | Connecting peptide | GGHPGDVR |
| 72 | Connecting peptide | RRHPGDVGG |
| 73 | Insulin lispro B-chain | FVNQHLCGSHLVEALYLVCGERGFFYTKPT |
| 74 | Insulin aspart B-chain | FVNQHLCGSHLVEALYLVCGERGFFYTDKT |
| 75 | Insulin glulisine | FVKQHLCGSHLVEALYLVCGERGFFYTPET |
| 76 | Insulin degludec, desB30, Lys B29 conjugated to hexadecandioic acid (B29N(epsilon)-omega-carboxypentadeca-noyl-gamma-L-glutamyl desB30 human insulin) | FVNQHLCGSHLVEALYLVCGERGFFYTPK* |
| 77 | Insulin glargine A-chain | GIVEQCCTSICSLYQLENYCG |
| 78 | Insulin glargine B-chain | FVNQHLCGSHLVEALYLVCGERGFFYTPKRR |
| 79 | ArgA0 | RGIVEQCCTSICSLYQLENYCN |
| 80 | ArgA0A21 | RGIVEQCCTSICSLYQLENYCG |
| 81 | Insulin degludec, desB30, Lys B29 conjugated to myristic acid | FVNQHLCGSHLVEALYLVCGERGFFYTPK* |
| 82 | TA57 pro | QPIDDTESQTTSVNLMADDTESAFATQTNSGGLDVVGLISMAKR |

| SEQ ID NO: | Description | Sequence |
|---|---|---|
| 83 | N-terminal spacer | EEGEPK |
| 84 | C peptide "AAK" | AAK |
| 85 | Saccharomyces cerevisiae mating factor pre-signal peptide (DNA) | ATGAGATTCCCATCCATCTTCACTGCTGTTTTGTTCGCTGCTTCT TCTGCTTTGGCT |
| 86 | Saccharomyces cerevisiae mating factor pre-signal peptide (protein) | MRFPSIFTAVLFAASSALA |
| 87 | DNA encodes Tricoderma reesei α1,2-mannosidase catalytic domain | CGCGCCGGATCTCCCAACCCTACGAGGGCGGCAGCAGTCAAG GCCGCATTCCAGACGTCGTGGAACGCTTACCACCATTTTGCCTT TCCCCATGACGACCTCCACCCGGTCAGCAACAGCTTTGATGATG AGAGAAACGGCTGGGGCTCGTCGGCAATCGATGGCTTGGACAC GGCTATCCTCATGGGGGATGCCGACATTGTGAACACGATCCTTC AGTATGTACCGCAGATCAACTTCACCACGACTGCGGTTGCCAAC CAAGGCATCTCCGTGTTCGAGACCAACATTCGGTACCTCGGTG GCCTGCTTTCTGCCTATGACCTGTTGCGAGGTCCTTTCAGCTCC TTGGCGACAAACCAGACCCTGGTAAACAGCCTTCTGAGGCAGG CTCAAACACTGGCCAACGGCCTCAAGGTTGCGTTCACCACTCCC AGCGGTGTCCCGGACCCTACCGTCTTCTTCAACCCTACTGTCCG GAGAAGTGGTGCATCTAGCAACAACGTCGCTGAAATTGGAAGC CTGGTGCTCGAGTGGACACGGTTGAGCGACCTGACGGGAAACC CGCAGTATGCCCAGCTTGCGCAGAAGGGCGAGTCGTATCTCCT GAATCCAAAGGGAAGCCCGGAGGCATGGCCTGGCCTGATTGGA ACGTTTGTCAGCACGAGCAACGGTACCTTTCAGGATAGCAGCG GCAGCTGGTCCGGCCTCATGGACAGCTTCTACGAGTACCTGAT CAAGATGTACCTGTACGACCCGGTTGCGTTTGCACACTACAAGG ATCGCTGGGTCCTTGCTGCCGACTCGACCATTGCGCATCTCGC CTCTCACCCGTCGACGCGCAAGGACTTGACCTTTTTGTCTTCGT ACAACGGACAGTCTACGTCGCCAAACTCAGGACATTTGGCCAGT TTTGCCGGTGGCAACTTCATCTTGGGAGGCATTCTCCTGAACGA GCAAAAGTACATTGACTTTGGAATCAAGCTTGCCAGCTCGTACT TTGCCACGTACAACCAGACGGCTTCTGGAATCGGCCCCGAAGG CTTCGCGTGGGTGGACAGCGTGACGGGCGCCGGCGGCTCGCC GCCCTCGTCCCAGTCCGGGTTCTACTCGTCGGCAGGATTCTGG GTGACGGCACCGTATTACATCCTGCGCCGGAGACGCTGGAGA GCTTGTACTACGCATACCGCGTCACGGGCGACTCCAAGTGGCA GGACCTGGCGTGGGAAGCGTTCAGTGCCATTGAGGACGCATGC CGCGCCGGCAGCGCGTACTCGTCCATCAACGACGTGACGCAG GCCAACGGCGGGGGTGCCTCTGACGATATGGAGAGCTTCTGGT TTGCCGAGGCGCTCAAGTATGCGTACCTGATCTTTGCGGAGGA GTCGGATGTGCAGGTGCAGGCCAACGGCGGGAACAAATTTGTC TTTAACACGGAGGCGCACCCCTTTAGCATCCGTTCATCATCACG ACGGGGCGGCCACCTTGCTTAA |
| 88 | Sequence of the 5'-region to knock into the PpPRO1 locus: | GAAGGGCCATCGAATTGTCATCGTCTCCTCAGGTGCCATCGCTG TGGGCATGAAGAGAGTCAACATGAAGCGGAAACCAAAAAAGTTA CAGCAAGTGCAGGCATTGGCTGCTATAGGACAAGGCCGTTTGA TAGGACTTTGGGACGACCTTTTCCGTCAGTTGAATCAGCCTATT GCGCAGATTTTACTGACTAGAACGGATTTGGTCGATTACACCCA GTTTAAGAACGCTGAAAATACATTGGAACAGCTTATTAAAATGGG TATTATTCCTATTGTCAATGAGAATGACACCCTATCCATTCAAGA AATCAAATTTGGTGACAATGACACCTTATCCGCCATAACAGCTG GTATGTGTCATGCAGACTACCTGTTTTTGGTGACTGATGTGGAC TGTCTTTACACGGATAACCCTCGTACGAATCCGGACGCTGAGCC AATCGTGTTAGTTAGAAATATGAGGAATCTAAACGTCAATACCGA AAGTGGAGGTTCCGCCGTAGGAACAGGAGGAATGACAACTAAA TTGATCGCAGCTGATTTGGGTGTATCTGCAGGTGTTACAACGAT TATTTGCAAAAGTGAACATCCCGAGCAGATTTTGGACATTGTAGA GTACAGTATCCGTGCTGATAGAGTCGAAAATGAGGCTAAATATC TGGTCATCAACGAAGAGGAAACTGTGGAACAATTTCAAGAGATC AATCGGTCAGAACTGAGGGAGTTGAACAAGCTGGACATTCCTTT GCATACACGTTTCGTTGGCCACAGTTTTAATGCTGTTAATAACAA AGAGTTTTGGTTACTCCATGGACTAAAGGCCAACGGAGCCATTA TCATTGATCCAGGTTGTTATAAGGCTATCACTAGAAAAAACAAAG CTGGTATTCTTCCAGCTGGAATTATTTCCGTAGAGGGTAATTTCC ATGAATACGAGTGTGTTGATGTTAAGGTAGGACTAAGAGATCCA GATGACCCACATTCACTAGACCCCAATGAAGAACTTTACGTCGT |

| SEQ ID NO: | Description | Sequence |
|---|---|---|
| | | TGGCCGTGCCCGTTGTAATTACCCCAGCAATCAAATCAACAAAA TTAAGGGTCTACAAAGCTCGCAGATCGAGCAGGTTCTAGGTTAC GCTGACGGTGAGTATGTTGTTCACAGGGACAACTTGGCTTTCCC AGTATTTGCCGATCCAGAACTGTTGGATGTTGTTGAGAGTACCC TGTCTGAACAGGAGAGAGAATCCAAACCAAATAAATAG |
| 89 | Sequence of the 3'-region to knock into the PpPRO1 locus: | AATTTCACATATGCTGCTTGATTATGTAATTATACCTTGCGTTCG ATGGCATCGATTTCCTCTTCTGTCAATCGCGCATCGCATTAAAAG TATACTTTTTTTTTTTTCCTATAGTACTATTCGCCTTATTATAAACT TTGCTAGTATGAGTTCTACCCCCAAGAAAGAGCCTGATTTGACT CCTAAGAAGAGTCAGCCTCCAAAGAATAGTCTCGGTGGGGGTA AAGGCTTTAGTGAGGAGGGTTTCTCCCAAGGGGACTTCAGCGC TAAGCATATACTAAATCGTCGCCCTAACACCGAAGGCTCTTCTG TGGCTTCGAACGTCATCAGTTCGTCATCATTGCAAAGGTTACCA TCCTCTGGATCTGGAAGCGTTGCTGTGGGAAGTGTGTTGGGAT CTTCGCCATTAACTCTTTCTGGAGGGTTCCACGGGCTTGATCCA ACCAAGAATAAAATAGACGTTCCAAAGTCGAAACAGTCAAGGAG ACAAAGTGTTCTTTCTGACATGATTTCCACTTCTCATGCAGCTAG AAATGATCACTCAGAGCAGCAGTTACAAACTGGACAACAATCAG AACAAAAGAAGAAGATGGTAGTCGATCTTCTTTTTCTGTTTCTT CCCCCGCAAGAGATATCCGGCACCCAGATGTACTGAAAACTGTC GAGAAACATCTTGCCAATGACAGCGAGATCGACTCATCTTTACA ACTTCAAGGTGGAGATGTCACTAGAGGCATTTATCAATGGGTAA CTGGAGAAAGTAGTCAAAAAGATAACCCGCCTTTGAAACGAGCA AATAGTTTTAATGATTTTTCTTCTGTGCATGGTGACGAGGTAGGC AAGGCAGATGCTGACCACGATCGTGAAAGCGTATTCGACGAGG ATGATATCTCCATTGATGATATCAAAGTTCCGGGAGGGATGCGT CGAAGTTTTTTATTACAAAAGCATAGAGACCAACAACTTTCTGGA CTGAATAAAACGGCTCACCAACCAAAACAACTTACTAAACCTAAT TTCTTCACGAACAACTTTATAGAGTTTTTGGCATTGTATGGGCAT TTTGCAGGTGAAGATTTGGAGGAAGACGAAGATGAAGATTTAGA CAGTGGTTCCGAATCAGTCGCAGTCAGTGATAGTGAGGGAGAA TTCAGTGAGGCTGACAACAATTTGTTGTATGATGAAGAGTCTCTC CTATTAGCACCTAGTACCTCCAACTATGCGAGATCAAGAATAGG AAGTATTCGTACTCCTACTTATGGATCTTTCAGTTCAAATGTTGG TTCTTCGTCTATTCATCAGCAGTTAATGAAAAGTCAAATCCCGAA GCTGAAGAAACGTGGACAGCACAAGCATAAAACACAATCAAAAA TACGCTCGAAGAAGCAAACTACCACCGTAAAAGCAGTGTTGCTG CTATTAAA |
| 90 | Portion of human insulin A-chain | GIVEQCCTSICSLYQLENYC |
| 91 | CTP + K | SSSSKAPPPSLPSPSRLPGPSDTPILPQK |
| 92 | CTP + R | SSSSKAPPPSLPSPSRLPGPSDTPILPQR |
| 93 | CTP + KR | SSSSKAPPPSLPSPSRLPGPSDTPILPQKR |
| 94 | CTP + RR | SSSSKAPPPSLPSPSRLPGPSDTPILPQRR |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A composition comprising a conjugate comprising:
An O-glycosylated insulin or insulin analogue having an A-chain peptide comprising the amino acid sequence GIVEQCCTSICSLYQLENYC (SEQ ID NO: 90); a B-chain peptide comprising the amino acid sequence HLCGSHLVEALYLVCGERGFF (SEQ ID NO:3), and a carboxy terminal portion (CTP) peptide comprising amino acids 112-118 to 145 of the beta subunit of human chorionic gonadotropin (hCGβ) that includes at least one O-glycosylation site of the CTP peptide, wherein at least one amino acid residue of the CTP peptide is covalently linked to an O-glycan wherein the O-glycan in the composition is a mannose, mannobiose, mannotriose, or mannotetrose; and wherein the insulin or insulin analogue optionally further includes up to 17 amino acid substitutions and the CTP is covalently linked by peptide bond to the N-terminus of the B-chain, the C-terminus of the A-chain, the C-terminus of the B-chain, or the CTP peptide is a connecting peptide that covalently links the B-chain to the A-chain to produce a single-chain insulin or insulin analogue having the structure (B-chain)-(CTP peptide)-(A-chain); and a pharmaceutically acceptable carrier or salt.

2. The composition of claim 1, wherein the CTP peptide comprises the amino acid sequence of SEQ ID NO: 1.

3. The composition of claim 1, wherein the composition comprises the conjugate wherein greater than 50 mole % of the O-glycans are mannotriose and mannotetrose.

4. The composition of claim 1, wherein the composition comprises the conjugate wherein greater than 80 mole % of the O-glycans are mannotriose and mannotetrose.

5. The composition of claim 1, wherein the mannose residues are covalently linked to an adjacent mannose residue by α1,2-linkage.

6. The composition of claim 1, wherein the composition comprises the conjugate wherein greater than 95 mole % of the O-glycans are mannose.

7. The composition of claim 1, wherein the composition lacks detectable β-linked mannose, phosphomannose, or β-linked mannose and phosphomannose.

8. The composition of claim 1, wherein the insulin or insulin analogue is a heterodimer or a single-chain.

9. A pharmaceutical formulation comprising:
(a) a multiplicity of conjugates comprising O-glycosylated insulin or insulin analogues, each O-glycosylated insulin or insulin analogue having a carboxy terminal portion (CTP) peptide comprising amino acids 112-118 to 145 of the beta subunit of human chorionic gonadotropin (hCGβ) that includes at least one O-glycosylation site of the CTP peptide, wherein at least one amino acid residue of the CTP peptide is covalently linked to an O-glycan wherein the O-glycan in the composition is a mannose, mannobiose, mannotriose, or mannotetrose, and
(b) a pharmaceutically acceptable carrier or salt.

10. The composition of claim 9, wherein the CTP peptide comprises the amino acid sequence of SEQ ID NO: 1.

11. The composition of claim 9, wherein the composition comprises the conjugate wherein greater than 50 mole % of the O-glycans are mannotriose and mannotetrose.

12. The composition of claim 9, wherein the composition comprises the conjugate wherein greater than 80 mole % of the O-glycans are mannotriose and mannotetrose.

13. The composition of claim 9, wherein the mannose residues are covalently linked to an adjacent mannose residue by α1,2-linkage.

14. The composition of claim 9, wherein the composition comprises the conjugate wherein greater than 95 mole % of the O-glycans are mannose.

15. The composition of claim 9, wherein the composition lacks detectable β-linked mannose, phosphomannose, or β-linked mannose and phosphomannose.

16. The composition of claim 9, wherein the insulin or insulin analogue is a heterodimer or a single-chain.

* * * * *

SEQUENCE LISTING

<160> NUMBER OF SEQ ID NOS: 94

<210> SEQ ID NO 1
<211> LENGTH: 28
<212> TYPE: PRT
<213> ORGANISM: Artificial Sequence
<220> FEATURE:
<223> OTHER INFORMATION: Human CTP peptide

<400> SEQUENCE: 1

Ser Ser Ser Ser Lys Ala Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 21
<212> TYPE: PRT
<213> ORGANISM: Artificial Sequence
<220> FEATURE:
<223> OTHER INFORMATION: B-chain peptide core sequence

<400> SEQUENCE: 3

His Leu Cys Gly Ser His Leu Val Glu Ala Leu Tyr Leu Val Cys Gly
1               5                   10                  15

Glu Arg Gly Phe Phe
            20

<210> SEQ ID NO 4
<211> LENGTH: 30
<212> TYPE: PRT
<213> ORGANISM: Homo sapiens

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 5
<211> LENGTH: 35
<212> TYPE: PRT
<213> ORGANISM: Homo sapiens

<400> SEQUENCE: 5

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Lys Arg
        35

<210> SEQ ID NO 6
<211> LENGTH: 110
<212> TYPE: PRT
<213> ORGANISM: Artificial Sequence
<220> FEATURE:
<223> OTHER INFORMATION: Human pre-proinsulin

<400> SEQUENCE: 6

Met Ala Leu Trp Met Arg Leu Leu Pro Leu Leu Ala Leu Leu Ala Leu
1               5                   10                  15

```
Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
 50                  55                  60

Gln Val Glu Leu Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 7
<211> LENGTH: 85
<212> TYPE: PRT
<213> ORGANISM: Saccharomyces cerevisiae

<400> SEQUENCE: 7

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
 50                  55                  60

Phe Ile Asn Thr Thr Ile Ala Ser Ile Ala Ala Lys Glu Glu Gly Val
65                  70                  75                  80

Ser Leu Glu Lys Arg
                85

<210> SEQ ID NO 8
<211> LENGTH: 934
<212> TYPE: DNA
<213> ORGANISM: Pichia pastoris

<400> SEQUENCE: 8
aacatccaaa gacgaaaggt tgaatgaaac cttttgcca tccgacatcc acaggtccat      60
tctcacacat aagtgccaaa cgcaacagga ggggatacac tagcagcaga ccgttgcaaa    120
cgcaggacct ccactcctct tctcctcaac acccactttt gccatcgaaa accagcccaa    180
gttattgggc ttgattggag ctcgctcatt ccaattcctt ctattaggct actaacacca    240
tgactttatt agcctgtcta tcctggcccc cctggcgagg ttcatgtttg tttatttccg    300
aatgcaacaa gctccgcatt acacccgaac atcactccag atgagggctt tctgagtgtg    360
gggtcaaata gtttcatgtt ccccaaatgg cccaaaactg acagtttaaa cgctgtcttg    420
gaacctaata tgacaaaagc gtgatctcat ccaagatgaa ctaagtttgg ttcgttgaaa    480
tgctaacggc cagttggtca aaagaaact  tccaaaagtc ggcataccgt ttgtcttgtt    540
tggtattgat tgacgaatgc tcaaaaataa tctcattaat gcttagcgca gtctctctat    600
cgcttctgaa ccccggtgca cctgtgccga aacgcaaatg gggaaacacc cgcttttgg     660 atgattatgc attgtctcca cattgtatgc ttccaagatt ctggtgggaa tactgctgat    720
agcctaacgt tcatgatcaa aatttaactg ttctaacccc tacttgacag caatatataa    780
```

```
acagaaggaa gctgccctgt cttaaacctt tttttttatc atcattatta gcttactttc    840
ataattgcga ctggttccaa ttgacaagct tttgatttta acgactttta acgacaactt    900
gagaagatca aaaacaact  aattattcga aacg                                934

<210> SEQ ID NO 9
<211> LENGTH: 260
<212> TYPE: DNA
<213> ORGANISM: Pichia pastoris

<400> SEQUENCE: 9
tcaagaggat gtcagaatgc catttgcctg agagatgcag gcttcatttt gatactttt     60 tatttgtaac ctatatagta taggatttt  tttgtcattt tgtttcttct cgtacgagct    120
tgctcctgat cagcctatct cgcagctgat gaatatcttg tggtaggggt ttgggaaaat    180
cattcgagtt tgatgttttt cttggtattt cccactcctc ttcagagtac agaagattaa    240
gtgagacgtt cgtttgtgca                                                260

<210> SEQ ID NO 10
<211> LENGTH: 375
<212> TYPE: DNA
<213> ORGANISM: Streptoalloteichus hindustanus

<400> SEQUENCE: 10
atggccaagt tgaccagtgc cgttccggtg ctcaccgcgc gcgacgtcgc cggagcggtc    60
gagttctgga ccgaccggct cgggttctcc cgggacttcg tggaggacga cttcgccggt    120
gtggtccggg acgacgtgac cctgttcatc agcgcggtcc aggaccaggt ggtgccggac    180
aacaccctgg cctgggtgtg ggtgcgcggc ctggacgagc tgtacgccga gtggtcggag    240
gtcgtgtcca cgaacttccg ggacgcctcc gggccggcca tgaccgagat cggcgagcag    300 ccgtggggc  gggagttcgc cctgcgcgac ccggccggca actgcgtgca cttcgtggcc    360
gaggagcagg actga                                                     375

<210> SEQ ID NO 11
<211> LENGTH: 427
<212> TYPE: DNA
<213> ORGANISM: Saccharomyces cerevisiae

<400> SEQUENCE: 11
gatcccccac acaccatagc ttcaaaatgt ttctactcct ttttactct  tccagatttt    60 ctcggactcc gcgcatcgcc gtaccacttc aaaacaccca agcacagcat actaaatttc    120
ccctctttct tcctctaggg tgtcgttaat tacccgtact aaaggtttgg aaaagaaaaa    180
agagaccgcc tcgtttcttt tcttcgtcg  aaaaaggcaa taaaaatttt tatcacgttt    240 cttttcttg  aaaatttttt ttttttgattt tttttctcttt cgatgacctc ccattgatat    300
ttaagttaat aaacggtctt caatttctca gtttcagtt  tcattttct  tgttctatta    360 caactttttt tacttcttgc tcattagaaa gaaagcatag caatctaatc taagttttaa    420
ttacaaa                                                              427

<210> SEQ ID NO 12
<211> LENGTH: 293
<212> TYPE: DNA
<213> ORGANISM: Saccharomyces cerevisiae

<400> SEQUENCE: 12
acaggcccct ttccctttgt cgatatcatg taattagtta tgtcacgctt acattcacgc    60
```

```
cctcctccca catccgctct aaccgaaaag gaaggagtta gacaacctga agtctaggtc    120
cctatttatt ttttttaata gttatgttag tattaagaac gttatttata tttcaaattt    180
ttcttttttt tctgtacaaa cgcgtgtacg catgtaacat tatactgaaa accttgcttg    240
agaaggtttt gggacgctcg aaggctttaa tttgcaagct gccggctctt aag            293
```

<210> SEQ ID NO 13
<211> LENGTH: 1793
<212> TYPE: DNA
<213> ORGANISM: Pichia pastoris

<400> SEQUENCE: 13

```
ggtttctcaa ttactatata ctactaacca tttacctgta gcgtatttct tttccctctt     60
cgcgaaagct caagggcatc ttcttgactc atgaaaaata tctggatttc ttctgacaga    120
tcatcaccct tgagcccaac tctctagcct atgagtgtaa gtgatagtca tcttgcaaca    180
gattattttg gaacgcaact aacaaagcag atacacccct cagcagaatc ctttctggat    240
attgtgaaga atgatcgcca agtcacagt cctgagacag ttcctaatct ttaccccatt     300
tacaagttca tccaatcaga cttcttaacg cctcatctgg cttatatcaa gcttaccaac    360
agttcagaaa ctcccagtcc aagtttcttg cttgaaagtg cgaagaatgg tgacaccgtt    420
gacaggtaca cctttatggg acattccccc agaaaaataa tcaagactgg gcctttagag    480
ggtgctgaag ttgacccctt ggtgcttctg gaaaagaac tgaagggcac cagacaagcg     540
caacttcctg gtattcctcg tctaagtggt ggtgccatag gatacatctc gtacgattgt    600
attaagtact ttgaaccaaa aactgaagga aaactgaaag atgttttgca acttccggaa    660
gcagctttga tgttgttcga cacgatcgtg gcttttgaca atgtttatca agattccag    720 gtaattggaa acgtttctct atccgttgat gactcggacg aagctattct tgagaaatat    780
tataagacaa gagaagaagt ggaaaagatc agtaaagtgg tatttgacaa taaaactgtt    840
ccctactatg aacagaaaga tattattcaa ggccaaacgt tcacctctaa tattggtcag    900
gaagggtatg aaaaccatgt tcgcaagctg aaagaacata ttctgaaagg agacatcttc    960
caagctgttc cctctcaaag ggtagccagg ccgacctcat gcacccttt caacatctat   1020 cgtcatttga aactgtcaa tccttctcca tacatgttct atattgacta tctagacttc   1080
caagttgttg gtgcttcacc tgaattacta gttaaatccg acaacaacaa caaaatcatc   1140
acacatccta ttgctggaac tcttcccaga ggtaaaacta tcgaagagga cgacaattat   1200
gctaagcaat tgaagtcgtc tttgaaagac agggccgagc acgtcatgct ggtagatttg   1260
gccagaaatg atattaaccg tgtgtgtgag cccaccagta ccacggttga tcgtttattg   1320 actgtgggaga gattttctca tgtgatgcat cttgtgtcag aagtcagtgg aacattgaga   1380
ccaaacaaga ctcgcttcga tgctttcaga tccatttttcc cagcaggaac cgtctccggt   1440
gctccgaagg taagagcaat gcaactcata ggagaattgg aaggagaaaa gagaggtgtt   1500 tatgcgggg ccgtaggaca ctggtcgtac gatggaaat cgatggacac atgtattgcc     1560
ttaagaacaa tggtcgtcaa ggacggtgtc gcttaccttc aagccggagg tggaattgtc   1620
tacgattctg acccctatga cgagtacatc gaaaccatga acaaaatgag atccaacaat   1680
aacaccatct tggaggctga gaaaatctgg accgataggt tggccagaga cgagaatcaa   1740
agtgaatccg aagaaaacga tcaatgaacg gaggacgtaa gtaggaattt atg          1793
```

<210> SEQ ID NO 14

<211> LENGTH: 3029
<212> TYPE: DNA
<213> ORGANISM: Saccharomyces cerevisiae

<400> SEQUENCE: 14

| | | | | | |
|---|---|---|---|---|---|
| aggcctcgca | acaacctata | attgagttaa | gtgcctttcc | aagctaaaaa | gtttgaggtt | 60 |
| ataggggctt | agcatccaca | cgtcacaatc | tcgggtatcg | agtatagtat | gtagaattac | 120 |
| ggcaggaggt | ttcccaatga | acaaaggaca | ggggcacggt | gagctgtcga | aggtatccat | 180 |
| tttatcatgt | ttcgtttgta | caagcacgac | atactaagac | atttaccgta | tgggagttgt | 240 |
| tgtcctagcg | tagttctcgc | tcccccagca | aagctcaaaa | aagtacgtca | tttagaatag | 300 |
| tttgtgagca | aattaccagt | cggtatgcta | cgttagaaag | gcccacagta | ttcttctacc | 360 |
| aaaggcgtgc | ctttgttgaa | ctcgatccat | tatgagggct | tccattattc | cccgcatttt | 420 |
| tattactctg | aacaggaata | aaaagaaaaa | acccagttta | ggaaattatc | cggggggcgaa | 480 |
| gaaatacgcg | tagcgttaat | cgaccccacg | tccagggttt | ttccatggag | gtttctggaa | 540 |
| aaactgacga | ggaatgtgat | tataaatccc | tttatgtgat | gtctaagact | tttaaggtac | 600 |
| gcccgatgtt | tgcctattac | catcatagag | acgtttcttt | tcgaggaatg | cttaaacgac | 660 |
| tttgtttgac | aaaaatgttg | cctaagggct | ctatagtaaa | ccatttggaa | gaaagatttg | 720 |
| acgactttt | ttttttggat | ttcgatccta | taatccttcc | tcctgaaaag | aaacatataa | 780 |
| atagatatgt | attattcttc | aaaacattct | cttgttcttg | tgcttttttt | ttaccatata | 840 |
| tcttactttt | tttttctct | cagagaaaca | agcaaaacaa | aaagcttttc | ttttcactaa | 900 |
| cgtatatgat | gcttttgcaa | gctttccttt | tccttttggc | tggttttgca | gccaaaatat | 960 |
| ctgcatcaat | gacaaacgaa | actagcgata | gacctttggt | ccacttcaca | cccaacaagg | 1020 |
| gctggatgaa | tgacccaaat | gggttgtggt | acgatgaaaa | agatgccaaa | tggcatctgt | 1080 |
| actttcaata | caacccaaat | gacaccgtat | ggggtacgcc | attgttttgg | ggccatgcta | 1140 |
| cttccgatga | tttgactaat | tgggaagatc | aacccattgc | tatcgctccc | aagcgtaacg | 1200 |
| attcaggtgc | tttctctggc | tccatggtgg | ttgattacaa | caacacgagt | gggttttca | 1260 |
| atgatactat | tgatccaaga | caaagatgcg | ttgcgatttg | gacttataac | actcctgaaa | 1320 |
| gtgaagagca | atacattagc | tattctcttg | atggtggtta | cactttact | gaataccaaa | 1380 |
| agaaccctgt | tttagctgcc | aactccactc | aattcagaga | tccaaaggtg | ttctggtatg | 1440 |
| aaccttctca | aaaatggatt | atgacggctg | ccaaatcaca | agactacaaa | attgaaattt | 1500 |
| actcctctga | tgacttgaag | tcctggaagc | tagaatctgc | atttgccaat | gaaggtttct | 1560 |
| taggctacca | atacgaatgt | ccaggtttga | ttgaagtccc | aactgagcaa | gatccttcca | 1620 |
| aatcttattg | ggtcatgttt | atttctatca | acccaggtgc | acctgctggc | ggttccttca | 1680 |
| accaatattt | tgttggatcc | ttcaatggta | ctcattttga | agcgtttgac | aatcaatcta | 1740 |
| gagtggtaga | ttttggtaag | gactactatg | ccttgcaaac | tttcttcaac | actgacccaa | 1800 |
| cctacggttc | agcattaggt | attgcctggg | cttcaaactg | ggagtacagt | gcctttgtcc | 1860 |
| caactaaccc | atggagatca | tccatgtctt | tggtccgcaa | gttttctttg | aacactgaat | 1920 |
| atcaagctaa | tccagagact | gaattgatca | atttgaaagc | cgaaccaata | ttgaacatta | 1980 |
| gtaatgctgg | tcctggtct | cgttttgcta | ctaacacaac | tctaactaag | gccaattctt | 2040 |
| acaatgtcga | tttgagcaac | tcgactggta | ccctagagtt | tgagttggtt | tacgctgtta | 2100 |
| acaccacaca | aaccatatcc | aaatccgtct | ttgccgactt | atcactttgg | ttcaagggtt | 2160 |
| tagaagatcc | tgaagaatat | ttgagaatgg | gttttgaagt | cagtgcttct | tccttcttt | 2220 |

```
tggaccgtgg taactctaag gtcaagtttg tcaaggagaa cccatatttc acaaacagaa    2280
tgtctgtcaa caaccaacca ttcaagtctg agaacgacct aagttactat aaagtgtacg    2340
gcctactgga tcaaaacatc ttggaattgt acttcaacga tggagatgtg gtttctacaa    2400 ataccta ctt catgaccacc ggtaacgctc taggatctgt gaacatgacc actggtgtcg    2460
ataatttgtt ctacattgac aagttccaag taagggaagt aaaatagagg ttataaaact    2520
tattgtcttt tttattttt tcaaaagcca ttctaaaggg ctttagctaa cgagtgacga    2580
atgtaaaact ttatgatttc aagaatacc tccaaccat tgaaaatgta tttttatttt    2640
tattttctcc cgaccccagt tacctggaat tgttcttta tgtactttat ataagtataa    2700
ttctcttaaa aattttact actttgcaat agacatcatt ttttcacgta ataaacccac    2760
aatcgtaatg tagttgcctt acactactag gatggaccct tttgccttta tctgttttgt    2820
tactgacaca atgaaaccgg gtaaagtatt agttatgtga aaatttaaaa gcattaagta    2880
gaagtatacc atattgtaaa aaaaaaaagc gttgtcttct acgtaaaagt gttctcaaaa    2940
agaagtagtg agggaaatgg ataccaagct atctgtaaca ggagctaaaa aatctcaggg    3000
aaaagcttct ggtttgggaa acggtcgac                                       3029
```

<210> SEQ ID NO 15
<211> LENGTH: 898
<212> TYPE: DNA
<213> ORGANISM: Artificial Sequence
<220> FEATURE:
<223> OTHER INFORMATION: Sequence of the 5'-Region used for knock out of
      PpURA5

<400> SEQUENCE: 15

```
atcggccttt gttgatgcaa gttttacgtg gatcatggac taaggagttt tatttggacc     60
aagttcatcg tcctagacat tacggaaagg gttctgctcc tcttttttgga aacttttttgg   120 aacctctgag tatgacagct tggtggattg tacccatggt atggcttcct gtgaatttct   180
attttttcta cattggattc accaatcaaa acaaattagt cgccatggct ttttggcttt   240
tgggtctatt tgtttggacc ttcttggaat atgcttttgca tagattttttg ttccacttgg   300 actactatct tccagagaat caaattgcat ttaccattca tttcttattg catgggatac   360
accactattt accaatggat aaatacagat tggtgatgcc acctacactt ttcattgtac   420
tttgctaccc aatcaagacg ctcgtctttt ctgttctacc atattacatg gcttgttctg   480
gatttgcagg tggattcctg ggctatatca tgtatgatgt cactcattac gttctgcatc   540
actccaagct gcctcgttat ttccaagagt tgaagaaata tcatttggaa catcactaca   600
agaattacga gttaggcttt ggtgtcactt ccaaattctg ggacaaagtc tttgggactt   660
atctgggtcc agacgatgtg tatcaaaaga caaattagag tatttataaa gttatgtaag   720
caaatagggg ctaatagga aagaaaaatt ttggttcttt atcagagctg gctcgcgcgc   780 agtgttttttc gtgctccttt gtaatagtca tttttgacta ctgttcagat tgaaatcaca   840
ttgaagatgt cactcgaggg gtaccaaaaa aggttttttgg atgctgcagt ggcttcgc      898
```

<210> SEQ ID NO 16
<211> LENGTH: 1060
<212> TYPE: DNA
<213> ORGANISM: Artificial Sequence
<220> FEATURE:
<223> OTHER INFORMATION: Sequence of the 3'-Region used for knock out of
      PpURA5

```
<400> SEQUENCE: 16
ggtcttttca acaaagctcc attagtgagt cagctggctg aatcttatgc acaggccatc      60
attaacagca acctggagat agacgttgta tttggaccag cttataaagg tattcctttg     120
gctgctatta ccgtgttgaa gttgtacgag ctcggcggca aaaaatacga aaatgtcgga     180
tatgcgttca atagaaaaga aaagaaagac cacggagaag gtggaagcat cgttggagaa     240
agtctaaaga ataaaagagt actgattatc gatgatgtga tgactgcagg tactgctatc     300
aacgaagcat ttgctataat tggagctgaa ggtgggagag ttgaaggtag tattattgcc     360
ctagatagaa tggagactac aggagatgac tcaaatacca gtgctaccca ggctgttagt     420
cagagatatg gtaccctgt cttgagtata gtgacattgg accatattgt ggcccatttg     480
ggcgaaactt tcacagcaga cgagaaatct caaatggaaa cgtatagaaa aaagtatttg     540
cccaaataag tatgaatctg cttcgaatga atgaattaat ccaattatct tctcaccatt     600
attttcttct gtttcggagc tttgggcacg gcggcgggtg gtgcgggctc aggttcccct     660
tcataaacag atttagtact tggatgctta atagtgaatg gcgaatgcaa aggaacaatt     720
tcgttcatct ttaacccttt cactcggggt acacgttctg gaatgtaccc gccctgttgc     780
aactcaggtg gaccgggcaa ttcttgaact ttctgtaacg ttgttggatg ttcaaccaga     840
aattgtccta ccaactgtat tagttttcct ttggtcttat attgttcatc gagatacttc     900
ccactctcct tgatagccac tctcactctt cctggattac caaaatcttg aggatgagtc     960
ttttcaggct ccaggatgca aggtatatcc aagtacctgc aagcatctaa tattgtcttt    1020
gccaggggt tctccacacc atactccttt tggcgcatgc                            1060

<210> SEQ ID NO 17
<211> LENGTH: 957
<212> TYPE: DNA
<213> ORGANISM: Artificial Sequence
<220> FEATURE:
<223> OTHER INFORMATION: Sequence of the PpURA5 auxotrophic marker

<400> SEQUENCE: 17
tctagaggga cttatctggg tccagacgat gtgtatcaaa agacaaatta gagtatttat      60
aaagttatgt aagcaaatag gggctaatag ggaaagaaaa attttggttc tttatcagag     120
ctggctcgcg cgcagtgttt ttcgtgctcc tttgtaatag tcattttga ctactgttca     180
gattgaaatc acattgaaga tgtcactgga ggggtaccaa aaaaggtttt tggatgctgc     240
agtggcttcg caggccttga agtttggaac tttcaccttg aaaagtggaa gacagtctcc     300
atacttcttt aacatgggtc ttttcaacaa agctccatta gtgagtcagc tggctgaatc     360
ttatgctcag gccatcatta acagcaacct ggagatagac gttgtatttg gaccagctta     420
taaggtatt cctttggctg ctattaccgt gttgaagttg tacgagctgg gcggcaaaaa     480
atacgaaaat gtcggatatg cgttcaatag aaaagaaaag aaagaccacg gagaaggtgg     540
aagcatcgtt ggagaaagtc taaagaataa aagagtactg attatcgatg atgtgatgac     600
tgcaggtact gctatcaacg aagcatttgc tataattgga gctgaaggtg ggagagttga     660
aggttgtatt attgccctag atagaatgga gactacagga gatgactcaa ataccagtgc     720
tacccaggct gttagtcaga gatatggtac ccctgtcttg agtatagtga cattggacca     780
tattgtggcc catttgggcg aaactttcac agcagacgag aaatctcaaa tggaaacgta     840
tagaaaaaag tatttgccca aataagtatg aatctgcttc gaatgaatga attaatccaa     900
ttatcttctc accattattt tcttctgttt cggagctttg ggcacggcgg cggatcc        957
```

<210> SEQ ID NO 18
<211> LENGTH: 709
<212> TYPE: DNA
<213> ORGANISM: Escherichia coli

<400> SEQUENCE: 18

```
cctgcactgg atggtggcgc tggatggtaa gccgctggca agcggtgaag tgcctctgga      60
tgtcgctcca caaggtaaac agttgattga actgcctgaa ctaccgcagc cggagagcgc     120
cgggcaactc tggctcacag tacgcgtagt gcaaccgaac gcgaccgcat ggtcagaagc     180
cgggcacatc agcgcctggc agcagtggcg tctggcggaa aacctcagtg tgacgctccc     240
cgccgcgtcc cacgccatcc cgcatctgac caccagcgaa atggattttt gcatcgagct     300
gggtaataag cgttggcaat taaccgcca gtcaggcttt cttcacaga tgtggattgg       360
cgataaaaaa caactgctga cgccgctgcg cgatcagttc acccgtgcac cgctggataa     420
cgacattggc gtaagtgaag cgacccgcat tgaccctaac gcctgggtcg aacgctggaa     480
ggcggcgggc cattaccagg ccgaagcagc gttgttgcag tgcacggcag atacacttgc     540
tgatgcggtg ctgattacga ccgctcacgc gtggcagcat caggggaaaa ccttatttat     600
cagccggaaa acctaccgga ttgatggtag tggtcaaatg gcgattaccg ttgatgttga     660
agtggcgagc gatacaccgc atccggcgcg gattggcctg aactgccag                 709
```

<210> SEQ ID NO 19
<211> LENGTH: 2875
<212> TYPE: DNA
<213> ORGANISM: Artificial Sequence
<220> FEATURE:
<223> OTHER INFORMATION: Sequence of the 5'-Region used for knock out of PpOCH1

<400> SEQUENCE: 19

```
aaaacctttt ttcctattca aacacaaggc attgcttcaa cacgtgtgcg tatccttaac      60
acagatactc catacttcta ataatgtgat agacgaatac aaagatgttc actctgtgtt     120
gtgtctacaa gcatttctta ttctgattgg ggatattcta gttacagcac taaacaactg     180
gcgatacaaa cttaaattaa ataatccgaa tctagaaaat gaacttttgg atggtccgcc     240
tgttggttgg ataaatcaat accgattaaa tggattctat tccaatgaga gagtaatcca     300
agacactctg atgtcaataa tcatttgctt gcaacaacaa acccgtcatc taatcaaagg     360
gtttgatgag gcttaccttc aattgcagat aaactcattg ctgtccactg ctgtattatg     420
tgagaatatg ggtgatgaat ctggtcttct ccactcagct aacatggctg tttgggcaaa     480
ggtggtacaa ttatacggag atcaggcaat agtgaaattg ttgaatatgg ctactggacg     540
atgcttcaag gatgtacgtc tagtaggagc cgtgggaaga ttgctggcag aaccagttgg     600
cacgtcgcaa caatccccaa gaatgaaat aagtgaaaac gtaacgtcaa agacagcaat     660
ggagtcaata ttgataacac cactggcaga gcggttcgta cgtcgttttg gagccgatat     720
gaggctcagc gtgctaacag cacgattgac aagaagactc tcgagtgaca gtaggttgag     780
taaagtattc gcttagattc ccaaccttcg ttttattctt tcgtagacaa agaagctgca     840
tgcgaacata gggacaactt ttataaatcc aattgtcaaa ccaacgtaaa accctctggc     900
accattttca acatatattt gtgaagcagt acgcaatatc gataaatact caccgttgtt     960
tgtaacagcc ccaacttgca tacgccttct aatgacctca aatggataag ccgcagcttg    1020
tgctaacata ccagcagcac cgcccgcggt cagctgcgcc cacacatata aaggcaatct    1080
```

```
acgatcatgg gaggaattag ttttgaccgt caggtcttca agagttttga actcttcttc    1140
ttgaactgtg taacctttta aatgacggga tctaaatacg tcatggatga gatcatgtgt    1200
gtaaaaactg actccagcat atggaatcat tccaaagatt gtaggagcga acccacgata    1260
aaagtttccc aaccttgcca aagtgtctaa tgctgtgact tgaaatctgg gttcctcgtt    1320
gaagaccctg cgtactatgc ccaaaaactt tcctccacga gccctattaa cttctctatg    1380
agtttcaaat gccaaacgga cacggattag gtccaatggg taagtgaaaa acacagagca    1440
aaccccagct aatgagccgg ccagtaaccg tcttggagct gtttcataag agtcattagg    1500
gatcaataac gttctaatct gttcataaca tacaaatttt atggctgcat agggaaaaat    1560
tctcaacagg gtagccgaat gaccctgata tagacctgcg acaccatcat acccatagat    1620
ctgcctgaca gccttaaaga gcccgctaaa agacccggaa aaccgagaga actctggatt    1680
agcagtctga aaagaatctt tcactctgtc tagtggagca attaatgtct tagcggcact    1740
tcctgctact ccgccagcta ctcctgaata gatcacatac tgcaaagact gcttgtcgat    1800
gaccttgggg ttatttagct tcaagggcaa ttttttgggac attttggaca caggagactc    1860
agaaacagac acagagcgtt ctgagtcctg gtgctcctga cgtaggccta gaacaggaat    1920
tattggcttt atttgtttgt ccatttcata ggcttggggt aatagataga tgacagagaa    1980
atagagaaga cctaatattt tttgttcatg gcaaatcgcg ggttcgcggt cgggtcacac    2040
acggagaagt aatgagaaga gctggtaatc tggggtaaaa gggttcaaaa gaaggtcgcc    2100
tggtagggat gcaatacaag gttgtcttgg agtttacatt gaccagatga tttggctttt    2160
tctctgttca attcacattt ttcagcgaga atcggattga cggagaaatg gcggggtgtg    2220
gggtggatag atggcagaaa tgctcgcaat caccgcgaaa gaaagacttt atggaataga    2280
actactgggt ggtgtaagga ttacatagct agtccaatgg agtccgttgg aaaggtaaga    2340
agaagctaaa accggctaag taactaggga agaatgatca gactttgatt tgatgaggtc    2400
tgaaaatact ctgctgcttt ttcagttgct ttttccctgc aacctatcat tttccttttc    2460
ataagcctgc ctttctgtt tcacttata tgagttccgc cgagacttcc ccaaattctc    2520
tcctggaaca ttctctatcg ctctccttcc aagttgcgcc ccctggcact gcctagtaat    2580
attaccacgc gacttatatt cagttccaca atttccagtg ttcgtagcaa atatcatcag    2640
ccatggcgaa ggcagatggc agtttgctct actataatcc tcacaatcca cccagaaggt    2700
attacttcta catggctata ttcgccgttt ctgtcatttg cgttttgtac ggaccctcac    2760
aacaattatc atctccaaaa atagactatg atccattgac gctccgatca cttgatttga    2820
agactttgga agctccttca cagttgagtc caggcaccgt agaagataat cttcg         2875
```

<210> SEQ ID NO 20
<211> LENGTH: 997
<212> TYPE: DNA
<213> ORGANISM: Artificial Sequence
<220> FEATURE:
<223> OTHER INFORMATION: Sequence of the 3'-Region used for knock out of
      PpOCH1

<400> SEQUENCE: 20

```
aaagctagag taaaatagat atagcgagat tagagaatga ataccttctt ctaagcgatc      60
gtccgtcatc atagaatatc atggactgta tagtttttttt tttgtacata taatgattaa     120
acggtcatcc aacatctcgt tgacagatct ctcagtacgc gaaatccctg actatcaaag     180
caagaaccga tgaagaaaaa aacaacagta acccaaacac cacaacaaac actttatctt     240
```

```
ctcccccca acaccaatca tcaaagagat gtcggaacca acaccaagaa agcaaaaact        300
aaccccatat aaaaacatcc tggtagataa tgctggtaac ccgctctcct tccatattct        360
gggctacttc acgaagtctg accggtctca gttgatcaac atgatcctcg aaatgggtgg        420
caagatcgtt ccagacctgc ctcctctggt agatggagtg ttgttttga cagggggatta       480 caagtctatt gatgaagata ccctaaagca actgggggac gttccaatat acagagactc       540
cttcatctac cagtgttttg tgcacaagac atctcttccc attgacactt tccgaattga       600
caagaacgtc gacttggctc aagatttgat caatagggcc cttcaagagt ctgtggatca       660
tgtcacttct gccagcacag ctgcagctgc tgctgttgtt gtcgctacca acggcctgtc       720
ttctaaacca gacgctcgta ctagcaaaat acagttcact cccgaagaag atcgttttat       780
tcttgacttt gttaggagaa atcctaaacg aagaaacaca catcaactgt acactgagct       840
cgctcagcac atgaaaaacc atacgaatca ttctatccgc cacagatttc gtcgtaatct       900
ttccgctcaa cttgattggg tttatgatat cgatccattg accaaccaac ctcgaaaaga       960
tgaaaacggg aactacatca aggtacaagg ccttcca                                 997

<210> SEQ ID NO 21
<211> LENGTH: 2159
<212> TYPE: DNA
<213> ORGANISM: Kluyveromyces lactis

<400> SEQUENCE: 21
aaacgtaacg cctggcactc tattttctca aacttctggg acggaagagc taaatattgt         60
gttgcttgaa caaacccaaa aaaacaaaaa aatgaacaaa ctaaaactac acctaaataa        120
accgtgtgta aaacgtagta ccatattact agaaaagatc acaagtgtat cacacatgtg        180
catctcatat tacatctttt atccaatcca ttctctctat cccgtctgtt cctgtcagat        240
tctttttcca taaaagaag aagaccccga atctcaccgg tacaatgcaa aactgctgaa        300 aaaaaagaa agttcactgg atacgggaac agtgccagta ggcttcacca catggacaaa        360
acaattgacg ataaaataag caggtgagct tcttttttcaa gtcacgatcc ctttatgtct       420
cagaaacaat atatacaagc taaacccttt tgaaccagtt ctctcttcat agttatgttc       480
acataaattg cgggaacaag actccgctgg ctgtcaggta cacgttgtaa cgttttcgtc       540
cgcccaatta ttagcacaac attggcaaaa agaaaaactg ctcgttttct ctacaggtaa       600
attacaattt ttttcagtaa ttttcgctga aaaatttaaa gggcaggaaa aaaagacgat       660
ctcgactttg catagatgca agaactgtgg tcaaaacttg aaatagtaat tttgctgtgc       720
gtgaactaat aaatatatat atatatatat atatatattt gtgtattttg tatatgtaat       780
tgtgcacgtc ttggctattg gatataagat tttcgcgggt tgatgacata gagcgtgtac       840
tactgtaata gttgtatatt caaaagctgc tgcgtggaga aagactaaaa tagataaaaa       900
gcacacattt tgacttcggt accgtcaact tagtgggaca gtcttttata tttggtgtaa       960
gctcatttct ggtactattc gaaacagaac agtgttttct gtattaccgt ccaatcgttt      1020
gtcatgagtt ttgtattgat tttgtcgtta gtgttcggag gatgttgttc caatgtgatt      1080
agtttcgagc acatggtgca aggcagcaat ataaatttgg gaaatattgt tacattcact      1140
caattcgtgt ctgtgacgct aattcagttg cccaatgctt tggacttctc tcactttccg      1200
tttaggttgc gacctagaca cattcctctt aagatccata tgttagctgt gttttttgttc      1260 tttaccagtt cagtcgccaa taacagtgtg tttaaatttg acatttccgt tccgattcat      1320
```

```
attatcatta gattttcagg taccactttg acgatgataa taggttgggc tgtttgtaat    1380
aagaggtact ccaaacttca ggtgcaatct gccatcatta tgacgcttgg tgcgattgtc    1440
gcatcattat accgtgacaa agaattttca atggacagtt taaagttgaa tacggattca    1500
gtgggtatga cccaaaaatc tatgtttggt atctttgttg tgctagtggc cactgccttg    1560
atgtcattgt tgtcgttgct caacgaatgg acgtataaca agtacgggaa acattggaaa    1620
gaaactttgt tctattcgca tttcttggct ctaccgttgt ttatgttggg gtacacaagg    1680
ctcagagacg aattcagaga cctcttaatt tcctcagact caatggatat tcctattgtt    1740
aaattaccaa ttgctacgaa acttttcatg ctaatagcaa ataacgtgac ccagttcatt    1800
tgtatcaaag gtgttaacat gctagctagt aacacggatg ctttgacact ttctgtcgtg    1860
cttctagtgc gtaaatttgt tagtctttta ctcagtgtct acatctacaa gaacgtccta    1920
tccgtgactg catacctagg gaccatcacc gtgttcctgg gagctggttt gtattcatat    1980
ggttcggtca aaactgcact gcctcgctga acaatccac gtctatga tactcgtttc    2040 agaattttt tgatttctg ccggatatgg tttctcatct ttacaatcgc attcttaatt    2100
ataccagaac gtaattcaat gatcccagtg actcgtaact cttatatgtc aatttaagc    2159
```

<210> SEQ ID NO 22
<211> LENGTH: 870
<212> TYPE: DNA
<213> ORGANISM: Artificial Sequence
<220> FEATURE:
<223> OTHER INFORMATION: Sequence of the 5'-Region used for knock out of
      PpBMT2

<400> SEQUENCE: 22

```
ggccgagcgg gcctagattt tcactacaaa tttcaaaact acgcggattt attgtctcag     60
agagcaattt ggcatttctg agcgtagcag gaggcttcat aagattgtat aggaccgtac    120
caacaaattg ccgaggcaca acacggtatg ctgtgcactt atgtggctac ttccctacaa    180
cggaatgaaa ccttcctctt tccgcttaaa cgagaaagtg tgtcgcaatt gaatgcaggt    240
gcctgtgcgc cttggtgtat tgttttgag ggcccaattt atcaggcgcc ttttttcttg    300
gttgttttcc cttagcctca agcaaggttg gtctatttca tctccgcttc tataccgtgc    360
ctgatactgt tggatgagaa cacgactcaa cttcctgctg ctctgtattg ccagtgtttt    420
gtctgtgatt tggatcggag tcctccttac ttggaatgat aataatcttg gcggaatctc    480
cctaaacgga ggcaaggatt ctgcctatga tgatctgcta tcattgggaa gcttcaacga    540
catggaggtc gactcctatg tcaccaacat ctacgacaat gctccagtgc taggatgtac    600
ggatttgtct tatcatggat tgttgaaagt cacccccaaag catgacttag cttgcgattt    660
ggagttcata agagctcaga ttttggacat tgacgtttac tccgccataa aagacttaga    720
agataaagcc ttgactgtaa acaaaaggt tgaaaaacac tggtttacgt tttatggtag    780
ttcagtcttt ctgcccgaac acgatgtgca ttacctggtt agacgagtca tcttttcggc    840
tgaaggaaag gcgaactctc cagtaacatc                                     870
```

<210> SEQ ID NO 23
<211> LENGTH: 1733
<212> TYPE: DNA
<213> ORGANISM: Artificial Sequence
<220> FEATURE:
<223> OTHER INFORMATION: Sequence of the 3'-Region used for knock out of
      PpBMT2

<400> SEQUENCE: 23

```
ccatatgatg ggtgtttgct cactcgtatg gatcaaaatt ccatggtttc ttctgtacaa      60
cttgtacact tatttggact tttctaacgg tttttctggt gatttgagaa gtccttattt     120
tggtgttcgc agcttatccg tgattgaacc atcagaaata ctgcagctcg ttatctagtt     180
tcagaatgtg ttgtagaata caatcaattc tgagtcagtt tgggtgggt cttggcgacg      240
ggaccgttat atgcatctat gcagtgttaa ggtacataga atgaaaatgt aggggttaat     300
cgaaagcatc gttaatttca gtagaacgta gttctattcc ctacccaaat aatttgccaa     360
gaatgcttcg tatccacata cgcagtggac gtagcaaatt tcactttgga ctgtgaccte     420
aagtcgttat cttctacttg gacattgatg gtcattacg aatccacaaa gaattggata      480
gcctctcgtt ttatctagtg cacagcctaa tagcacttaa gtaagagcaa tggacaaatt     540
tgcatagaca ttgagctaga tacgtaactc agatcttgtt cactcatggt gtactcgaag     600
tactgctgga accgttacct cttatcattt cgctactggc tcgtgaaact actggatgaa     660
aaaaaaaaaa gagctgaaag cgagatcatc ccattttgtc atcatacaaa ttcacgcttg     720
cagttttgct tcgttaacaa gacaagatgt ctttatcaaa gacccgtttt tcttcttga     780
agaatacttc cctgttgagc acatgcaaac catatttatc tcagatttca ctcaacttgg     840
gtgcttccaa gagaagtaaa attcttccca ctgcatcaac ttccaagaaa cccgtagacc     900
agtttctctt cagccaaaag aagttgctcg ccgatcaccg cggtaacaga ggagtcagaa     960
ggtttcacac ccttccatcc cgatttcaaa gtcaaagtgc tgcgttgaac caaggttttc    1020
aggttgccaa agcccagtct gcaaaaacta gttccaaatg gcctattaat tcccataaaa    1080
gtgttggcta cgtatgtatc ggtacctcca ttctggtatt tgctattgtt gtcgttggtg    1140
ggttgactag actgaccgaa tccggtcttt ccataacgga gtggaaacct atcactggtt    1200
cggttccccc actgactgag gaagactgga agttggaatt tgaaaaatac aaacaaagcc    1260
ctgagtttca ggaactaaat tctcacataa cattggaaga gttcaagttt atattttcca    1320
tggaatgggg acatagattg ttgggaaggg tcatcggcct gtcgtttgtt cttcccacgt    1380
tttacttcat tgcccgtcga agtgttcca aagatgttgc attgaaactg cttgcaatat    1440
gctctatgat aggattccaa ggtttcatcg gctggtggat ggtgtattcc ggattggaca    1500
aacagcaatt ggctgaacgt aactccaaac caactgtgtc tccatatcgc ttaactaccc    1560
atcttggaac tgcatttgtt atttactgtt acatgattta cacagggctt caagttttga    1620
agaactataa gatcatgaaa cagcctgaag cgtatgttca aattttcaag caaattgcgt    1680
ctccaaaatt gaaaactttc aagagactct cttcagttct attaggcctg gtg           1733

<210> SEQ ID NO 24
<211> LENGTH: 981
<212> TYPE: DNA
<213> ORGANISM: Mus musculus

<400> SEQUENCE: 24
atgtctgcca acctaaaata tctttccttg ggaattttgg tgtttcagac taccagtctg      60
gttctaacga tgcggtattc taggactta aaagaggagg ggcctcgtta tctgtcttct      120
acagcagtgg ttgtggctga attttgaag ataatggcct gcatcttttt agtctacaaa      180
gacagtaagt gtagtgtgag agcactgaat agagtactgc atgatgaaat tcttaataag     240
cccatggaaa ccctgaagct cgctatcccg tcagggatat atactcttca gaacaactta     300
ctctatgtgg cactgtcaaa cctagatgca gccacttacc aggttacata tcagttgaaa     360
```

```
atacttacaa cagcattatt ttctgtgtct atgcttggta aaaaattagg tgtgtaccag    420
tggctctccc tagtaattct gatggcagga gttgcttttg tacagtggcc ttcagattct    480
caagagctga actctaagga cctttcaaca ggctcacagt ttgtaggcct catggcagtt    540
ctcacagcct gtttttcaag tggctttgct ggagtttatt ttgagaaaat cttaaaagaa    600
acaaaacagt cagtatggat aaggaacatt caacttggtt tctttggaag tatatttgga    660
ttaatgggtg tatacgttta tgatggagaa ttggtctcaa agaatggatt ttttcaggga    720
tataatcaac tgacgtggat agttgttgct ctgcaggcac ttggaggcct tgtaatagct    780
gctgtcatca aatatgcaga taacatttta aaaggatttg cgacctcctt atccataata    840
ttgtcaacaa taatatctta tttttggttg caagattttg tgccaaccag tgtcttttc    900 cttggagcca tccttgtaat agcagctact ttcttgtatg gttacgatcc caaacctgca    960
ggaaatccca ctaaagcata g                                              981
```

<210> SEQ ID NO 25
<211> LENGTH: 486
<212> TYPE: DNA
<213> ORGANISM: Pichia pastoris

<400> SEQUENCE: 25

```
tttttgtaga aatgtcttgg tgtcctcgtc caatcaggta gccatctctg aaatatctgg     60
ctccgttgca actccgaacg acctgctggc aacgtaaaat tctccggggt aaaacttaaa    120
tgtggagtaa tggaaccaga aacgtctctt cccttctctc tccttccacc gcccgttacc    180
gtccctagga aattttactc tgctggagag cttcttctac ggccccttg cagcaatgct    240 cttcccagca ttacgttgcg ggtaaaacgg aggtcgtgta cccgacctag cagcccaggg    300
atggaaaagt cccggccgtc gctggcaata tagcgggcg gacgcatgtc atgagattat    360
tggaaaccac cagaatcgaa tataaaaggc gaacacctt cccaattttg gtttctcctg    420
acccaaagac tttaaattta atttatttgt ccctatttca atcaattgaa caactatcaa    480
aacaca                                                               486
```

<210> SEQ ID NO 26
<211> LENGTH: 21
<212> TYPE: PRT
<213> ORGANISM: Artificial Sequence
<220> FEATURE:
<223> OTHER INFORMATION: Ypslss

<400> SEQUENCE: 26

Met Lys Leu Lys Thr Val Arg Ser Ala Val Leu Ser Ser Leu Phe Ala
1               5                   10                  15

Ser Gln Val Leu Gly
            20

<210> SEQ ID NO 27
<211> LENGTH: 1128
<212> TYPE: DNA
<213> ORGANISM: Artificial Sequence
<220> FEATURE:
<223> OTHER INFORMATION: Sequence of the 5'-Region used for knock out of
      PpMNN4L1

<400> SEQUENCE: 27

```
gatctggcca ttgtgaaact tgacactaaa gacaaaactc ttagagtttc caatcactta     60
ggagacgatg tttcctacaa cgagtacgat ccctcattga tcatgagcaa tttgtatgtg    120
```

```
aaaaaagtca tcgaccttga caccttggat aaaagggctg aggaggtgg  aaccacctgt    180 gcaggcggtc tgaaagtgtt caagtacgga tctactacca aatatacatc tggtaacctg    240
aacggcgtca ggttagtata ctggaacgaa ggaaagttgc aaagctccaa atttgtggtt    300
cgatcctcta attactctca aaagcttgga ggaaacagca acgccgaatc aattgacaac    360
aatggtgtgg gttttgcctc agctggagac tcaggcgcat ggattctttc caagctacaa    420
gatgttaggg agtaccagtc attcactgaa aagctaggtg aagctacgat gagcattttc    480
gatttccacg gtcttaaaca ggagacttct actacagggc ttggggtagt tggtatgatt    540
cattcttacg acggtgagtt caaacagttt ggtttgttca ctccaatgac atctattcta    600
caaagacttc aacgagtgac caatgtagaa tggtgtgtag cgggttgcga agatggggat    660
gtggacactg aaggagaaca cgaattgagt gatttggaac aactgcatat gcatagtgat    720
tccgactagt caggcaagag agagccctca aatttacctc tctgcccctc ctcactcctt    780
ttggtacgca taattgcagt ataaagaact tgctgccagc cagtaatctt atttcatacg    840
cagttctata tagcacataa tcttgcttgt atgtatgaaa tttaccgcgt tttagttgaa    900
attgtttatg ttgtgtgcct tgcatgaaat ctctcgttag ccctatcctt acatttaact    960
ggtctcaaaa cctctaccaa ttccattgct gtacaacaat atgaggcggc attactgtag   1020
ggttggaaaa aaattgtcat tccagctaga gatcacacga cttcatcacg cttattgctc   1080
ctcattgcta aatcatttac tcttgacttc gacccagaaa agttcgcc                1128

<210> SEQ ID NO 28
<211> LENGTH: 1231
<212> TYPE: DNA
<213> ORGANISM: Artificial Sequence
<220> FEATURE:
<223> OTHER INFORMATION: Sequence of the 3'-Region used for knock out of
      PpMNN4L1

<400> SEQUENCE: 28
gcatgtcaaa cttgaacaca acgactagat agttgttttt tctatataaa acgaaacgtt     60 atcatctttta ataatcattg aggtttaccc ttatagttcc gtattttcgt ttccaaactt    120
agtaatcttt tggaaatatc atcaaagctg gtgccaatct tcttgtttga agtttcaaac    180
tgctccacca agctacttag agactgttct aggtctgaag caacttcgaa cacagagaca    240
gctgccgccg attgttcttt tttgtgtttt tcttctggaa gaggggcatc atcttgtatg    300
tccaatgccc gtatcctttc tgagttgtcc gacacattgt ccttcgaaga gtttcctgac    360
attgggcttc ttctatccgt gtattaattt tgggttaagt tcctcgtttg catagcagtg    420
gatacctcga ttttttttggc tcctatttac ctgacataat attctactat aatccaactt    480
ggacgcgtca tctatgataa ctaggctctc ctttgttcaa aggggacgtc ttcataatcc    540
actggcacga agtaagtctg caacgaggcg cttttgcaa cagaacgata gtgtcgtttc    600
gtacttggac tatgctaaac aaaaggatct gtcaaacatt tcaaccgtgt ttcaaggcac    660
tctttacgaa ttatcgacca agaccttcct agacgaacat ttcaacatat ccaggctact    720
gcttcaaggt ggtgcaaatg ataaaggtat agatattaga tgtgtttggg acctaaaaca    780
gttcttgcct gaagattccc ttgagcaaca ggcttcaata gccaagttag agaagcagta    840
ccaaatcggt aacaaaaggg ggaagcatat aaaaccttta ctattgcgac aaaatccatc    900
cttgaaagta aagctgtttg ttcaatgtaa agcatacgaa acgaaggagg tagatcctaa    960
gatggttaga gaacttaacg ggacatactc cagctgcatc ccatattacg atcgctggaa   1020
```

```
gactttttc atgtacgtat cgcccaccaa cctttcaaag caagctaggt atgattttga    1080
cagttctcac aatccattgg ttttcatgca acttgaaaaa acccaactca aacttcatgg    1140
ggatccatac aatgtaaatc attacgagag ggcgaggttg aaaagtttcc attgcaatca    1200
cgtcgcatca tggctactga aaggccttaa c                                    1231
```

<210> SEQ ID NO 29
<211> LENGTH: 937
<212> TYPE: DNA
<213> ORGANISM: Artificial Sequence
<220> FEATURE:
<223> OTHER INFORMATION: Sequence of the 5'-Region used for knock out of
      PpPNO1 and PpMNN4

<400> SEQUENCE: 29

```
tcattctata tgttcaagaa aagggtagtg aaaggaaaga aaaggcatat aggcgaggga     60
gagttagcta gcatacaaga taatgaagga tcaatagcgg tagttaaagt gcacaagaaa    120
agagcacctg ttgaggctga tgataaagct ccaattacat tgccacagag aaacacagta    180
acagaaatag gaggggatgc accacgagaa gagcattcag tgaacaactt tgccaaattc    240 ataacccccaa gcgctaataa gccaatgtca aagtcggcta ctaacattaa tagtacaaca    300
actatcgatt ttcaaccaga tgtttgcaag gactacaaac agacaggtta ctgcggatat    360
ggtgacactt gtaagttttt gcacctgagg atgatttca aacagggatg gaaattagat    420
agggagtggg aaaatgtcca aaagaagaag cataatactc tcaaaggggt taaggagatc    480
caaatgttta atgaagatga gctcaaagat atcccgttta aatgcattat atgcaaagga    540
gattacaaat cacccgtgaa aacttcttgc aatcattatt tttgcgaaca atgtttcctg    600
caacggtcaa gaagaaaacc aaattgtatt atatgtggca gagacacttt aggagttgct    660
ttaccagcaa agaagttgtc ccaatttctg gctaagatac ataataatga aagtaataaa    720
gtttagtaat tgcattgcgt tgactattga ttgcattgat gtcgtgtgat actttcaccg    780
aaaaaaaaca cgaagcgcaa taggagcggt tgcatattag tccccaaagc tatttaattg    840
tgcctgaaac tgttttttaa gctcatcaag cataattgta tgcattgcga cgtaaccaac    900
gtttaggcgc agtttaatca tagcccactg ctaagcc                              937
```

<210> SEQ ID NO 30
<211> LENGTH: 1906
<212> TYPE: DNA
<213> ORGANISM: Artificial Sequence
<220> FEATURE:
<223> OTHER INFORMATION: Sequence of the 3'-Region used for knock out of
      PpPNO1 and PpMNN4

<400> SEQUENCE: 30

```
cggaggaatg caaataataa tctccttaat tacccactga taagctcaag agacgcggtt     60
tgaaaacgat ataatgaatc atttggattt tataataaac cctgacagtt tttccactgt    120
attgttttaa cactcattgg aagctgtatt gattctaaga agctagaaat caatacggcc    180
atacaaaaga tgacattgaa taagcaccgg cttttttgat tagcatatac cttaaagcat    240
gcattcatgg ctacatagtt gttaaagggc ttcttccatt atcagtataa tgaattacat    300
aatcatgcac ttatatttgc ccatctctgt tctctcactc ttgcctgggt atattctatg    360
aaattgcgta tagcgtgtct ccagttgaac cccaagcttg gcgagtttga agagaatgct    420
aaccttgcgt attccttgct tcaggaaaca ttcaaggaga acaggtcaa gaagccaaac    480 attttgatcc ttcccgagtt agcattgact ggctacaatt ttcaaagcca gcagcggata    540
```

```
gagcctttt  tggaggaaac  aaccaaggga  gctagtaccc  aatgggctca  aaaagtatcc      600
aagacgtggg  attgctttac  tttaatagga  tacccagaaa  aaagtttaga  gagccctccc      660
cgtatttaca  acagtgcggt  acttgtatcg  cctcagggaa  aagtaatgaa  caactacaga      720
aagtccttct  tgtatgaagc  tgatgaacat  tggggatgtt  cggaatcttc  tgatgggttt      780
caaacagtag  atttattaat  tgaaggaaag  actgtaaaga  catcatttgg  aatttgcatg      840
gatttgaatc  cttataaatt  tgaagctcca  ttcacagact  tcgagttcag  tggccattgc      900
ttgaaaaccg  gtacaagact  cattttgtgc  ccaatggcct  ggttgtcccc  tctatcgcct      960
tccattaaaa  aggatcttag  tgatatagag  aaaagcagac  ttcaaaagtt  ctaccttgaa     1020
aaaatagata  ccccggaatt  tgacgttaat  tacgaattga  aaaagatga   agtattgccc     1080 acccgtatga  atgaaacgtt  ggaaacaatt  gactttgagc  cttcaaaacc  ggactactct     1140
aatataaatt  attggatact  aaggttttt   cccttctga   ctcatgtcta  taaacgagat     1200
gtgctcaaag  agaatgcagt  tgcagtctta  tgcaaccgag  ttggcattga  gagtgatgtc     1260
ttgtacggag  gatcaaccac  gattctaaac  ttcaatggta  agttagcatc  gacacaagag     1320
gagctggagt  tgtacgggca  gactaatagt  ctcaaccca   gtgtggaagt  attggggggcc    1380 cttggcatgg  gtcaacaggg  aattctagta  cgagacattg  aattaacata  atatacaata    1440
tacaataaac  acaaataaag  aatacaagcc  tgacaaaaat  tcacaaatta  ttgcctagac    1500
ttgtcgttat  cagcagcgac  cttttccaa   tgctcaattt  cacgatatgc  cttttctagc    1560
tctgctttaa  gcttctcatt  ggaattggct  aactcgttga  ctgcttggtc  agtgatgagt    1620
ttctccaagg  tccatttctc  gatgttgttg  ttttcgtttt  cctttaatct  cttgatataa    1680
tcaacagcct  tctttaatat  ctgagccttg  ttcgagtccc  ctgttggcaa  cagagcggcc    1740
agttccttta  ttccgtggtt  tatattttct  cttctacgcc  tttctacttc  tttgtgattc    1800
tctttacgca  tcttatgcca  ttcttcagaa  ccagtggctg  gcttaaccga  atagccagag    1860
cctgaagaag  ccgcactaga  agaagcagtg  gcattgttga  ctatgg                    1906
```

<210> SEQ ID NO 31
<211> LENGTH: 411
<212> TYPE: DNA
<213> ORGANISM: Artificial Sequence
<220> FEATURE:
<223> OTHER INFORMATION: Sequence of the 5'-Region used for knock out of
      BMT1

<400> SEQUENCE: 31

```
catatggtga  gagccgttct  gcacaactag  atgttttcga  gcttcgcatt  gtttcctgca       60
gctcgactat  tgaattaaga  tttccggata  tctccaatct  cacaaaaact  tatgttgacc      120
acgtgctttc  ctgaggcgag  gtgttttata  tgcaagctgc  caaaaatgga  aaacgaatgg      180
ccatttttcg  cccaggcaaa  ttattcgatt  actgctgtca  taaagacagt  gttgcaaggc      240
tcacattttt  ttttaggatc  cgagataaag  tgaatacagg  acagcttatc  tctatatctt      300
gtaccattcg  tgaatcttaa  gagttcggtt  aggggggactc  tagttgaggg  ttggcactca     360
cgtatggctg  ggcgcagaaa  taaaattcag  gcgcagcagc  acttatcgat  g               411
```

<210> SEQ ID NO 32
<211> LENGTH: 692
<212> TYPE: DNA
<213> ORGANISM: Artificial Sequence
<220> FEATURE:
<223> OTHER INFORMATION: Sequence of the 3'-Region used for knock out of

BMT1

<400> SEQUENCE: 32

```
gaattcacag ttataaataa aaacaaaaac tcaaaaagtt tgggctccac aaaataactt        60
aatttaaatt tttgtctaat aaatgaatgt aattccaaga ttatgtgatg caagcacagt       120
atgcttcagc cctatgcagc tactaatgtc aatctcgcct gcgagcgggc ctagattttc       180
actacaaatt tcaaaactac gcggatttat tgtctcagag agcaatttgg catttctgag       240
cgtagcagga ggcttcataa gattgtatag gaccgtacca acaaattgcc gaggcacaac       300
acggtatgct gtgcacttat gtggctactt ccctacaacg gaatgaaacc ttcctctttc       360
cgcttaaacg agaaagtgtg tcgcaattga atgcaggtgc ctgtgcgcct tggtgtattg       420
tttttgaggg cccaatttat caggcgcctt ttttcttggt tgttttccct tagcctcaag       480
caaggttggt ctatttcatc tccgcttcta taccgtgcct gatactgttg gatgagaaca       540
cgactcaact tcctgctgct ctgtattgcc agtgttttgt ctgtgatttg gatcggagtc       600
ctccttactt ggaatgataa taatcttggc ggaatctccc taaacggagg caaggattct       660
gcctatgatg atctgctatc attgggaagc tt                                    692
```

<210> SEQ ID NO 33
<211> LENGTH: 1043
<212> TYPE: DNA
<213> ORGANISM: Artificial Sequence
<220> FEATURE:
<223> OTHER INFORMATION: Sequence of the 5'-Region used for knock out of BMT4

<400> SEQUENCE: 33

```
aagcttgttc accgttggga cttttccgtg gacaatgttg actactccag gagggattcc        60
agctttctct actagctcag caataatcaa tgcagcccca ggcgcccgtt ctgatggctt       120
gatgaccgtt gtattgcctg tcactatagc caggggtagg gtccataaag gaatcatagc       180
agggaaatta aaagggcata ttgatgcaat cactcccaat ggctctcttg ccattgaagt       240
ctccatatca gcactaactt ccaagaagga ccccttcaag tctgacgtga tagagcacgc       300
ttgctctgcc acctgtagtc ctctcaaaac gtcaccttgt gcatcagcaa agactttacc       360
ttgctccaat actatgacgg aggcaattct gtcaaaattc tctctcagca attcaaccaa       420
cttgaaagca aattgctgtc tcttgatgat ggagactttt ttccaagatt gaaatgcaat       480
gtgggacgac tcaattgctt cttccagctc ctcttcggtt gattgaggaa cttttgaaac       540
cacaaaattg gtcgttgggt catgtacatc aaaccattct gtagatttag attcgacgaa       600
agcgttgttg atgaaggaaa aggttggata cggtttgtcg gtctctttgg tatggccggt       660
ggggtatgca attgcagtag aagataattg gacagccatt gttgaaggta gagaaaaggt       720
cagggaactt gggggttatt tataccattt taccccacaa ataacaactg aaaagtaccc       780
attccatagt gagaggtaac cgacggaaaa agacgggccc atgttctggg accaatagaa       840
ctgtgtaatc cattgggact aatcaacaga cgattggcaa tataatgaaa tagttcgttg       900
aaaagccacg tcagctgtct tttcattaac tttggtcgga cacaacattt tctactgttg       960
tatctgtcct actttgctta tcatctgcca cagggcaagt ggatttcctt ctcgcgcggc      1020
tgggtgaaaa cggttaacgt gaa                                             1043
```

<210> SEQ ID NO 34
<211> LENGTH: 695
<212> TYPE: DNA

<213> ORGANISM: Artificial Sequence
<220> FEATURE:
<223> OTHER INFORMATION: Sequence of the 3'-Region used for knock out of BMT4

<400> SEQUENCE: 34

```
gccttggggg acttcaagtc tttgctagaa actagatgag gtcaggccct cttatggttg    60
tgtcccaatt gggcaatttc actcacctaa aaagcatgac aattatttag cgaaataggt   120
agtatatttt ccctcatctc ccaagcagtt tcgttttgc atccatatct ctcaaatgag    180
cagctacgac tcattagaac cagagtcaag taggggtgag ctcagtcatc agccttcgtt   240
tctaaaacga ttgagttctt ttgttgctac aggaagcgcc ctagggaact ttcgcacttt   300
ggaaatagat tttgatgacc aagagcggga gttgatatta gagaggctgt ccaaagtaca   360
tgggatcagg ccggccaaat tgattggtgt gactaaacca ttgtgtactt ggacactcta   420
ttacaaaagc gaagatgatt tgaagtatta caagtcccga agtgttagag gattctatcg   480
agcccagaat gaaatcatca accgttatca gcagattgat aaactcttgg aaagcggtat   540
cccatttca ttattgaaga actacgataa tgaagatgtg agagacggcg accctctgaa    600
cgtagacgaa gaaacaaatc tacttttggg gtacaataga gaaagtgaat caagggaggt   660
atttgtggcc ataatactca actctatcat taatg                              695
```

<210> SEQ ID NO 35
<211> LENGTH: 546
<212> TYPE: DNA
<213> ORGANISM: Artificial Sequence
<220> FEATURE:
<223> OTHER INFORMATION: Sequence of the 5'-Region used for knock out of BMT3

<400> SEQUENCE: 35

```
gatatctccc tggggacaat atgtgttgca actgttcgtt gttggtgccc cagtccccca    60
accggtacta atcggtctat gttcccgtaa ctcatattcg gttagaacta gaacaataag   120
tgcatcattg ttcaacattg tggttcaatt gtcgaacatt gctggtgctt atatctacag   180
ggaagacgat aagcctttgt acaagagagg taacagacag ttaattggta tttctttggg   240
agtcgttgcc ctctacgttg tctccaagac atactacatt ctgagaaaca gatggaagac   300
tcaaaaatgg gagaagctta gtgaagaaga gaaagttgcc tacttggaca gagctgagaa   360
ggagaacctg ggttctaaga ggctggactt tttgttcgag agttaaactg cataattttt   420
tctaagtaaa tttcatagtt atgaaatttc tgcagcttag tgtttactgc atcgtttact   480
gcatcaccct gtaaataatg tgagcttttt tccttccatt gcttggtatc ttccttgctg   540
ctgttt                                                              546
```

<210> SEQ ID NO 36
<211> LENGTH: 378
<212> TYPE: DNA
<213> ORGANISM: Artificial Sequence
<220> FEATURE:
<223> OTHER INFORMATION: Sequence of the 3'-Region used for knock out of BMT3

<400> SEQUENCE: 36

```
acaaaacagt catgtacaga actaacgcct ttaagatgca gaccactgaa aagaattggg    60
tcccattttt cttgaaagac gaccaggaat ctgtccattt tgtttactcg ttcaatcctc   120
tgagagtact caactgcagt cttgataacg gtgcatgtga tgttctatt gagttaccac    180
```

```
atgattttgg catgtcttcc gagctacgtg gtgccactcc tatgctcaat cttcctcagg    240
caatcccgat ggcagacgac aaagaaattt gggtttcatt cccaagaacg agaatatcag    300
attgcgggtg ttctgaaaca atgtacaggc caatgttaat gctttttgtt agagaaggaa    360
caaacttttt tgctgagc                                                  378
```

<210> SEQ ID NO 37
<211> LENGTH: 2577
<212> TYPE: DNA
<213> ORGANISM: Leishmania major

<400> SEQUENCE: 37

```
atgggtaaaa gaaagggaaa ctccttggga gattctggtt ctgctgctac tgcttccaga     60
gaggcttctg ctcaagctga agatgctgct tcccagacta agactgcttc tccacctgct    120
aaggttatct tgttgccaaa gactttgact gacgagaagg acttcatcgg tatcttccca    180
tttccattct ggccagttca cttcgttttg actgttgttg ctttgttcgt tttggctgct    240
tcctgtttcc aggctttcac tgttagaatg atctccgttc aaatctacgg ttacttgatc    300
cacgaatttg acccatggtt caactacaga gctgctgagt acatgtctac tcacggatgg    360
agtgcttttt tctcctggtt cgattacatg tcctggtatc cattgggtag accagttggt    420
tctactactt acccaggatt gcagttgact gctgttgcta tccatagagc tttggctgct    480
gctggaatgc caatgtcctt gaacaatgtt tgtgttttga tgccagcttg gtttggtgct    540
atcgctactg ctactttggc tttctgtact tacgaggctt ctggttctac tgttgctgct    600
gctgcagctg ctttgtcctt ctccattatc cctgctcact tgatgagatc catggctggt    660
gagttcgaca acgagtgtat tgctgttgct gctatgttgt tgactttcta ctgttgggtt    720
cgttccttga gaactagatc ctcctggcca atcggtgttt tgacaggtgt tgcttacggt    780
tacatggctg ctgcttgggg aggttacatc ttcgttttga acatggttgc tatgcacgct    840
ggtatctctt ctatggttga ctgggctaga aacacttaca acccatcctt gttgagagct    900
tacactttgt tctacgttgt tggtactgct atcgctgttt gtgttccacc agttggaatg    960
tctccattca agtccttgga gcagttggga gctttgttgg ttttggtttt cttgtgtgga   1020
ttgcaagttt gtgaggtttt gagagctaga gctggtgttg aagttagatc cagagctaat   1080
ttcaagatca gagttagagt tttctccgtt atggctggtg ttgctgcttt ggctatctct   1140
gttttggctc caactggtta ctttggtcca ttgtctgtta gagttagagc tttgtttgtt   1200
gagcacacta gaactggtaa cccattggtt gactccgttg ctgaacatca accagcttct   1260
ccagaggcta tgtgggcttt cttgcatgtt tgtggtgtta cttggggatt gggttccatt   1320
gttttggctg tttccacttt cgttcactac tccccatcta aggttttctg gttgttgaac   1380
tccggtgctg tttactactt ctccactaga atggctagat tgttgttgtt gtccggtcca   1440
gctgcttgtt tgtccactgg tatcttcgtt ggtactatct tggaggctgc tgttcaattg   1500
tctttctggg actccgatgc tactaaggct aagaagcagc aaaagcaggc tcaaagacac   1560
caaagaggtg ctggtaaagg ttctggtaga gatgacgcta agaacgctac tactgctaga   1620
gctttctgtg acgttttcgc tggttcttct ttggcttggg gtcacagaat ggttttgtcc   1680
attgctatgt gggctttggt tactactact gctgtttcct tcttctcctc cgaatttgct   1740
tctcactcca ctaagttcgc tgaacaatcc tccaacccaa tgatcgtttt cgctgctgtt   1800
gttcagaaca gagctactgg aaagccaatg aacttgttgg ttgacgacta cttgaaggct   1860
tacgagtggt tgagagactc tactccagag gacgctagag ttttggcttg gtgggactac   1920
```

```
ggttaccaaa tcactggtat cggtaacaga acttccttgg ctgatggtaa cacttggaac    1980
cacgagcaca ttgctactat cggaaagatg ttgacttccc cagttgttga agctcactcc    2040
cttgttagac acatggctga ctacgttttg atttgggctg gtcaatctgg tgacttgatg    2100
aagtctccac acatggctag aatcggtaac tctgttacc acgacatttg tccagatgac     2160
ccattgtgtc agcaattcgg tttccacaga acgattact ccagaccaac tccaatgatg     2220
agagcttcct tgttgtacaa cttgcacgag gctggaaaaa gaaagggtgt taaggttaac    2280
ccatctttgt tccaagaggt ttactcctcc aagtacggac ttgttagaat cttcaaggtt    2340
atgaacgttt ccgctgagtc taagaagtgg gttgcagacc cagctaacag agtttgtcac    2400
ccacctggtt cttggatttg tcctggtcaa tacccacctg ctaaagaaat ccaagagatg    2460
ttggctcaca gagttccatt cgaccaggtt acaaacgctg acagaaagaa caatgttggt    2520
tcctaccaag aggaatacat gagaagaatg agagagtccg agaacagaag ataatag      2577

<210> SEQ ID NO 38
<211> LENGTH: 1215
<212> TYPE: DNA
<213> ORGANISM: Saccharomyces cerevisiae

<400> SEQUENCE: 38
atgtcagaag atcaaaaaag tgaaaattcc gtaccttcta aggttaatat ggtgaatcgc      60
accgatatac tgactacgat caagtcattg tcatggcttg acttgatgtt gccatttact     120
ataattctct ccataatcat tgcagtaata atttctgtct atgtgccttc ttcccgtcac     180
acttttgacg ctgaaggtca tcccaatcta atgggagtgt ccattccttt gactgttggt     240
atgattgtaa tgatgattcc cccgatctgc aaagtttcct gggagtctat tcacaagtac     300
ttctacagga gctatataag gaagcaacta gccctctcgt tattttgaa ttgggtcatc      360 ggtcctttgt tgatgacagc attggcgtgg atggcgctat tcgattataa ggaataccgt     420
caaggcatta ttatgatcgg agtagctaga tgcattgcca tggtgctaat ttggaatcag     480
attgctggag agacaatga tctctgcgtc gtgcttgtta ttacaaactc gcttttacag      540
atggtattat atgcaccatt gcagatattt tactgttatg ttatttctca tgaccacctg     600
aatacttcaa atagggtatt attcgaagag gttgcaaagt ctgtcggagt ttttctcggc     660
ataccactgg gaattggcat tatcatacgt ttgggaagtc ttaccatagc tggtaaaagt     720
aattatgaaa aatacatttt gagatttatt tctccatggg caatgatcgg atttcattac     780
actttatttg ttatttttat tagtagaggt tatcaattta tccacgaaat tggttctgca     840
atattgtgct ttgtcccatt ggtgctttac ttctttattg catggttttt gaccttcgca     900
ttaatgaggt acttatcaat atctaggagt gatacacaaa gagaatgtag ctgtgaccaa     960
gaactacttt taagagggt ctggggaaga aagtcttgtg aagctagctt ttctattacg     1020
atgacgcaat gtttcactat ggcttcaaat aattttgaac tatccctggc aattgctatt    1080
tccttatatg gtaacaatag caagcaagca atagctgcaa catttgggcc gttgctagaa    1140
gttccaattt tattgatttt ggcaatagtc gcgagaatcc ttaaaccata ttatatatgg    1200
aacaatagaa attaa                                                     1215

<210> SEQ ID NO 39
<211> LENGTH: 600
<212> TYPE: DNA
<213> ORGANISM: Pichia pastoris
```

<400> SEQUENCE: 39

```
gttcttcgct tggtcttgta tctccttaca ctgtatcttc ccatttgcgt ttaggtggtt    60
atcaaaaact aaaaggaaaa atttcagatg tttatctcta aggttttttc tttttacagt   120
ataacacgtg atgcgtcacg tggtactaga ttacgtaagt tattttggtc cggtgggtaa   180
gtgggtaaga atagaaagca tgaaggttta caaaaacgca gtcacgaatt attgctactt   240
cgagcttgga accaccccaa agattatatt gtactgatgc actaccttct cgattttgct   300
cctccaagaa cctacgaaaa acatttcttg agccttttca acctagacta cacatcaagt   360
tatttaaggt atgttccgtt aacatgtaag aaaaggagag gatagatcgt ttatggggta   420
cgtcgcctga ttcaagcgtg accattcgaa gaataggcct tcgaaagctg aataaagcaa   480
atgtcagttg cgattggtat gctgacaaat tagcataaaa agcaatagac tttctaacca   540
cctgtttttt tccttttact ttatttatat tttgccaccg tactaacaag ttcagacaaa   600
```

<210> SEQ ID NO 40
<211> LENGTH: 1144
<212> TYPE: DNA
<213> ORGANISM: Pichia pastoris

<400> SEQUENCE: 40

```
caaatgcaag aggacattag aaatgtgttt ggtaagaaca tgaagccgga ggcatacaaa    60
cgattcacag atttgaagga ggaaaacaaa ctgcatccac cggaagtgcc agcagccgtg   120
tatgccaacc ttgctctcaa aggcattcct acggatctga gtgggaaata tctgagattc   180
acagacccac tattggaaca gtaccaaacc tagtttggcc gatccatgat tatgtaatgc   240
atatagtttt tgtcgatgct cacccgtttc gagtctgtct cgtatcgtct tacgtataag   300
ttcaagcatg tttaccaggt ctgttagaaa ctcctttgtg agggcaggac ctattcgtct   360
cggtcccgtt gtttctaaga gactgtacag ccaagcgcag aatggtggca ttaaccataa   420
gaggattctg atcggacttg gtctattggc tattggaacc acccttacg ggacaaccaa   480
ccctaccaag actcctattg catttgtgga accagccacg gaaagagcgt taaggacgg   540
agacgtctct gtgattttg ttctcggagg tccaggagct ggaaaaggta cccaatgtgc    600
caaactagtg agtaattacg gatttgttca cctgtcagct ggagacttgt tacgtgcaga   660
acagaagagg gaggggtcta agtatggaga gatgatttcc cagtatatca gagatggact   720
gatagtacct caagaggtca ccattgcgct cttggagcag gccatgaagg aaaacttcga   780
gaaagggaag acacggttct tgattgatgg attccctcgt aagatggacc aggccaaaac   840
ttttgaggaa aaagtcgcaa agtccaaggt gacacttttc tttgattgtc ccgaatcagt   900
gctccttgag agattactta aaagaggaca gacaagcgga agagaggatg ataatgcgga   960
gagtatcaaa aaaagattca aacattcgt ggaaacttcg atgcctgtgg tggactattt  1020
cgggaagcaa ggacgcgttt tgaaggtatc ttgtgaccac cctgtggatc aagtgtattc  1080
acaggttgtg tcggtgctaa aagagaaggg gatctttgcc gataacgaga cggagaataa  1140
ataa                                                               1144
```

<210> SEQ ID NO 41
<211> LENGTH: 255
<212> TYPE: DNA
<213> ORGANISM: Artificial Sequence
<220> FEATURE:
<223> OTHER INFORMATION: DNA encodes Saccharomyces cerevisiae mating factor pre-propeptide

<400> SEQUENCE: 41

```
atgagatttc cttcaattttt tactgcagtt ttattcgcag catcctccgc attagctgct      60
ccagtcaaca ctacaacaga agatgaaacg gcacaaattc cggctgaagc tgtcatcggt     120
tactcagatt tagaaggga tttcgatgtt gctgttttgc cattttccaa cagcacaaat     180
aacgggttat tgtttataaa tactactatt gccagcattg ctgctaaaga agaaggggta     240
tctctcgaga aaagg                                                      255
```

<210> SEQ ID NO 42
<211> LENGTH: 237
<212> TYPE: DNA
<213> ORGANISM: Artificial Sequence
<220> FEATURE:
<223> OTHER INFORMATION: DNA encodes SCI (C peptide CTP)

<400> SEQUENCE: 42

```
tttgttaacc aacatttgtg tggttctcac cttgttgaag ctttgtacct tgtctgcgga      60
gagagaggat ttttctatac tcctaagaca tcttcctcaa gtaaagcccc acctccatca     120
ttgccttctc catccagact tcctggtcca tccgataccc ctattttgcc acaaggaatc     180
gtcgaacagt gttgcacttc aatttgtagt ttgtaccagc ttgagaacta ttgcaat        237
```

<210> SEQ ID NO 43
<211> LENGTH: 79
<212> TYPE: PRT
<213> ORGANISM: Artificial Sequence
<220> FEATURE:
<223> OTHER INFORMATION: SCI (C peptide CTP)

<400> SEQUENCE: 43

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Ser Ser
            20                  25                  30

Ser Ser Lys Ala Pro Pro Pro Ser Leu Pro Ser Pro Ser Arg Leu Pro
        35                  40                  45

Gly Pro Ser Asp Thr Pro Ile Leu Pro Gln Gly Ile Val Glu Gln Cys
    50                  55                  60

Cys Thr Ser Ile Cys Ser Leu Tyr Gln Leu Glu Asn Tyr Cys Asn
65                  70                  75
```

<210> SEQ ID NO 44
<211> LENGTH: 240
<212> TYPE: DNA
<213> ORGANISM: Artificial Sequence
<220> FEATURE:
<223> OTHER INFORMATION: DNA encodes SCI (C peptide CTP+K)

<400> SEQUENCE: 44

```
tttgttaacc aacatttgtg tggttctcac cttgttgaag ctttgtacct tgtctgcgga      60
gagagaggat ttttctatac tcctaagaca tcttcctcaa gtagagcccc acctccatca     120
ttgccttctc catccagact tcctggtcca tccgataccc ctattttgcc acaaaaagga     180
atcgtcgaac agtgttgcac ttcaatttgt agtttgtacc agcttgagaa ctattgcaat     240
```

<210> SEQ ID NO 45
<211> LENGTH: 80
<212> TYPE: PRT
<213> ORGANISM: Artificial Sequence
<220> FEATURE:

<223> OTHER INFORMATION: SCI (C peptide CTP+K)

<400> SEQUENCE: 45

Phe Val Asn Gln His Leu Cys Gly Ser His Leu Val Glu Ala Leu Tyr
1               5                   10                  15
Leu Val Cys Gly Glu Arg Gly Phe Phe Tyr Thr Pro Lys Thr Ser Ser
            20                  25                  30
Ser Ser Arg Ala Pro Pro Ser Leu Pro Ser Pro Ser Arg Leu Pro
        35                  40                  45
Gly Pro Ser Asp Thr Pro Ile Leu Pro Gln Lys Gly Ile Val Glu Gln
    50                  55                  60
Cys Cys Thr Ser Ile Cys Ser Leu Tyr Gln Leu Glu Asn Tyr Cys Asn
65                  70                  75                  80

<210> SEQ ID NO 46
<211> LENGTH: 246
<212> TYPE: DNA
<213> ORGANISM: Artificial Sequence
<220> FEATURE:
<223> OTHER INFORMATION: DNA encodes SCI (N-spacer CTP)

<400> SEQUENCE: 46
tcttcctcaa gtagagcacc acctccatca ttgccttctc catccagact tcctggtcca      60
tccgataccc ctattttgcc acaatttgtt aaccagcatt tgtgtggatc tcaccttgtt     120
gaagctttgt accttgtctg cggagagaga ggattttttct atactcctaa gacagctgcc    180
aaaggtattg tcgaacaatg ttgcacttca atctgtagtt tgtaccagct gagaactat     240 tgcaat                                                                246

<210> SEQ ID NO 47
<211> LENGTH: 82
<212> TYPE: PRT
<213> ORGANISM: Artificial Sequence
<220> FEATURE:
<223> OTHER INFORMATION: SCI (N-spacer CTP)

<400> SEQUENCE: 47

Ser Ser Ser Ser Arg Ala Pro Pro Pro Ser Leu Pro Ser Pro Ser Arg
1               5                   10                  15
Leu Pro Gly Pro Ser Asp Thr Pro Ile Leu Pro Gln Phe Val Asn Gln
            20                  25                  30
His Leu Cys Gly Ser His Leu Val Glu Ala Leu Tyr Leu Val Cys Gly
        35                  40                  45
Glu Arg Gly Phe Phe Tyr Thr Pro Lys Thr Ala Ala Lys Gly Ile Val
    50                  55                  60
Glu Gln Cys Cys Thr Ser Ile Cys Ser Leu Tyr Gln Leu Glu Asn Tyr
65                  70                  75                  80
Cys Asn

<210> SEQ ID NO 48
<211> LENGTH: 249
<212> TYPE: DNA
<213> ORGANISM: Artificial Sequence
<220> FEATURE:
<223> OTHER INFORMATION: DNA encodes SCI (N-spacer CTP +K)

<400> SEQUENCE: 48
tcttcctcaa gtagagcacc acctccatca ttgccttctc catccagact tcctggtcca      60
tccgataccc ctattttgcc acaaaagttt gttaaccagc atttgtgtgg atctcacctt     120

```
gttgaagctt tgtaccttgt ctgcggagag agaggatttt tctatactcc taagacagct    180
gccaaaggta ttgtcgaaca atgttgcact tcaatctgta gtttgtacca gcttgagaac    240
tattgcaat                                                            249
```

<210> SEQ ID NO 49
<211> LENGTH: 83
<212> TYPE: PRT
<213> ORGANISM: Artificial Sequence
<220> FEATURE:
<223> OTHER INFORMATION: SCI (N-spacer CTP +K)

<400> SEQUENCE: 49

```
Ser Ser Ser Ser Arg Ala Pro Pro Ser Leu Pro Ser Pro Ser Arg
1               5                   10                  15

Leu Pro Gly Pro Ser Asp Thr Pro Ile Leu Pro Gln Lys Phe Val Asn
                20                  25                  30

Gln His Leu Cys Gly Ser His Leu Val Glu Ala Leu Tyr Leu Val Cys
            35                  40                  45

Gly Glu Arg Gly Phe Phe Tyr Thr Pro Lys Thr Ala Ala Lys Gly Ile
        50                  55                  60

Val Glu Gln Cys Cys Thr Ser Ile Cys Ser Leu Tyr Gln Leu Glu Asn
65                  70                  75                  80

Tyr Cys Asn
```

<210> SEQ ID NO 50
<211> LENGTH: 321
<212> TYPE: DNA
<213> ORGANISM: Artificial Sequence
<220> FEATURE:
<223> OTHER INFORMATION: DNA encodes SCI (N-spacer CTP; C-peptide CTP)

<400> SEQUENCE: 50

```
tcttcctcaa gtaaggctcc acctccatca ttgccatctc cttccagact tccaggtcct     60
agtgatacac caattttgcc tcaatttgtt aaccagcatt tgtgtggatc tcaccttgtt    120
gaagctttgt accttgtctg cggagagaga ggattttttct atactccaaa gacatcttcc   180
tcaagtaaag ccccctccacc ttccttgcca tcacctagta gacttccagg tccttctgac   240
accccaattt tgcctcaagg aatcgtcgaa cagtgttgca cttctatctg ttccttgtac    300
caacttgaga actattgcaa t                                              321
```

<210> SEQ ID NO 51
<211> LENGTH: 107
<212> TYPE: PRT
<213> ORGANISM: Artificial Sequence
<220> FEATURE:
<223> OTHER INFORMATION: SCI (N-spacer CTP; C-peptide CTP)

<400> SEQUENCE: 51

```
Ser Ser Ser Ser Lys Ala Pro Pro Ser Leu Pro Ser Pro Ser Arg
1               5                   10                  15

Leu Pro Gly Pro Ser Asp Thr Pro Ile Leu Pro Gln Phe Val Asn Gln
                20                  25                  30

His Leu Cys Gly Ser His Leu Val Glu Ala Leu Tyr Leu Val Cys Gly
            35                  40                  45

Glu Arg Gly Phe Phe Tyr Thr Pro Lys Thr Ser Ser Ser Lys Ala
        50                  55                  60

Pro Pro Pro Ser Leu Pro Ser Pro Ser Arg Leu Pro Gly Pro Ser Asp
```

```
                65                  70                  75                  80
Thr Pro Ile Leu Pro Gln Gly Ile Val Glu Gln Cys Cys Thr Ser Ile
                    85                  90                  95
Cys Ser Leu Tyr Gln Leu Glu Asn Tyr Cys Asn
                100                 105

<210> SEQ ID NO 52
<211> LENGTH: 324
<212> TYPE: DNA
<213> ORGANISM: Artificial Sequence
<220> FEATURE:
<223> OTHER INFORMATION: DNA encodes SCI (N-spacer CTP; C-peptide CTP+K)

<400> SEQUENCE: 52
tcttcttctt ctagagcccc acctccatca ttgccatctc cttccagact tccaggtcct        60
agtgatacac caattttgcc tcaatttgtt aaccagcatt tgtgtggatc tcaccttgtt       120
gaagctttgt accttgtctg cggagagaga ggattttttct atactccaaa gacatcttcc      180
tcaagtagag cccctccacc ttccttgcca tcacctagta gacttccagg tccttctgac       240
accccaattt tgcctcaaaa aggaatcgtc gaacagtgtt gcacttctat ctgttccttg       300
taccaacttg agaactattg caat                                              324

<210> SEQ ID NO 53
<211> LENGTH: 108
<212> TYPE: PRT
<213> ORGANISM: Artificial Sequence
<220> FEATURE:
<223> OTHER INFORMATION: SCI (N-spacer CTP; C-peptide CTP+K)

<400> SEQUENCE: 53

Ser Ser Ser Ser Arg Ala Pro Pro Ser Leu Pro Ser Pro Ser Arg
1               5                   10                  15
Leu Pro Gly Pro Ser Asp Thr Pro Ile Leu Pro Gln Phe Val Asn Gln
                20                  25                  30
His Leu Cys Gly Ser His Leu Val Glu Ala Leu Tyr Leu Val Cys Gly
                35                  40                  45
Glu Arg Gly Phe Phe Tyr Thr Pro Lys Thr Ser Ser Ser Ser Arg Ala
            50                  55                  60
Pro Pro Ser Leu Pro Ser Pro Ser Arg Leu Pro Gly Pro Ser Asp
65                  70                  75                  80
Thr Pro Ile Leu Pro Gln Lys Gly Ile Val Glu Gln Cys Cys Thr Ser
                85                  90                  95
Ile Cys Ser Leu Tyr Gln Leu Glu Asn Tyr Cys Asn
                100                 105

<210> SEQ ID NO 54
<211> LENGTH: 10
<212> TYPE: DNA
<213> ORGANISM: Artificial Sequence
<220> FEATURE:
<223> OTHER INFORMATION: 5' MylI leader sequence

<400> SEQUENCE: 54
gagtcctctt                                                               10

<210> SEQ ID NO 55
<211> LENGTH: 14
<212> TYPE: DNA
<213> ORGANISM: Artificial Sequence
<220> FEATURE:
```

<223> OTHER INFORMATION: 3' stop-stop-FseI sequence

<400> SEQUENCE: 55
taatagggcc ggcc                                                    14

<210> SEQ ID NO 56
<211> LENGTH: 12
<212> TYPE: PRT
<213> ORGANISM: Artificial Sequence
<220> FEATURE:
<223> OTHER INFORMATION: Connecting peptide

<400> SEQUENCE: 56

Gly Ala Gly Ser Ser Ser Arg Arg Ala Pro Gln Thr
1               5                   10

<210> SEQ ID NO 57
<211> LENGTH: 9
<212> TYPE: PRT
<213> ORGANISM: Artificial Sequence
<220> FEATURE:
<223> OTHER INFORMATION: Connecting peptide

<400> SEQUENCE: 57

Gly Ala Gly Ser Ser Ser Arg Arg Ala
1               5

<210> SEQ ID NO 58
<211> LENGTH: 8
<212> TYPE: PRT
<213> ORGANISM: Artificial Sequence
<220> FEATURE:
<223> OTHER INFORMATION: Connecting peptide

<400> SEQUENCE: 58

Gly Ala Gly Ser Ser Ser Arg Arg
1               5

<210> SEQ ID NO 59
<211> LENGTH: 6
<212> TYPE: PRT
<213> ORGANISM: Artificial Sequence
<220> FEATURE:
<223> OTHER INFORMATION: Connecting peptide

<400> SEQUENCE: 59

Gly Gly Gly Pro Arg Arg
1               5

<210> SEQ ID NO 60
<211> LENGTH: 7
<212> TYPE: PRT
<213> ORGANISM: Artificial Sequence
<220> FEATURE:
<223> OTHER INFORMATION: Connecting peptide

<400> SEQUENCE: 60

Gly Gly Gly Pro Gly Ala Gly
1               5

<210> SEQ ID NO 61
<211> LENGTH: 7
<212> TYPE: PRT
<213> ORGANISM: Artificial Sequence
<220> FEATURE:
<223> OTHER INFORMATION: Connecting peptide

```
<400> SEQUENCE: 61

Gly Gly Gly Gly Gly Lys Arg
1               5

<210> SEQ ID NO 62
<211> LENGTH: 7
<212> TYPE: PRT
<213> ORGANISM: Artificial Sequence
<220> FEATURE:
<223> OTHER INFORMATION: Connecting peptide

<400> SEQUENCE: 62

Gly Gly Gly Pro Gly Lys Arg
1               5

<210> SEQ ID NO 63
<211> LENGTH: 7
<212> TYPE: PRT
<213> ORGANISM: Artificial Sequence
<220> FEATURE:
<223> OTHER INFORMATION: Connecting peptide

<400> SEQUENCE: 63

Val Gly Leu Ser Ser Gly Gln
1               5

<210> SEQ ID NO 64
<211> LENGTH: 7
<212> TYPE: PRT
<213> ORGANISM: Artificial Sequence
<220> FEATURE:
<223> OTHER INFORMATION: Connecting peptide

<400> SEQUENCE: 64

Thr Gly Leu Gly Ser Gly Arg
1               5

<210> SEQ ID NO 65
<211> LENGTH: 7
<212> TYPE: PRT
<213> ORGANISM: Artificial Sequence
<220> FEATURE:
<223> OTHER INFORMATION: Connecting peptide

<400> SEQUENCE: 65

Arg Arg Gly Pro Gly Gly Gly
1               5

<210> SEQ ID NO 66
<211> LENGTH: 7
<212> TYPE: PRT
<213> ORGANISM: Artificial Sequence
<220> FEATURE:
<223> OTHER INFORMATION: Connecting peptide

<400> SEQUENCE: 66

Arg Arg Gly Gly Gly Gly Gly
1               5

<210> SEQ ID NO 67
<211> LENGTH: 9
<212> TYPE: PRT
<213> ORGANISM: Artificial Sequence
<220> FEATURE:
<223> OTHER INFORMATION: Connecting peptide

<400> SEQUENCE: 67
```

Gly Gly Ala Pro Gly Asp Val Lys Arg
1               5

<210> SEQ ID NO 68
<211> LENGTH: 9
<212> TYPE: PRT
<213> ORGANISM: Artificial Sequence
<220> FEATURE:
<223> OTHER INFORMATION: Connecting peptide

<400> SEQUENCE: 68

Arg Arg Ala Pro Gly Asp Val Gly Gly
1               5

<210> SEQ ID NO 69
<211> LENGTH: 9
<212> TYPE: PRT
<213> ORGANISM: Artificial Sequence
<220> FEATURE:
<223> OTHER INFORMATION: Connecting peptide

<400> SEQUENCE: 69

Gly Gly Tyr Pro Gly Asp Val Leu Arg
1               5

<210> SEQ ID NO 70
<211> LENGTH: 9
<212> TYPE: PRT
<213> ORGANISM: Artificial Sequence
<220> FEATURE:
<223> OTHER INFORMATION: Connecting peptide

<400> SEQUENCE: 70

Arg Arg Tyr Pro Gly Asp Val Gly Gly
1               5

<210> SEQ ID NO 71
<211> LENGTH: 8
<212> TYPE: PRT
<213> ORGANISM: Artificial Sequence
<220> FEATURE:
<223> OTHER INFORMATION: Connecting peptide

<400> SEQUENCE: 71

Gly Gly His Pro Gly Asp Val Arg
1               5

<210> SEQ ID NO 72
<211> LENGTH: 9
<212> TYPE: PRT
<213> ORGANISM: Artificial Sequence
<220> FEATURE:
<223> OTHER INFORMATION: Connecting peptide

<400> SEQUENCE: 72

Arg Arg His Pro Gly Asp Val Gly Gly
1               5

<210> SEQ ID NO 73
<211> LENGTH: 30
<212> TYPE: PRT
<213> ORGANISM: Artificial Sequence
<220> FEATURE:
<223> OTHER INFORMATION: Insulin lispro B-chain

<400> SEQUENCE: 73

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 74
<211> LENGTH: 30
<212> TYPE: PRT
<213> ORGANISM: Artificial Sequence
<220> FEATURE:
<223> OTHER INFORMATION: Insulin aspart B-chain

<400> SEQUENCE: 74

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 75
<211> LENGTH: 30
<212> TYPE: PRT
<213> ORGANISM: Artificial Sequence
<220> FEATURE:
<223> OTHER INFORMATION: Insulin glulisine

<400> SEQUENCE: 75

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr
            20                  25                  30

<210> SEQ ID NO 76
<211> LENGTH: 29
<212> TYPE: PRT
<213> ORGANISM: Artificial Sequence
<220> FEATURE:
<223> OTHER INFORMATION: Insulin degludec, desB30, Lys B29 conjugated to
      hexadecandioic acid (B29N(epsilon)-omega-carboxypentadecanoyl-
      gamma-L-glutamyl desB30 human insulin)

<400> SEQUENCE: 76

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 77
<211> LENGTH: 21
<212> TYPE: PRT
<213> ORGANISM: Artificial Sequence
<220> FEATURE:
<223> OTHER INFORMATION: Insulin glargine A-chain

<400> SEQUENCE: 77

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 78
<211> LENGTH: 31
<212> TYPE: PRT
<213> ORGANISM: Artificial Sequence
<220> FEATURE:
<223> OTHER INFORMATION: Insulin glargine B-chain
```

-continued

```
<400> SEQUENCE: 78

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Arg Arg
            20                  25                  30

<210> SEQ ID NO 79
<211> LENGTH: 22
<212> TYPE: PRT
<213> ORGANISM: Artificial Sequence
<220> FEATURE:
<223> OTHER INFORMATION: ArgA0

<400> SEQUENCE: 79

Arg Gly Ile Val Glu Gln Cys Cys Thr Ser Ile Cys Ser Leu Tyr Gln
1               5                   10                  15

Leu Glu Asn Tyr Cys Asn
            20

<210> SEQ ID NO 80
<211> LENGTH: 22
<212> TYPE: PRT
<213> ORGANISM: Artificial Sequence
<220> FEATURE:
<223> OTHER INFORMATION: ArgA0A21

<400> SEQUENCE: 80

Arg Gly Ile Val Glu Gln Cys Cys Thr Ser Ile Cys Ser Leu Tyr Gln
1               5                   10                  15

Leu Glu Asn Tyr Cys Gly
            20

<210> SEQ ID NO 81
<211> LENGTH: 29
<212> TYPE: PRT
<213> ORGANISM: Artificial Sequence
<220> FEATURE:
<223> OTHER INFORMATION: Insulin degludec, desB30, Lys B29 conjugated to
      myristic acid

<400> SEQUENCE: 81

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 82
<211> LENGTH: 44
<212> TYPE: PRT
<213> ORGANISM: Artificial Sequence
<220> FEATURE:
<223> OTHER INFORMATION: TA57 pro

<400> SEQUENCE: 82

Gln Pro Ile Asp Asp Thr Glu Ser Gln Thr Thr Ser Val Asn Leu Met
1               5                   10                  15

Ala Asp Asp Thr Glu Ser Ala Phe Ala Thr Gln Thr Asn Ser Gly Gly
            20                  25                  30

Leu Asp Val Val Gly Leu Ile Ser Met Ala Lys Arg
        35                  40

<210> SEQ ID NO 83
```

```
<211> LENGTH: 6
<212> TYPE: PRT
<213> ORGANISM: Artificial Sequence
<220> FEATURE:
<223> OTHER INFORMATION: N-terminal spacer

<400> SEQUENCE: 83

Glu Glu Gly Glu Pro Lys
1               5

<210> SEQ ID NO 84
<211> LENGTH: 3
<212> TYPE: PRT
<213> ORGANISM: Artificial Sequence
<220> FEATURE:
<223> OTHER INFORMATION: C peptide "AAK"

<400> SEQUENCE: 84

Ala Ala Lys
1

<210> SEQ ID NO 85
<211> LENGTH: 57
<212> TYPE: DNA
<213> ORGANISM: Artificial Sequence
<220> FEATURE:
<223> OTHER INFORMATION: Saccharomyces cerevisiae mating factor pre-
      signal peptide (DNA)

<400> SEQUENCE: 85
atgagattcc catccatctt cactgctgtt ttgttcgctg cttcttctgc tttggct        57

<210> SEQ ID NO 86
<211> LENGTH: 19
<212> TYPE: PRT
<213> ORGANISM: Artificial Sequence
<220> FEATURE:
<223> OTHER INFORMATION: Saccharomyces cerevisiae mating factor pre-
      signal peptide (protein)

<400> SEQUENCE: 86

Met Arg Phe Pro Ser Ile Phe Thr Ala Val Leu Phe Ala Ala Ser Ser
1               5                   10                  15

Ala Leu Ala

<210> SEQ ID NO 87
<211> LENGTH: 1494
<212> TYPE: DNA
<213> ORGANISM: Artificial Sequence
<220> FEATURE:
<223> OTHER INFORMATION: DNA encodes Tricoderma reesei ?1,2-mannosidase
      catalytic domain

<400> SEQUENCE: 87
cgcgccggat ctcccaaccc tacgagggcg gcagcagtca aggccgcatt ccagacgtcg        60
tggaacgctt accaccattt tgcctttccc catgacgacc tccacccggt cagcaacagc       120
tttgatgatg agagaaacgg ctggggctcg tcggcaatcg atggcttgga cacggctatc       180
ctcatggggg atgccgacat tgtgaacacg atccttcagt atgtaccgca gatcaacttc       240
accacgactg cggttgccaa ccaaggcatc tccgtgttcg agaccaacat tcggtacctc       300
ggtggcctgc tttctgccta tgacctgttg cgaggtcctt tcagctcctt ggcgacaaac       360
cagaccctgt aaacagcct tctgaggcag gctcaaacac tggccaacgg cctcaaggtt       420
gcgttcacca ctcccagcgg tgtcccggac cctaccgtct tcttcaaccc tactgtccgg       480
```

```
agaagtggtg catctagcaa caacgtcgct gaaattggaa gcctggtgct cgagtggaca    540
cggttgagcg acctgacggg aaacccgcag tatgcccagc ttgcgcagaa gggcgagtcg    600
tatctcctga atccaagggg aagcccggag gcatggcctg gcctgattgg aacgtttgtc    660
agcacgagca acgtacctt tcaggatagc agcggcagct ggtccggcct catggacagc     720
ttctacgagt acctgatcaa gatgtacctg tacgacccgg ttgcgtttgc acactacaag    780
gatcgctggg tccttgctgc cgactcgacc attgcgcatc tcgcctctca cccgtcgacg    840
cgcaaggact tgaccttttt gtcttcgtac aacggacagt ctacgtcgcc aaactcagga    900
catttggcca gttttgccgg tggcaacttc atcttgggag gcattctcct gaacgagcaa    960
aagtacattg actttggaat caagcttgcc agctcgtact ttgccacgta caaccagacg   1020
gcttctggaa tcggcccga aggcttcgcg tgggtggaca gcgtgacggg cgccggcggc    1080
tcgccgccct cgtcccagtc cgggttctac tcgtcggcag gattctgggt gacggcaccg   1140
tattacatcc tgcggccgga gacgctggag agcttgtact acgcataccg cgtcacgggc   1200
gactccaagt ggcaggacct ggcgtgggaa gcgttcagtg ccattgagga cgcatgccgc   1260
gccggcagcg cgtactcgtc catcaacgac gtgacgcagg ccaacggcgg gggtgcctct   1320
gacgatatgg agagcttctg gtttgccgag gcgctcaagt atgcgtacct gatctttgcg   1380
gaggagtcgg atgtgcaggt gcaggccaac ggcgggaaca aatttgtctt taacacggag   1440
gcgcacccct ttagcatccg ttcatcatca cgacggggcg gccaccttgc ttaa          1494
```

<210> SEQ ID NO 88
<211> LENGTH: 1231
<212> TYPE: DNA
<213> ORGANISM: Artificial Sequence
<220> FEATURE:
<223> OTHER INFORMATION: Sequence of the 5'-region to knock into the
      PpPRO1 locus

<400> SEQUENCE: 88

```
gaagggccat cgaattgtca tcgtctcctc aggtgccatc gctgtgggca tgaagagagt     60
caacatgaag cggaaaccaa aaaagttaca gcaagtgcag gcattggctg ctataggaca    120
aggccgtttg ataggacttt gggacgacct tttccgtcag ttgaatcagc ctattgcgca    180
gattttactg actagaacgg atttggtcga ttacacccag tttaagaacg ctgaaaatac    240
attggaacag cttattaaaa tgggtattat tcctattgtc aatgagaatg cacccctatc    300
cattcaagaa atcaaatttg gtgacaatga caccttatcc gccataacag ctggtatgtg    360
tcatgcagac tacctgttt tggtgactga tgtggactgt ctttacacgg ataaccctcg     420
tacgaatccg gacgctgagc caatcgtgtt agttagaaat atgaggaatc taaacgtcaa    480
taccgaaagt ggaggttccg ccgtaggaac aggaggaatg acaactaaat tgatcgcagc    540
tgatttgggt gtatctgcag gtgttacaac gattatttgc aaaagtgaac atcccgagca    600
gattttggac attgtagagt acagtatccg tgctgataga gtcgaaaatg aggctaaata    660
tctggtcatc aacgaagagg aaactgtgga acaatttcaa gagatcaatc ggtcagaact    720
gagggagttg aacaagctgg acattccttt gcatacacgt ttcgttggcc acagttttaa    780
tgctgttaat aacaaagagt tttggttact ccatggacta aaggccaacg gagccattat    840
cattgatcca ggttgttata aggctatcac tagaaaaaac aaagctggta ttcttccagc    900
tggaattatt tccgtagagg gtaatttcca tgaatacgac tgtgttgatg ttaaggtagg    960
actaagagat ccagatgacc cacattcact agaccccaat gaagaacttt acgtcgttgg   1020
```

```
ccgtgcccgt tgtaattacc ccagcaatca aatcaacaaa attaagggtc tacaaagctc    1080
gcagatcgag caggttctag gttacgctga cggtgagtat gttgttcaca gggacaactt    1140
ggctttccca gtatttgccg atccagaact gttggatgtt gttgagagta ccctgtctga    1200
acaggagaga gaatccaaac caaataaata g                                   1231
```

<210> SEQ ID NO 89
<211> LENGTH: 1425
<212> TYPE: DNA
<213> ORGANISM: Artificial Sequence
<220> FEATURE:
<223> OTHER INFORMATION: Sequence of the 3'-region to knock into the
      PpPRO1 locus

<400> SEQUENCE: 89

```
aatttcacat atgctgcttg attatgtaat tataccttgc gttcgatggc atcgatttcc      60
tcttctgtca atcgcgcatc gcattaaaag tatacttttt ttttttttcct atagtactat    120 tcgccttatt ataaactttg ctagtatgag ttctaccccc aagaaagagc ctgatttgac    180
tcctaagaag agtcagcctc caaagaatag tctcggtggg ggtaaaggct ttagtgagga    240
gggtttctcc caaggggact tcagcgctaa gcatatacta atcgtcgcc ctaacaccga     300 aggctcttct gtggcttcga acgtcatcag ttcgtcatca ttgcaaaggt taccatcctc    360
tggatctgga agcgttgctg tgggaagtgt gttgggatct tcgccattaa ctctttctgg    420
agggttccac gggcttgatc caaccaagaa taaaatagac gttccaaagt cgaaacagtc    480
aaggagacaa agtgttcttt ctgacatgat ttccacttct catgcagcta gaaatgatca    540
ctcagagcag cagttacaaa ctggacaaca atcagaacaa aagaagaag atggtagtcg     600 atcttctttt tctgtttctt cccccgcaag agatatccgg cacccagatg tactgaaaac    660
tgtcgagaaa catcttgcca atgacagcga gatcgactca tctttacaac ttcaaggtgg    720
agatgtcact agaggcattt atcaatgggt aactggagaa agtagtcaaa agataaccc    780 gcctttgaaa cgagcaaata gttttaatga ttttcttct gtgcatggtg acgaggtagg     840
caaggcagat gctgaccacg atcgtgaaag cgtattcgac gaggatgata tctccattga    900
tgatatcaaa gttccgggag ggatgcgtcg aagttttta ttacaaaagc atagagacca    960
acaactttct ggactgaata aaacggctca ccaaccaaaa caacttacta aacctaattt    1020
cttcacgaac aactttatag agtttttggc attgtatggg cattttgcag gtgaagattt    1080
ggaggaagac gaagatgaag atttagacag tggttccgaa tcagtcgcag tcagtgatag    1140
tgagggagaa ttcagtgagg ctgacaacaa tttgttgtat gatgaagagt ctctcctatt    1200
agcacctagt acctccaact atgcgagatc aagaatagga agtattcgta ctcctactta    1260
tggatctttc agttcaaatg ttggttcttc gtctattcat cagcagttaa tgaaaagtca    1320
aatcccgaag ctgaagaaac gtggacagca caagcataaa acacaatcaa aaatacgctc    1380
gaagaagcaa actaccaccg taaaagcagt gttgctgcta ttaaa                    1425
```

<210> SEQ ID NO 90
<211> LENGTH: 20
<212> TYPE: PRT
<213> ORGANISM: Artificial Sequence
<220> FEATURE:
<223> OTHER INFORMATION: Portion of human insulin A-chain

<400> SEQUENCE: 90

Gly Ile Val Glu Gln Cys Cys Thr Ser Ile Cys Ser Leu Tyr Gln Leu

Glu Asn Tyr Cys
            20

<210> SEQ ID NO 91
<211> LENGTH: 29
<212> TYPE: PRT
<213> ORGANISM: Artificial Sequence
<220> FEATURE:
<223> OTHER INFORMATION: CTP+K

<400> SEQUENCE: 91

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln Lys
            20                  25

<210> SEQ ID NO 92
<211> LENGTH: 29
<212> TYPE: PRT
<213> ORGANISM: Artificial Sequence
<220> FEATURE:
<223> OTHER INFORMATION: CTP+R

<400> SEQUENCE: 92

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln Arg
            20                  25

<210> SEQ ID NO 93
<211> LENGTH: 30
<212> TYPE: PRT
<213> ORGANISM: Artificial Sequence
<220> FEATURE:
<223> OTHER INFORMATION: CTP+KR

<400> SEQUENCE: 93

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln Lys Arg
            20                  25                  30

<210> SEQ ID NO 94
<211> LENGTH: 30
<212> TYPE: PRT
<213> ORGANISM: Artificial Sequence
<220> FEATURE:
<223> OTHER INFORMATION: CTP+RR

<400> SEQUENCE: 94

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln Arg Arg
            20                  25                  30